(12) United States Patent
Choi et al.

(10) Patent No.: US 9,937,151 B2
(45) Date of Patent: *Apr. 10, 2018

(54) CARBAPENEM ANTIBACTERIALS WITH GRAM-NEGATIVE ACTIVITY

(71) Applicant: FOB Synthesis, Inc., Kennesaw, GA (US)

(72) Inventors: Woo-Baeg Choi, Sandy Springs, GA (US); Ewa Gruszecka-Kowalik, Atlanta, GA (US); Hyung-Yeul Joo, Kennesaw, GA (US); Shuangpei Liu, Marietta, GA (US); Shuli Mao, Atlanta, GA (US); Yongfeng Li, Marietta, GA (US); Deog-Il Kim, Marietta, GA (US)

(73) Assignee: FOB Synthesis, Inc., Kennesaw, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/692,973

(22) Filed: Apr. 22, 2015

(65) Prior Publication Data

US 2015/0306071 A1 Oct. 29, 2015

Related U.S. Application Data

(63) Continuation of application No. 13/713,520, filed on Dec. 13, 2012, now Pat. No. 9,149,461, which is a continuation of application No. PCT/US2011/040883, filed on Jun. 17, 2011.

(60) Provisional application No. 61/356,398, filed on Jun. 18, 2010.

(51) Int. Cl.
*A61K 31/407* (2006.01)
*C07D 477/10* (2006.01)
*A61K 45/06* (2006.01)
*C07D 477/16* (2006.01)

(52) U.S. Cl.
CPC ............ *A61K 31/407* (2013.01); *A61K 45/06* (2013.01); *C07D 477/10* (2013.01); *C07D 477/16* (2013.01)

(58) Field of Classification Search
None
See application file for complete search history.

(56) References Cited

U.S. PATENT DOCUMENTS

| | | | |
|---|---|---|---|
| 4,424,230 | A | 1/1984 | Christensen et al. |
| 4,782,051 | A | 11/1988 | Christensen et al. |
| 4,933,333 | A | 6/1990 | Sunagawa et al. |
| 4,943,569 | A | 7/1990 | Sunagawa |
| 4,962,103 | A | 10/1990 | Sunagawa et al. |
| 5,011,832 | A | 4/1991 | Dininno et al. |
| 5,034,384 | A | 7/1991 | Greenlee et al. |
| 5,064,954 | A | 11/1991 | Uyeo et al. |
| 5,122,604 | A | 6/1992 | Sunagawa et al. |
| 6,255,300 | B1 | 7/2001 | Dininno et al. |
| 6,310,055 | B2 | 10/2001 | Dininno et al. |
| 6,399,597 | B1 | 6/2002 | Cama et al. |
| 7,683,049 | B2 | 3/2010 | Choi et al. |

FOREIGN PATENT DOCUMENTS

| | | |
|---|---|---|
| EP | 0017992 | 4/1980 |
| EP | 0184844 | 6/1986 |
| EP | 0185315 | 6/1986 |
| EP | 0208889 | 1/1987 |
| EP | 0292191 | 11/1988 |
| EP | 0481116 A1 | 10/1990 |
| JP | 2001491 | 1/1990 |
| JP | 4-164091 | 6/1992 |
| JP | 2000136133 | 5/2000 |
| WO | WO 92-02521 | 2/1992 |
| WO | WO 2005-123066 | 12/2005 |
| WO | WO2005123066 | * 12/2005 |

OTHER PUBLICATIONS

Lippard the Art of Chemistry, Nature 2002, vol. 416, pp. 587.*
Zhanel et al. Ertapenem: review of a new carbapenem, Expert rev. Anti Infect. Ther. (2005) vol. 3, pp. 23-39.*
Aldridge, K., "Ertapenem (MK-0826), a New Carbapenem: Comparative In Vitro Activity Against Clinically Significant Anaerobes," *Diagn. Microbial. Infect. Dis.*, 2002, pp. 181-186, 44(2).
Arnould et al., "New Applications of the Mitsonobu Reaction in the Synthesis of C-2 N-Methy Carbapenems", Tetrahedron Letters, 1992, vol. 33, No. 47, pp. 7133-7136.
Bouffard et al., "Thienamycin Total Synthesis. 1. Synthesis of Azetidinone Precursors of (±)-Thienamycin and Its Stereoisomers," *J. Org. Chem.*, 1980, pp. 1130-1142, 45.
Cunha, B., "Ertapenem: A Review of Its Microbiologic, Pharmocokinetic and Clinical Aspects," *Drugs of Today*, 2002, pp. 195-213, 38 (3).
Edwards et al., "In Vitro Antibacterial Activity of SM-7338, a Carbapenem Antibiotic with Stability to Dehydropeptidase I," *Antimicrob. Agents Chemother.*, 1989, pp. 215-222, 33 (2).
Hazumi et al., "Mechanism of Enhanced Antipseudomonal Activity of BO-2727, a New Injectable 1-β-Methyl Carbapenem," *Antimicrob. Agents Chemother.*, 1995, pp. 702-706, 39 (3).
Johnston et al., "Total Synthesis of (±)-Thienamycin", *J. Am. Chem. Soc.*, 1978, pp. 313-315, 100.
Kahan et al., "Thienamycin, a New β-Lactam Antibiotic I. Discovery, Taxonomy, Isolation and Physical Properties," *J. Antibiot.*, 1979, pp. 1-12, 32.
Krein et al., "A Convenient Synthesis of 2-(Alkylamino) Pyridines," *J. Org. Chem.*, 2002, pp. 4965-4967, 67.
Leanza et al., "N-Acetimidoyl-and N-Formimidoylthienamycin Derivatives: Antipseudomonal β-Lactam Antibiotics," *J. Med. Chem.*, 1979, pp. 1435-1436, 22.

(Continued)

*Primary Examiner* — Kendra D Carter
*Assistant Examiner* — Taina D Matos Negron
(74) *Attorney, Agent, or Firm* — King & Spalding

(57) ABSTRACT

The present invention provides β-methyl carbapenem compounds and pharmaceutical compositions useful in the treatment of bacterial infections and methods for treating such infections using such compounds and/or compositions. The invention includes administering an effective amount of a carbapenem compound or salt and/or prodrug thereof to a host in need of such a treatment.

32 Claims, No Drawings

(56) References Cited

OTHER PUBLICATIONS

Legua et al., "Safety and Local Tolerability of Intramuscularly Administered Ertapenem Diluted in Lidocaine: A Prospective, Randomized, Double-Blind Study Versus Intramuscular Ceftriaxone," *Clin. Therapeut.*, 2002, pp. 434-444, 24 (3).

Majumdar et al., "Pharmacokinetics of Ertapenem in Healthy Young Volunteers," *Antimicrob. Agents Chemother.*, 2002, pp. 3506-3511, 46 (11).

Martins et al., "Design, Synthesis, and Biological Activity of a Novel Non-Cisplatin-type Platinum-Acridine Pharmacophore," *J. Med. Chem.*, 2001, pp. 4492-4496, 44.

Marvel et al., "The Structure of Urea-Formaldehyde Resins," *J. Am. Chem. Soc.*, 1946, pp. 16811686, 68 (9).

Nakagawa et al., "In Vitro Activity of a New Carbapenem Antibiotic, BO-2727, with Potent Antipseudomnal Activity," *Antimicrob. Agents Chemother.*, 1993, pp. 2756-2759, 37 (12).

Neu et al., "In Vitro Activity and β-Lactamase Stability of a New Carpabenem, SM-7338," *Agents Chemother.*, 1989, pp. 1009-1018, 33 (7).

Saino et al., "Purification and Properties of Inducible Penicillin β-Lactamase Isolated from *Pseudomonas maltophilia*," *Antimicrob. Agents Chemother.*, 1982, pp. 564-570, 22 (4).

Salzmann et al., "A Sterocontrolled Synthesis of (±)-Thienamycin," *J. Am. Chem. Soc.*, 1980, pp. 6161-6163, 102.

Shah et al., "Ertapenem, the First of a New Group of Carbapenems," *J. Antimicrob. Chemother.*, 2003, pp. 538-542, 52.

Shimada et al, "Overview of a New Carbapenem, Panipenem/Betamipron," *Drugs Exp Clin Res.*, 1994, pp. 241-245, 20 (6).

Tiraby et al., "A Standard Numbering Scheme for the Class A β-Lactamases," *Biochem. J.*, 1991, pp. 269-270, 276 (pt.1).

Weaver et al., "Thienamycin: New Beta-Lactam Antibiotic with Potent Broad-Spectrum Activity," *Antimicrob. Agents Chemother.*, 1979, pp. 518-521, 15 (4).

Wilkening et al., "Synthesis and Activity of 2(Sulfonamido)Methylcarbapenems: Discovery of a Novel, Anti-MRSA 1,8-Napthosultam Pharmacophore", Bioorganic and Medicinal Chemistry Letters 9, 1999, pp. 673-678.

Yadav et al., "Reactions on a Solid Surface. A Simple, Economical, and Efficient Acylation of Alcohols and Amines over $Al_2O_3$", *J. Org. Chem.*, 2004, pp. 577-580, 69.

Yotsujii et al., "Properties of Novel β-*Lactamase Produced by Bacteroides fragilis,*" *Antimicrob. Agents Chemother.*, 1983, pp. 925-929, 24 (6).

International Search Report with Written Opinion of the Searching Authority dated Nov. 3, 2005 for PCT/US05/20518.

Humphrey, Journal of the American Chemical Society (1999), 121 (49), 11261-11266.

Imuta, Mitsuru et al. "Synthesis and Antibacterial Activity of 2-Functionalized-Vinyl 1B-Methylcarbapenems and Related Compounds," Bioorganic & Medicinal Chemistry Letters 1993, vol. 3, No. 11, pp. 2199-2204.

Aihara, Kazuhiro et al.. "CP0569, A New Broad-Spectrum Injectable Carbapenem," Bioorganic & Medicinal Chemistry 2003, vol. 11, pp. 3475-3485.

Chabala, John et al. "The Preparation and Reactions of 2-Azidocarbapenems," Tetrahedron Letters 1985, vol. 26, No. 44, pp. 5407-5410.

International Preliminary Report on Patentability for PCT/US2011/040883, dated Dec. 19, 2012.

\* cited by examiner

CARBAPENEM ANTIBACTERIALS WITH GRAM-NEGATIVE ACTIVITY

CROSS REFERENCE TO RELATED APPLICATIONS

This application is a continuation of U.S. patent application Ser.No. 13/713,520, filed Dec. 13, 2012, which is a continuation of International Application No. PCT/US2011/040883 filed on Jun. 17, 2011 and claims priority to U.S. Provisional Patent Application No. 61/356,398, filed Jun. 18, 2010. The entire contents of each of the above-identified patent applications are hereby incorporated by reference.

FIELD OF THE INVENTION

This application provides novel carbapenem compounds and their salts, methods of treatment of gram-negative bacterial infections with an effective amount of the compounds and pharmaceutical compositions including the compounds.

BACKGROUND

The worldwide exploitation of antibiotics to treat infectious diseases has grown dramatically over the last forty years. In 1954, two million pounds of antibiotics were produced in the United States. Today, the figure exceeds 50 million pounds. According to the Centers Disease Control (CDC), humans consume 235 million doses of antibiotics annually.

Widespread misuse or overuse of antibiotics has fostered the spread of antibiotic resistance and has contributed to the development of a serious public health problem. Antibiotic resistance occurs when bacteria that cause infection are not killed by the antibiotics taken to stop the infection. The bacteria survive and continue to multiply, causing more harm. For example, the bacterium *Staphylococous aureus* is a major cause of hospital acquired infections that, historically, responded satisfactorily to the antibiotic vancomycin. Recently, however, many strains of *S. aureus* have been found to be resistant to vancomycin. Moreover, the death rates for some communicable diseases such as tuberculosis have started to rise again, in part because of increases in bacterial resistance to antibiotics.

Antibiotics are used therapeutically to treat bacterial infections. Several types of antibiotics, classified according to their mechanism of action, are currently employed. The known types of antibiotics include, e.g. cell wall synthesis inhibitors, cell membrane inhibitors, protein synthesis inhibitors and inhibitors that bind to or affect the synthesis of DNA or RNA.

Cell wall synthesis inhibitors, such as beta lactam antibiotics, generally inhibit some step in the synthesis of bacterial peptidoglycan. Penicillin is generally effective against non-resistant *streptococcus*, gonococcus and *staphylococcus*. Amoxycillin and Ampicillin have broadened spectra against Gram-negative bacteria. Cephalosporins are generally used as penicillin substitutes, against Gram-negative bacteria and in surgical prophylaxis. Monobactams are generally useful for the treatment of allergic individuals.

Numerous antibiotic agents, suitable for use in the treatment of bacteria-related diseases and disorders, are known and disclosed, e.g. in *The Physician's Desk Reference (PDR)*, Medical Economics Company (Montvale, N.J.), (53$^{rd}$ Ed.), 1999; *Mayo Medical Center Formulary*, Unabridged Version, Mayo Clinic (Rochester, Minn.), January 1998; *Merck Index: An Encyclopedia of Chemicals, Drugs and Biologicals*, (11$^{th}$ Ed.), Merck & Co., Inc. (Rahway, N.J.), 1989; University of Wisconsin Antimicrobial Use Guide, http://www.medsch.wisc.edu/clinsci/5amcg/amcg.html; *Introduction on the Use of the Antibiotics Guideline, of Specific Antibiotic Classes*, Thomas Jefferson University, http://jeffline.tju.edu/CWIS/OAC/antibiotics_guide/intro.html; and references cited therein.

The first carbapenem to be isolated was thienamycin, shown below, which was isolated from *Streptomyces cattleya* (U.S. Pat. No. 3,950,357) and was shown to have strong antibacterial activity, including potency against *Pseudomonas* spp. and β-lactamase stability (Kahan, J. S., et al., *J. Antibiot.*, 32, pp. 1-12 (1979); Bodey, G. P., et al., *Antimicrob. Agents Chemother.*, 15, pp. 518-521 (1979). The racemic synthesis of thienamycin was reported shortly thereafter by Merck (Johnston, D. B. R., et al., *J. Am. Chem. Soc.*, 100, pp. 313-315 (1978); Bouffard, F. A., et al., *J. Org. Chem.*, 45, 1130-1142 (1980)), as well as an asymmetric total synthesis (Salzmann, T. N., et al., *J. Am. Chem. Soc.* 102, pp. 6161-6163 (1980)). The nucleus and amino-containing side chain of this molecule,

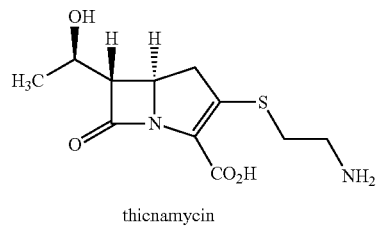 [SMILES: C[C@@H](O)[C@H]1C(=O)N2C(C(=O)O)=C(SCCN)C[C@H]12]

thienamycin however, contributed to its chemical instability. In addition to its potential to be hydrolyzed by the zinc-activated β-lactamase that is present in *Bacillus* species, *Xanthomonas*, *Pseudomonas*, and *Bacteroides* species (Saino, Y., et al., *Antimicrob. Agents Chemother.*, 22, pp. 564-570 (1982); Yotsujii, A., et al., *Antimicrob. Agents Chemother.*, 24, pp. 925-929 (1983)), chemical stability issues associated with the intermolecular aminolysis of the azetidinone (β-lactam) ring of one molecule of thienamycin by the primary amine in the cysteamine side chain of another thienamycin molecule, resulted in the use of thienamycin as a drug candidate to be abandoned.

As a result of the problems associated with thienamycin, N-formimidoyl thienamycin, known as imipenem, was synthesized (Leanza, W. J., et al., *J. Med. Chem.*, 22, pp. 1435-1436 (1979)). This compound bears a more basic amidine functionality on the 2' side chain, which is protonated at physiological pH, preventing the compound from initiating a nucleophilic attack on another imipenem molecule.

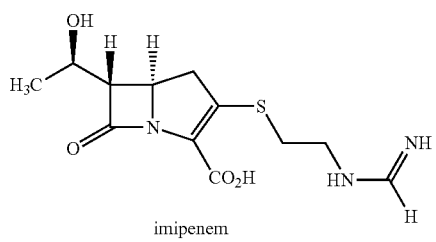 [SMILES: C[C@@H](O)[C@H]1C(=O)N2C(C(=O)O)=C(SCCNC=N)C[C@H]12]

imipenem

However, poor urinary tract recovery from test subjects revealed an instability of this compound to the mammalian β-lactamase renal dehydropeptidase-I (DHP-I) (Shimada, J., et al., *Drugs Exp Clin Res.*, 20, pp. 241-245 (1994)). Consequently, the compound cilastatin was developed for use in co-administration in order to prevent hydrolysis and degredation by DHP-I; this combination therapy is currently prescribed under the name Primaxin® (Merck Frosst Std).

In response to the problem of carbapenems to destruction by renal dehydropeptidase-1, the carbapenem antibiotic meropenem (SM7338) (shown below), was developed (see, Edwards, J. R., et al., *Antimicrob. Agents Chemother.*, 33, pp. 215-222 (1989); Neu, H. C., et al., *Antimicrob. Agents Chemother.*, 33, pp. 1009-1018 (1989)).

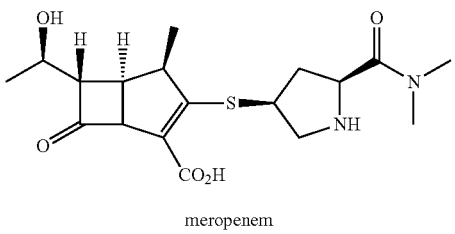 [SMILES: C[C@@H](O)[C@H]1C(=O)C2C(C(=O)O)=C(S[C@@H]3CN[C@H](C(=O)N(C)C)C3)[C@H](C)[C@@H]21]

meropenem

This compound was shown to be active against a large number of Gram-negative bacteria. The drug is currently prescribed for intravenous use (Merrem® IV; AstraZeneca) in the treatment of intra-abdominal infections and bacterial meningitis.

The carbapenem ertapenem (formerly MK-0826; Cunha, B. A., *Drugs of Today*, 38, pp. 195-213 (2002)) was the first of a group of carbapenems with potential against methicillin-resistant staphylococci (MRS) shown to be useful as a long-acting, parenteral carbapenem (Shah, P. M., et al., *J. Antimicrob. Chemother.*, 52, pp. 538-542 (2003); Aldridge, K. E., *Diagn. Microbiol. Infect. Dis.*, 44(2), pp. 181-6 (2002)). It is suitable for administration both as a single-agent (e.g., co-administration with a compound such as cilastatin is not required), or by the intravenous or intramuscular route (Legua, P., et al., *Clin. Therapeut.*, 24, pp. 434-444 (2002); Majumdar, A. K., et al., *Antimicrob. Agents Chemother.*, 46, pp. 3506-3511 (2002)). Ertapenem has received regulatory approval in both the United States (November, 2001) and the European Union (April, 2002).

One carbapenem having a fused pyrazole ring system (L-627; Biapenem) was developed by Lederle Ltd. (Japan), and introduced a methyl radical at the 1-β postion of the carbapenem skeleton (see, U.S. Pat. No. 4,866,171). This structural modification reportedly gave biapenem stability against hydrolysis by kidney dehydropeptidase, making co-administration of a dehydropeptidase inhibitor unnecessary.

More recently, a new, injectable 1-β-methyl carbapenem antibiotic having an (R)-1-hydroxymethyl-methylaminopropyl group exhibiting both broad spectrum, potent antibacterial activity (BO-2727) and having antipseudomonal activity has been reported (Nakagawa, S., et al., *Antimicrob. Agents Chemother.*, 37, pp. 2756-2759 (1993); Hazumi, N., et al., *Antimicrob. Agents Chemother.*, 39, pp. 702-706 (1995).

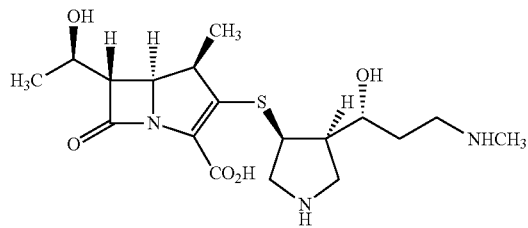

BO-2727

Since the discovery of thienamycin having a potential antimicrobial activity against Gram-negative and Gram-positive bacteria, studies on the syntheses of carbapenem derivatives which are analogous to thienamycin have been widely developed. As a result, it was found that carbapenem derivatives having, as their 2-side chain, a substituent derived from 4-hydroxy-proline exhibit a potential antimicrobial activity and are useful as medicines or as intermediates for compounds possessing antimicrobial activity.

1-β-methyl carbapenem antibiotics, are particularly well known for treating a broad spectrum of gram-negative and gram-positive bacterial infections. See for example U.S. Pat. Nos. 4,962,103 4,933,333; 4,943,569; 5,122,604; 5,034,384 and 5,011,832.

U.S. Pat. No. 6,255,300 to Merck & Co. describes certain carbapenem antibacterial agents in which the carbapenem nucleus is substituted with an iodo-phenyl linked through a methyl-oxygen linkage. The patent states that these compounds are useful against gram positive bacterial infections. Similarly, U.S. Pat. No. 6,310,055 provides carbapenem compounds with aromatic side chains that are halogen substituted, linked thorough an alkoxy unsaturated group.

European Publication No. 0 292 191 to Merck & Co. describes certain 2-(substituted methyl)-1-alkylcarbapenem compounds useful as antibiotic agents.

U.S. Pat. No. 6,399,597, also to Merck & Co. describes certain napthosultam compounds that are allegedly useful in the treatment of certain drug resistant bacterial infections.

U.S. Pat. No. 7,683,049 to FOB Synthesis, Inc. describes certain β-methyl carbapenem compounds for the treatment of gram-negative bacterial infections.

Because of the drug-resistance challenges associated with treating bacterial infections, there remains a need for new antimicrobial agents.

Therefore, it is one object of the present invention to provide novel β-methylcompounds carbapenems that are effective antimicrobial agents.

It is another object of the present invention to provide methods for the treatment of gram-negative bacteria, which optionally can be drug-resistant and/or multi-drug resistant. m

SUMMARY OF THE INVENTION

In one embodiment of the present invention, carbapenem compounds of the general Formula (I):

Formula I

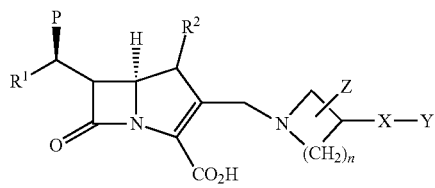

or a pharmaceutically acceptable salt, ester or prodrug thereof, are described,
wherein
$R^1$ and $R^2$ are each independently selected from H or alkyl;
P is H, OH, halogen, or hydroxyl protected by a hydroxyl protecting group;
n is 0, 1 or 2;
X is —$(CR_2)_m$— or —C(=O)—;
m is 0, 1 or 2;
Y is CN, OR, SR' or NRR';
each R is independently selected from H, alkyl or haloalkyl; and
R' is H, alkyl, $NR_2$; C(=O)R; $SO_2R$; $SO_2NR_2$; C(=NR)$NR_2$; C(=O)$NR_2$; $CR_2C$(=O)$NR_2$; C(=NR)R; C(=NR)$NRSO_2R$; C(=NR)NRC(=O)R; C(=O)$CR_2NRSO_2NR_2$; or C(=O)$CR_2NRC$(=NR)$NR_2$; and
Z is H, alkyl, halo, CN, OR, SR' or NRR'.

In another embodiment, carbapenem compounds of Formula IV:

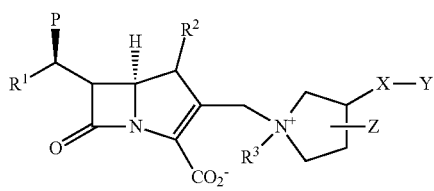

or a pharmaceutically acceptable salt, ester or prodrug thereof, are described
wherein
$R^1$, $R^2$ and $R^3$ are each independently selected from H or alkyl;
P is H, OH, halogen, or hydroxyl protected by a hydroxyl protecting group;
X is —$(CR_2)_m$— or —C(=O)—;
m is 0, 1 or 2;
Y is CN, OR, SR or NRR';
each R is independently selected from H, alkyl or haloalkyl; and
R' is H, alkyl, $NR_2$; C(=O)R; $SO_2R$; $SO_2NR_2$; C(=NR)$NR_2$; C(=O)$NR_2$; $CR_2C$(=O)$NR_2$; C(=NR)R; C(=NR)$NRSO_2R$; C(=NR)NRC(=O)R; C(=O)$CR_2NRSO_2NR_2$; or C(=O)$CR_2NRC$(=NR)$NR_2$; and
Z is H, alkyl, halo, CN, OR, SR' or NRR'.

In another embodiment, carbapenem compounds of Formula VI:

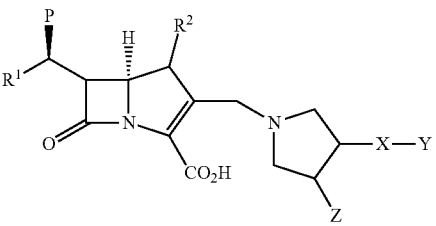

or a pharmaceutically acceptable salt, ester or prodrug thereof, are described
wherein
$R^1$ and $R^2$ are each independently selected from H or alkyl;
P is H, OH, halogen, or hydroxyl protected by a hydroxyl protecting group;
X is —$(CR_2)_m$— or —C(=O)—;
m is 0, 1 or 2;
Y is CN, OR, SR' or NRR';
each R is independently selected from H, alkyl or haloalkyl;
R' is H, alkyl, $NR_2$; C(=O)R; $SO_2R$; $SO_2NR_2$; C(=NR)$NR_2$; C(=O)$NR_2$; $CR_2C$(=O)$NR_2$; C(=NR)R; C(=NR)$NRSO_2R$; C(=NR)NRC(=O)R; C(=O)$CR_2NRSO_2NR_2$; or C(=O)$CR_2NRC$(=NR)$NR_2$; and
Z is H, alkyl, halo, CN, OR, SR' or NRR'.

In a particular embodiment, the present invention describes the following compound:

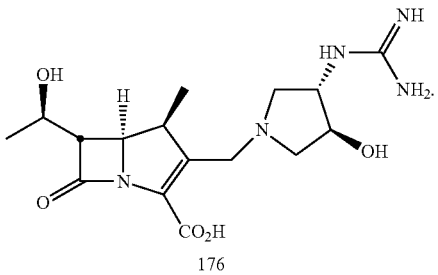 [SMILES: C[C@@H](O)[C@H]1C(=O)N2C(C(=O)O)=C(CN3C[C@H](NC(=N)N)[C@@H](O)C3)[C@H](C)[C@H]12]

176

In another particular embodiment, the present invention describes the following compound:

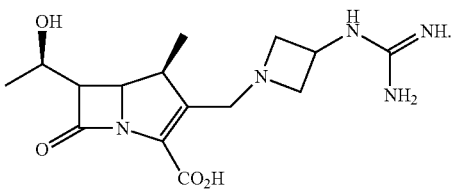

89

The present invention also provides a pharmaceutical composition including a compound of the invention, or a pharmaceutically acceptable salt and/or prodrug thereof, optionally with a pharmaceutically acceptable carrier or diluent.

In one embodiment, the invention provides a pharmaceutical composition comprising a compound of the invention, or a pharmaceutically acceptable salt and/or prodrug therein, in combination with one or more other antimicrobial agents, optionally with a pharmaceutically acceptable carrier or diluent.

In another embodiment, the invention provides a method of preventing or treating a bacterial infection in a host, typically an animal, and most typically a human, including administering to the host a therapeutic amount of a compound of the present invention, or a pharmaceutically acceptable salt and/or prodrug therein, optionally in a pharmaceutically acceptable carrier or diluent.

In a separate embodiment, the invention provides a method of preventing or treating a gram-negative bacterial infection in a host that includes administering a therapeutic amount of a compound of the present invention, or a pharmaceutically acceptable salt and/or prodrug therein, in combination or alternation with one or more other antimicrobial agents, optionally in a pharmaceutically acceptable carrier or diluent.

In one principal embodiment, the bacterial infection is due to a gram-negative bacteria. In another embodiment, the bacterial infection is from a drug resistant and/or multiple-drug resistant gram-negative bacteria.

The invention also provides a compound of the present invention for use in medical therapy, and the use in the preparation of a medicament for the treatment of bacterial infections, particularly gram negative bacterial infections, alone or in combination with another agent.

DETAILED DESCRIPTION OF THE INVENTION

The invention provides carbapenem compounds or their pharmaceutically acceptable salts or prodrugs, pharmaceutical compositions containing these compounds and methods of their use in the treatment or prevention of gram-negative bacterial infections.

Definitions

The numbering system for the carbapenem compounds used in this specification is set out below, wherein the numbering of the carbapenem nucleus is in accordance with standards in the art (see, Tiraby, G., et al., *Biochem J,* 276 (pt. 1), pp. 269-270 (1991)).

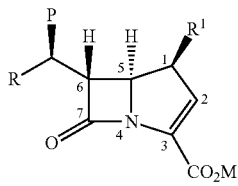

Whenever a range is presented herein it should be understood to include each element of the range. For example, the range "$C_1$ to $C_4$" alkyl independently includes $C_1$, $C_2$, $C_3$ and $C_4$ alkyl groups. When such a range is stated, each element has been contemplated and the range is used merely for convenience.

Generally, while the compounds, compositions and methods are described in terms of "comprising" various components or steps, the compounds, compositions and methods can also "consist essentially of" or "consist of" the various components and steps.

The term "alkyl", as used herein, unless otherwise specified, includes a saturated straight, branched, or cyclic, primary, secondary, or tertiary hydrocarbon of $C_1$ to $C_{10}$. The term includes both substituted and unsubstituted alkyl groups. Moieties with which the alkyl group can be substituted are selected from the group consisting of hydroxyl, halo (F, Cl, Br, I), amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference. When the alkyl group is said to be substituted with an alkyl group, this is used interchangeably with "branched alkyl group". Specific examples of alkyls and/or substituted alkyls includes, but are not limited to, methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl.

The term "lower alkyl", as used herein, and unless otherwise specified, refers to a $C_1$ to $C_4$ saturated straight, branched, or if appropriate, a cyclic (for example, cyclopropyl) alkyl group, including both substituted and unsubstituted forms. Unless otherwise specifically stated in this application, when alkyl is a suitable moiety, lower alkyl is typical. Similarly, when alkyl or lower alkyl is a suitable moiety, unsubstituted alkyl or lower alkyl is typical.

Cycloalkyl is a species of alkyl containing from 3 to 15 carbon atoms, without alternating or resonating double bonds between carbon atoms. It may contain from 1 to 4 rings, which are fused.

The term "alkenyl" includes a hydrocarbon radical straight, branched or cyclic containing from 2 to 10 carbon atoms and at least one carbon to carbon double bond. Examples of alkenyl groups include ethenyl, propenyl, butenyl and cyclohexenyl.

The term "alkynyl" refers to a hydrocarbon radical straight or branched, containing from 2 to 10 carbon atoms and at least one carbon to carbon triple bond. Examples of alkynyl groups include ethynyl, propynyl and butynyl.

"Alkoxy" includes $C_1$-$C_4$ alkyl-O—, with the alkyl group optionally substituted as described herein.

The term "alkylamino" or "arylamino" refers to an amino group that has one or two alkyl or aryl substituents, respectively.

"Aryl" refers to aromatic rings e.g., phenyl, substituted phenyl, biphenyl, and the like, as well as rings which are fused, e.g., naphthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. The typical aryl groups are phenyl, naphthyl and phenanthrenyl. The term includes both substituted and unsubstituted moieties. The aryl group can be substituted with one or more moieties selected from the group consisting of bromo, chloro, fluoro, iodo, hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991. Typical substituted aryls include phenyl and naphthyl.

The term "alkaryl" or "alkylaryl" refers to an alkyl group with an aryl substituent. The term "aralkyl" or "arylalkyl" refers to an aryl group with an alkyl substituent.

The term "heteroaryl" or "heteroaromatic", as used herein, refers to an aromatic group that includes at least one sulfur, oxygen, nitrogen or phosphorus in the aromatic ring. Heteroaryl or heteroaromatic compounds include monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one, two or three additional carbon atoms are optionally replaced by a heteroatom selected from oxygen, sulfur or nitrogen heteroatom. Examples of this type are pyrrole, pyridine, oxazole, thiazole and oxazine. Additional nitrogen atoms may be present together with the first nitrogen and oxygen or sulfur, giving, e.g., thiadiazole. Examples include the following.

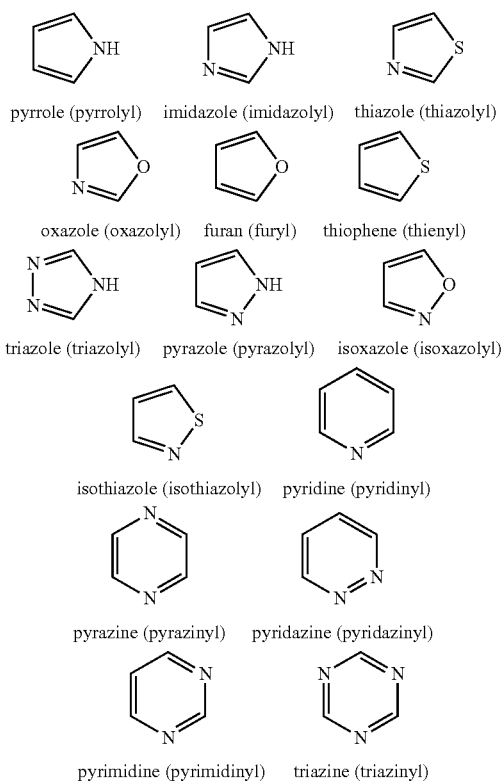

The heteroaryl or heteroaromatic group can be optionally substituted with one or more substituent selected from halogen, haloalkyl, alkyl, alkoxy, hydroxy, carboxyl derivatives, amido, amino, alkylamino, dialkylamino. Functional oxygen and nitrogen groups on the heterocyclic or heteroaryl group can be protected as necessary or desired. Suitable protecting groups are well known to those skilled in the art, and include trimethylsilyl, dimethylhexylsilyl, t-butyldimethylsilyl, and t-butyl-diphenylsilyl, trityl or substituted trityl, alkyl groups, acyl groups such as acetyl and propionyl, methanesulfonyl, and p-toluenylsulfonyl.

"Heterarylium" refers to heteroaryl groups bearing a quaternary nitrogen atom and thus a positive charge. Examples include the following.

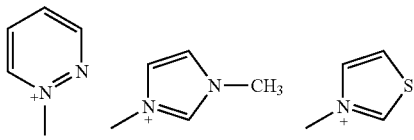

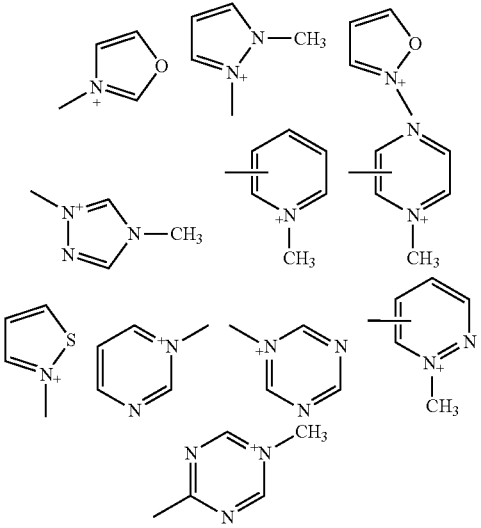

When a charge is shown on a particular nitrogen atom in a ring, which contains one or more additional nitrogen atoms, it is understood that the charge may reside on a different nitrogen atom in the ring by virtue of charge resonance that occurs.

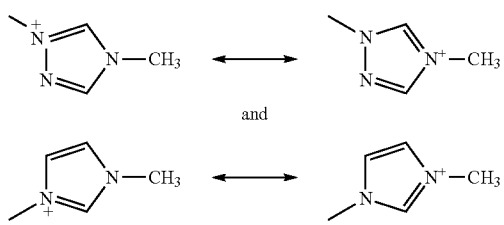

The term "heterocycloalkyl" refers to a cycloalkyl group (nonaromatic) in which one of the carbon atoms in the ring is replaced by a heteroatom selected from O, S or N, and in which up to three additional carbon atoms may be replaced by heteroatoms.

The terms "quaternary nitrogen" and "positive charge" refer to tetravalent, positively charged nitrogen atoms including, e.g., the positively charged nitrogen in a tetraalkylammonium group (e. g. tetramethylammonium), heteroarylium, (e.g., N-methyl-pyridinium), basic nitrogens which are protonated at physiological pH, and the like. Cationic groups thus encompass positively charged nitrogen-containing groups, as well as basic nitrogens which are protonated at physiologic pH.

The term "heteroatom" refers to oxygen, sulfur, nitrogen, phosphorus, and selenium, selected on an independent basis.

Halogen and "halo", as used herein, includes bromine, chlorine, fluorine and iodine.

The term acyl refers to a carboxylic acid ester in which the non-carbonyl moiety of the ester group is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl.

Aryl groups in the esters typically include a phenyl group. The term "lower acyl" refers to an acyl group in which the non-carbonyl moiety is lower alkyl.

"Carboxylate anion" refers to a negatively charged group —COO.

"Guanidinyl" refers to the group: $H_2NC(NH)NH—$.

"Carbamimidoyl" refers to the group: $H_2NC(NH)—$.

"Ureido" refers to the group: $H_2NC(O)NH—$.

When a group is "optionally interrupted", this includes one or more of the interrupting moieties in combination, as well as said moieties located at either or both ends of the chain. Thus, it includes terminating the group as well.

When a group is termed "substituted", unless otherwise indicated, this means that the group contains from 1 to 4 substituents thereon. With respect to R, $R^a$, $R^b$ and $R^c$, the substituents available on alkyl groups are selected from the values of $R^d$. Many of the variable groups are optionally substituted with up to four $R^i$ groups. With respect to $R^e$, $R^f$ and $R^g$, when these variables represent substituted alkyl, the substituents available thereon are selected from the values of $R^i$.

When a functional group is termed "protected", this means that the group is in modified form to preclude undesired side reactions at the protected site, and unless otherwise defined refers to a group that is added to an oxygen, nitrogen, or phosphorus atom to prevent its further reaction or for other purposes. In some of the carbapenem compounds of the present invention, M is a readily removable carboxyl protecting group, and/or P represents a hydroxyl which is protected by a hydroxylprotecting group. Such protecting groups are used to protectively block the hydroxyl or carboxyl group during the synthesis procedures and are readily removable by procedures that will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile and catalytic hydrogenation.

A wide variety of oxygen and nitrogen protecting groups are known to those skilled in the art of organic synthesis. Suitable protecting groups for the compounds of the present invention will be recognized from the present application taking into account the level of skill in the art, and with reference to standard textbooks, such as Greene, T. W. and Wuts, P. M., *Protective Groups in Organic Synthesis*, $3^{rd}$ Ed., Wiley, New York (1991). Examples of carboxyl protecting groups include allyl, benzhydryl, 2-naphthylmethyl, benzyl (Bn), silyl such as t-butyldimethylsilyl (TBDMS), phenacyl, p-methoxybenzyl, o-nitrobenzyl, p-methoxyphenyl, p-nitrobenzyl, 4-pyridylmethyl and t-butyl. Examples of suitable C-6 hydroxyethyl protecting groups include triethylsilyl (TES), t-butyldimethylsilyl (TBDMS), o-nitrobenzyloxycarbonyl (ONB), p-nitrobenzyloxycarbonyl (PNB), benzyloxycarbonyl (CBz), allyloxycarbonyl (Alloc), t-butyloxycarbonyl (Boc), 2,2,2-trichloroethyloxycarbonyl (Troc), and the like.

The phrase "pharmaceutically acceptable ester, salt or hydrate," refers to those salts, esters and hydrated forms of the compounds of the present invention, which would be apparent to the pharmaceutical chemist. i.e., those which are substantially non-toxic and which may favorably affect the pharmacokinetic properties of said compounds, such as palatability, absorption, distribution, metabolism and excretion. Other factors that are also important in the selection are cost of the raw materials, ease of crystallization, yield, stability, solubility, hygroscopicity and flowability of the resulting bulk drug.

"Pharmaceutically acceptable salts" include salts that retain the desired biological activity of the parent compound and do not impart undesired toxicological effects. These salts can take the form —COOM, where M is a positive charge, which is balanced by a counterion. These include salts formed with cations such as sodium, potassium, $NH_4^+$, magnesium, zinc, ammonium, or alkylammonium cations such as tetramethylammonium, tetrabutylammonium, choline, triethylhydroammonium, meglumine, triethanolhydroammonium, calcium, and calcium polyamines such as spermine and spermidine. These can also include salts formed from elemental anions such as chloride, bromide, and iodide. They can also include acid addition salts, for example, salts derived from inorganic or organic acids. Included among such salts are the following: acetate, adipate, alginate, ascorbic acid, aspartate, benzoate, benzenesulfonate, bisulfate, butyrate, citrate, camphorate, camphorsulfonate, cyclopentancpropionate, digluconate, dodecylsulfate, ethanesulfonate, fumarate, glucoheptanoate, gluconic acid, glycerophosphate, hemisulfate, heptanoate, hexanoate, hydrochloride, hydrobromide, hydroiodide, 2-hvdroxvethanesulfonate, lactate, maleate, methanesulfonate, 2-naphthalenesulfonate, nicotinate, nitric acid, oxalate, palmitic acid, pamoate, pectinate, persulfate, 3-phenylpropionate, phosphoric acid, picrate, pivalate, polygalacturonic acid; polyglutamic acid, propionate, p-toluenesulfonic acid, succinate, sulfuric acid, tannic acid, tartrate, thiocyanate, tosylate and undecanoate.

The term "prodrug" includes a compound that, when administered to an animal, is converted under physiological conditions to a compound of the invention, for example a pharmaceutically acceptable ester.

The pharmaceutically acceptable esters are such as would be readily apparent to a medicinal chemist, and include, for example, those described in detail in U.S. Pat. No. 4,309, 438. Included within such pharmaceutically acceptable esters are those, which are hydrolyzed under physiological conditions, such as pivaloyloxymethyl, acetoxymethyl, phthalidyl, indanyl and methoxymethyl. These are also referred to as "biolabile esters", which are biologically hydrolysable. Examples of biolabile esters include compounds in which M represents an alkoxyalkyl, alkylcarbonyloxyalkyl, alkoxycarbonyloxyalkyl, cycloalkoxyalkyl, alkenyloxyalkyl, aryloxyalkyl, alkoxyaryl, alkylthioalkyl, cycloalkylthioalkyl, alkenylthioalkyl, arylthioalkyl or alkylthioaryl group. These groups can be substituted in the alkyl or aryl portions thereof with acyl or halo groups. The following M species are examples of biolabile ester forming moieties: acetoxymethyl, 1-acetoxyethyl, 1-acetoxypropyl, pivaloyloxymethyl, 1isopropyloxycarbonyloxyethyl, 1-cyclohexyloxycarbonyloxyethyl, phthalidyl and (2-oxomethyl-1,3-dioxolenyl)methyl.

The term "host", as used herein, refers to a unicellular or multicellular organism in which the bacteria can replicate, including cell lines and animals. Alternatively, the host can be carrying a part of the bacterial particles, whose replication and/or function can be altered by the compounds of the present invention. The term host refers to infected cells, cells transfected with all or part of the bacteria and animals, such as, primates (including chimpanzees) and, in one embodiment, the host is a human. Veterinary applications are also encompassed by the present invention.

The term "treatment" as used herein, includes an approach for obtaining beneficial or desired results including clinical results, including alleviation of symptoms, diminishment of extent of disease, stabilization (i.e., not worsening) state of disease, preventing spread of disease, preventing or reducing occurrence or recurrence of disease, delay or slowing of disease progression, and reduction of incidence of disease or symptoms. As used herein, the phrase "anti-bacterially effective amount" means an amount effective for treating the bacterial infection.

Compounds of the Invention

In one embodiment, the compound is a compound of Formula I,

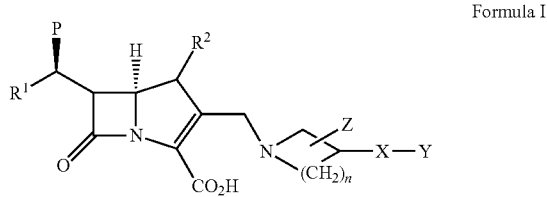

Formula I or a pharmaceutically acceptable salt, ester or prodrug thereof,
wherein
$R^1$ and $R^2$ are each independently selected from H or alkyl;
P is H, OH, halogen, or hydroxyl protected by a hydroxyl protecting group;
n is 0, 1 or 2;
X is —$(CR_2)_m$— or —C(=O)—;
m is 0, 1 or 2;
Y is CN, OR, SR' or NRR';
each R is independently selected from H, alkyl or haloalkyl;
R' is H, alkyl, $NR_2$; C(=O)R; $SO_2R$; $SO_2NR_2$; C(=NR)$NR_2$; C(=O)$NR_2$; $CR_2C$(=O)$NR_2$; C(=NR)R; C(=NR)$NRSO_2R$; C(=NR)NRC(=O)R; C(=O)$CR_2NRSO_2NR_2$; or C(=O)$CR_2NRC$(=NR)$NR_2$; and
Z is H, alkyl, halo, CN, OR, SR' or NRR'.

In one embodiment, $R^1$ is H. In one embodiment, $R^1$ is alkyl, for example $CH_3$. In one embodiment, $R^2$ is H. In one embodiment, $R^2$ is alkyl, for example $CH_3$. In one embodiment, both $R^1$ and $R^2$ are alkyl, for example $CH_3$.

In one embodiment, P is H. In one embodiment, P is OH. In one embodiment, P is halogen. In one embodiment, P is hydroxyl protected by a hydroxyl protecting group. In a particular embodiment, P is OH or hydroxyl protected by a hydroxyl protecting group.

In one embodiment, n is 0. In one embodiment, n is 1. In another embodiment, n is 2. In one embodiment, n is 1 or 2. In one embodiment, n is not 0.

In one embodiment, X is —$(CR_2)_m$—. In one subembodiment, m is 0. In another subembodiment, m is 1. In another subembodiment, m is 2. In one embodiment, X is —C(=O)—.

In one embodiment, at least one R is H. In one embodiment, at least two Rs are H. In one embodiment, at least one R is alkyl, for example $CH_3$, $CH_2CH_3$ or $CH_2CH_2CH_3$. In one embodiment, at least one R is haloalkyl, for example $CF_3$.

In one embodiment, Y is CN. In another embodiment, Y is OR. In a particular embodiment, Y is OH. In one embodiment, Y is SR', for example SH or S(alkyl). In one embodiment, Y is SR' and R' is C(=NR)$NR_2$, for example C(=NH)$NH_2$, C(=NCH$_3$)$NH_2$, C(=NCH$_3$)$NHCH_3$, C(=NCH$_3$)N(CH$_3$)$_2$, C(=NR)NH(CH$_3$), or C(=NCF$_3$)$NH_2$. In one embodiment, Y is NRR'. In a subembodiment, Y is NHR'. In another subembodiment, Y is N(alkyl)R', for example N(CH$_3$)R'.

In one embodiment, R' is H. In one embodiment, R' is alkyl, for example $CH_3$. In one embodiment, R' is $NR_2$, for example $NH_2$, NHR, $NHCH_3$, or N(CH$_3$)$_2$. In another embodiment, R' is C(=O)R, for example C(=O)$CH_3$ or C(=O)$CF_3$. In another embodiment, R' is $SO_2R$, for example $SO_2CH_3$. In another embodiment, R' is $SO_2NR_2$, for example $SO_2NH_2$. In another embodiment, R' is C(=NR)$NR_2$, for example C(=NH)$NH_2$, C(=NCH$_3$)$NH_2$, C(=NCH$_3$)NHCH$_3$, C(=NCH$_3$)N(CH$_3$)$_2$, C(=NR)NH(CH$_3$), or C(=NCF$_3$)$NH_2$. In another embodiment, R' is C(=O)$NR_2$, for example C(=O)$NH_2$, C(=O)NHR, C(=O)NHCH$_3$ or C(=O)N(CH$_3$)$_2$. In another embodiment, R' is C(=NR)R, for example C(=NH)H, C(=NH)R or C(=NH)CH$_3$. In another embodiment, R' is C(=NR)NRSO$_2$R, for example C(=NH)NHSO$_2$H, C(=NH)NHSO$_2$R, or C(=NH)NHSO$_2$CH$_3$. In another embodiment, R' is C(=NR)NRC(=O)R, for example C(=NH)NHC(=O)R or C(=NH)NHC(=O)CH$_3$. In another embodiment, R' is C(=O)$CR_2NRSO_2NR_2$, for example C(=O)CH$_2$NHSO$_2$NR$_2$, C(=O)CH$_2$NHSO$_2$NH$_2$, or C(=O)CH$_2$NHSO$_2$N(CH$_3$)$_2$. In another embodiment, R' is C(=O)$CR_2NRC$(=NR)$NR_2$, for example C(=O)CH$_2$NHC(=NH)$NR_2$, C(=O)CH$_2$NHC(=NH)$NH_2$ or C(=O)CH$_2$NHC(=NH)N(CH$_3$)$_2$.

In certain embodiments, Y is CN, $NR_2$, SC(=NR)$NR_2$, C(=O)$NR_2$; C(=O)$NRSO_2R$; C(=O)$NRSO_2NR_2$; NRC(=NR)$NR_2$; $NRSO_2NR_2$; NRC(O)$NR_2$; $NRCR_2C$(O)$NR_2$; NRCR(=NR); $CR_2NRC$(=NR)$NR_2$; NRC(=NR)NRSO$_2$R; NRC(=NR)NRC(O)R; C(O)NRCR$_2$C(O)$NR_2$; C(O)NRC(=NR)$NR_2$; OR; NRC(O)CR$_2$NRSO$_2$NR$_2$; or NRC(O)CR$_2$NRC(=NR)$NR_2$.

In one embodiment, Z is H. In another embodiment, Z is alkyl. In one embodiment, Z is CN. In another embodiment, Z is halo. In certain embodiments, Z is OR, for example OH.

In one embodiment, Z is SR', for example SH or S(alkyl). In one embodiment, Z is NRR'. In a subembodiment, Z is NHR'. In another subembodiment, Z is N(alkyl)R', for example N(CH$_3$)R'.

In one embodiment, $R^1$ is alkyl; $R^2$ is alkyl; P is hydroxyl or hydroxyl protected by a hydroxyl protecting group; n is 0, 1 or 2; m is 0; and Y is —CN. In another embodiment, $R^1$ is alkyl; $R^2$ is alkyl; P is hydroxyl or hydroxyl protected by a hydroxyl protecting group; n is 0, 1 or 2; m is 0; and Y is OR. In another embodiment, $R^1$ is alkyl; $R^2$ is alkyl; P is hydroxyl or hydroxyl protected by a hydroxyl protecting group; n is 0, 1 or 2; m is 0 or 1; and Y is NRR'.

In one embodiment, when Y is CN, X is not —C(=O)—. In another embodiment, $R^1$ is alkyl; $R^2$ is alkyl; P is hydroxyl or hydroxyl protected by a hydroxyl protecting group; n is 0, 1 or 2; X is —C(=O)—; and Y is OR. In another embodiment, $R^1$ is alkyl; $R^2$ is alkyl; P is hydroxyl or hydroxyl protected by a hydroxyl protecting group; n is 0, 1 or 2; X is —C(=O)—; and Y is NRR'.

In one embodiment, $R^1$ is alkyl; $R^2$ is alkyl; P is hydroxyl or hydroxyl protected by a hydroxyl protecting group; n is 1 or 2; m is 0; and Y is —CN. In another embodiment, $R^1$ is alkyl; $R^2$ is alkyl; P is hydroxyl or hydroxyl protected by a hydroxyl protecting group; n is 1 or 2; m is 0; and Y is OR. In another embodiment, $R^1$ is alkyl; $R^2$ is alkyl; P is hydroxyl or hydroxyl protected by a hydroxyl protecting group; n is 1 or 2; m is 0 or 1; and Y is NRR'. In one embodiment, $R^1$ is alkyl; $R^2$ is alkyl; P is hydroxyl or hydroxyl protected by a hydroxyl protecting group; n is 1 or 2; X is —C(=O)—; and Y is OR. In another embodiment, $R^1$ is alkyl; $R^2$ is alkyl;

P is hydroxyl or hydroxyl protected by a hydroxyl protecting group; n is 1 or 2; X is —C(=O)—; and Y is NRR'.
In one embodiment, the compound of Formula I is selected from the group consisting of:
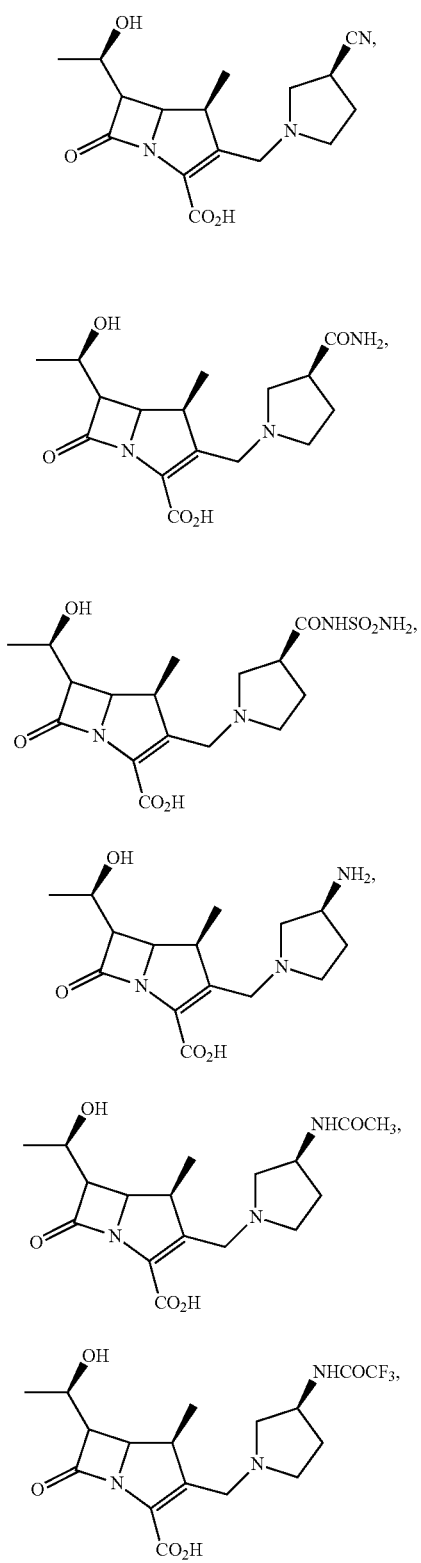
-continued
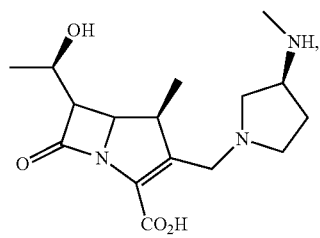
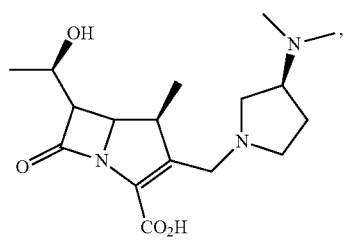
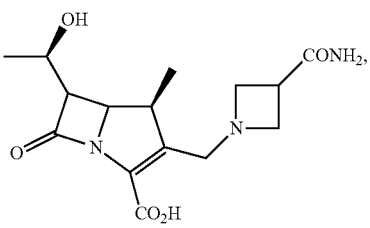
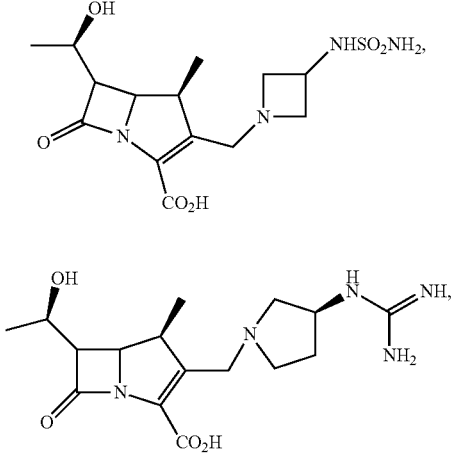
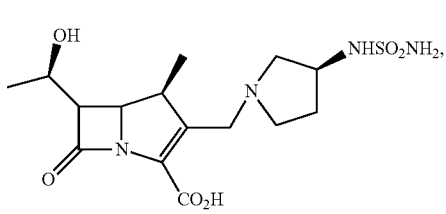
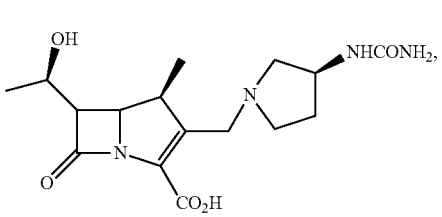

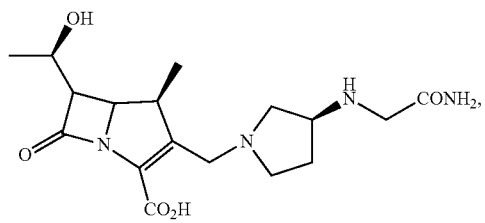 83
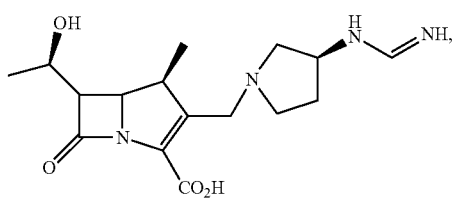 84
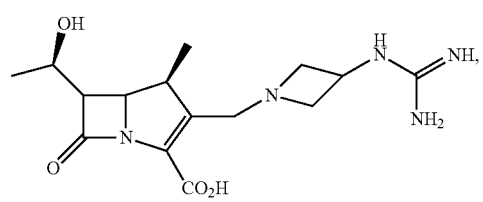 89
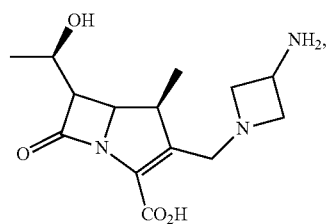 93
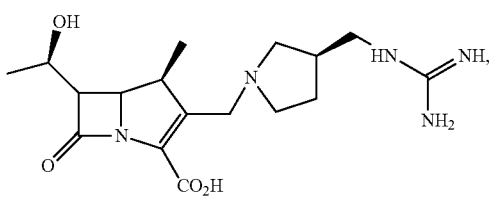 99
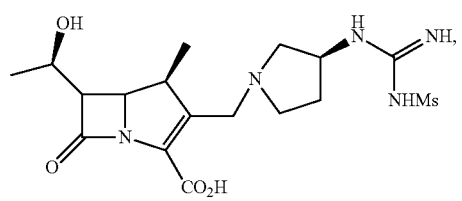 106
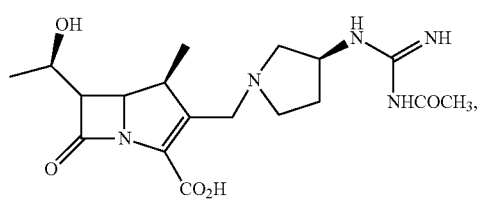 111
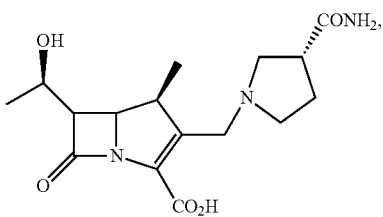 115
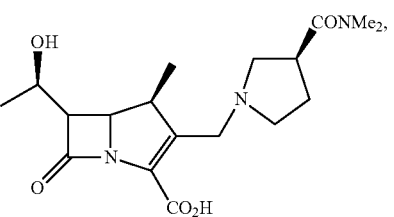 120
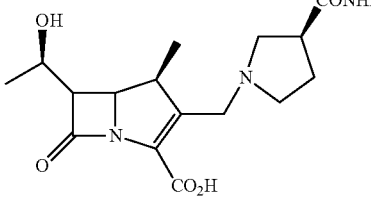 127
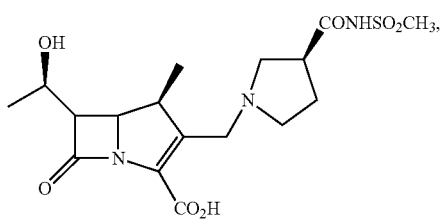 132
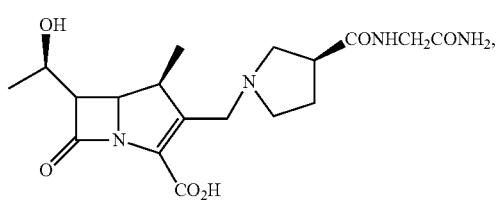 137
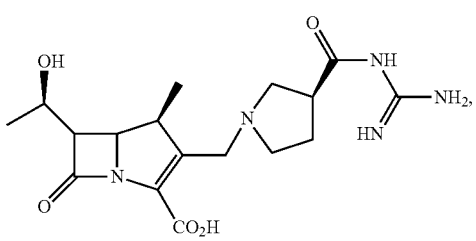 143
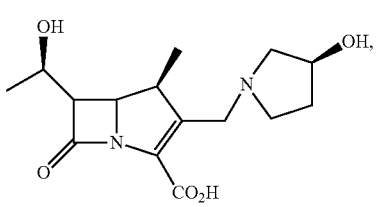 146

-continued

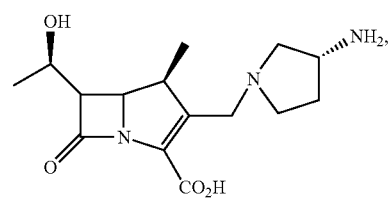
151

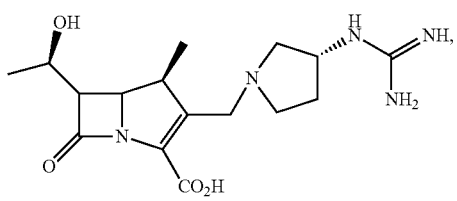
156

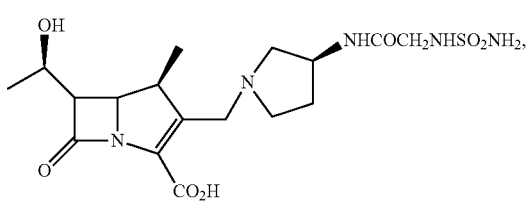
163

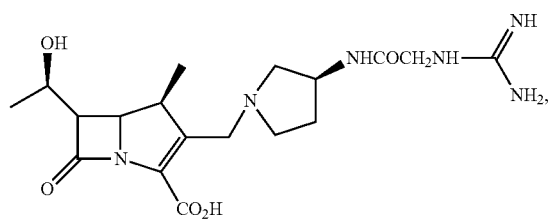
167

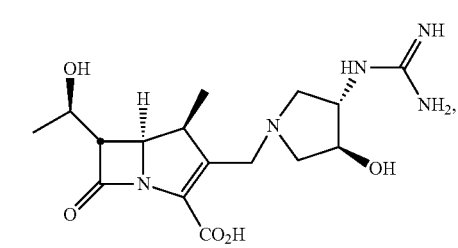
176

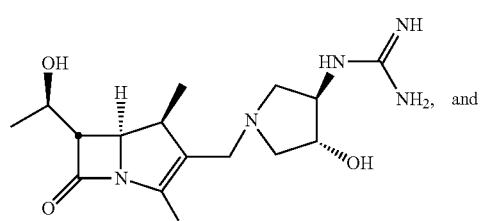
178

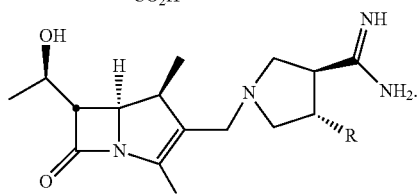
185a R = H
185b R = OH

In one embodiment, the compound is compound 7. In another embodiment, the compound is compound 12. In another embodiment, the compound is compound 19. In another embodiment, the compound is compound 27. In another embodiment, the compound is compound 32. In another embodiment, the compound is compound 43. In another embodiment, the compound is compound 46. In another embodiment, the compound is compound 49. In another embodiment, the compound is compound 64. In another embodiment, the compound is compound 89. In another embodiment, the compound is compound 99. In another embodiment, the compound is compound 137. In another embodiment, the compound is compound 146. In another embodiment, the compound is compound 151. In another embodiment, the compound is compound 156.

In another embodiment, the compound is a compound of Formula II,

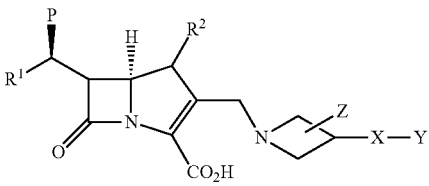
Formula II or a pharmaceutically acceptable salt, ester or prodrug thereof,
wherein
$R^1$ and $R^2$ are each independently selected from H or alkyl;
P is H, OH, halogen, or hydroxyl protected by a hydroxyl protecting group;
X is —$(CR_2)_m$— or —C(=O)—;
m is 0, 1 or 2;
Y is CN, OR, SR' or NRR';
each R is independently selected from H, alkyl or haloalkyl;
R' is H, alkyl, $NR_2$; C(=O)R; $SO_2R$; $SO_2NR_2$; C(=NR)$NR_2$; C(=O)$NR_2$; $CR_2C$(=O)$NR_2$; C(=NR)R; C(=NR)$NRSO_2R$; C(=NR)NRC(=O)R; C(=O)$CR_2NRSO_2NR_2$; or C(=O)$CR_2NRC$(=NR)$NR_2$; and
Z is H, alkyl, halo, CN, OR, SR' or NRR'

In one embodiment, $R^1$ is H. In one embodiment, $R^1$ is alkyl, for example $CH_3$. In one embodiment, $R^2$ is H. In one embodiment, $R^2$ is alkyl, for example $CH_3$. In one embodiment, both $R^1$ and $R^2$ are alkyl, for example $CH_3$.

In one embodiment, P is H. In one embodiment, P is OH. In one embodiment, P is halogen. In one embodiment, P is hydroxyl protected by a hydroxyl protecting group. In a particular embodiment, P is OH or hydroxyl protected by a hydroxyl protecting group.

In one embodiment, X is —$(CR_2)_m$—. In one subembodiment, m is 0. In another subembodiment, m is 1. In another subembodiment, m is 2. In one embodiment, X is —C(=O)—.

In one embodiment, at least one R is H. In one embodiment, at least two Rs are H. In one embodiment, at least one R is alkyl, for example $CH_3$, $CH_2CH_3$ or $CH_2CH_2CH_3$. In one embodiment, at least one R is haloalkyl, for example $CF_3$.

In one embodiment, Z is H. In one embodiment, Z is halogen. In another embodiment, Z is alkyl. In one embodiment, Z is CN. In another embodiment, Z is halo. In certain embodiments, Z is OR, for example OH. In one embodiment, Z is SR', for example SH or S(alkyl). In one embodiment, Z is halogen, for example mono- or multi-F or Cl. In one embodiment, Z is NRR'. In a subembodiment, Z is NHR'. In another subembodiment, Z is N(alkyl)R', for example N(CH₃)R'.

In one embodiment, Y is CN. In another embodiment, Y is OR. In a particular embodiment, Y is OH. In one embodiment, Y is SR', for example SH or S(alkyl). In one embodiment, Y is SR' and R' is C(=NR)NR₂, for example C(=NH)NH₂, C(=NCH₃)NH₂, C(=NCH₃)NHCH₃, C(=NCH₃)N(CH₃)₂, C(=NR)NH(CH₃), or C(=NCF₃)NH₂. In one embodiment, Y is NRR'. In a subembodiment, Y is NHR'. In another subembodiment, Y is N(alkyl)R', for example N(CH₃)R'.

In one embodiment, R' is H. In one embodiment, R' is alkyl, for example CH₃. In one embodiment, R' is NR₂, for example NH₂, NHR, NHCH₃, or N(CH₃)₂. In another embodiment, R' is C(=O)R, for example C(=O)CH₃ or C(=O)CF₃. In another embodiment, R' is SO₂R, for example SO₂CH₃. In another embodiment, R' is SO₂NR₂, for example SO₂NH₂. In another embodiment, R' is C(=NR)NR₂, for example C(=NH)NH₂, C(=NCH₃)NH₂, C(=NCH₃)NHCH₃, C(=NCH₃)N(CH₃) 2, C(=NR)NH (CH₃), or C(=NCF₃)NH₂. In another embodiment, R' is C(=O)NR₂, for example C(=O)NH₂, C(=O)NHR, C(=O)NHCH₃ or C(=O)N(CH₃)₂. In another embodiment, R' is C(=NR)R, for example C(=NH)H, C(=NH)R or C(=NH)CH₃. In another embodiment, R' is C(=NR)NRSO₂R, for example C(=NH)NHSO₂H, C(=NH)NHSO₂R, or C(=NH)NHSO₂CH₃. In another embodiment, R' is C(=NR)NRC(=O)R, for example C(=NH)NHC(=O)R or C(=NH)NHC(=O)CH₃. In another embodiment, R' is C(=O)CR₂NRSO₂NR₂, for example C(=O)CH₂NHSO₂NR₂, C(=O)CH₂NHSO₂NH₂, or C(=O)CH₂NHSO₂N(CH₃)₂. In another embodiment, R' is C(=O)CR₂NRC(=NR)NR₂, for example C(=O)CH₂NHC(=NH)NR₂, C(=O)CH₂NHC(=NH)NH₂ or C(=O)CH₂NHC(=NH)N(CH₃)₂.

In a particular embodiment, Y is NH₂, NHC(=NH)NH₂, or NHSO₂NH₂.

In one embodiment, the compound of Formula II is selected from the group consisting of

49

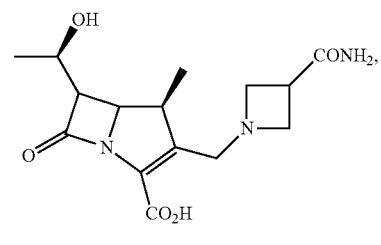

58

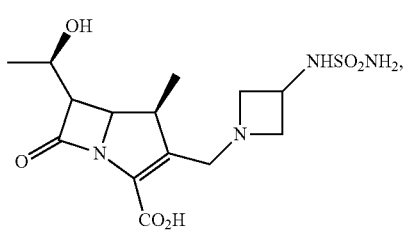

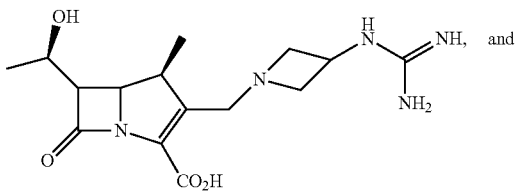

89

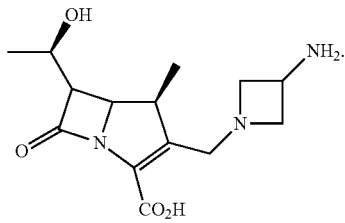

93

In another embodiment, the compound is a compound of Formula III,

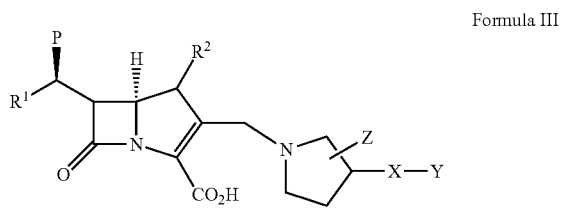

Formula III or a pharmaceutically acceptable salt, ester or prodrug thereof,
wherein
R¹ and R² are each independently selected from H or alkyl;
P is H, OH, halogen, or hydroxyl protected by a hydroxyl protecting group;
X is —(CR₂)ₘ— or —C(=O)—;
m is 0, 1 or 2;
Y is CN, OR, SR' or NRR';
each R is independently selected from H, alkyl or haloalkyl;
R' is H, alkyl, NR₂; C(=O)R; SO₂R; SO₂NR₂; C(=NR)NR₂; C(=O)NR₂; CR₂C(=O)NR₂; C(=NR)R; C(=NR)NRSO₂R; C(=NR)NRC(=O)R; C(=O)CR₂NRSO₂NR₂; or C(=O)CR₂NRC(=NR)NR₂; and
Z is H, alkyl, halo, CN, OR, SR' or NRR'.

In one embodiment, R¹ is H. In one embodiment, R¹ is alkyl, for example CH₃. In one embodiment, R² is H. In one embodiment, R² is alkyl, for example CH₃. In one embodiment, both R¹ and R² are alkyl, for example CH₃.

In one embodiment, P is H. In one embodiment, P is OH. In one embodiment, P is halogen. In one embodiment, P is hydroxyl protected by a hydroxyl protecting group. In a particular embodiment, P is OH or hydroxyl protected by a hydroxyl protecting group.

In one embodiment, X is —(CR₂)ₘ—. In one subembodiment, m is 0. In another subembodiment, m is 1. In another subembodiment, m is 2. In one embodiment, X is —C(=O)—.

In one embodiment, at least one R is H. In one embodiment, at least two Rs are H. In one embodiment, at least one R is alkyl, for example CH₃, CH₂CH₃ or CH₂CH₂CH₃. In one embodiment, at least one R is haloalkyl, for example CF₃.

In one embodiment, Y is CN. In another embodiment, Y is OR. In a particular embodiment, Y is OH. In one embodiment, Y is SR', for example SH or S(alkyl). In one embodiment, Y is SR' and R' is C(=NR)NR₂, for example C(=NH)NH₂, C(=NCH₃)NH₂, C(=NCH₃)NHCH₃, C(=NCH₃)N(CH₃)₂, C(=NR)NH(CH₃), or C(=NCF₃)NH₂. In one embodiment, Y is NRR'. In a subembodiment, Y is NHR'. In another subembodiment, Y is N(alkyl)R', for example N(CH₃)R'.

In one embodiment, Z is H. In one embodiment, Z is halogen. In another embodiment, Z is alkyl. In one embodiment, Z is CN. In another embodiment, Z is halo. In certain embodiments, Z is OR, for example OH. In one embodiment, Z is SR', for example SH or S(alkyl). In one embodiment, Z is halogen, for example mono- or multi-F or Cl. In one embodiment, Z is NRR'. In a subembodiment, Z is NHR'. In another subembodiment, Z is N(alkyl)R', for example N(CH₃)R'.

In one embodiment, R' is H. In one embodiment, R' is alkyl, for example CH₃. In one embodiment, R' is NR₂, for example NH₂, NHR, NHCH₃, or N(CH₃)₂. In another embodiment, R' is C(=O)R, for example C(=O)CH₃ or C(=O)CF₃. In another embodiment, R' is SO₂R, for example SO₂CH₃. In another embodiment, R' is SO₂NR₂, for example SO₂NH₂. In another embodiment, R' is C(=NR)NR₂, for example C(=NH)NH₂, C(=NCH₃)NH₂, C(=NCH₃)NHCH₃, C(=NCH₃)N(CH₃)₂, C(=NR)NH(CH₃), or C(=NCF₃)NH₂. In another embodiment, R' is C(=O)NR₂, for example C(=O)NH₂, C(=O)NHR, C(=O)NHCH₃ or C(=O)N(CH₃)₂. In another embodiment, R' is C(=NR)R, for example C(=NH)H, C(=NH)R or C(=NH)CH₃. In another embodiment, R' is C(=NR)NRSO₂R, for example C(=NH)NHSO₂H, C(=NH)NHSO₂R, or C(=NH)NHSO₂CH₃. In another embodiment, R' is C(=NR)NRC(=O)R, for example C(=NH)NHC(=O)R or C(=NH)NHC(=O)CH₃. In another embodiment, R' is C(=O)CR₂NRSO₂NR₂, for example C(=O)CH₂NHSO₂NR₂, C(=O)CH₂NHSO₂NH₂, or C(=O)CH₂NHSO₂N(CH₃)₂. In another embodiment, R' is C(=O)CR₂NRC(=NR)NR₂, for example C(=O)CH₂NHC(=NH)NR₂, C(=O)CH₂NHC(=NH)NH₂ or C(=O)CH₂NHC(=NH)N(CH₃)₂.

In one embodiment, the compound of Formula III is selected from the group consisting of:

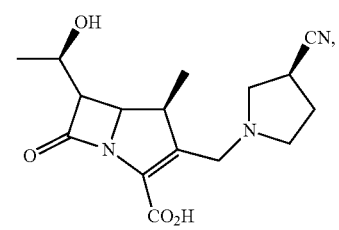
7

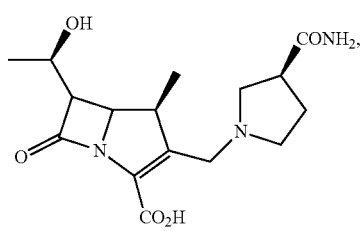
12

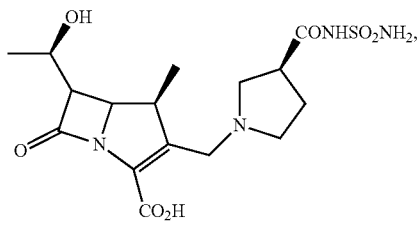
19

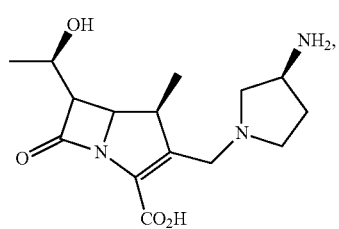
27

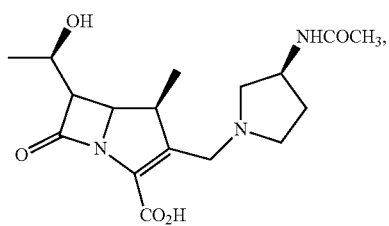
32

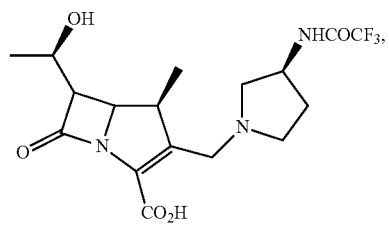
37

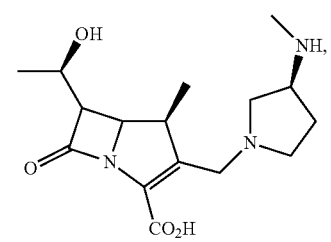
43

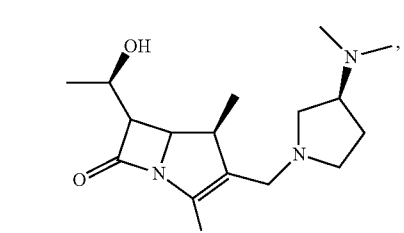
46

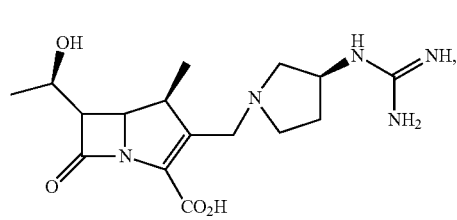
64

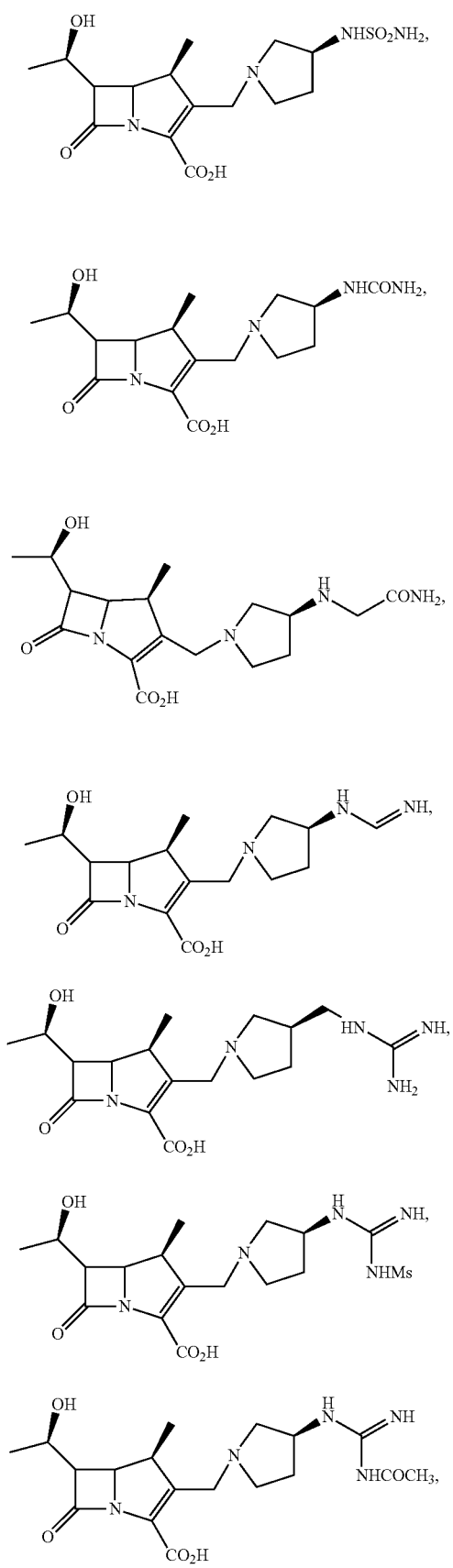
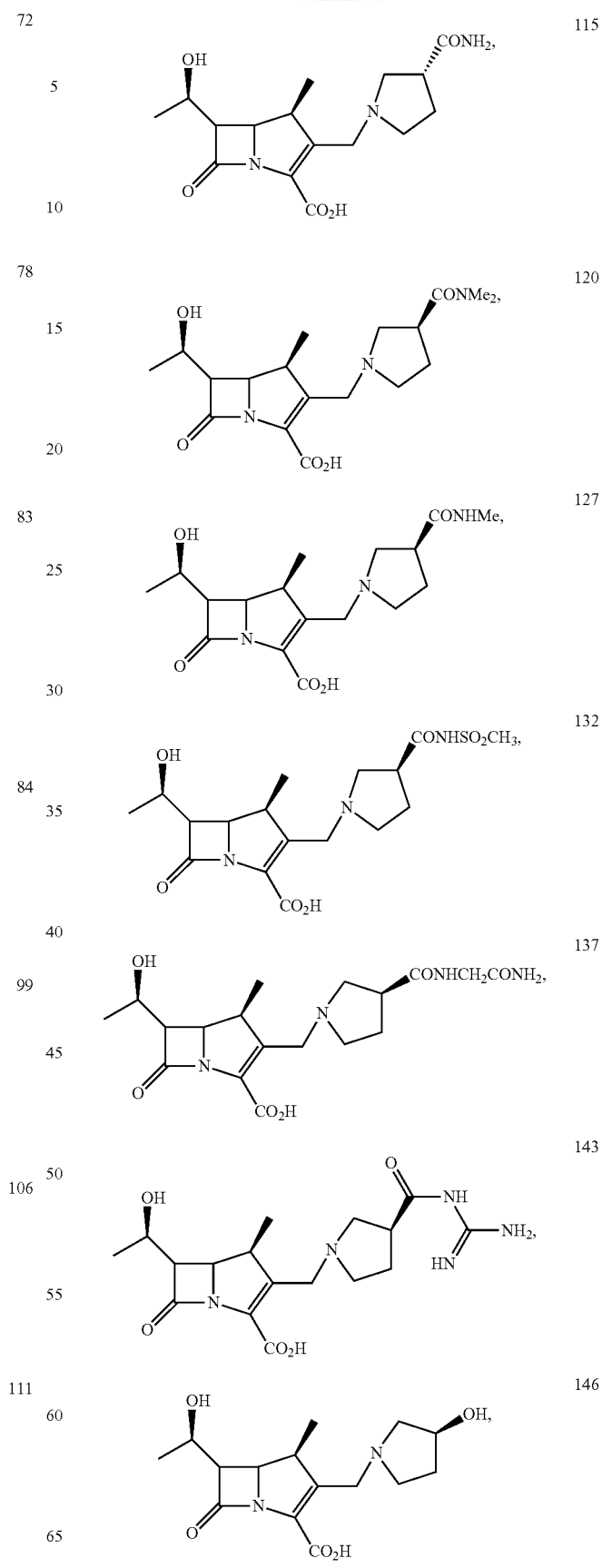

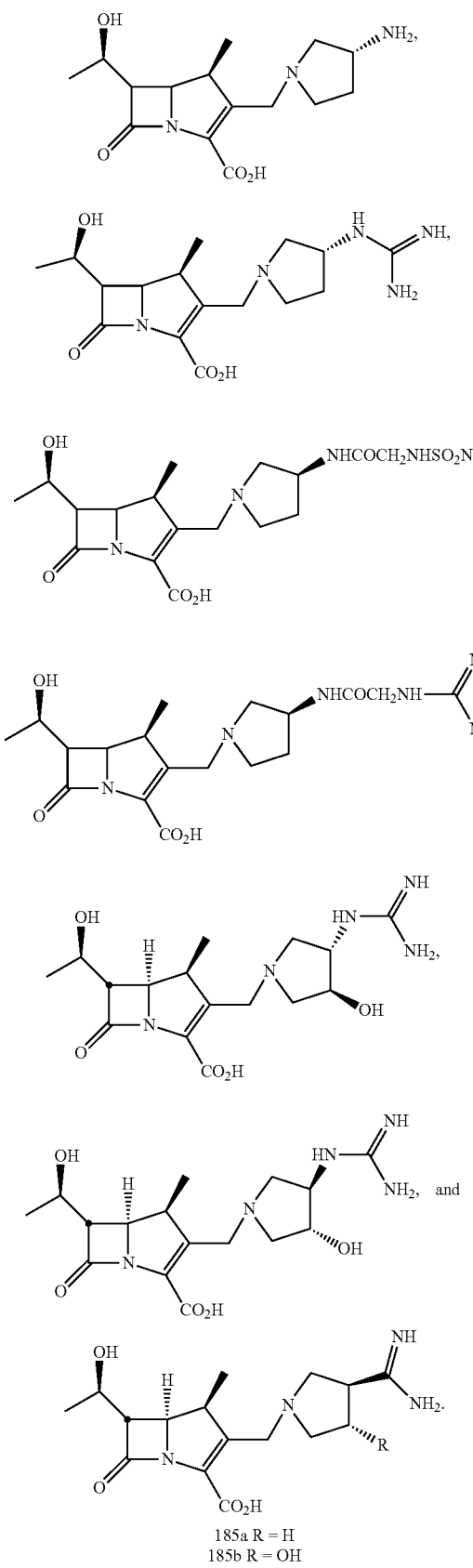

185a R = H
185b R = OH

In another particular embodiment, the compound is a compound of Formula IV,

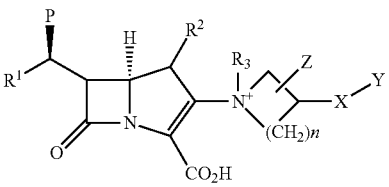

or a pharmaceutically acceptable salt, ester or prodrug thereof,
wherein
R$^1$, R$^2$ and R$^3$ are each independently selected from H or alkyl;
P is H, OH, halogen, or hydroxyl protected by a hydroxyl protecting group;
n is 0, 1, or 2
X is —(CR$_2$)$_m$— or —C(═O)—;
m is 0, 1 or 2;
Y is CN, OR, SR' or NRR';
each R is independently selected from H, alkyl or haloalkyl;
R' is H, alkyl, NR$_2$; C(═O)R; SO$_2$R; SO$_2$NR$_2$; C(═NR)NR$_2$; C(═O)NR$_2$; CR$_2$C(═O)NR$_2$; C(═NR)R; C(═NR)NRSO$_2$R; C(═NR)NRC(═O)R; C(═O)CR$_2$NRSO$_2$NR$_2$; or C(═O)CR$_2$NRC(═NR)NR$_2$; and
Z is H, alkyl, halo, CN, OR, SR' or NRR'.

In one embodiment, R$^1$ is H. In one embodiment, R$^1$ is alkyl, for example CH$_3$. In one embodiment, R$^2$ is H. In one embodiment, R$^2$ is alkyl, for example CH$_3$. In one embodiment, both R$^1$ and R$^2$ are alkyl, for example CH$_3$.

In one embodiment, P is H. In one embodiment, P is OH. In one embodiment, P is halogen. In one embodiment, P is hydroxyl protected by a hydroxyl protecting group. In a particular embodiment, P is OH or hydroxyl protected by a hydroxyl protecting group.

In one embodiment, n is 0. In one embodiment, n is 1. In another embodiment, n is 2. In one embodiment, n is 1 or 2. In one embodiment, n is 0.

In one embodiment, X is —(CR$_2$)$_m$—. In one subembodiment, m is 0. In another subembodiment, m is 1. In another subembodiment, m is 2. In one embodiment, X is —C(═O)—.

In one embodiment, at least one R is H. In one embodiment, at least two Rs are H. In one embodiment, at least one R is alkyl, for example CH$_3$, CH$_2$CH$_3$ or CH$_2$CH$_2$CH$_3$. In one embodiment, at least one R is haloalkyl, for example CF$_3$.

In one embodiment, Y is CN. In another embodiment, Y is OR. In a particular embodiment, Y is OH. In one embodiment, Y is SR', for example SH or S(alkyl). In one embodiment, Y is SR' and R' is C(═NR)NR$_2$, for example C(═NH)NH$_2$, C(═NCH$_3$)NH$_2$, C(═NCH$_3$)NHCH$_3$, C(═NCH$_3$)N(CH$_3$)$_2$, C(═NR)NH(CH$_3$), or C(═NCF$_3$)NH$_2$. In one embodiment, Y is NRR'. In a subembodiment, Y is NHR'. In another subembodiment, Y is N(alkyl)R', for example N(CH$_3$)R'.

In one embodiment, R' is H. In one embodiment, R' is alkyl, for example CH$_3$. In one embodiment, R' is NR$_2$, for example NH$_2$, NHR, NHCH$_3$, or N(CH$_3$)$_2$. In another embodiment, R' is C(═O)R, for example C(═O)CH$_3$ or C(═O)CF$_3$. In another embodiment, R' is SO$_2$R, for example SO$_2$CH$_3$. In another embodiment, R' is SO$_2$NR$_2$, for example SO₂NH₂. In another embodiment, R' is C(=NR)NR₂, for example C(=NH)NH₂, C(=NCH₃)NH₂, C(=NCH₃)NHCH₃, C(=NCH₃)N(CH₃)₂, C(=NR)NH(CH₃), or C(=NCF₃)NH₂. In another embodiment, R' is C(=O)NR₂, for example C(=O)NH₂, C(=O)NHR, C(=O)NHCH₃ or C(=O)N(CH₃)₂. In another embodiment, R' is C(=NR)R, for example C(=NH)H, C(=NH)R or C(=NH)CH₃. In another embodiment, R' is C(=NR)NRSO₂R, for example C(=NH)NHSO₂H, C(=NH)NHSO₂R, or C(=NH)NHSO₂CH₃. In another embodiment, R' is C(=NR)NRC(=O)R, for example C(=NH)NHC(=O)R or C(=NH)NHC(=O)CH₃. In another embodiment, R' is C(=O)CR₂NRSO₂NR₂, for example C(=O)CH₂NHSO₂NR₂, C(=O)CH₂NHSO₂NH₂, or C(=O)CH₂NHSO₂N(CH₃)₂. In another embodiment, R' is C(=O)CR₂NRC(=NR)NR₂, for example C(=O)CH₂NHC(=NH)NR₂, C(=O)CH₂NHC(=NH)NH₂ or C(=O)CH₂NHC(=NH)N(CH₃)₂.

In one embodiment, Y is CN, NR₂, SC(=NR)NR₂, C(=O)NR₂, C(=O)NRSO₂R; C(=O)NRSO₂NR₂; NRC(=NR)NR₂; NRSO₂NR₂; NRC(O)NR₂; NRCR₂C(O)NR₂; NRCR(=NR); CR₂NRC(=NR)NR₂; NRC(=NR)NRSO₂R; NRC(=NR)NRC(O)R; C(O)NRCR₂C(O)NR₂; C(O)NRC(=NR)NR₂; OR; NRC(O)CR₂NRSO₂NR₂; or NRC(O)CR₂NRC(=NR)NR₂.

In one embodiment, Z is H. In one embodiment, Z is halogen. In another embodiment, Z is alkyl. In one embodiment, Z is CN. In another embodiment, Z is halo. In certain embodiments, Z is OR, for example OH. In one embodiment, Z is SR', for example SH or S(alkyl). In one embodiment, Z is halogen, for example mono- or multi-F or Cl. In one embodiment, Z is NRR'. In a subembodiment, Z is NHR'. In another subembodiment, Z is N(alkyl)R', for example N(CH₃)R'.

In one embodiment, R¹ is alkyl; R² is alkyl; P is hydroxyl or hydroxyl protected by a hydroxyl protecting group; n is 0, 1 or 2; m is 0; and Y is —CN. In another embodiment, R¹ is alkyl; R² is alkyl; P is hydroxyl or hydroxyl protected by a hydroxyl protecting group; n is 0, 1 or 2; m is 0; and Y is OR. In another embodiment, R¹ is alkyl; R² is alkyl; P is hydroxyl or hydroxyl protected by a hydroxyl protecting group; n is 0, 1 or 2; m is 0 or 1; and Y is NRR'.

In one embodiment, when Y is CN, X is not —C(=O)—. In another embodiment, R¹ is alkyl; R² is alkyl; P is hydroxyl or hydroxyl protected by a hydroxyl protecting group; n is 0, 1 or 2; X is —C(=O)—; and Y is OR. In another embodiment, R¹ is alkyl; R² is alkyl; P is hydroxyl or hydroxyl protected by a hydroxyl protecting group; n is 0, 1 or 2; X is —C(=O)—; and Y is NRR'.

In one embodiment, R¹ is alkyl; R² is alkyl; P is hydroxyl or hydroxyl protected by a hydroxyl protecting group; n is 1 or 2; m is 0; and Y is —CN. In another embodiment, R¹ is alkyl; R² is alkyl; P is hydroxyl or hydroxyl protected by a hydroxyl protecting group; n is 1 or 2; m is 0; and Y is OR. In another embodiment, R¹ is alkyl; R² is alkyl; P is hydroxyl or hydroxyl protected by a hydroxyl protecting group; n is 1 or 2; m is 0 or 1; and Y is NRR'. In one embodiment, R¹ is alkyl; R² is alkyl; P is hydroxyl or hydroxyl protected by a hydroxyl protecting group; n is 1 or 2; X is —C(=O)—; and Y is OR. In another embodiment, R¹ is alkyl; R² is alkyl; P is hydroxyl or hydroxyl protected by a hydroxyl protecting group; n is 1 or 2; X is —C(=O)—; and Y is NRR'.

In another particular embodiment, the compound is a compound of Formula V,

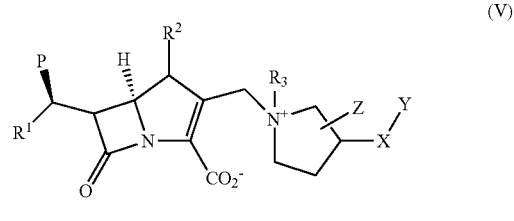

(V)

or a pharmaceutically acceptable salt, ester or prodrug thereof,
wherein
R¹, R² and R³ are each independently selected from H or alkyl;
P is H, OH, halogen, or hydroxyl protected by a hydroxyl protecting group;
X is —(CR₂)ₘ— or —C(=O)—;
m is 0, 1 or 2;
Y is CN, OR, SR' or NRR';
each R is independently selected from H, alkyl or haloalkyl;
R' is H, alkyl, NR₂; C(=O)R; SO₂R; SO₂NR₂; C(=NR)NR₂; C(=O)NR₂; CR₂C(=O)NR₂; C(=NR)R; C(=NR)NRSO₂R; C(=NR)NRC(=O)R; C(=O)CR₂NRSO₂NR₂; or C(=O)CR₂NRC(=NR)NR₂; and
Z is H, alkyl, halo, CN, OR, SR' or NRR'.

In one embodiment, R¹ is H. In one embodiment, R¹ is alkyl, for example CH₃. In one embodiment, R² is H. In one embodiment, R² is alkyl, for example CH₃. In one embodiment, both R¹ and R² are alkyl, for example CH₃.

In one embodiment, P is H. In one embodiment, P is OH. In one embodiment, P is halogen. In one embodiment, P is hydroxyl protected by a hydroxyl protecting group. In a particular embodiment, P is OH or hydroxyl protected by a hydroxyl protecting group.

In one embodiment, X is —(CR₂)ₘ—. In one subembodiment, m is 0. In another subembodiment, m is 1. In another subembodiment, m is 2. In one embodiment, X is —C(=O)—.

In one embodiment, at least one R is H. In one embodiment, at least two Rs are H. In one embodiment, at least one R is alkyl, for example CH₃, CH₂CH₃ or CH₂CH₂CH₃. In one embodiment, at least one R is haloalkyl, for example CF₃.

In one embodiment, Z is H. In one embodiment, Z is halogen. In another embodiment, Z is alkyl. In one embodiment, Z is CN. In another embodiment, Z is halo. In certain embodiments, Z is OR, for example OH. In one embodiment, Z is SR', for example SH or S(alkyl). In one embodiment, Z is halogen, for example mono- or multi-F or Cl. In one embodiment, Z is NRR'. In a subembodiment, Z is NHR'. In another subembodiment, Z is N(alkyl)R', for example N(CH₃)R'.

In one embodiment, Y is CN. In another embodiment, Y is OR. In a particular embodiment, Y is OH. In one embodiment, Y is SR', for example SH or S(alkyl). In one embodiment, Y is SR' and R' is C(=NR)NR₂, for example C(=NH)NH₂, C(=NCH₃)NH₂, C(=NCH₃)NHCH₃, C(=NCH₃)N(CH₃)₂, C(=NR)NH(CH₃), or C(=NCF₃)NH₂. In one embodiment, Y is NRR'. In a subembodiment, Y is NHR'. In another subembodiment, Y is N(alkyl)R', for example N(CH₃)R'.

In one embodiment, R' is H. In one embodiment, R' is alkyl, for example CH₃. In one embodiment, R' is NR₂, for example NH₂, NHR, NHCH₃, or N(CH₃)₂. In another embodiment, R' is C(=O)R, for example C(=O)CH₃ or C(=O)CF₃. In another embodiment, R' is SO₂R, for example SO₂CH₃. In another embodiment, R' is SO₂NR₂, for example SO₂NH₂. In another embodiment, R' is C(=NR)NR₂, for example C(=NH)NH₂, C(=NCH₃)NH₂, C(=NCH₃)NHCH₃, C(=NCH₃)N(CH₃) 2, C(=NR)NH (CH₃), or C(=NCF₃)NH₂. In another embodiment, R' is C(=O)NR₂, for example C(=O)NH₂, C(=O)NHR, C(=O)NHCH₃ or C(=O)N(CH₃)₂. In another embodiment, R' is C(=NR)R', for example C(=NH)H, C(=NH)R or C(=NH)CH₃. In another embodiment, R' is C(=NR) NRSO₂R, for example C(=NH)NHSO₂H, C(=NH) NHSO₂R, or C(=NH)NHSO₂CH₃. In another embodiment, R' is C(=NR)NRC(=O)R, for example C(=NH)NHC (=O)R or C(=NH)NHC(=O)CH₃. In another embodiment, R' is C(=O)CR₂NRSO₂NR₂, for example C(=O) CH₂NHSO₂NR₂, C(=O)CH₂NHSO₂NH₂, or C(=O) CH₂NHSO₂N(CH₃)₂. In another embodiment, R' is C(=O) CR₂NRC(=NR)NR₂, for example C(=O)CH₂NHC (=NH)NR₂, C(=O)CH₂NHC(=NH)NH₂ or C(=O) CH₂NHC(=NH)N(CH₃)₂.

In one embodiment, the compound of Formula IV is the compound:

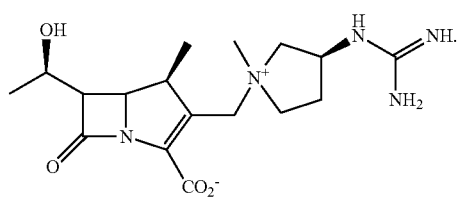

In another particular embodiment, the compound is a compound of Formula VI,

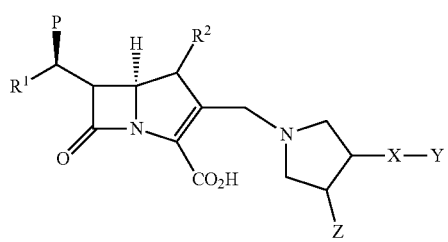

or a pharmaceutically acceptable salt, ester or prodrug thereof,
wherein
R¹ and R² are each independently selected from H or alkyl;
P is H, OH, halogen, or hydroxyl protected by a hydroxyl protecting group;
X is —(CR₂)ₘ— or —C(=O)—;
m is 0, 1 or 2;
Y is CN, OR, SR' or NRR';
each R is independently selected from H, alkyl or haloalkyl;
R' is H, alkyl, NR₂; C(=O)R; SO₂R; SO₂NR₂; C(=NR) NR₂; C(=O)NR₂; CR₂C(=O)NR₂; C(=NR)R; C(=NR)NRSO₂R; C(=NR)NRC(=O)R; C(=O) CR₂NRSO₂NR₂; or C(=O)CR₂NRC(=NR)NR₂; and
Z is H, alkyl, halo, CN, OR, SR' or NRR'.

In one embodiment, R¹ is H. In one embodiment, R¹ is alkyl, for example CH₃. In one embodiment, R² is H. In one embodiment, R² is alkyl, for example CH₃. In one embodiment, both R¹ and R² are alkyl, for example CH₃.

In one embodiment, P is H. In one embodiment, P is OH. In one embodiment, P is halogen. In one embodiment, P is hydroxyl protected by a hydroxyl protecting group. In a particular embodiment, P is OH or hydroxyl protected by a hydroxyl protecting group.

In one embodiment, X is —(CR₂)ₘ—. In one subembodiment, m is 0. In another subembodiment, m is 1. In another subembodiment, m is 2. In one embodiment, X is —C(=O)—.

In one embodiment, at least one R is H. In one embodiment, at least two Rs are H. In one embodiment, at least one R is alkyl, for example CH₃, CH₂CH₃ or CH₂CH₂CH₃. In one embodiment, at least one R is haloalkyl, for example CF₃.

In one embodiment, Y is CN. In another embodiment, Y is OR. In a particular embodiment, Y is OH. In one embodiment, Y is SR', for example SH or S(alkyl). In one embodiment, Y is SR' and R' is C(=NR)NR₂, for example C(=NH) NH₂, C(=NCH₃)NH₂, C(=NCH₃)NHCH₃, C(=NCH₃)N (CH₃)₂, C(=NR)NH(CH₃), or C(=NCF₃)NH₂. In one embodiment, Y is NRR'. In a subembodiment, Y is NHR'. In another subembodiment, Y is N(alkyl)R', for example N(CH₃)R'.

In one embodiment, Z is H. In one embodiment, Z is halogen. In another embodiment, Z is alkyl. In one embodiment, Z is CN. In another embodiment, Z is halo. In certain embodiments, Z is OR, for example OH. In one embodiment, Z is SR', for example SH or S(alkyl). In one embodiment, Z is halogen, for example mono- or multi-F or Cl. In one embodiment, Z is NRR'. In a subembodiment, Z is NHR'. In another subembodiment, Z is N(alkyl)R', for example N(CH₃)R'.

In one embodiment, the Z substituent and the X—Y substituent are in a cis-configuration with respect to each other. In another embodiment, the Z substituent and the X—Y substituent are in a trans-configuration with respect to each other. In a preferred embodiment, Z is hydroxyl. In another preferred embodiment, m is 0 and Y is NRR', where R is H and R' is C(=NR)NR₂. In yet another preferred embodiment, Z is hydroxyl, m is 0 and Y is NRR', where R is H and R' is C(=NR)NR₂.

In one embodiment, R' is H. In one embodiment, R' is alkyl, for example CH₃. In one embodiment, R' is NR₂, for example NH₂, NHR, NHCH₃, or N(CH₃)₂. In another embodiment, R' is C(=O)R, for example C(=O)CH₃ or C(=O)CF₃. In another embodiment, R' is SO₂R, for example SO₂CH₃. In another embodiment, R' is SO₂NR₂, for example SO₂NH₂. In another embodiment, R' is C(=NR)NR₂, for example C(=NH)NH₂, C(=NCH₃)NH₂, C(=NCH₃)NHCH₃, C(=NCH₃)N(CH₃) 2, C(=NR)NH (CH₃), or C(=NCF₃)NH₂. In another embodiment, R' is C(=O)NR₂, for example C(=O)NH₂, C(=O)NHR, C(=O)NHCH₃ or C(=O)N(CH₃)₂. In another embodiment, R' is C(=NR)R, for example C(=NH)H, C(=NH)R or C(=NH)CH₃. In another embodiment, R' is C(=NR) NRSO₂R, for example C(=NH)NHSO₂H, C(=NH) NHSO₂R, or C(=NH)NHSO₂CH₃. In another embodiment, R' is C(=NR)NRC(=O)R, for example C(=NH)NHC (=O)R or C(=NH)NHC(=O)CH₃. In another embodiment, R' is C(=O)CR₂NRSO₂NR₂, for example C(=O) CH₂NHSO₂NR₂, C(=O)CH₂NHSO₂NH₂, or C(=O) CH₂NHSO₂N(CH₃)₂. In another embodiment, R' is C(=O) CR₂NRC(=NR)NR₂, for example C(=O)CH₂NHC (=NH)NR₂, C(=O)CH₂NHC(=NH)NH₂ or C(=O) CH₂NHC(=NH)N(CH₃)₂.

In one embodiment, the compound of Formula VI is selected from the group consisting of:
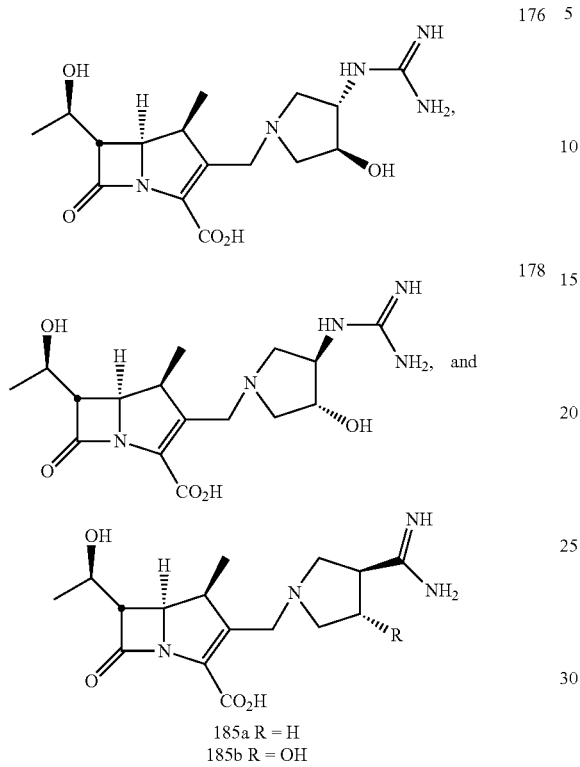
176
178 and
185a R = H
185b R = OH
In certain embodiments, the compound is selected from the group consisting of:
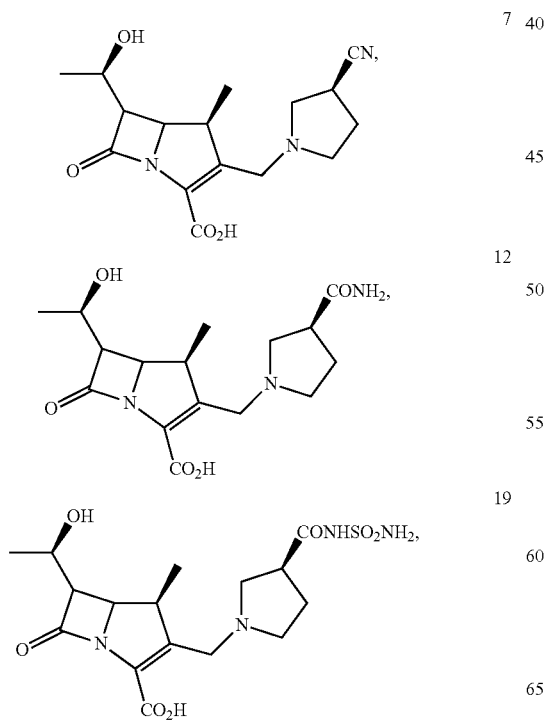
7
12
19
-continued
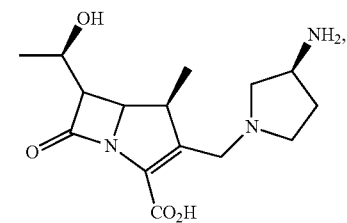
27
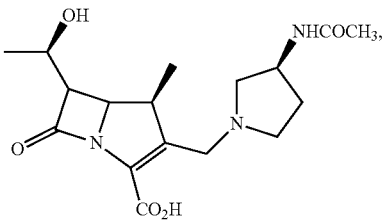
32
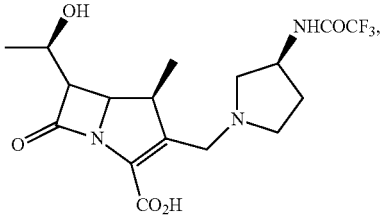
37
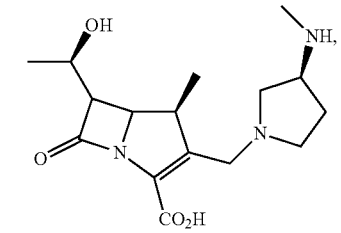
43
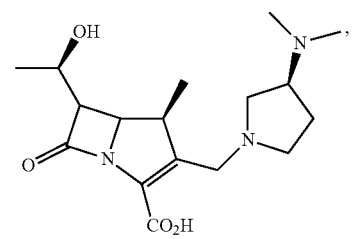
46
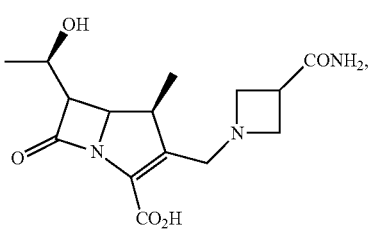
49
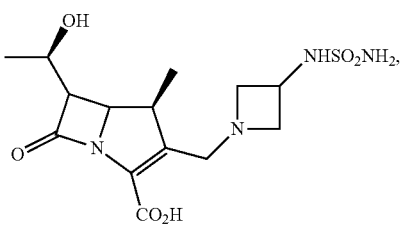
58

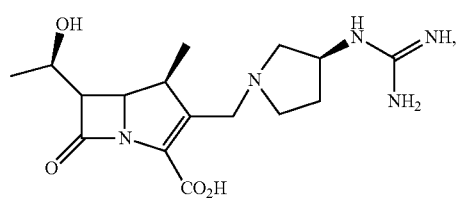
64
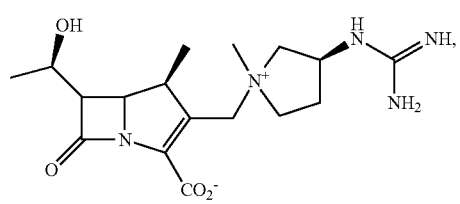
67
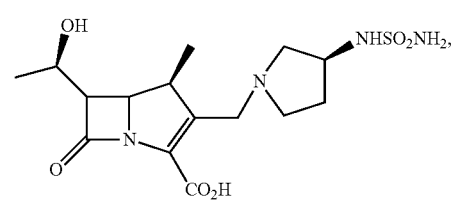
72
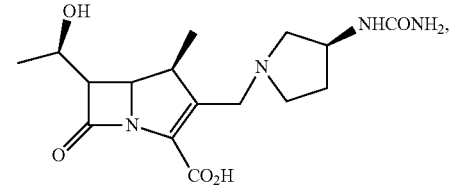
78
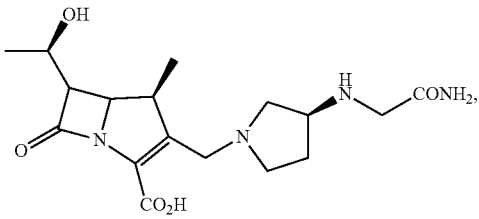
83
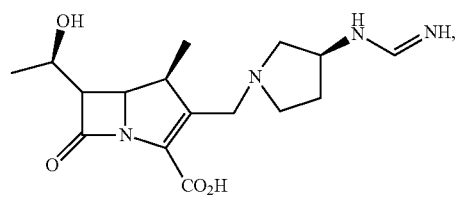
84
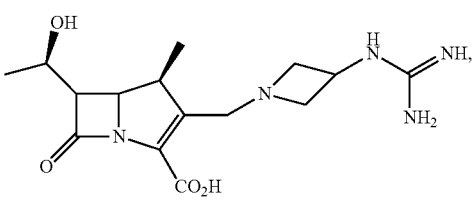
89
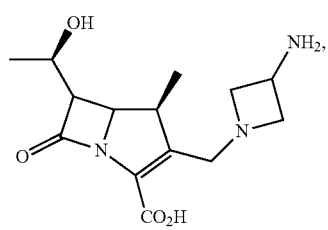
93
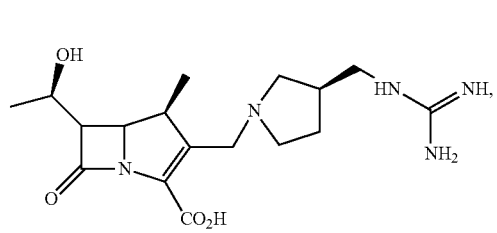
99
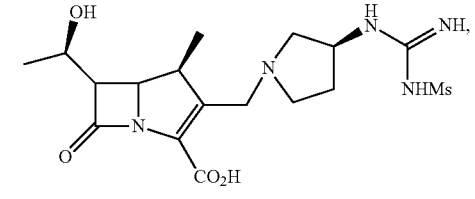
106
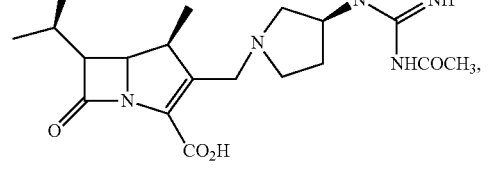
111
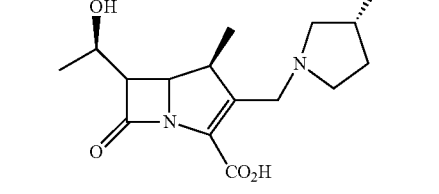
115
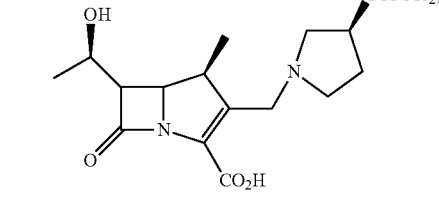
120
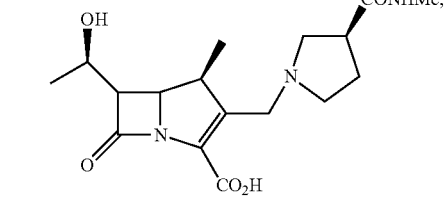
127

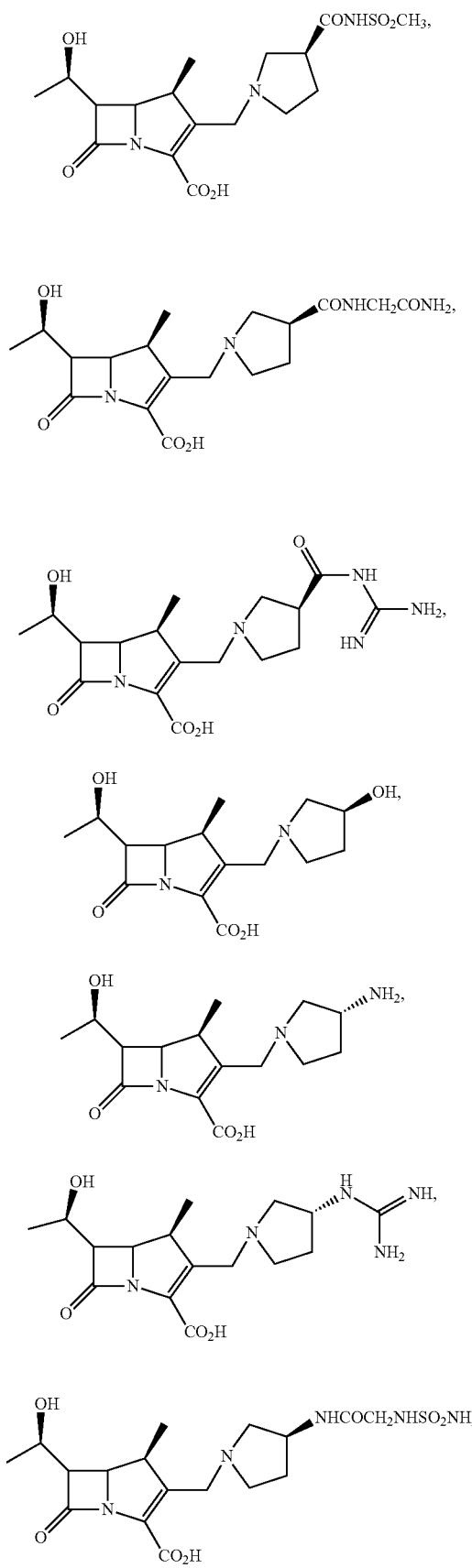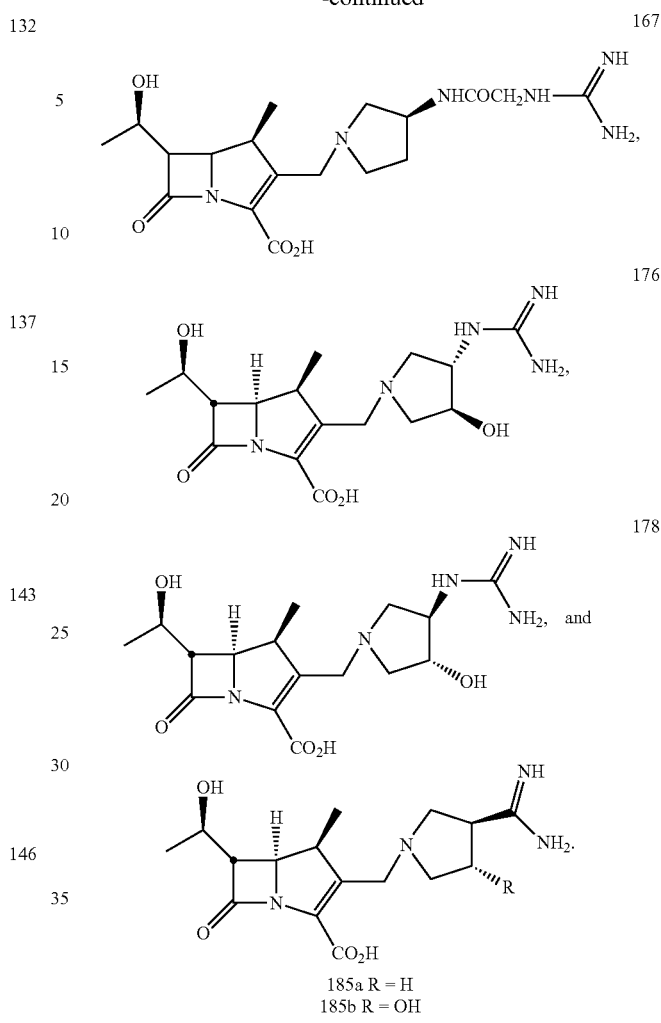

Method of Treatment

The present invention also provides a method of preventing or treating a bacterial infection, in a host, for example an animal, and typically a human, including administering a therapeutic amount of a compound of the present invention, or a pharmaceutically acceptable salt and/or prodrug therein, optionally in a pharmaceutically acceptable carrier or diluent where the bacterial infection is due to gram-negative bacteria. In one embodiment, the bacterial infection is a drug resistant and/or multiple-drug resistant bacterial infection.

The invention also provides a compound of the present invention for use in medical therapy.

The present invention also provides a use of a therapeutic amount of a compound of the present invention, or a pharmaceutically acceptable salt and/or prodrug therein, optionally in a pharmaceutically acceptable carrier or diluent, for preventing or treating a gram-negative bacterial infection, in a host, such as an animal, and typically a human.

The distinctive feature of gram-negative bacteria is the presence of a double membrane surrounding each bacterial cell. Although all bacteria have an inner cell membrane, gram-negative bacteria have a unique outer membrane. This outer membrane excludes certain drugs and antibiotics from penetrating the cell, partially accounting for why gram-negative bacteria are generally more resistant to antibiotics than are gram-positive bacteria. The pathogenic capability of gram-negative bacteria is usually associated with certain components of their cell walls, particularly the lipopolysaccharide (endotoxin) layer.

The outer membrane of gram-negative bacteria is rich in lipopolysaccharide. If gram-negative bacteria enter the bloodstream, lipopolysaccharide can trigger a cascade of events, including high fever and a drop in blood pressure. Unlike Gram-positive bacteria, which assume a violet color in Gram staining, Gram-negative bacteria incorporate the counterstain rather than the primary stain. Because the cell wall of Gram (−) bacteria is high in lipid content and low in peptidoglycan content, the primary crystal-violet escapes from the cell when the decolorizer is added. Most enteric (bowel related) illnesses can also be attributed to this group of bacteria.

Examples of gram-negative bacteria include *Aeromonas* sp., *Acinetobacter* sp. such as *Acinetobacter baumannii*(or *A. calcoaceticus*), *Actinobacillus actinomycetemcomitans*, *Bacteroides* sp. such as *Bacteroides fragilis*, *Bartonella*, *Bdellovibrio* spp., *Bordetella pertussis*, *Brucella* sp., *Burkholderia cepacia*, *Burkholderia*, *pseudomallei*, *Campylobacter* sp., *Capnocytophaga* sp., *Cardiobacterium hominis*, *Chlamydia trachomatis*, *Citrobacter* sp., *Eikenella corrodens*, *Enterobacter* sp., *Escherichia coli*, *Francisella tularensis*, *Flavobacterium* sp., *Fusobacterium* sp., *Helicobacter pylori*, *Haemophilus influenzae*, *Haemophilus ducreyi*, *Klebsiella* spp. such as *Klebsiella pneumoniae*, *Kingella kingae*, *Legionella* spp. such as *Legionella pneumophila*, *Moraxella catarrhalis*, *Morganella*, *Neisseria gonorrhoeae*, *Neisseria meningitidis*, *Pasteurella pestis*, *Pasteurella multocida*, *Plesiomonas shigelloides*, *Prevotella* sp., *Proteus* spp., *Providencia*, *Pseudomonas* spp. such as *Pseudomonas aeruginosa*, *Salmonella* spp. such as *Salmonella enteriditis* and *Salmonella typhi*, *Serratia marcescens*, *Shigella* spp., *Vibrio cholerae*, *Vibrio parahaemolyticus*, *Vibrio vulnificus*, *Veillonella* sp., *Xanthomonas maltophilia* or *Stenotrophomonas maltophila*, *Yersinia pestis*, *Yersinia enterocolitica*. Additionally, some organisms simply tend not to be well differentiated by gram staining, despite any known phylogenetic affiliation with the gram-negatives or gram-positives. *Rickettsia prowazekii*, *Rickettsia rickettsii* and *Treponema pallidum*. Chlamydias are small, gram-negative, peptidoglycan-less cocci that are obligate intracellular parasites of animals. *Spirochetes* are chemoheterotrophic bacteria whose cells are tightly coiled or resemble a stretched spring with gram-negative-like cell envelopes. *Spirochetes* include *Spirillum minus*, *Borrelia burgdorferi* (Lyme disease), *Leptospira* spp. (leptospirosis) and *Treponema pallidum* (syphilis). Rickettsias and actinomycetes are also gram-negative pleomorphic bacilli and coccobacilli that are obligate intracellular parasites of eucaryotes transmitted generally by insects and ticks.

The present invention also provides a use of a therapeutic amount of a compound of the present invention, or a pharmaceutically acceptable salt and/or prodrug therein, optionally in a pharmaceutically acceptable carrier or diluent, in the manufacture of a medicament for preventing or treating a gram-negative bacterial infection, in a host, such as an animal, and typically a human.

The invention also includes methods of inhibiting bacterial infection in a host. Inhibition of bacterial replication or treatment of an infection in a cell can be measured by showing a reduction in bacterial replication in a cell to a level lower than the level in an otherwise identical cell, which was not administered the compound of the invention. The reduction can be by about 80%, 85%, 90%, 95%, about 99.9% or more. The level of bacterial replication in a cell can be assessed by any known methods. For example, the level of bacterial replication in a cell can be assessed by evaluating the number of bacterial particles or amount of a bacterial component, such as a bacterial protein, a bacterial enzyme, or bacterial nucleic acid, in the cell or in fluid or debris associated with the cell. The number of infectious bacteria in a cell can be evaluated, for example, in a plaque assay. The level of a bacterial component such as a bacterial protein or enzyme in a cell can be evaluated using standard analytical techniques of protein biochemistry, such as, for example, using an activity assay for a bacterial enzyme, or using Western blotting or quantitative gel electrophoresis for a bacterial protein. Bacterial nucleic acid levels in a cell can be evaluated using standard analytical techniques such as Northern blotting and Southern Blotting or quantitation by polymerase chain reaction (PCR).

As used herein, to inhibit bacterial replication in a host means to reduce the bacterial load in a host to a level, which is lower than the level of the bacterial load in an otherwise identical host, which was not administered the compound. Bacterial load in a mammal can be reduced by about 1 to 12 $\log_{10}$ or more relative to an otherwise identical mammal, which was not administered the compound. Bacterial load in a mammal can be assessed by a number of methods known in the art such as, for example, obtaining a tissue or fluid sample from the mammal and assessing the amount of bacterial components in the mammal contained therein using technology which is either immunological, biochemical or molecular biological in nature and which is well known to the skilled artisan and which are described elsewhere herein. Inhibition of bacterial replication in a cell is assessed using similar or identical assays as those used to assess bacterial load in a mammal.

Combination and Alternation Therapies

In one embodiment of the invention, one or more therapeutic agents, including particularly antimicrobial agents such as antibiotic agents that are effective against gram negative bacteria, can be used in combination and/or alternation with the compound/composition of the present invention to achieve a additive and/or synergistic therapeutic effect.

The active compounds can be administered in combination, alternation or sequential steps with another anti-bacterial agent. In combination therapy, effective dosages of two or more agents are administered together, whereas in alternation or sequential-step therapy, an effective dosage of each agent is administered serially or sequentially. The dosages given will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions. In some embodiments, an anti-bacterial agent exhibits an $EC_{50}$ of 10-15 μM or less, or typically less than 1-5 μM.

In one particular embodiment, the combination includes a β-lactamase inhibitor, such as clavulanic acid, which has been used as in the delivery of prophylactic amounts of antibiotics in patients. Although clavulanic acid does have some degree of bacterial activity, its principal role is as a beta-lactamase inhibitor. Clavulanic acid has a similar structure to the beta-lactam antibiotics but binds irreversibly to the beta-lactamase enzymes. Used in combination with the beta-lactam antibiotics, it has become one of the most prescribed antibiotics in the western world prolonging the effective life of antibiotics such as Ampicillin (as in GSK's Augmentin®).

It is possible that drug-resistant variants of bacteria can emerge after prolonged treatment with an anti-bacterial agent. The efficacy of a drug against the bacterial infection can be prolonged, augmented, or restored by administering the compound in combination or alternation with a second, and perhaps third, anti-bacterial agent, for example with a different site of activity than the principle drug. Alternatively, the pharmacokinetics, biodistribution or other parameter of the drug can be altered by such combination or alternation therapy.

Suitable antibiotic agents are disclosed, e.g. in Physician's Desk 30 Reference (PDR), Medical Economics Company (Montvale, N.J.), (53rd Ed.), 1999; Mayo Medical Center Formulary, Unabridged Version, Mayo Clinic (Rochester, Minn.), January 1998; Merck Index An Encyclopedia of Chemicals, Drugs and Biologicals, (11th Ed.), Merck & Co., Inc. (Rahway, N.J.), 1989; University of Wisconsin Antimicrobial Use Guide, http://www.medsch.wisc.edu/clinsci/5amcg/amcg.html; Introduction on the Use of the Antibiotics Guideline, of Specific Antibiotic Classes, Thomas Jefferson University, http://jeffiine.tju.edu/CWIS/OAC/antibiotics_guide/intro.html; and references cited therein.

Nonlimiting examples of agents that can be used in combination or alternation with the compounds of the invention include: aminoglycosides, β-lactam antibiotics, cephalosporius, macrolides, miscellaneous antibiotics, penicillins, tetracyclines, antifungals, antimalarial agents, antituberculosis agents, antibacterials, leprostatics, miscellaneous anti-infectives, quinolones, sulfonamides, urinary anti-infectives, nasal antibiotics, opthalmic antibiotics, opthalmic antibacterials, opthalmicquinalones, opthalmic sulfonamides, skin and mucous membrane antibiotics, skin and mucous membrane antifungals, skin and mucous membrane antibacterials, skin and mucous membrane miscellaneous anti-infectives, skin and mucous membranescabicides and pedulicides, skin and mucous membrane antincoplasts, nitrofurans and oxazolidinones.

Specific compounds include, for example, Amikacin (amikacin sulfate); Craramyein (gentamicin sulfate); Nebcin (tobramycin sulfate); Netromycin (netilmicin sulfate); Streptomycin Sulfate; and TOBI (tobramycin), Azactam (aztreonam); Cefotan (cefotetan); Lorabid (loracarbef); Mefoxin (cefoxitin); Merrem (meropenem); and Primaxin (imipenem and cilastatin for injectable suspension); Ancef (cefazolin); Ceclor (cefaclor); Cedax (ceffibuten); Cefizox (ceffizoxime sodium); Cefobid (cefoperazone sodium); Ceftin (cefuroxime axetil); Cefzil (cefprozil); Ceptaz (ceftazidime); Claforan (cefotaxime); Duricef (cefadroxil monohydrate); Fortaz (ceftazidime); Keflex (cephalexin); Keftab (cephalexin HCl); Kefurox (cefuroxime); Kcfzol (ccfazolin); Mandol (cefamandole nafatc); Maxipimc (cefepime HCl); Monocid (cefonicidsodium); Omnicef (cefdinir); Rocephin (ceftriaxone); Suprax (cefixime); Tazicef (ceftazidime); Tazidime (ceftazidime); Vantin (cefpodoxime proxetil); and Zinacef5(cefuroxime); Biaxin (clarithromycin); Dynabac (dirithromycin); E.E.S. 200 (Erythromycin Ethylsuccinate); E.E.S. 400 (Erythromycin Ethylsuccinate); EryPed 200 (Erythromycin Ethylsuccinate); EryPed 400 (Erythromycin Ethylsuccinate); Ery-Tab (Erythromycin delayed-release tablets); Erythrocin Stearate (Erythromycin stearate); Ilosone (erythromycinestolate); PCE Dispertab (erythromycin particles in tablets); Pediazole (erythromycin ethylsuccinate and sulfisoxazole acetyl for oral suspension); Tao (troleandomycin); Zithromax (azithromycin); and Erythromycin; Cleocin HCl (clindamycin hydrochloride); Cleotin Phosphate (elindamycin phosphate); Coly-Mycin M (colistimethate sodium); and Vancocin HCl (vancomycin hydrochloride); Amoxil (amoxicillin); Augmentin (amoxicillin/clavulanate potassium); Bicillin C-R 900/300 (Penicillin G benzathine and Penicillin G procaine suspension); Bicillin C-R (Penicillin G benzathine and Penicillin G procaine suspension); Bicillin L-A (Penicillin G benzathine suspension); Geoeillin (carbencillin indanyl sodium); Mezlin (sterile mezlocillinsodium); Omnipen (ampicillin); Pen-Vee K (penicillin V potassium); Pfizerpen (penicillin G potassium); Pipracil (piperacillin sodium); Speetrobid (bacampicillin-HCl); Ticar (tiearcillin disodium); Timentin (ticarcillin disodium and clavulanate potassium); Unasyn (ampicillin sodium/sulbactam sodium); Zosyn (piperacillin sodium and tazobactam sodium); and Dicloxacillin Sodium; Achromycin V (tetracycline HCl); Declomycin (derneclocycline HCl); Dynacin (minocyline HCl); Minocin (minocyclinc hydrochloride); Monodox (Doxycycline monohydrate capsules); Terramycin (oxytetracyline); Vectrin (minocycline hydrochloride); Vibramycin Calcium (doxycycline sodium); Vibramycin Hyclate (doxycycline hyclate); Vibramycin Monohydrate (doxycycline monohydrate); Vibra-Tabs (doxycycline-hydrate); Declomycin (demeclocycline HCl); Vibramycin (doxycycline); Dynacin (Minocyline HCl); Terramycin (oxytetracyline HCl); Achromycin V capsules5 (tetracycline HCl); Linco-mycins; and Cleotin HCl (clindamycin HCl); Abelcet (amphotericin B lipid complex); AmBisome (amphotericin B); Amphotec (amphotericin B cholesterol sulfatecomplex); Ancobon (flucytosine); Diflucan (fluconazole); Fulvicin P/Gamma (ultramicrosize griseofulvin); Fulvicin P/G 165 and 330 (ultramicrosize griseofulvin); Grifulvin V (griseofulvin); GalsPEG (gxiseofulvin ultramicrosize); Lamisil (terbinafine hydrochloride); Nizoral (ketoconazole); Amphotericin B; Lotrimin (clotrimazole); Dapsone tablets (dapsone); Diflucan (fluconazole); Monistat-Derm cream (miconazole); Mycostalin Crc .am (nystatin); and Sporanox (itraconazole); Aralen hydrochloride (chloroquine HCl); Aralen phosphate (chloroquine phosphatc); Dataprim (pyrimethamine); Ladam (mefloquine HCl); and Plaquenil (hydroxychloroqnine sulfate); Capastat sulfate (capreomycinsulfate); Myambutol (ethambutol hydrochloride); Mycobutin (rifabutin capsules); Nydrazid (isoniazid injection); Paser (aminosalicylic acid); Prifiin (rifapentine); Pyrazinamide tablets (pyrazinamide); Rifadin (rifampin capsules); Rifadin IV (rifampin for injection); Rifamate (rifampin and isoniazid); Rifater (rifampin, isoniazid and pyrazinamide); Seromycin (cycloserine capsules); Streptomycin-Sulfate; Tice BCG (BCG vaccine); Cycloserine (seromycin capsules); Urised (Methenamine); and Trecator-SC (ethionamide tablets); Alferon N (interferon alfa-n3); Crixivan (indinavir sulfate); Cytovene (ganciclovir); Cytovene-IV (ganciclovir sodium); Epivir (lamivudine); Famvir (famciclovir); Flumadine (rimantadine HCl); Foscavir (foscamet sodium); Hivid (zalcitabine); Intron A (interferon alfa-2b); Invirase (saquinavir mesylate); Norvir (ritonavir); Rebetron combination therapy, which contains Rebetrol (ribavirin) and Intron A (inteferon alfa-2b); Rescriptor (delavirdine mesylate); Retrovir (ziduvudine); Retrovir IV (ziduvudine); Symmetrel (amantadine HCl); Synagis (palivizumab); Valtrex (valacyclovir HCl); Videx (didanosine); Viracept (nelfinavir mesylate); Viramune (nevirapine); Virazole (ribavirin); Vistide (cidofovir); Zerit (stavudine (d4T)); Symmetrel Syrup (amantadine HCl); Combivir Tablets (lamiduvine); and Zovirax (acyclovir); Dapsone Tablets (dapsone); Daraprim (pyrimethamine); Flagyl 375 (metronidazole); Flagyl ER Tablets (metronidazole); Flagyl I.V. (metronidazole); Furoxone (furazolidone); Mepron (atovaquone); and Neutrexin (tfirnetrexate glucuronate); Cipro (ciprofloxacin HCl); Floxin (ofloxacin); Levaquin (levofloxacin); Mazaquin (lomcfioxacin HCl); Noroxin (norfloxacin); Penetrex (enoxacin); Raxar (grepafloxacin HCl); Trovan (trovafioxacin mesylate); and Zagam (sparfloxacin); Bactrim. (trimethoprim and sulfamethoxazole); Bactrim DS (Irimethoprim and sulfamethoxazole double strength); Pediazole (erythromycin ethylsuccinate and sulfisoxazole acetyl); Septra (trimethoprim and sulfamethoxazole); Septra DS (trimethoprim and sulfamethoxazole); Co-Trimoxazole, Sulfadiazine, Battrim I.V. Infusion (sulfamethoxazole); Sulfapyridine and Pediazole (erythromycin ethylsuccinate and sulfisoxazole acetyl); Furadantin (nitrofurantoin); Macrobid (nitrofurantoin monohydrate macrocrystals); Macrodantin (nitrofurantoin macrocrystals); Monurol Sachet (fosfomycin tromethamine); NegGram Caplets (nalidixic acid); Septra (trimethoprim and sulfamethoxazole); Septra DS(trimethoprim and sulfamethoxazole); Urised (a combination of the antisepticsmethenamine, methylene blue, phenyl salicylate, benzoic acid and parasympatholytics (atropine sulfate) hyoscyamine); (oxytetracyclinc HCl, sulfamethizole and phenazopyridine HCl); (methenaminc mandelatc); Bactroban (mupirocin); Chloromycetin opthalmic (chloramphenical); Cortisporin (neomycin and polymyxin [3 sulfates and hydrocortisone acetate cream); Ilotycin (erythromycin opthalmic ointment); NeoDecadron (neomycin sulfate-dexamethasone sodium phosphate); Polytrim (tfimethoprirn and polythyxin [3 sulfate opthalmic solution); Terra-Cortril (oxytetracycline HCl and hydrocortisone acetate); Terramycin (oxytetracycline); and TobraDex (tobramycin and dexamethasone opthalmic suspension and ointment); Vita-A opthalmic ointment, (vidatabine); (norfloxacinopthalmic solution; Ciloxan opthalmic solution and ointment (Ciprofloxacin HCl); and Ocuflox opthalmic solution (ofioxacin), Blephamide opthalmicointment (sulfacetamide sodium and prednisolone acetate); and Blephamideopthalmic suspension (sulfacetamide sodium and predrdsolone acetate); A/T/S (erythromycin); Bactroban (mupirocin); Benzamycin (erythromycin-benzoyl peroxide topical gel); Betadine (povidone-odine); Cleotin T (clindamy cinphosphate topical solution); Clindets (clindamycin phosphate pledgets); Cortispofin (neomycin, polymyxin B sulfates and hydrocortisone acetate cream); Emgel (erythromycin); Erycette (erythromycin topical solution); Garamycin (gentamicin sulfate); Klaron (sodium sulfacetamide lotion); Mycostatin (nystatin cream); Theramycin Z (erythromycin topical solution); T-Stat (erythromycin); Chloromycetin (chloramphenicol opthalmic ointment); Cortisporin (neomycin and polymyxin B sulfates, bacitracin zinc and hydrocortisone opthalmic ointment); Ilotycin (erythromycin); NeoDeeadron (neomycin sulfate-dexamethasone sodium phosphate); Polytrim (trimethoprim and polymyxin B sulfate); Terra-Cortril (oxytetracycline HCl and hydrocortisone acetate); Terramycin (oxytetracyclinc); Exclderm (sulconazole nitrate); Fungizone (amphotcricin B oral suspension); Lamisil (terbinafine hydrochloride cream); Loprox (ciclopiroxolamine); Lotrimin (clotrimazole); Lotrisone (clotrimazole and betamethasone dipropionate); Mentax (butenafine HCl); Monistat-Denn (miconazole nitrate); Mycelex (clotrimazole); Mycostatin (nystatin); Naffin (nattifine HCl); Nizoral Ocetoconazole); Nystop (nystatin); Oxistat (oxiconazole nitrate); Selsun Rx (2.5% selenium sulfide lotion); and Spectazole (econazole nitrate); Denavir (penciclovir cream); and Zovirax (acyclovir); Benzashave Coenzoyl peroxide); Betadine (povidone-iodine); Betasept (chlorhexidine gluconate); Cetaphil (soap substitute); Clorpactin WCS-90 (sodium oxychlorosene); Dapsone Tablets (dapsone); Desquam-E Coenzoyl peroxide); Desquam-X (benzoyl peroxide); Hibiclens (chlorhexidine gluconate); Hibistat (ehlorhexidine gluconate); Impregon (tetrachlorosalicylanilide 2%); MetroCream (metronidazole); MetroGel (metronidazole); Noritate (metronidazole); pHisoHex (hexachlorophene detergent cleanser); Sulfacet-R (sodium sulfacetamide 10% and sulfur 5%); Sulfamylon (materfide acetate); Tfiaz Cocnzoyl peroxide); and Vanoxide-HC Coenzoyl peroxide hydrocortisone); Acticin (permethrin); Elimite (permethrin); Eurax (crotamiton); Efudex (fluoro-uracil); Fluoroplex.

Pharmaceutical Compositions

Hosts, including humans can be treated by administering to the patient an effective amount of the active compound or a pharmaceutically acceptable prodrug or salt thereof in the presence of a pharmaceutically acceptable carrier or diluent. The active materials can be administered by any appropriate route, for example, orally, parenterally, intravenously, intradermally, subcutaneously, or topically, in liquid or solid form.

An optional dose of the compound for treatment of a bacterial (such as a gram negative bacteria) infection is about 1 to 50 mg/kg, or 1 to 20 mg/kg, of body weight per day, more generally 0.1 to about 100 mg per kilogram body weight of the recipient per day. The effective dosage range of the pharmaceutically acceptable salts and prodrugs can be calculated based on the weight of the parent nucleoside to be delivered. If the salt or prodrug exhibits activity in itself, the effective dosage can be estimated as above using the weight of the salt or prodrug, or by other means known to those skilled in the art.

Optionally, the active ingredient should be administered to achieve peak plasma concentrations of the active compound of from about 0.2 to 70 M, e.g., about 1.0 to 10 uM. This may be achieved, for example, by the intravenous injection of a 0.1 to 5% solution of the active ingredient, optionally in saline, or administered as a bolus of the active ingredient. The concentration of active compound in the drug composition will depend on absorption, inactivation and excretion rates of the drug as well as other factors known to those of skill in the art. It is to be further understood that for any particular subject, specific dosage regimens should be adjusted according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

The compound is conveniently administered in unit any suitable dosage form, including but not limited to one containing 7 to 3000 mg, or 70 to 1400 mg of active ingredient per unit dosage form. A dosage of 50-1000 mg is optimal.

The active compound can be administered in a pharmaceutically acceptable carrier available in the art, and can be administered by a chosen route of administration. Pharmaceutical compositions can be prepared, packaged, or sold in a variety of formulations which can be suitable for one or more routes of administration such as, for example, oral, intravenous, intramuscular, topical, subcutaneous, rectal, vaginal, parenteral, pulmonary, intranasal, buccal, ophthalmic, or another route of administration. The active materials can be administered in liquid or solid form. Other contemplated formulations include projected nanoparticles, liposomal preparations, resealed erythrocytes containing the active ingredient, and immunologically-based formulations.

The active compound may be administered intravenously or intraperitoneally by infusion or injection. Solutions of the active compound or its salts may be prepared in water or saline, optionally mixed with a non-toxic surfactant. Dispersions may be prepared in glycerol, liquid polyethylene glycols, triacetin, and mixtures thereof, and in oils. Under ordinary conditions of storage and use, these preparations contain a preservative to prevent growth of microorganisms.

Pharmaceutical dosage forms suitable for injection or infusion may include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form is optionally sterile, fluid, and stable under conditions of manufacture and storage. The liquid carrier or vehicle may be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof.

For oral therapeutic administration, the active compound can be combined with one or more excipients and used in the form of ingestible tablets, buccal tablets, troches, capsules, elixirs, suspensions, syrups, wafers, and the like. Such compositions and preparations can contain at least 0.1% (w/w) of active compound. The percentage of the compositions and preparations can, of course, be varied, for example from about 0.1% to nearly 100% of the weight of a given unit dosage form. The amount of active compound in such therapeutically useful compositions is such that an effective dosage level will be obtained upon administration.

The tablets, troches, pills, capsules, and the like may also contain one or more of the following: binders, such as microcrystalline cellulose, gum tragacanth, *acacia*, corn starch, or gelatin; excipients, such as dicalcium phosphate, starch or lactose; a disintegrating agent, such as corn starch, potato starch, alginic acid, primogel, and the like; a lubricant, such as magnesium stearate or Sterotes; a glidant, such as colloidal silicon dioxide; a sweetening agent, such as sucrose, fructose, lactose, saccharin, or aspartame; a flavoring agent such as peppermint, methylsalicylate, oil of wintergreen, or cherry flavoring; and a peptide antibacterial agent, such as envuvirtide (Fuzeon™). When the unit dosage form is a capsule, it can contain, in addition to materials of the above type, a liquid carrier, such as a vegetable oil or a polyethylene glycol. Various other materials may be present as coatings or to otherwise modify the physical form of the solid unit dosage form.

In one embodiment, the active compounds are prepared with carriers that will protect the compound against rapid elimination from the body, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, and polylacetic acid. Methods for preparation of such formulations will be apparent to those skilled in the art. The materials may also be obtained commercially from Alza Corporation.

The compounds/compositions of the present invention are optionally administered in a controlled release formulation, which can be a degradable or nondegradable polymer, hydrogel or ganogel or other physical construct that modifies the bioabsorption, half-life or biodegradation of the active agent(s). The controlled release formulation can be a material that is painted or otherwise applied onto the afflicted site, either internally or externally. In one embodiment, the invention provides a biodegradable bolus or implant. The controlled release formulation with appropriated selected imaging agent can be used to coat a transplanted organ or tissue to prevent rejection. It can alternatively be implanted or otherwise applied near the site of potential infection.

Other formulations can also be developed. For example, the compounds can be administered in liposomal suspensions (including liposomes targeted to infected cells with monoclonal antibodies to bacterial antigens). These may be prepared according to methods known to those skilled in the art, for example, as described in U.S. Pat. No. 4,522,811. For example, liposome formulations may be prepared in a variety of lipid(s) (such as stearoyl phosphatidyl ethanolamine, stearoyl phosphatidyl choline, arachadoyl phosphatidyl choline, and cholesterol).

A pharmaceutical composition of the invention may be prepared, packaged, or sold in a formulation suitable for rectal administration. Such a composition may be in the form of, for example, a suppository, a retention enema preparation, and a solution for rectal or colonic irrigation. A pharmaceutical composition of the invention may also be prepared, packaged, or sold in a formulation suitable for vaginal administration. Such a composition may be in the form of, for example, a suppository, an impregnated or coated vaginally-insertable material such as a tampon, a douche preparation, or a solution for vaginal irrigation.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration, which can include particles wherein at least 98% of the particles by weight have a diameter greater than 0.5 nanometers and at least 95% of the particles by number have a diameter less than 7 nanometers. Typically least 95% of the particles by weight have a diameter greater than 1 nanometer and at least 90% of the particles by number have a diameter less than 6 nanometers. The active ingredient can also be in the form of droplets of a solution or suspension, for example those that have an average diameter in the range from about 0.1 to about 200 nanometers.

The formulations described herein as being useful for pulmonary delivery are also useful for intranasal delivery of a pharmaceutical composition of the invention. Another formulation suitable for intranasal administration is a coarse powder comprising the active ingredient and having an average particle from about 0.2 to 500 micrometers.

A pharmaceutical composition of the invention may be prepared, packaged, or sold in a formulation suitable for ophthalmic administration. For topical administration, the present compounds can be applied in pure form, i.e., as a liquid. However, typically, the compounds are administered to the skin as compositions or formulations, in combination with a dermatologically acceptable carrier. Useful solid carriers include finely divided solids such as talc, clay, microcrystalline cellulose, silica, alumina, and the like. Useful liquid carriers include water, alcohols, glycols, and blends of two or more of these, in which the present compounds can be dissolved or dispersed at effective levels, optionally with the aid of non-toxic surfactants. Adjuvants such as fragrances and additional antimicrobial agents can be added to optimize properties for a given use. The resulting liquid compositions can be applied using absorbent pads, used to impregnate bandages or other dressings, or sprayed onto the affected area using pump-type or aerosol sprayers.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

The compound or a pharmaceutically acceptable prodrug or salts thereof can also be mixed with other active materials that do not impair the desired action, or with materials that supplement the desired action, such as antibiotics, antifungals, anti-inflammatories, or other antibacterials, including other nucleoside compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposale syringes or multiple dose vials made of glass or plastic. If administered intravenously, useful carriers are physiological saline or phosphate buffered saline (PS).

The concentration of the compound(s) in a liquid composition, such as a lotion, will, for example, range from about 0.1% to about 95% by weight, or from about 0.5% to about 25% by weight. The concentration in a semi-solid or solid composition such as a gel or a powder will, for example, range from about 0.1% to 100% by weight, or about 0.5% to about 5% by weight. Single doses for intravenous injection, subcutaneous, intramuscular or topical administration, infusion, ingestion or suppository will generally be from about 0.001 to about 5000 mg, and be administered from about 1 to about 3 times daily, to yield levels of about 0.01 to about 500 mg/kg, for adults.

The invention also includes one or more compounds disclosed herein, or any combination thereof, or salt thereof, in an amount effective to inhibit bacterial (such as a gram negative bacteria) replication in a host. The compound can be useful for inhibiting bacterial replication in a cell or neutralization (i.e. inactivation) of extracellular bacteria.

The invention also includes a kit for administering a compound of the invention, a pharmaceutically acceptable salt thereof, or a pharmaceutical composition, to a host for treatment of a bacterial (such as gram negative bacteria) infection. Typically, the host is a human. The kit comprises one or more compounds of the invention, or a combination thereof, and optionally an instructional material, which describes adventitially administering the composition to the mammal by any of the routes of administration described herein. In another embodiment, this kit comprises a (typically sterile) solvent suitable for dissolving or suspending the composition of the invention prior to administering the compound to the mammal.

EXAMPLES

Nuclear magnetic resonance (NMR) spectra were obtained on a Varian INOVA 400 (400 MHz) spectrometer; chemical shifts (δ) are reported in parts per million (ppm), and the signals are described as s (singlet), d (doublet), t (triplet), q (quartet), bs r (broad singlet), dd (doublet of doublet), dt (triplet of doublet), and m (multiplet). All reactions were monitored using thin layer chromatography (TLC; 200 mm silica gel GF plates) on Analtech or HPLC. Dry dichloromethane, acetonitrile, DMF, and THF were obtained by drying over 4 Å molecular sieves.

Abbreviations
ACN: Acetonitrile
DBU: 1,8-Diazabicyclo[5.4.0]undec-7-ene
DCM: Dichloromethane
DIEA: Diisopropylethyl-amine
DI H$_2$O: Deionized water
DMAP: 4-(Dimethylamino)pyridine
DMF: N,N-Dimethylformamide
EDC: N-(3-Dimethylaminopropyl)-N-ethylcarbodiimide
HOBT: 1-Hydroxybenzotriazole
IPA: iso-Propanol
LDA: Lithium diisopropylamide
TBS or TBDMS: tert-Butyldimethylsilyl
TBSOTf: tert-Butyldimethylsilyl trifluoromethanesulfonate
LAH: Lithium aluminum hydride
Pt/C: Platinum on carbon
PNB: para-Nitrobenzyl
TES: Triethylsilyl
TFA: Trifluoroacetic acid
THF: Tetrahydrofuran
General Synthesis Methods
Preparation of the Carbapenem Intermediate (CPI)

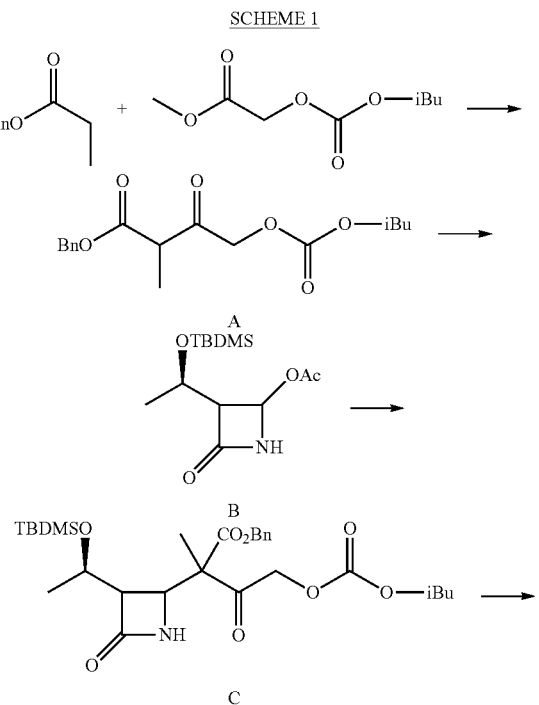

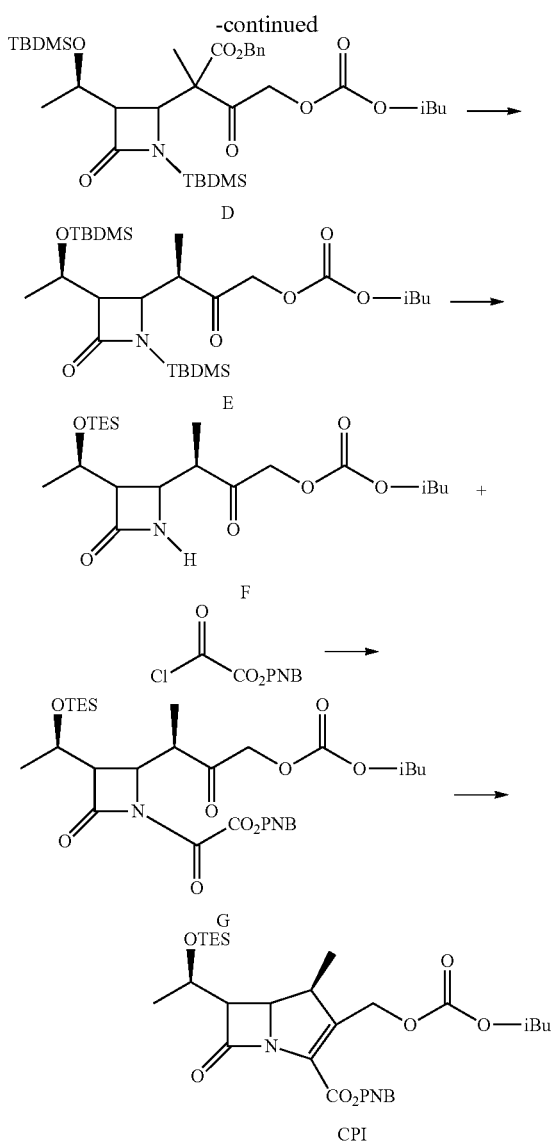

Carbapenem Intermediate (CPI) was prepared according to the synthetic scheme shown in Scheme 1. In the first step of the process, benzyl propionate is reacted with isobutoxycarbonyloxy acetic acid methyl ester in a solvent at low temperature in the presence of LDA to form ketoester A. The ketoester A is then contacted with the acetoxyazetidinone B (prepared by any number of known, synthetic routes) in a solvent, and sodium carbonate is added. The reaction ages for a period of time at a temperature such that the reaction goes substantially to completion, generating the target lactam C.

The lactam C is dissolved in a solvent, such as DMF, to which a suitable base (such as DIEA) and TBSOTf are added, and the mixture allowed to age for a period of time at a temperature. Following workup, the bis-TBS-ketoester D is isolated.

The crude ketoester D is dissolved in ethyl acetate in an appropriate reaction vessel.

Formic acid and a catalyst, such as Pd/C, are added to the reaction vessel, and the entire mixture is hydrogenated at an appropriate hydrogen pressure (40-50 psi) for a period of time such that the decarboxylation reaction proceeds to completion. The reaction mixture is filtered over a pad of Celite®, and the solvent is removed under vacuum. Product E is isolated following purification by column chromatography.

The bis-TBDMS ketolactam E is then de-silylated using 2 N HCl in ACN and the product is isolated after a standard aqueous workup. The crude product is dissolved in a solvent, such as DCM, and allowed to react with triethylsilyl chloride and imidazole for several hours (monitored by TLC) at rt. Following aqueous workup, O-TES ketolactam F was isolated and purified on silica gel.

N-PNB, O-TES ketolactam G is produced by reacting ketolactam F with p-nitrobenzyl oxalylchloride in a suitable solvent (DCM, for example) in the presence of a base (DIEA, for example). The mixture is allowed to age for a period of time (and at an appropriate temperature) to effect a substantially complete reaction as monitored by an appropriate means (e.g., TLC or HPLC). Following workup in a usual manner, intermediate G was isolated.

To a solution of compound G is a suitable solvent was added triethylphosphite, and the mixture heated to reflux until complete by TLC. Following workup and purification in the appropriate manner, CPI was isolated.

Preparation of Gram-Negative Active Carbapenems

The 1-β-methylcarbapenem compounds possessing Gram-negative activity were synthesized using the methods described above and as illustrated in Scheme 2 below, unless otherwise noted. In general, a series of secondary or cyclic amines (H) were coupled to CPI in DMF using a combination of $Pd_2(dba)_3CHCl_3$ with $P(OEt)_3$ at rt to produce the coupled intermediate I. In some cases, 2,6-lutidine (Method B), TsOH (Method C), or DIEA (Method D) were added to drive the reaction to completion. The secondary or cyclic amines were either purchased from commercial sources or prepared by alkylation or substitution reactions of N-Boc-protected primary amines followed by cleavage of the Boc protecting group with TFA/water in DCM Removal of the TES protecting group in the series of intermediate I was accomplished as described in Method E.

Lastly, the PNB group(s) in intermediate J were removed by hydrogenation of the corresponding PNB esters using Methods F, G or H and the final products K were isolated.

SCHEME 2

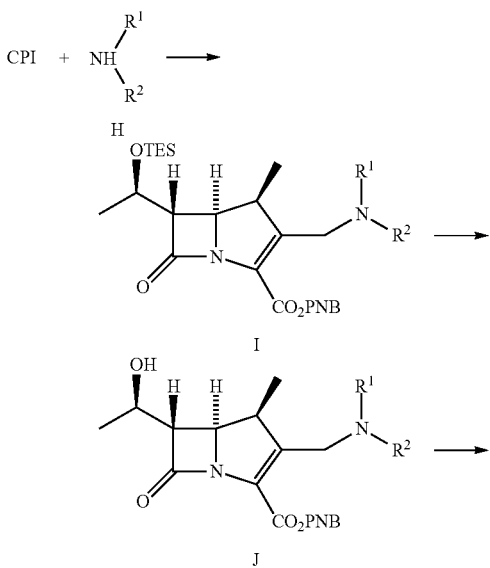

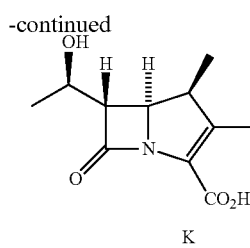

K

Step 1: General Procedure for the Palladium Coupling Reaction
Method A:

To an oven-dried round-bottomed flask was added anhydrous DMF. This was degassed at rt with two cycles of nitrogen/vacuum. Then $Pd_2(dba)_3CHCl_3$ and $P(OEt)_3$ were added. The solution was degassed with two nitrogen/vacuum cycles and aged for 20 min. Then neutralized amine dissolved in DMF and CPI were added and the resulting mixture was degassed with two nitrogen/vacuum cycles, and was allowed to stir at rt. After the consumption of CPI, solvent was removed in vacuo and the resulting residue was purified by $SiO_2$ column chromatography to provide the desired coupled product.
Method B:

To an oven-dried round-bottomed flask was added anhydrous DMF. This was degassed at rt with two cycles of nitrogen/vacuum. Then $Pd_2(dba)_3CHCl_3$ and $P(OEt)_3$ were added. The solution was degassed with two nitrogen/vacuum cycles and aged for 20 min. Then amine (TFA salt) and CPI were added, followed by 2,6-lutidine and the resulting mixture was degassed with two nitrogen/vacuum cycles, and was allowed to stir at rt. After the consumption of CPI, solvent was removed in vacuo and the resulting residue was purified by $SiO_2$ column chromatography to provide the desired coupled product and its de-TES product.
Method C:

To an oven-dried round-bottomed flask were added anhydrous DMF and 4 Å molecular sieves. This was degassed at rt with two cycles of nitrogen/vacuum. Then $Pd_2(dba)_3 CHCl_3$ and $P(OEt)_3$ were added. The solution was degassed with two nitrogen/vacuum cycles and aged for 20 min. Then amine and CPI were added, followed by TsOH and the resulting mixture was degassed with two nitrogen/vacuum cycles, and was allowed to stir at rt. After the consumption of CPI, solvent was removed in vacuo and the resulting residue was purified by $SiO_2$ column chromatography to provide the desired coupled product.
Method D:

To an oven-dried round-bottomed flask was added anhydrous toluene and THF (10 to 1 ratio). This was degassed at ice-bath with two cycles of nitrogen/vacuum. Then $Pd_2(dba)_3CHCl_3$ and $P(OEt)_3$ were added. The solution was degassed with two nitrogen/vacuum cycles and aged for 20 min. Then amine (TFA salt) and CPI were added, followed by DIEA and the resulting mixture was degassed with two nitrogen/vacuum cycles, and was allowed to stir at rt. After the consumption of CPI, solvent was removed in vacuo and the resulting residue was purified by $SiO_2$ column chromatography to provide the desired coupled product.
Step 2: General Procedure for the Removal of the TES Protecting Group
Method E:

To a round-bottomed flask charged with TES compound was added anhydrous THF and DMF under $N_2$. This was cooled to 0° C. and then AcOH was added followed by $Me_4NF.4H_2O$. After stirring overnight at 0° C., the crude mixture was quenched with DI water, followed by addition of saturated $NaHCO_3$ to adjust pH 7. Then this was extracted with EtOAc or a mixture of DCM and MeOH. The combined organic layer was dried ($Na_2SO_4$) and concentrated in vacuo. The crude material was purified by $SiO_2$ column chromatography to provide the desired OH product.
Step 3: General Procedure for the Removal of the PNB Protecting Group
Method F:

To a round-bottomed flask charged with OH compound was added THF, IPA, DI water and phosphate buffer (pH 6, 0.35 M). This was degassed and charged with $N_2$. Then Pt/C was added, followed by degassing and charging with $H_2$ ($H_2$ balloon). After stirring at 0° C. until the consumption of SM, cold DI water was added. The crude mixture was filtered through Celite and the filtrate was extracted with cold EtOAc twice. The separated aqueous layer was concentrated in vacuo. The crude material was purified by SP-207 resin with IPA and DI water as eluent. The column fractions were concentrated under reduced pressure at 6° C. to remove IPA and then lyophilized to afford the final product.
Method G:

To solution of OH compound in THF and phosphate buffer (pH 6.0, 0.35 M) was added Zinc dust at 10° C. and aged over until the consumption of SM. The mixture was diluted with cold DI water, filtered through on a pad of Celite, and the pad was washed with water and ethyl acetate. After separation, the aqueous layer was lyophilized and then purified on HP-20 or SP-207 resins with a solvent gradient system (from 100% water to 45% i-PrOH in water). The column fractions containing product were then concentrated under vacuum and lyophilized to afford the final product.
Method H:

It was dissolved OH compound in a glass vessel of parr-hydrogenation with a mixed solvent of THF/iso-propanol/DI-water/phosphate buffer (pH 6, 0.35 M). To the mixture was added Pt catalyst (5% or 10% on Carbon), degassed under vacuum, and charged with $H_2$ gas to 30 psi. After shaking about 30 min until no more pressure change, the reaction mixture was cooled down to zero degree and diluted with DI water. The mixture was filtered through on a pad of Celite and the pad was washed with water. After washing with ethyl acetate, the aqueous layer was lyophilized and then purified on SP-207 resin with a solvent gradient system (from 100% water to 45% i-PrOH in water). The column fractions containing product were then concentrated under vacuum and lyophilized to afford desired final carbapenem derivative.

Example 1

Synthesis of Compound 7

SCHEME 3

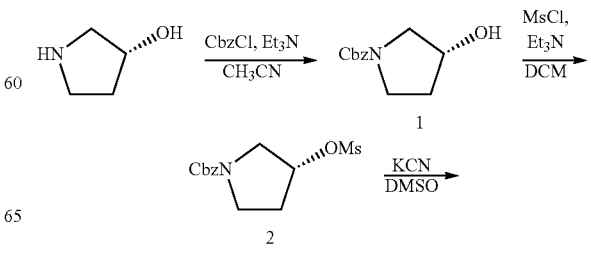

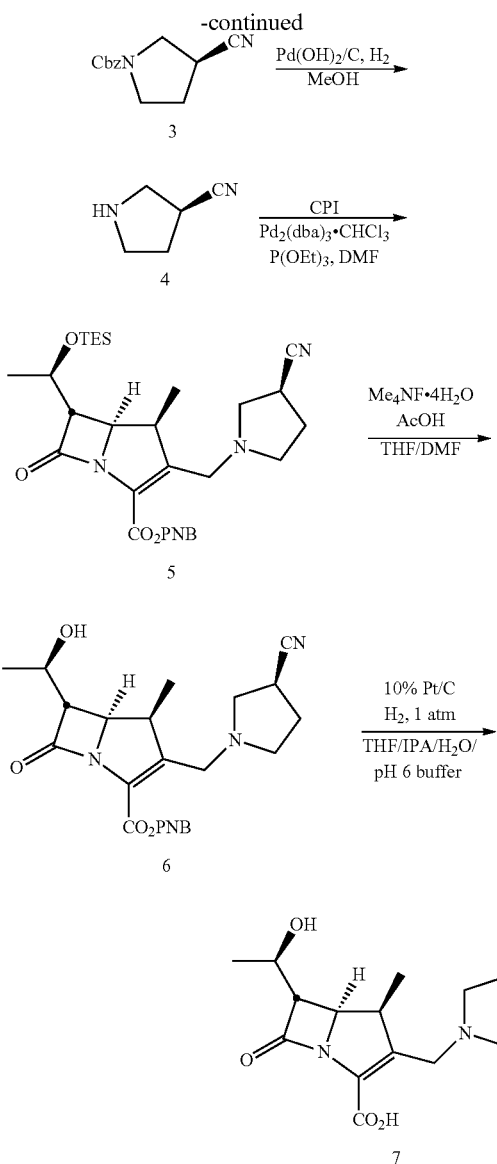

Step 1:

In a 500 mL oven-dried round-bottomed flask charged with (R)-3-pyrrolidinol (5.15 g, 58 mmol) was added dry CH₃CN (200 mL) to give a light brown solution under N₂. Then Et₃N (16.2 mL, 0.12 mol) was added dropwise. This was cooled to 0° C. and then CbzCl (48 mL, 83 mmol) was added dropwise. The temperature was allowed to warm up to rt gradually. After stirring for 24 h, solvent was removed in vacuo. The residue was treated with DCM and DI water. Organic layer was separated and the aqueous layer was extracted with DCM once. The combined organic layer was dried (Na₂SO₄) and concentrated in vacuo. The crude material was purified by SiO₂ column chromatography eluting with Hexane:EtOAc=1:1 to provide the desired alcohol 1 (12.6 g, 98%).

$^1$H NMR (CDCl₃, 400 MHz): δ 7.37-7.30 (m, 5H), 5.14 (s, 2H), 4.52-4.46 (m, 1H), 3.60-3.41 (m, 4H), 2.01-1.95 (m, 2H), 1.61 (br s, 1H).

Step 2:

In a 1 L oven-dried round-bottomed flask charged with alcohol 1 (12.6 g, 56.9 mmol) was added dry DCM (250 mL) to give a colorless solution under N₂. This was cooled to 0° C. and Et₃N (16 mL, 0.11 mol) was added. After 10 min, MsCl (6.5 mL, 84 mmol) was added dropwise. The temperature was allowed to warm up to rt gradually. After 14 h, DI water was added. The organic layer was separated, washed with DI water once, brine once, dried (Na₂SO₄) and concentrated in vacuo. The crude material was purified by SiO₂ column chromatography eluting from Hexane:EtOAc=2:1 to 1:1 to provide the desired mesylate 2 (14.7 g, 86%) as a yellow oil.

$^1$H NMR (CDCl₃, 400 MHz): δ 7.38-7.30 (m, 5H), 5.30-5.28 (m, 1H), 5.14 (d, J=2.8 Hz, 2H), 3.81-3.74 (m, 1H), 3.70-3.51 (m, 3H), 3.04 (s, 3H), 2.36-2.27 (m, 1H), 2.21-2.09 (m, 1H).

Step 3:

In a 150 mL oven-dried round-bottomed flask charged with mesylate 2 (4.12 g, 0.014 mol) was added dry DMSO (30 mL) under N₂. This was treated with KCN (1.94 g, 0.03 mol) at rt. The mixture was heated to 80° C. After 21 h, the flask was removed from oil-bath. After cooling to rt, sat NaHCO₃ was added, which was extracted with EtOAc (×4). The combined organic layer was dried (Na₂SO₄) and concentrated in vacuo. The crude material was purified by SiO₂ column chromatography eluting from Hexane:EtOAc=3:1 to 2:1 to provide the desired cyanate 3 (2.23 g, 70%) as a yellow oil.

$^1$H NMR (CDCl₃, 400 MHz): δ 7.37-7.30 (m, 5H), 5.14 (d, J=1.6 Hz, 2H), 3.78-3.47 (m, 4H), 3.15-3.07 (m, 1H), 2.27-2.16 (m, 2H).

Step 4:

To a 250 mL two-neck flask was added a MeOH solution of cyanate 3 (0.53 g, 2.3 mmol) under N₂. Then 20 mol % Pd(OH)₂/C (0.16 g, 0.23 mmol) was added, followed by vacuum and charging with H₂, this was repeated twice. After stirring for 1 h under hydrogen balloon, TLC showed no SM. Then the crude mixture was filtered through Celite and washed with MeOH. The filtrate was concentrated to give the crude amine 4 (0.13 g, 61%) as a light yellow oil which was used directly for the next step.

$^1$H NMR (CDCl₃, 400 MHz): δ 3.25-3.09 (m, 2H), 3.00-2.86 (m, 2H), 2.70-2.38 (m, 1H), 2.26-2.02 (m, 2H).

Step 5:

According to General Method A, CPI (1.54 g, 2.6 mmol), side chain 4 (0.25 g, 2.6 mmol), Pd₂(dba)₃CHCl₃ (0.14 g, 0.135 mmol) and P(OEt)₃ (0.15 mL, 0.86 mmol) in DMF (53 mL) were reacted for 17.5 h to afford the TES product 5 (0.39 g, 26%).

$^1$H NMR (CDCl₃, 400 MHz): δ 8.22 (d, J=8.8 Hz, 2H), 7.66 (d, J=9.2 Hz, 2H), 5.44 (d, J=13.6 Hz, 1H), 5.22 (d, J=14.0 Hz, 1H), 4.29-4.20 (m, 2H), 4.14-4.07 (m, 1H), 3.89 (d, J=14.4 Hz, 1H), 3.38 (d, J=14.8 Hz, 1H), 3.36-3.29 (m, 1H), 3.26-3.23 (m, 1H), 3.05-2.98 (m, 1H), 2.87-2.83 (m, 1H), 2.77-2.71 (m, 2H), 2.62-2.56 (m, 1H), 2.27-2.18 (m, 1H), 2.17-2.08 (m, 1H), 1.25 (d, J=7.0 Hz, 3H), 1.17 (d, J=7.2 Hz, 3H), 0.94 (t, J=8.0 Hz, 9H), 0.60 (q, J=8.0 Hz, 6H).

Step 6:

According to General Method E, TES compound 5 (390 mg), Me₄NF·4H₂O (0.17 g), AcOH (79 μL) in THF (15 mL) and DMF (5 mL) were reacted for 7.5 h to afford the desired OH product 6 (240 mg, 77%) as a white glassy solid.

$^1$H NMR (CDCl₃, 400 MHz): δ 8.24 (d, J=8.8 Hz, 2H), 7.67 (d, J=8.8 Hz, 2H), 5.49 (d, J=13.6 Hz, 1H), 5.22 (d, J=13.6 Hz, 1H), 4.30-4.26 (m, 1H), 4.24 (dd, J=10.0, 3.2 Hz, 1H), 3.89 (d, J=14.8 Hz, 1H), 3.40 (d, J=14.8 Hz, 1H), 3.40-3.37 (m, 1H), 3.30-3.28 (m, 1H), 3.05-2.98 (m, 2.87-2.83 (m, 1H), 2.78-2.69 (m, 2H), 2.61-2.55 (m, 1H), 2.27-2.09 (m, 2H), 1.72 (d, J=4.4 Hz, 1H), 1.36 (d, J=6.4 Hz, 3H), 1.19 (d, J=7.2 Hz, 3H).
Step 7:
According to General Method F, OH compound 6 (240 mg, 0.53 mmol), 10% Pt/C (280 mg) in IPA (10 mL), THF (20 mL), DI water (16 mL) and pH 6 buffer (7 mL) were reacted for 8 h to afford the desired final product 7 (18 mg, 11%).
$^1$H NMR (D$_2$O, 400 MHz): δ 4.21-4.13 (m, 2H), 3.72 (d, J=13.6 Hz, 1H), 3.45 (d, J=13.2 Hz, 1H), 3.37 (dd, J=6.4, 3.8 Hz, 1H), 3.26-3.14 (m, 2H), 2.99 (br s, 1H), 2.86 (br s, 2H), 2.67 (br s, 1H), 2.34-2.23 (m, 1H), 2.16-2.07 (m, 1H), 1.23 (d, J=6.4 Hz, 3H), 1.06 (d, J=7.2 Hz, 3H).

Example 2

Synthesis of Compound 12

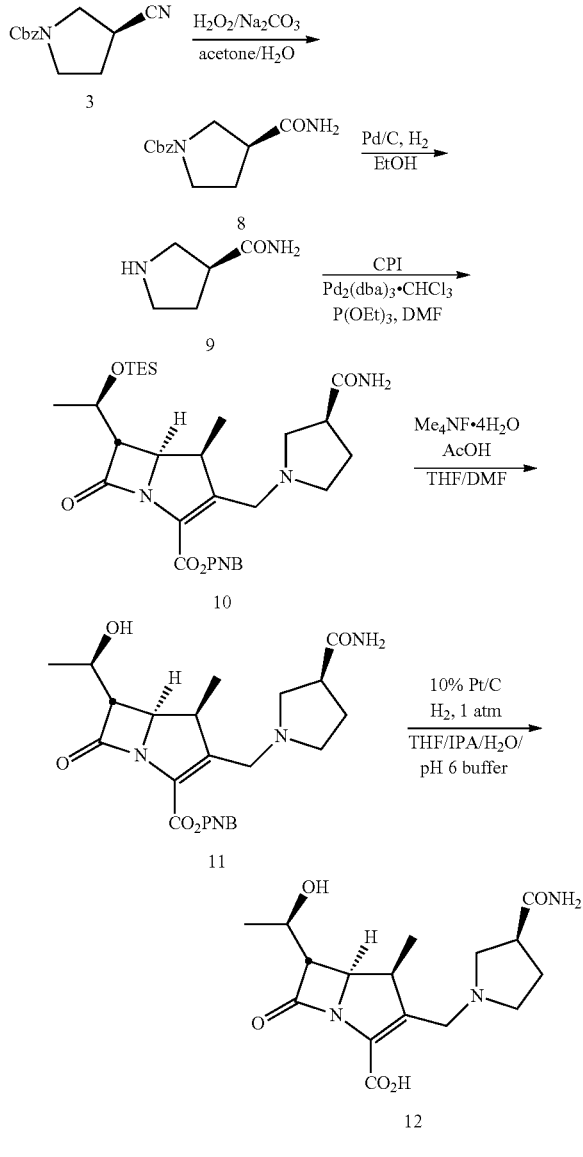

Step 1:
In a 150 mL round-bottomed flask charged with cyanate 3 (0.64 g, 2.78 mmol) was added acetone (15 mL), followed by DI water (4.9 mL) to give a colorless solution. Then 30% aqueous H$_2$O$_2$ (7.8 mL) was added, followed by Na$_2$CO$_3$ (0.97 g, 9.15 mmol). After stirring at rt for 20 h, the crude mixture was treated with EtOAc and brine. Organic layer was separated and the aqueous layer was extracted with EtOAc twice. The combined organic layer was dried (Na$_2$SO$_4$) and concentrated in vacuo. The crude material was purified by SiO$_2$ column chromatography eluting from Hexane:EtOAc=1:1 to EtOAc to provide the desired amide 8 (0.38 g, 55%) as a white solid.
$^1$H NMR (DMSO-d6, 400 MHz): δ 7.46 (br s, 1H), 7.39-7.31 (m, 5H), 6.97 (br s, 1H), 5.05 (s, 2H), 3.53-3.24 (m, 4H), 2.94-2.87 (m, 1H), 2.04-1.93 (m, 2H).
Step 2:
To a 100 mL two-neck flask was added an EtOH solution of amide 8 (0.38 g, 1.53 mmol). This was vacuumed and charged with N$_2$. Then 10 mol % Pd/C (82 mg) was added, followed by vacuum and charging with H$_2$ (hydrogen balloon), this was repeated twice. After stirring for 1.5 h, TLC showed a lot of SM. The crude mixture was transferred to a Parr hydrogenation flask and was hydrogenated at 50 psi. After 1 h, TLC showed no SM. Then the crude mixture was filtered through Celite and washed with EtOH. The filtrate was concentrated in vacuo to give the crude amine 9 (0.15 g, 84%) which was used directly for the next step.
$^1$H NMR (DMSO-d6, 400 MHz): δ 7.31 (br s, 1H), 6.76 (br s, 1H), 2.92-2.87 (m, 1H), 2.80-2.59 (m, 4H), 1.82-1.67 (m, 2H).
Step 3:
According to General Method A, CPI (0.78 g, 1.3 mmol), side chain 9 (0.15 g, 1.3 mmol), Pd$_2$(dba)$_3$CHCl$_3$ (69 mg, 0.067 mmol) and P(OEt)$_3$ (77 μL, 0.44 mmol) in DMF (27 mL) were reacted for 27 h to afford the desired TES product 10 (0.38 g, 49%) as a yellow oil.
$^1$H NMR (CDCl$_3$, 400 MHz): δ 8.21 (d, J=8.8 Hz, 2H), 7.66 (d, J=9.2 Hz, 2H), 6.40 (br s, 1H), 5.44 (d, J=14.0 Hz, 1H), 5.35 (br s, 1H), 5.22 (d, J=14.0 Hz, 1H), 4.27-4.20 (m, 2H), 3.91 (d, J=14.4 Hz, 1H), 3.36 (d, J=14.8 Hz, 1H), 3.30-3.23 (m, 2H), 2.90-2.83 (m, 3H), 2.50-2.40 (m, 2H), 2.22-2.13 (m, 1H), 2.07-1.98 (m, 1H), 1.25 (d, J=6.0 Hz, 3H), 1.18 (d, J=7.2 Hz, 3H), 0.94 (t, J=8.0 Hz, 9H), 0.60 (q, J=8.0 Hz, 6H).
Step 4:
According to General Method E, TES compound 10 (380 mg, 0.65 mmol), Me$_4$NF.4H$_2$O (0.16 g, 0.99 mmol), AcOH (74 μL, 1.29 mmol) in THF (14 mL) and DMF (4.5 mL) were reacted for 15 h to afford the desired OH product 11 (300 mg, 95%) as a white glassy solid.
$^1$H NMR (CDCl$_3$, 400 MHz): δ 8.23 (d, J=8.8 Hz, 2H), 7.66 (d, J=8.8 Hz, 2H), 6.35 (br s, 1H), 5.48 (d, J=13.6 Hz, 1H), 5.32 (br s, 1H), 5.21 (d, J=13.6 Hz, 1H), 4.30-4.22 (m, 2H), 3.91 (d, J=14.4 Hz, 1H), 3.37 (d, J=14.8 Hz, 1H), 3.34-3.27 (m, 2H), 2.95-2.82 (m, 3H), 2.49-2.39 (m, 2H), 2.22-2.13 (m, 1H), 2.07-1.98 (m, 1H), 1.36 (d, J=6.4 Hz, 3H), 1.19 (d, J=7.6 Hz, 3H).
Step 5:
According to General Method F, OH compound 11 (0.29 g, 0.62 mmol), 10% Pt/C (300 mg) in IPA (7.5 mL), THF (15 mL), DI water (15 mL) and pH 6 buffer (6 mL) were reacted for 8 h to afford the desired product 12 (70 mg, 34%).
$^1$H NMR (D$_2$O, 400 MHz): δ 4.22-4.16 (m, 2H), 4.00 (br s, 2H), 3.44-3.42 (m, 2H), 3.28-3.14 (m, 4H), 2.36 (br s, 1H), 2.16 (br s, 1H), 1.22 (d, J=6.0 Hz, 3H), 1.11 (d, J=7.2 Hz, 3H).

Example 3

Synthesis of Compound 19

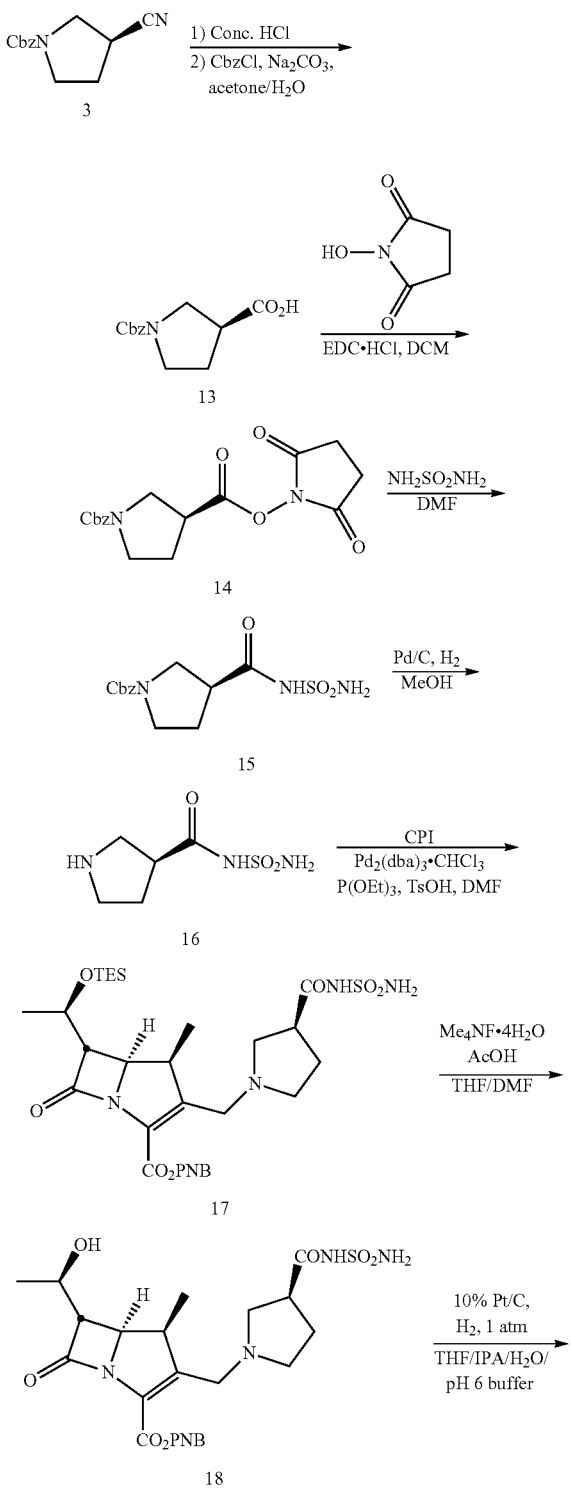

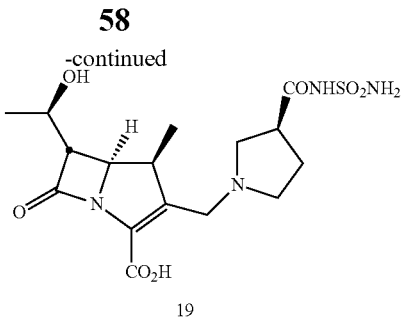

Step 1:

To a 100 mL round-bottomed flask charged with cyanate 3 (2 g, 8.7 mmol) was added concentrated HCl (20 mL). After refluxing for 4.5 h, solvent was removed in vacuo and was dried overnight by oil-pump. The crude material was re-dissolved in a mixture of acetone (20 mL) and DI water (20 mL). After cooling to 0° C., $Na_2CO_3$ (2.8 g, 26 mmol) was added, followed by dropwise addition of CbzCl (5.5 mL, 9.6 mmol). The reaction was allowed to warm up to rt gradually. After 7 h, solvent was removed in vacuo. Then DI water (8 mL) was added, which was extracted with Hexane: EtOAc=1:1 twice. The aqueous layer was acidified to pH 2 by adding concentrated HCl and 0.5 M $KHSO_4$. The aqueous layer was extracted with EtOAc (×4), dried ($Na_2SO_4$) and concentrated in vacuo to give the carboxylic acid 13 (1.46 g, 67%) which was used directly for the next step.

$^1$H NMR (CDCl$_3$, 400 MHz): δ 7.38-7.29 (m, 5H), 5.14 (d, J=2.8 Hz, 2H), 3.72-3.43 (m, 4H), 3.17-3.09 (m, 1H), 2.21-2.14 (m, 2H).

Step 2:

In a 150 mL round-bottomed flask charged with carboxylic acid 13 (1.48 g, 5.94 mmol) was added DCM (30 mL) to give a colorless solution under $N_2$. This was cooled to 0° C. and then N-hydroxysuccinamide (1.0 g, 8.7 mmol) and EDC.HCl (1.37 g, 7.15 mmol) were added.

This was allowed to warm up to rt gradually. After stirring for 18 h, solvent was removed in vacuo. The residue was treated with EtOAc and DI water. Organic layer was separated and washed with DI water (×3) and brine once, dried (MgSO$_4$) and concentrated in vacuo to give the desired product 14 (1.91 g, 93%) which was used directly for the next step.

$^1$H NMR (CDCl$_3$, 400 MHz): δ 7.37-7.29 (m, 5H), 5.14 (d, J=7.6 Hz, 2H), 3.82-3.49 (m, 4H), 3.44-3.37 (m, 1H), 2.86-2.82 (m, 4H), 2.37-2.30 (m, 2H).

Step 3:

In a 75 mL sealed tube was added a DMF (11 mL) solution of starting material 14 (1.9 g, 5.5 mmol), followed by sulfamide (1.07 g, 11 mmol). The mixture was heated to 90° C. for 16.5 h, after cooling to rt, the crude mixture was filtered and the solid was washed with DCM. The filtrate was concentrated in vacuo. The residue was treated with DCM and DI water. Aqueous layer was separated and extracted with DCM (×3). The combined organic layer was washed with brine once, dried (Na$_2$SO$_4$) and concentrated in vacuo. The crude material was purified by SiO$_2$ column chromatography eluting from 3% MeOH in DCM to 5% to 9% to provide the desired product 15 (0.74 g, 41%).

$^1$H NMR (CDCl$_3$, 400 MHz): δ 7.34-7.28 (m, 5H), 6.13 (br s, 1H), 6.00 (br s, 1H), 5.10 (d, J=2.0 Hz, 2H), 3.70-3.52 (m, 3H), 3.42-3.36 (m, 1H), 2.97-2.85 (m, 1H), 2.20-2.03 (m, 2H).

Step 4:

To a Parr hydrogenation flask was added a MeOH (23 mL) solution of starting material 15 (0.74 g, 2.26 mmol). This was vacuumed and charged with $H_2$. Then 0.24 g of Pd/C (10% on carbon) was added. This was hydrogenated at 50 psi for 2 h. Then the crude mixture was filtered through Celite and washed with MeOH. The filtrate was concentrated in vacuo to give the crude amine 16 (0.21 g, 48%) as a colorless oil which was used directly for the next step.

$^1$H NMR (CDCl$_3$, 400 MHz): δ 6.00 (br s, 1H), 5.19 (br s, 1H), 3.21-3.10 (m, 2H), 2.98-2.93 (m, 1H), 2.87-2.74 (m, 2H), 2.11-2.02 (m, 1H), 2.00-1.91 (m, 1H).

Step 5:

According to General Method C, CPI (0.59 g, 1.0 mmol), side chain 16 (0.21 g, 1.1 mmol), Pd$_2$(dba)$_3$CHCl$_3$ (52 mg, 0.05 mmol), P(OEt)$_3$ (59 μL, 0.33 mmol) and TsOH (97 mg, 0.5 mmol) in DMF (20 mL) were reacted for 16 h to afford the TES product 17 (0.53 g, 79%) as a light yellow glassy solid.

$^1$H NMR (CDCl$_3$, 400 MHz): δ 8.22 (d, J=8.8 Hz, 2H), 7.67 (d, J=8.8 Hz, 2H), 6.39 (bs, 1H), 5.45 (d, J=13.6 Hz, 1H), 5.22 (d, J=14.0 Hz, 1H), 5.13 (br s, 1H), 4.27-4.20 (m, 2H), 3.92 (d, J=14.4 Hz, 1H), 3.37 (d, J=14.0 Hz, 1H), 3.30-3.23 (m, 2H), 2.97-2.85 (m, 3H), 2.50-2.40 (m, 2H), 2.23-2.17 (m, 1H), 2.05-2.01 (m, 1H), 1.26 (d, J=6.0 Hz, 3H), 1.18 (d, J=7.6 Hz, 3H), 0.94 (t, J=8.0 Hz, 9H), 0.60 (q, J=8.0 Hz, 6H).

Step 6:

According to General Method E, TES compound 17 (0.52 g, 0.78 mmol), Me$_4$NF.4H$_2$O (0.19 g, 1.17 mmol), AcOH (89 μL, 1.55 mmol) in THF (17 mL) and DMF (5.6 mL) were reacted for 16.5 h to afford the desired OH product 18 (0.31 g, 72%) as an off-white glassy solid.

$^1$H NMR (CDCl$_3$, 400 MHz): δ 8.23 (d, J=8.8 Hz, 2H), 7.67 (d, J=8.8 Hz, 2H), 6.30 (br s, 1H), 5.49 (d, J=13.6 Hz, 1H), 5.22 (d, J=13.6 Hz, 1H), 5.14 (br s, 1H), 4.29-4.22 (m, 2H), 3.91 (d, J=14.4 Hz, 1H), 3.38 (d, J=14.8 Hz, 1H), 3.34-3.27 (m, 2H), 2.96-2.83 (m, 3H), 2.52-2.40 (m, 2H), 2.21-2.13 (m, 1H), 2.09-2.01 (m, 1H), 1.69 (bs, 1H), 1.36 (d, J=6.0 Hz, 3H), 1.20 (d, J=7.6 Hz, 3H).

Step 7:

According to General Method F, OH compound 18 (0.31 g, 0.56 mmol), 10% Pt/C (300 mg) in IPA (8 mL), THF (20 mL), DI water (22 mL) and pH=6 buffer (7 mL) were reacted for 5 h to afford the desired product 19 (95 mg, 41%).

$^1$H NMR (D$_2$O, 400 MHz): δ 4.26-4.22 (m, 2H), 4.15 (d, J=15.2 Hz, 1H), 4.09 (d, J=15.2 Hz, 1H), 3.50-3.38 (m, 7H), 3.28-3.20 (m, 1H), 2.50-2.42 (m, 1H), 2.27-2.18 (m, 1H), 1.28 (d, J=6.0 Hz, 3H), 1.18 (d, J=7.2 Hz, 3H).

Example 4

Synthesis of Compound 27

SCHEME 6

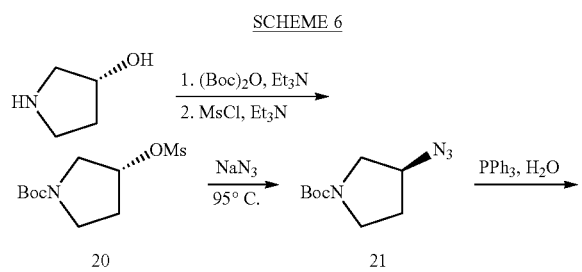

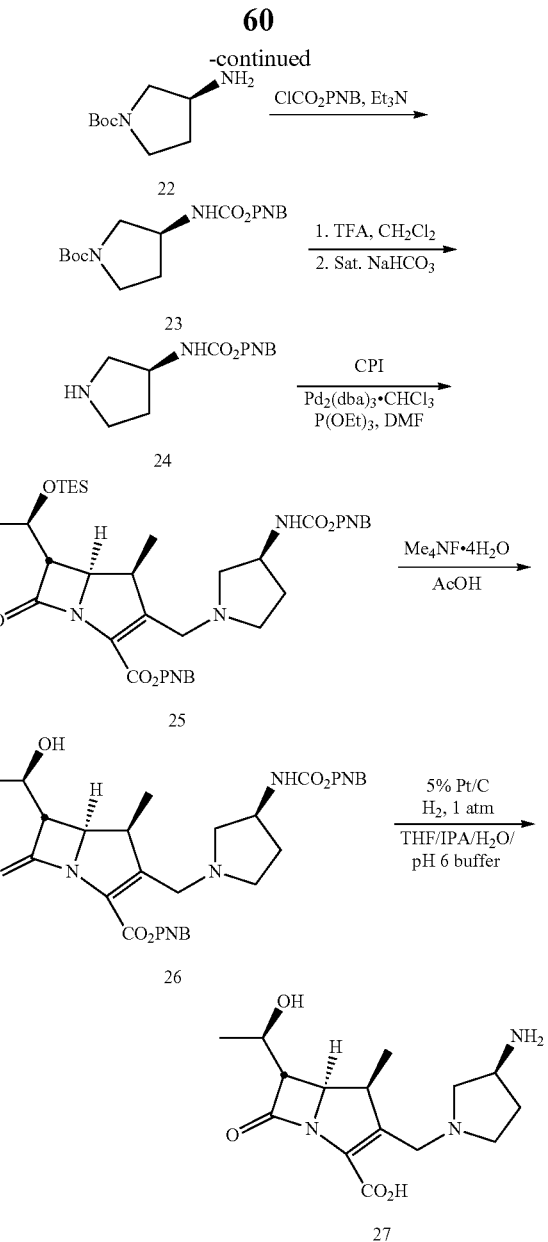

Step 1:

(R)-Pyrrolidinol (43.56 g, 0.5 mol) was dissolved in dry CH$_2$Cl$_2$ (1 L) and cooled with ice-bath to 0° C. To the solution was added Et$_3$N (139.4 mL, 1.0 mol), followed by dropwise addition of (Boc)$_2$O (130.95 g, 0.6 mol) in CH$_2$Cl$_2$ (160 mL), and keep stirring at 0° C. for 2 h. To the reaction mixture of Boc-protection was added more of Et$_3$N (139.4 mL, 1.0 mol), and followed by dropwise addition of MsCl (42.74 mL, 0.55 mol). After 2 h at 0° C., it was treated with H$_2$O (500 mL) for 10 min, separated, and the aqueous phase was extracted with CH$_2$Cl$_2$ (300 mL×2). The combined organic layers was washed with brine (500 mL), concentrated and purified by silica column chromatography to give N-Boc protected mesylate 20 as an oily product (123 g, 93%)

$^1$H NMR (CDCl$_3$, 400 MHz): δ 5.29-5.23 (m, 1H), 3.74-3.40 (m, 4H), 3.05 (s, 3H), 2.36-2.20 (m, 1H), 2.20-2.05 (m, 1H), 1.46 (s, 9H).

Step 2:

To a solution of mesylate 20 (19.8 g, 74.7 mmol) in DMF (250 mL) was added NaN$_3$ (7.28 g, 112 mmol), and aged at 95° C. for 20 h. After cooling down to rt, the mixture was concentrated under a reduced pressure, treated with H₂O (200 mL), and extracted with CH₂Cl₂ (100 mL×3). The combined organic layers was washed with brine (100 mL), concentrated and purified by silica column chromatography to afford the desired azide 21 (14.4 g, 90%).

¹H NMR (CDCl₃, 400 MHz): δ 4.16-4.10 (m, 1H), 3.54-3.32 (m, 4H), 2.12-1.94 (m, 2H), 1.45 (s, 9H).

Step 3:

A solution of azide 21 (14.4 g, 68.1 mmol) and H₂O (7.4 mL, 0.41 mol) in THF (200 mL) was cooled with ice-bath, then PPh₃ (35.73 g, 136.2 mmol) was added into the mixture as a solid in small portions. After the addition, the reaction mixture was slowly warmed up to rt and then submerged into an oil-bath preheated to 50° C. After 5 h, the mixture was concentrated in vacuo, treated with H₂O (100 mL) and CH₂Cl₂ (100 mL), and then acidified with 1N HCl to pH 2. The mixture was washed with DCM (100 mL×3), and the aqueous phase was then treated with 6 N NaOH to pH 10. After extraction with CH₂Cl₂ (100 mL×3), the organic layers were combined and washed with brine (100 mL), dried over Na₂SO₄, concentrated to give the desired amine 22 (12.16 g, 96%) which was used directly for the next step.

¹H NMR (CDCl₃, 400 MHz): δ 3.58-3.28 (m, 4H), 3.08-2.94 (m, 1H), 2.08-1.98 (m, 1H), 1.70-1.56 (m, 1H), 1.45 (s, 9H).

Step 4:

A solution of amine 22 (372 mg, 2 mmol) in dry CH₂Cl₂ (20 mL) was cooled to 0° C., then Et₃N (558 μL, 4 mmol) and ClCO₂PNB (517 mg, 2.4 mmol) were added into the solution. The reaction mixture was aged at 0° C. for 2 h, then it was treated with H₂O (20 mL) and separated, the aqueous layer was extracted with CH₂Cl₂ (20 mL×2). The combined organic layers was washed with brine (30 mL), concentrated and purified by silica gel column chromatography to give the desired carbamate 23 (0.35 g, 48%).

¹H NMR (CDCl₃, 400 MHz): δ 8.22 (d, J=8.8 Hz, 2H), 7.51 (d, J=8.8 Hz, 2H), 5.20 (s, 2H), 4.93 (d, J=6.4 Hz, 1H), 4.30-4.18 (m, 1H), 3.61 (dd, J=6.4, 11.6 Hz, 1H), 3.50-3.35 (m, 2H), 3.32-3.13 (m, 1H), 2.21-2.09 (m, 1H), 1.93-1.78 (m, 1H), 1.46 (s, 9H).

Step 5:

To a solution of TFA (1.1 mL, 14.4 mmol) in CH₂Cl₂ (10 mL) at 0° C. was added the carbamate 23 (0.35 g, 0.96 mmol). After overnight at 0° C., the mixture was concentrated, co-evaporated with hexane (5 mL×3) and then dried under high vacuum to give the de-Boc product as a TFA salt. The TFA salt was then neutralized with saturated NaHCO₃, extracted with 5% methanol in DCM to give compound 24 (0.21 g, 85%).

¹H NMR (CDCl₃, 400 MHz): δ 8.21 (d, J=8.4 Hz, 2H), 7.50 (d, J=8.4 Hz, 2H), 5.23 (s, 1H), 5.17 (s, 2H), 4.23-4.12 (m, 1H), 3.16-3.02 (m, 2H), 2.98-2.76 (m, 2H), 2.20-2.08 (m, 1H), 1.72-1.56 (m, 1H).

Step 6:

According to General Method A, CPI (0.25 g, 0.42 mmol), side chain 24 (0.11 g, 0.41 mmol), Pd₂(dba)₃CHCl₃ (22 mg, 0.021 mmol) and P(OEt)₃ (24 μL, 0.14 mmol) in DMF (9 mL) were reacted for 4 h to afford the desired TES product 25 (0.26 g, 85%) as a yellow oil.

¹H NMR (CDCl₃, 400 MHz): δ 8.22 (d, J=8.8 Hz, 4H), 7.66 (d, J=8.4 Hz, 2H), 7.50 (d, J=8.4 Hz, 2H), 5.44 (d, J=14.4 Hz, 1H), 5.23-5.17 (m, 3H), 5.02 (d, J=8.4 Hz, 1H), 4.27-4.18 (m, 3H), 3.85 (d, J=14.4 Hz, 1H), 3.34 (d, J=14.4 Hz, 1H), 3.31-3.23 (m, 2H), 2.79-2.74 (m, 1H), 2.64-2.60 (m, 1H), 2.54-2.51 (m, 1H), 2.48-2.42 (m, 1H), 2.32-2.21 (m, 1H), 1.25 (d, J=6.0 Hz, 3H), 1.17 (d, J=7.2 Hz, 3H), 0.94 (t, J=8.0 Hz, 9H), 0.60 (q, J=7.6 Hz, 6H).

Step 7:

According to General Method E, TES compound 25 (0.28 g, 0.38 mmol), Me₄NF.4H₂O (94 mg, 0.58 mmol), AcOH (43 μL, 0.75 mmol) in THF (8 mL) and DMF (2.7 mL) were reacted for 16 h to afford the desired OH product 26 (0.17 g, 71%).

¹H NMR (CDCl₃, 400 MHz): δ 8.22 (dd, J=8.8, 2.0 Hz, 4H), 7.66 (d, J=8.8 Hz, 2H), 7.50 (d, J=8.4 Hz, 2H), 5.48 (d, J=13.6 Hz, 1H), 5.21 (d, J=14.0 Hz, 1H), 5.18 (s, 2H), 5.02 (d, J=8.4 Hz, 1H), 4.27 (t, J=6.0 Hz, 1H), 4.22-4.19 (m, 2H), 3.84 (d, J=14.4 Hz, 1H), 3.36 (d, J=14.8 Hz, 1H), 3.36-3.26 (m, 2H), 2.82-2.77 (m, 1H), 2.58-2.52 (m, 2H), 2.45-2.39 (m, 1H), 2.32-2.21 (m, 1H), 1.36 (d, J=6.0 Hz, 3H), 1.18 (d, J=7.2 Hz, 3H).

Step 8:

According to General Method F, OH compound 26 (0.17 g, 0.27 mmol), 5% Pt/C (370 mg) in IPA (4 mL), THF (8 mL), DI water (8 mL) and phosphate buffer (pH 6, 3, mL) were reacted for 8 h to afford the desired final product 27 (12 mg, 14%).

¹H NMR (D₂O, 400 MHz): δ 4.27-4.22 (m, 2H), 3.84-3.80 (m, 2H), 3.63-3.60 (m, 1H), 3.45-3.43 (m, 1H), 3.26-3.18 (m, 2H), 2.91 (br s, 2H), 2.76 (br s, 1H), 2.39-2.30 (m, 1H), 1.89-1.84 (m, 1H), 1.28 (d, J=6.0 Hz, 3H), 1.13 (d, J=7.2 Hz, 3H).

Example 5

Synthesis of Compound 32

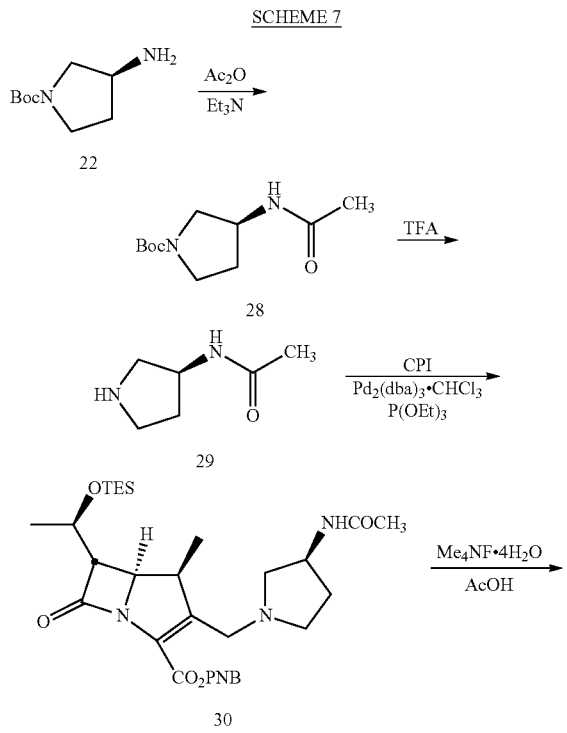

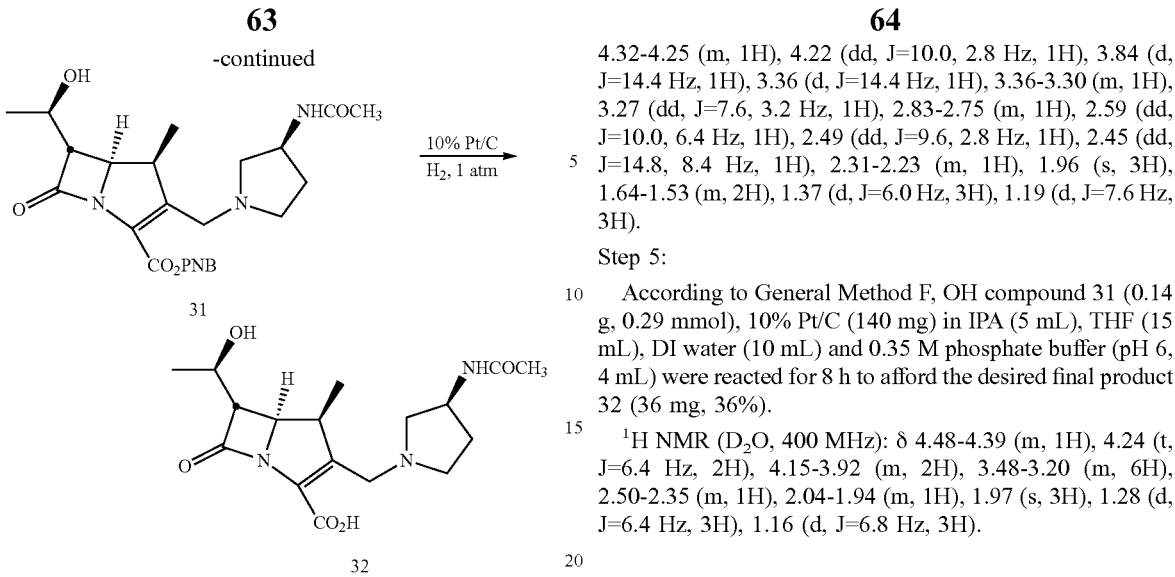

31

32

Step 1:

A solution of amine 22 (930 mg, 5 mmol) in dry CH$_2$Cl$_2$ (50 mL) was cooled to 0° C., then Et$_3$N (1.4 mL, 10 mmol) and acetic anhydride (567 μL, 6 mmol) were added into the solution, slowly warmed up to rt. After overnight, it was treated with H$_2$O (20 mL) and separated, the aqueous layer was extracted with CH$_2$Cl$_2$ twice (10 mL). The combined organic layers was washed with brine (30 mL), then concentrated and purified by silica gel column chromatography to give a desired amide 28 (0.69 g, 60%). $^1$H NMR (CDCl$_3$, 400 MHz): δ 6.36-6.06 (br s, 1H), 4.45-4.36 (m, 1H), 3.68-3.48 (m, 1H), 3.43-3.30 (m, 2H), 3.24-3.08 (m, 1H), 2.14-2.04 (m, 1H), 1.95 (s, 3H), 1.90-1.73 (m, 1H), 1.42 (s, 9H).

Step 2:

The similar procedure with side chain, 24, synthesis was used for de-protection of Boc group to afford the desired amine 29 in 86% yield.

$^1$H NMR (CDCl$_3$, 400 MHz): δ 4.54-4.46 (m, 1H), 3.48-3.38 (m, 1H), 3.32-3.17 (m, 3H), 2.25-2.14 (m, 1H), 2.06-1.96 (m, 1H), 1.92 (s, 3H).

Step 3:

According to General Method A, CPI (0.74 g, 1.25 mmol), side chain 29 (0.16 g, 1.25 mmol), Pd$_2$(dba)$_3$CHCl$_3$ (65 mg, 0.063 mmol) and P(OEt)$_3$ (72 μL, 0.41 mmol) in DMF (25 mL) were reacted for 24.5 h to afford the desired TES product 30 (0.27 g, 36%).

$^1$H NMR (CDCl$_3$, 400 MHz): δ 8.22 (dd, J=8.8, 1.6 Hz, 2H), 7.66 (d, J=8.8 Hz, 2H), 5.64 (d, J=8.0 Hz, 1H), 5.45 (d, J=14.0 Hz, 1H), 5.22 (d, J=14.0 Hz, 1H), 4.46-4.39 (m, 1H), 4.28-4.22 (m, 1H), 4.19 (dd, J=10.4, 3.2 Hz, 1H), 3.84 (d, J=14.4 Hz, 1H), 3.35 (d, J=14.4 Hz, 1H), 3.30-3.22 (m, 2H), 2.80-2.74 (m, 1H), 2.62-2.58 (m, 1H), 2.52-2.48 (m, 1H), 2.47-2.40 (m, 1H), 2.31-2.23 (m, 1H), 1.96 (s, 3H), 1.61-1.53 (m, 1H), 1.26 (d, J=6.4 Hz, 3H), 1.18 (d, J=7.2 Hz, 3H), 0.94 (t, J=8.0 Hz, 9H), 0.60 (q, J=7.6 Hz, 6H).

Step 4:

According to General Method E, TES compound 30 (0.27 g, 0.45 mmol), Me$_4$NF·4H$_2$O (0.11 g, 0.68 mmol), AcOH (51 μL, 0.89 mmol) in THF (10 mL) and DMF (2.5 mL) were reacted for 15.5 h to afford the desired OH product 31 (0.14 g, 64%).

$^1$H NMR (CDCl$_3$, 400 MHz): δ 8.23 (dd, J=8.8, 2.0 Hz, 2H), 7.66 (d, J=8.8 Hz, 2H), 5.65 (d, J=7.6 Hz, 1H), 5.49 (d, J=14.0 Hz, 1H), 5.22 (d, J=14.0 Hz, 1H), 4.47-4.38 (m, 1H), 4.32-4.25 (m, 1H), 4.22 (dd, J=10.0, 2.8 Hz, 1H), 3.84 (d, J=14.4 Hz, 1H), 3.36 (d, J=14.4 Hz, 1H), 3.36-3.30 (m, 1H), 3.27 (dd, J=7.6, 3.2 Hz, 1H), 2.83-2.75 (m, 1H), 2.59 (dd, J=10.0, 6.4 Hz, 1H), 2.49 (dd, J=9.6, 2.8 Hz, 1H), 2.45 (dd, J=14.8, 8.4 Hz, 1H), 2.31-2.23 (m, 1H), 1.96 (s, 3H), 1.64-1.53 (m, 2H), 1.37 (d, J=6.0 Hz, 3H), 1.19 (d, J=7.6 Hz, 3H).

Step 5:

According to General Method F, OH compound 31 (0.14 g, 0.29 mmol), 10% Pt/C (140 mg) in IPA (5 mL), THF (15 mL), DI water (10 mL) and 0.35 M phosphate buffer (pH 6, 4 mL) were reacted for 8 h to afford the desired final product 32 (36 mg, 36%).

$^1$H NMR (D$_2$O, 400 MHz): δ 4.48-4.39 (m, 1H), 4.24 (t, J=6.4 Hz, 2H), 4.15-3.92 (m, 2H), 3.48-3.20 (m, 6H), 2.50-2.35 (m, 1H), 2.04-1.94 (m, 1H), 1.97 (s, 3H), 1.28 (d, J=6.4 Hz, 3H), 1.16 (d, J=6.8 Hz, 3H).

Example 6

Synthesis of Compound 37

SCHEME 8

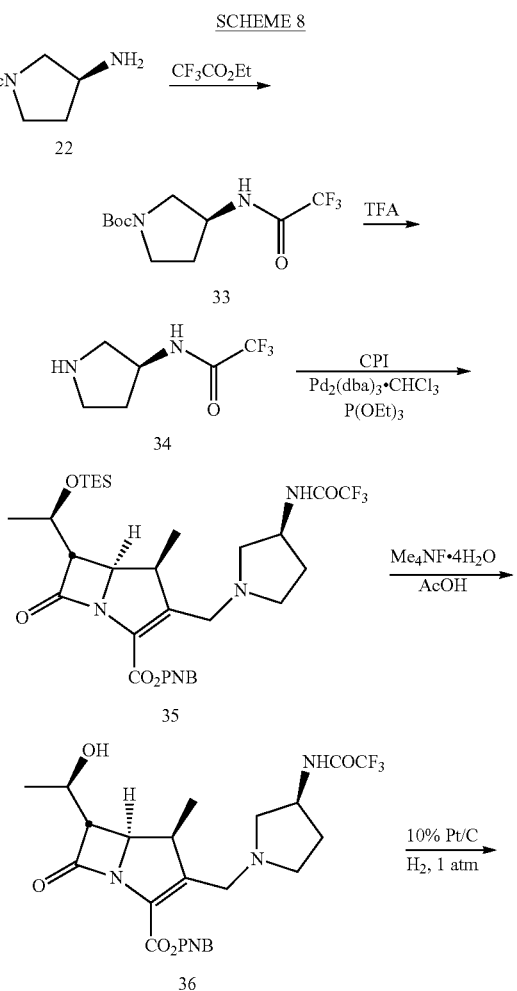

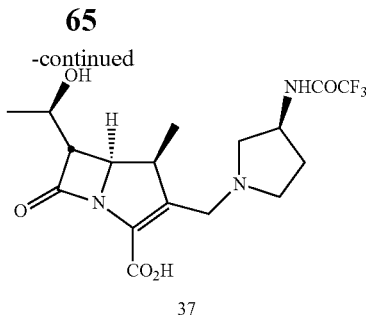

37

Step 1:

A solution of amine 22 (1.3 g, 7 mmol) in dry THF (70 mL) was cooled to 0° C., then ethyl trifluoroacetate (836 μL, 7 mmol) were added into the solution, aged at 0° C. overnight. After concentration, the residue was purified by silica gel column chromatography to give the desired amide 33 (0.28 g, 14%).

$^1$H NMR (CDCl$_3$, 400 MHz): δ 6.49 (d, J=6.0 Hz, 1H), 4.54-4.45 (m, 1H), 3.66 (dd, J=11.6, 6.0 Hz, 1H), 3.60-3.20 (m, 3H), 2.28-2.18 (m, 1H), 2.05-1.88 (m, 1H), 1.46 (s, 9H).

Step 2:

The similar procedure with side chain, 24, synthesis was used for de-protection of Boc group to afford the desired amine 34 in 83% yield.

$^1$H NMR (CDCl$_3$, 400 MHz): δ 4.69-4.61 (m, 1H), 3.54-3.45 (m, 1H), 3.43-3.33 (m, 1H), 3.30-3.22 (m, 1H), 2.38-2.27 (m, 1H), 2.19-2.09 (m, 1H).

Step 3:

According to General Method A, CPI (0.43 g, 0.73 mmol), side chain 34 (0.13 g, 0.73 mmol), Pd$_2$(dba)$_3$CHCl$_3$ (38 mg, 0.037 mmol) and P(OEt)$_3$ (42 μL, 0.24 mmol) in DMF (18 mL) were reacted for 42 h to afford the desired TES product 35 (0.3 g, 63%).

$^1$H NMR (CDCl$_3$, 400 MHz): δ 8.21 (dd, J=8.8, 2.0 Hz, 2H), 7.65 (d, J=9.2 Hz, 2H), 6.69 (br s, 1H), 5.44 (d, J=14.0 Hz, 1H), 5.21 (d, J=14.0 Hz, 1H), 4.48-4.42 (m, 1H), 4.27-4.21 (m, 1H), 4.18 (dd, J=10.4, 3.2 Hz, 1H), 3.87 (d, J=14.4 Hz, 1H), 3.36 (d, J=14.4 Hz, 1H), 3.27-3.19 (m, 2H), 2.91-2.86 (m, 1H), 2.64-2.61 (m, 1H), 2.57-2.53 (m, 1H), 2.47-2.41 (m, 1H), 2.36-2.27 (m, 1H), 1.74-1.66 (m, 1H), 1.26 (d, J=6.0 Hz, 3H), 1.17 (d, J=7.6 Hz, 3H), 0.93 (t, J=8.0 Hz, 9H), 0.59 (q, J=7.2 Hz, 6H).

Step 4:

According to General Method E, TES compound 35 (0.3 g, 0.46 mmol), Me$_4$NF·4H$_2$O (0.11 g, 0.68 mmole), AcOH (52 μL, 0.89 mmol) in THF (10 mL) and DMF (2.5 mL) were reacted for 15.5 h to afford the desired OH product 36 (0.14 g, 56%).

$^1$H NMR (CDCl$_3$, 400 MHz): δ 8.20 (dd, J=8.8, 1.6 Hz, 2H), 7.63 (d, J=8.8 Hz, 2H), 6.85 (br s, 1H), 5.45 (d, J=13.6 Hz, 1H), 5.18 (d, J=13.6 Hz, 1H), 4.48-4.41 (m, 1H), 4.28-4.21 (m, 2H), 3.87 (d, J=14.4 Hz, 1H), 3.35 (d, J=14.0 Hz, 1H), 3.32-3.25 (m, 2H), 2.93-2.87 (m, 1H), 2.65-2.53 (m, 3H), 2.44-2.36 (m, 1H), 2.36-2.27 (m, 1H), 1.74-1.66 (m, 1H), 1.32 (d, J=6.4 Hz, 3H), 1.17 (d, J=7.6 Hz, 3H).

Step 5:

According to General Method F, OH compound 36 (0.14 g, 0.26 mmol), 10% Pt/C (140 mg) in IPA (5 mL), THF (10 mL), DI water (10 mL) and 0.35 M phosphate buffer (pH 6, 4 mL) were reacted for 8 h to afford the desired final product 37 (26 mg, 25%).

$^1$H NMR (D$_2$O, 400 MHz): δ 4.57-4.48 (m, 1H), 4.25-4.20 (m, 2H), 3.95-3.82 (m, 2H), 3.51-3.40 (m, 3H), 3.27-3.18 (m, 2H), 2.50-2.35 (m, 1H), 2.10-1.93 (m, 1H), 1.28 (d, J=6.4 Hz, 3H), 1.14 (d, J=6.8 Hz, 3H).

Example 7

Synthesis of Compound 43

SCHEME 9

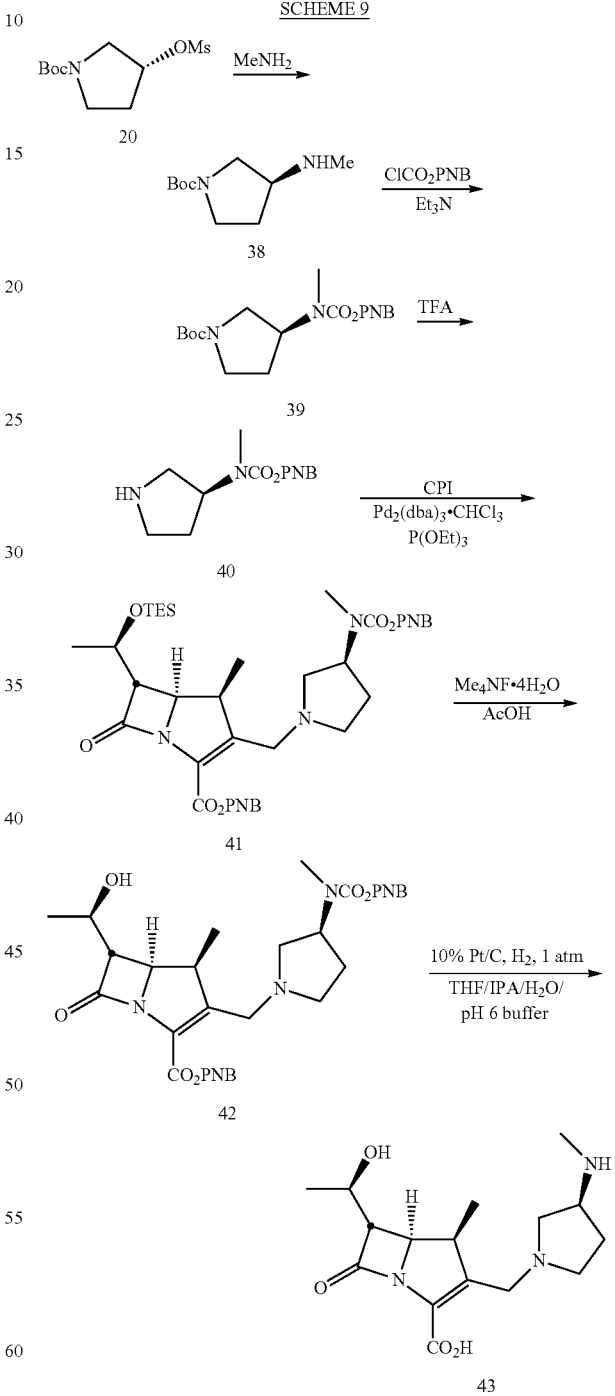

Step 1:

Mesylate 20 (1.33 g, 5 mmol) and 2 M solution of MeNH$_2$ in THF (25 mL, 50 mmol) were loaded to a sealed tube and aged at 95° C. for 60 h, then the reaction mixture was concentrated and the residue was purified by silica gel column chromatography to give the desired amine 38 (0.85 g, 85%).

$^1$H NMR (CDCl$_3$, 400 MHz): δ 3.58-3.28 (m, 3H), 3.26-3.02 (m, 2H), 2.43 (s, 3H), 2.08-1.98 (m, 1H), 1.76-1.63 (m, 1H), 1.45 (s, 9H).

Step 2:

The similar procedure with side chain, 23, synthesis was used for protection of nitrogen atom to afford the desired carbamate 39 in 93% yield.

$^1$H NMR (CDCl$_3$, 400 MHz): δ 8.22 (d, J=8.8 Hz, 2H), 7.51 (d, J=8.8 Hz, 2H), 5.23 (s, 2H), 4.90-4.60 (m, 1H), 3.62-3.44 (m, 2H), 3.38-3.12 (m, 2H), 2.88 (s, 3H), 2.10-1.90 (m, 2H), 1.45 (s, 9H).

Step 3:

The similar procedure with side chain, 24, synthesis was used for de-protection of Boc group to afford the desired amine 40 in 87% yield.

$^1$H NMR (DMSO-d$_6$, 400 MHz): δ 9.12-8.80 (br s, 2H), 8.24 (d, J=8.8 Hz, 2H), 7.64 (d, J=8.8 Hz, 2H), 5.24 (s, 2H), 4.82-4.65 (m, 1H), 3.42-3.48 (m, 2H), 3.22-3.08 (m, 2H), 2.85 (s, 3H), 2.17-2.06 (m, 1H), 2.03-1.91 (m, 1H).

Step 4:

According to General Method A, CPI (0.46 g, 0.78 mmol), side chain 40 (0.22 g, 0.78 mmol), Pd$_2$(dba)$_3$CHCl$_3$ (41 mg, 0.04 mmol) and P(OEt)$_3$ (45 µL, 0.26 mmol) in DMF (16 mL) were reacted for 24 h to afford the desired TES product 41 (0.33 g, 56%).

$^1$H NMR (CDCl$_3$, 400 MHz): δ 8.21 (dd, J=7.6, 2.0 Hz, 4H), 7.66 (d, J=8.8 Hz, 2H), 7.50 (d, J=8.8 Hz, 2H), 5.45 (d, J=14.0 Hz, 1H), 5.22 (d, J=14.0 Hz, 1H), 5.21 (s, 2H), 4.87 (br s, 1H), 4.28-4.22 (m, 1H), 4.18 (dd, J=10.0, 3.2 Hz, 1H), 3.77 (d, J=14.4 Hz, 1H), 3.37 (d, J=14.4 Hz, 1H), 3.31-3.23 (m, 2H), 2.91 (s, 3H), 2.83-2.78 (m, 1H), 2.64 (br s, 1H), 2.46 (t, J=8.4 Hz, 1H), 2.39 (dd, J=16.4, 8.0 Hz, 1H), 2.20-2.09 (m, 1H), 1.76 (br s, 1H), 1.26 (d, J=6.0 Hz, 3H), 1.18 (d, J=7.6 Hz, 3H), 0.94 (t, J=8.0 Hz, 9H), 0.59 (q, J=8.0 Hz, 6H).

Step 5:

According to General Method E, TES compound 41 (0.33 g, 0.44 mmol), Me$_4$NF.4H$_2$O (0.11 g, 0.68 mmol), AcOH (50 µL, 0.87 mmol) in THF (10 mL) and DMF (2.5 mL) were reacted for 16 h to afford the desired OH product 42 (0.18 g, 64%).

$^1$H NMR (CDCl$_3$, 400 MHz): δ 8.20 (d, J=8.4 Hz, 4H), 7.64 (d, J=8.4 Hz, 2H), 7.49 (d, J=8.0 Hz, 2H), 5.47 (d, J=13.6 Hz, 1H), 5.29 (s, 2H), 5.20 (d, J=13.6 Hz, 1H), 4.81 (br s, 1H), 4.27-4.20 (m, 2H), 3.76 (d, J=14.4 Hz, 1H), 3.36 (d, J=14.4 Hz, 1H), 3.32-3.27 (m, 2H), 2.91 (s, 3H), 2.83-2.79 (m, 1H), 2.45 (t, J=8.8 Hz, 1H), 2.38 (dd, J=16.4, 8.0 Hz, 1H), 2.13 (br s, 2H), 1.76 (br s, 1H), 1.34 (d, J=6.0 Hz, 3H), 1.19 (d, J=7.2 Hz, 3H).

Step 6:

According to General Method F, OH compound 42 (0.21 g, 0.33 mmol), 10% Pt/C (300 mg) in IPA (5 mL), THF (10 mL), DI water (10 mL) and 0.35 M phosphate buffer (pH 6, 4 mL) were reacted for 8 h to afford the desired final product 43 (29 mg, 27%).

$^1$H NMR (D$_2$O, 400 MHz): δ 4.25-4.18 (m, 2H), 3.74 (d, J=13.6 Hz, 1H), 3.68-3.61 (m, 1H), 3.48 (d, J=13.6 Hz, 1H), 3.43 (dd, J=6.0, 2.8 Hz, 2H), 3.25-3.18 (m, 1H), 3.12-3.06 (m, 1H), 2.81 (br s, 1H), 2.75-2.69 (m, 1H), 2.67-2.61 (m, 1H), 2.58 (s, 3H), 2.34-2.24 (m, 1H), 1.90-1.82 (m, 1H), 1.28 (d, J=6.0 Hz, 3H), 1.11 (d, J=7.6 Hz, 3H).

Example 8

Synthesis of Compound 46

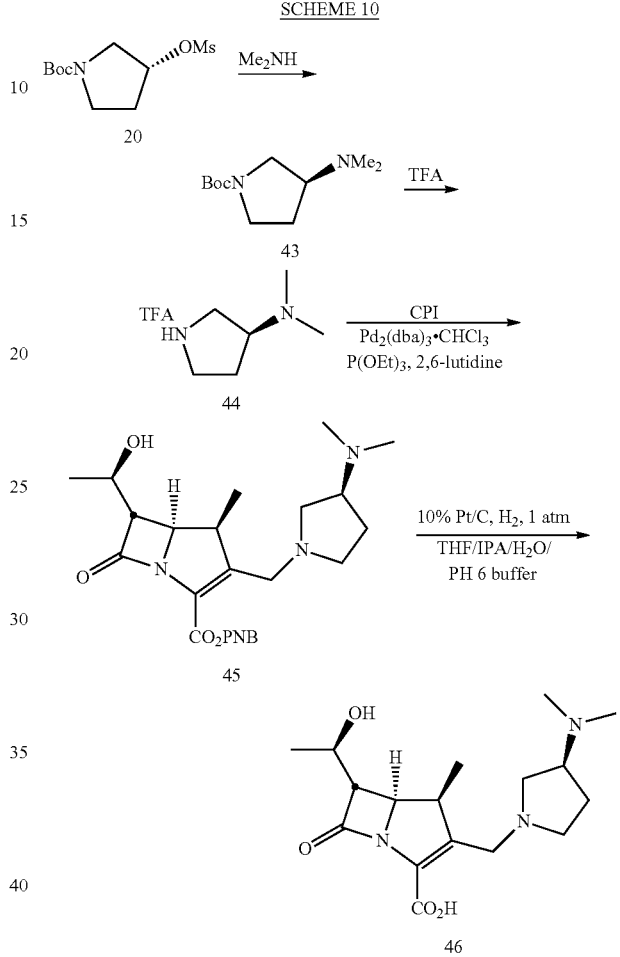

SCHEME 10

Step 1:

The similar procedure with side chain, 38, synthesis was used to afford the desired dimethyl amine 43 in 64% yield.

$^1$H NMR (CDCl$_3$, 400 MHz): δ 3.70-3.61 (m, 0.5H), 3.60-3.43 (m, 2H), 3.32-3.21 (m, 1H), 2.72-2.56 (m, 1.5H), 2.26 (s, 6H), 2.09-2.01 (m, 1H), 1.80-1.67 (m, 1H), 1.46 (s, 9H).

Step 2:

The similar procedure with side chain, 24, synthesis was used for de-protection of Boc group to afford the desired amine 44 as a TFA salt in quantitative yield.

$^1$H NMR (CDCl$_3$, 400 MHz): δ 4.10 (m, 1H), 3.82 (dd, J=12.4, 8.4 Hz, 1H), 3.62 (dd, J=12.4, 7.6 Hz, 1H), 3.52 (ddd, J=11.6, 8.4, 4.0 Hz, 1H), 3.40 (ddd, J=11.6, 10.0, 7.6 Hz, 1H), 2.88 (s, 6H), 2.54-2.44 (m, 1H), 2.35-2.23 (m, 1H).

Step 3:

According to General Method B, CPI (0.77 g, 1.3 mmol), side chain 44 (0.28 g, 1.3 mmol), Pd$_2$(dba)$_3$CHCl$_3$ (68 mg, 0.066 mmol), P(OEt)$_3$ (75 µL, 0.43 mmol) and 2,6-lutidine (0.3 mL, 2.58 mmol) in DMF (23 mL) were reacted for 74.5 h to afford the OH product 45 (0.17 g, 27%).

$^1$H NMR (CDCl$_3$, 400 MHz): δ 8.21 (d, J=8.8 Hz, 2H), 7.64 (d, J=8.8 Hz, 2H), 5.46 (d, J=13.6 Hz, 1H), 5.19 (d,

J=14.0 Hz, 1H), 4.29-4.21 (m, 2H), 3.89 (d, J=13.6 Hz, 1H), 3.68 (br s, 1H), 3.40 (d, J=14.4 Hz, 1H), 3.32 (t, J=8.4 Hz, 1H), 3.26 (dd, J=6.4, 2.8 Hz, 1H), 3.12 (d, J=8.8 Hz, 1H), 3.01-2.97 (m, 1H), 2.75 (s, 6H), 2.52 (br s, 2H), 2.25-2.18 (m, 1H), 2.12-2.03 (m, 1H), 1.33 (d, J=6.0 Hz, 3H), 1.15 (d, J=7.2 Hz, 3H).

Step 4:

According to General Method F, OH compound 45 (0.12 g, 0.25 mmol), 10% Pt/C (120 mg) in IPA (4 mL), THF (8 mL), DI water (8 mL) and 0.35 M phosphate buffer (pH=6, 3 mL) were reacted for 7 h to afford the desired final product 46 (20 mg, 23%).

$^1$H NMR (D$_2$O, 400 MHz): δ 4.28-4.14 (m, 2H), 3.86-3.75 (m, 1H), 3.62-3.43 (m, 3H), 3.17-3.11 (m, 2H), 3.02-2.75 (m, 3H), 2.55 (s, 6H), 2.33-2.20 (m, 1H), 2.01-1.86 (m, 1H), 1.26 (d, J=6.0 Hz, 3H), 1.11 (d, J=7.6 Hz, 3H).

Example 9

Synthesis of Compound 49

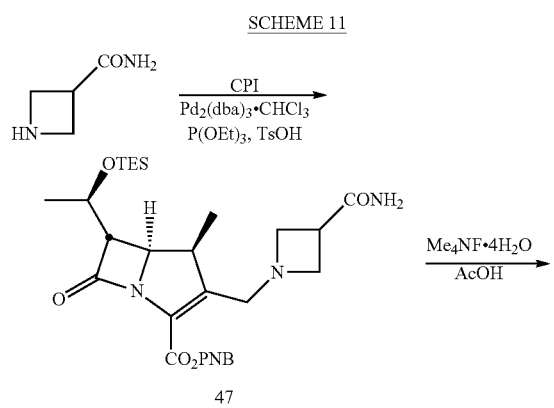
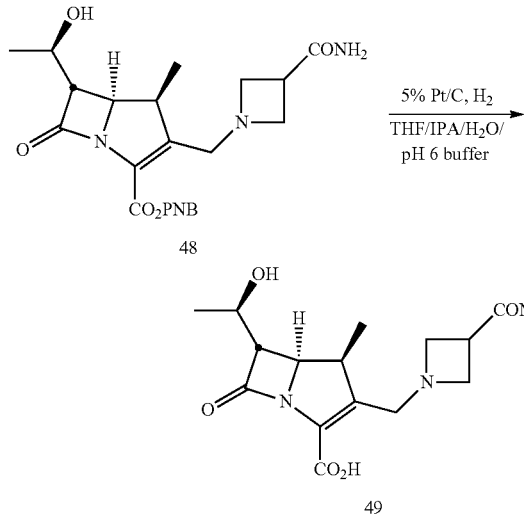

Step 1:

According to General Method C, CPI (3.48 g, 5.89 mmol), 3-azetidinecarboxylic amide (0.59 g, 5.89 mmol), Pd$_2$(dba)$_3$CHCl$_3$ (0.3 g, 0.29 mmol), P(OEt)$_3$ (0.34 mL, 1.95 mmol) and TsOH (0.56 g, 2.94 mmol) in DMF (100 mL) were reacted for 91 h to afford the desired TES product 47 (1.03 g, 31%).

$^1$H NMR (CDCl$_3$, 400 MHz): δ 8.22 (d, J=8.8 Hz, 2H), 7.67 (d, J=8.8 Hz, 2H), 6.04 (br s, 1H), 5.46 (d, J=13.6 Hz, 1H), 5.39 (br s, 1H), 5.23 (d, J=13.6 Hz, 1H), 4.27-4.21 (m, 1H), 4.18 (dd, J=10.4, 2.8 Hz, 1H), 3.98 (d, J=14.4 Hz, 1H), 3.50-3.36 (m, 4H), 3.27-3.19 (m, 3H), 3.13-3.06 (m, 1H), 1.25 (d, J=6.4 Hz, 3H), 1.16 (d, J=7.2 Hz, 3H), 0.94 (t, J=8.0 Hz, 9H), 0.59 (q, J=7.6 Hz, 6H).

Step 2:

According to General Method E, TES compound 47 (0.8 g, 1.4 mmol), Me$_4$NF.4H$_2$O (0.41 g, 2.5 mmol), AcOH (0.2 mL, 3.5 mmol) in THF (30 mL) and DMF (10 mL) were reacted for 15.5 h to afford the desired OH product 48 (0.35 g, 55%).

$^1$H NMR (CDCl$_3$, 400 MHz): δ 8.23 (d, J=8.8 Hz, 2H), 7.66 (d, J=8.8 Hz, 2H), 6.08 (br s, 1H), 5.55 (br s, 1H), 5.49 (d, J=13.6 Hz, 1H), 5.22 (d, J=13.6 Hz, 1H), 4.29-4.24 (m, 1H), 4.20 (dd, J=10.0, 3.2 Hz, 1H), 3.97 (d, J=14.4 Hz, 1H), 3.48-3.34 (m, 4H), 3.32-3.21 (m, 3H), 3.13-3.06 (m, 1H), 1.34 (d, J=6.4 Hz, 3H), 1.16 (d, J=7.2 Hz, 3H).

Step 3:

According to General Method F, OH compound 48 (0.35 g, 1.18 mmol), 5% Pt/C (300 mg) in IPA (10 mL), THF (20 mL), DI water (20 mL) and 0.35 M phosphate buffer (pH 6, 8 mL) were reacted for 23 h to afford the desired final product 49 (107 mg, 43%).

$^1$H NMR (D$_2$O, 400 MHz): δ 4.19-4.08 (m, 6H), 3.96 (br s, 1H), 3.95-3.85 (m, 1H), 3.58 (t, J=8.0 Hz, 1H), 3.40-3.39 (m, 1H), 3.16-3.08 (m, 1H), 1.21 (d, J=6.4 Hz, 3H), 1.09 (d, J=7.2 Hz, 3H).

Example 10

Synthesis of Compound 58

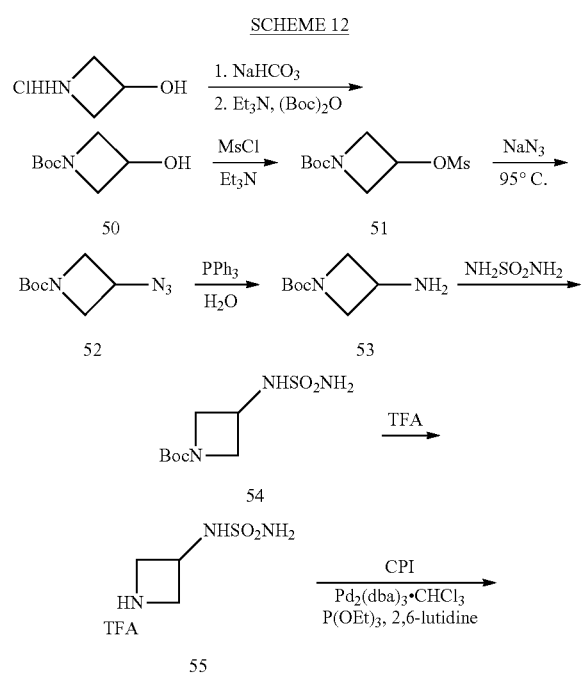

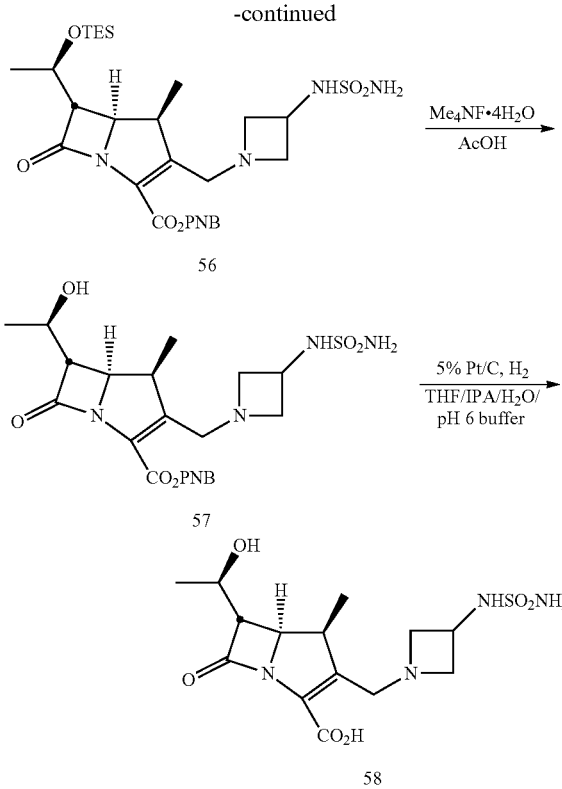

Step 1:

3-Hydroxyazetidine hydrochloride (10.96 g, 0.1 mol) was dissolved in H$_2$O (20 ml) and CH$_2$Cl$_2$ (200 mL) and cooled with ice-bath to 0° C. To the above solution was added NaHCO$_3$ (8.4 g, 0.1 mmol) slowly as a solid in small portions, aged at 0° C. for 10 min. After the addition, then Et$_3$N (20.9 mL, 0.15 mole) was added, followed by dropwise addition of solution of (Boc)$_2$O (24 g, 0.11 mol) in CH$_2$Cl$_2$ (30 mL), kept stirring at 0° C. for 1 h. The reaction mixture was treated with H$_2$O (200 mL), stirred for 10 min, and separated. The aqueous phase was extracted with CH$_2$Cl$_2$ (100 mL) twice, and the combined organic layers was washed with brine (200 mL), dried over anhydrous Na$_2$SO$_4$ and filtered. The filtrate was concentrated and dried over high vacuum to give the desired carbamate 50 as an oily product (crude 19.3 g, used for next step without further purification).

$^1$H NMR (CDCl$_3$, 400 MHz): δ 4.60-4.50 (m, 1H), 4.10 (ddd, J=9.6, 6.8, 0.8 Hz, 2H), 3.78 (ddd, J=9.6, 4.4, 0.8 Hz, 2H), 1.42 (s, 9H).

Step 2:

The carbamate 50 (4.36 g, 25.2 mmol) was dissolved in dry CH$_2$Cl$_2$ (200 mL) and cooled with ice-bath to 0° C. To the above solution was added Et$_3$N (7 mL, 50.34 mmol), followed by dropwise addition of MsCl (2.54 mL, 32.72 mmol). After 2 h at 0° C., the reaction mixture was treated with H$_2$O (100 mL), stirred for 10 min, and separated. The aqueous phase was extracted with CH$_2$Cl$_2$ (50 mL) twice, and the combined organic layers was washed with brine (100 mL), dried over anhydrous Na$_2$SO$_4$ and filtered. The filtrate was concentrated and dried over high vacuum to give the mesylate 51 as an oily product (crude 6.38 g, used for next step without further purification)

$^1$H NMR (CDCl$_3$, 400 MHz): δ 5.22-5.16 (m, 1H), 4.26 (ddd, J=10.4, 6.8, 1.2 Hz, 2H), 4.08 (ddd, J=10.4, 4.4, 1.2 Hz, 2H), 3.06 (s, 3H), 1.42 (s, 9H).

Step 3:

The similar procedure with side chain, 21, synthesis was used for azidation to afford the desired azide 52 in 92% yield.

$^1$H NMR (CDCl$_3$, 400 MHz): δ 4.24-4.16 (m, 3H), 3.91-3.86 (m, 2H), 1.43 (s, 9H).

Step 4:

The similar procedure with side chain, 22, synthesis was used for the reduction of azide to afford the desired amine 53 in quantitative yield.

$^1$H NMR (CDCl$_3$, 400 MHz): δ 4.13 (dd, J=8.4, 8.0 Hz, 2H), 3.80-3.70 (m, 1H), 3.56 (dd, J=9.2, 5.2 Hz, 2H), 1.42 (s, 9H).

Step 5:

To a 200 mL oven-dried round-bottomed flask charged with amine 53 (0.69 g, 4.0 mmol) was added dry 1,4-dioxane (40 mL) to give a colorless solution under N$_2$. Then sulfamide (0.77 g, 8.0 mmol) was added. This mixture was put into a pre-heated oil-bath (85° C.). After heating for 52 h, oil-bath was removed. The crude mixture was concentrated in vacuo. The residue was treated with DI water and DCM. The aqueous layer was separated and extracted with DCM (×5). The combined organic layer was dried (Na$_2$SO$_4$) and concentrated in vacuo. The crude material was purified by SiO$_2$ column chromatography eluting from 1% to 3% of MeOH in DCM to provide the desired product 54 (0.34 g, 34%).

$^1$H NMR (CDCl$_3$, 400 MHz): δ 5.73 (br s, 1H), 5.20 (br s, 1H), 5.16 (br s, 1H), 4.25-4.22 (m, 3H), 3.89 (d, J=4.8 Hz, 2H), 1.81 (br s, 1H), 1.43 (s, 9H).

Step 6:

The similar procedure with side chain, 24, synthesis was used for de-protection of Boc group to afford the desired amine 55 as a TFA salt in quantitative yield.

$^1$H NMR (DMSO-d6, 400 MHz): δ 8.74 (br s, 1H), 8.66 (br s, 1H), 7.52 (d, J=8.0 Hz, 1H), 6.85 (s, 2H), 4.25-4.16 (m, 1H), 4.08-4.07 (m, 2H), 3.90-3.87 (m, 2H).

Step 7:

According to General Method B, CPI (0.80 g, 1.35 mmol), side chain 55 (0.38 g, 1.35 mmol), Pd$_2$(dba)$_3$CHCl$_3$ (70 mg, 0.068 mmol), P(OEt)$_3$ (78 μL, 0.45 mmol) and 2,6-lutidine (0.31 mL, 2.67 mmol) in DMF (23 mL) were reacted for 73 h to afford the desired TES product 56 (0.24 g, 29%).

$^1$H NMR (CDCl$_3$, 400 MHz): δ 8.21 (d, J=8.8 Hz, 2H), 7.67 (d, J=8.8 Hz, 2H), 5.66 (br s, 1H), 5.44 (d, J=13.6 Hz, 1H), 5.29 (d, J=14.0 Hz, 1H), 4.73 (d, J=13.3 Hz, 1H), 4.40-4.01 (m, 10H), 3.79-3.62 (m, 3H), 3.35-3.28 (m, 2H), 1.22 (d, J=6.0 Hz, 3H), 1.14 (d, J=6.8 Hz, 3H), 0.92 (t, J=8.0 Hz, 9H), 0.58 (t, J=7.2 Hz, 6H).

Step 8:

According to General Method E, TES compound 56 (0.24 g, 0.38 mmol), Me$_4$NF.4H$_2$O (0.11 g, 0.68 mmol), AcOH (56 μL, 0.98 mmol) in THF (10 mL) and DMF (3 mL) were reacted for 18.5 h to afford the desired OH product 57 (0.17 g, 87%).

$^1$H NMR (CDCl$_3$, 400 MHz): δ 8.22 (d, J=8.4 Hz, 2H), 7.65 (d, J=8.4 Hz, 2H), 5.46 (d, J=13.6 Hz, 1H), 5.22 (d, J=13.6 Hz, 1H), 4.23-4.17 (m, 2H), 4.04-4.00 (m, 1H), 3.95 (d, J=14.4 Hz, 1H), 3.67-3.60 (m, 2H), 3.43 (d, J=14.8 Hz, 1H), 3.27-3.21 (m, 3H), 3.10 (t, J=6.8 Hz, 1H), 3.02 (t, J=6.8 Hz, 1H), 1.31 (d, J=6.0 Hz, 3H), 1.13 (d, J=7.2 Hz, 3H).

Step 9:

According to General Method F, OH compound 57 (0.17 g, 0.33 mmol), 5% Pt/C (270 mg) in IPA (4.5 mL), THF (9 mL), DI water (9 mL) and 0.35 M phosphate buffer (pH 6, 4 mL) were reacted for 8 h to afford the desired final product 58 (19 mg, 15%).

$^1$H NMR (D$_2$O, 400 MHz): δ 4.28 (br s, 2H), 4.21-4.13 (m, 4H), 3.87 (br s, 2H), 3.72-3.61 (m, 1H), 3.41-3.39 (m, 1H), 3.17-3.06 (m, 1H), 1.22 (d, J=6.0 Hz, 3H), 1.08 (d, J=7.2 Hz, 3H).

Example 11

Synthesis of Compound 64

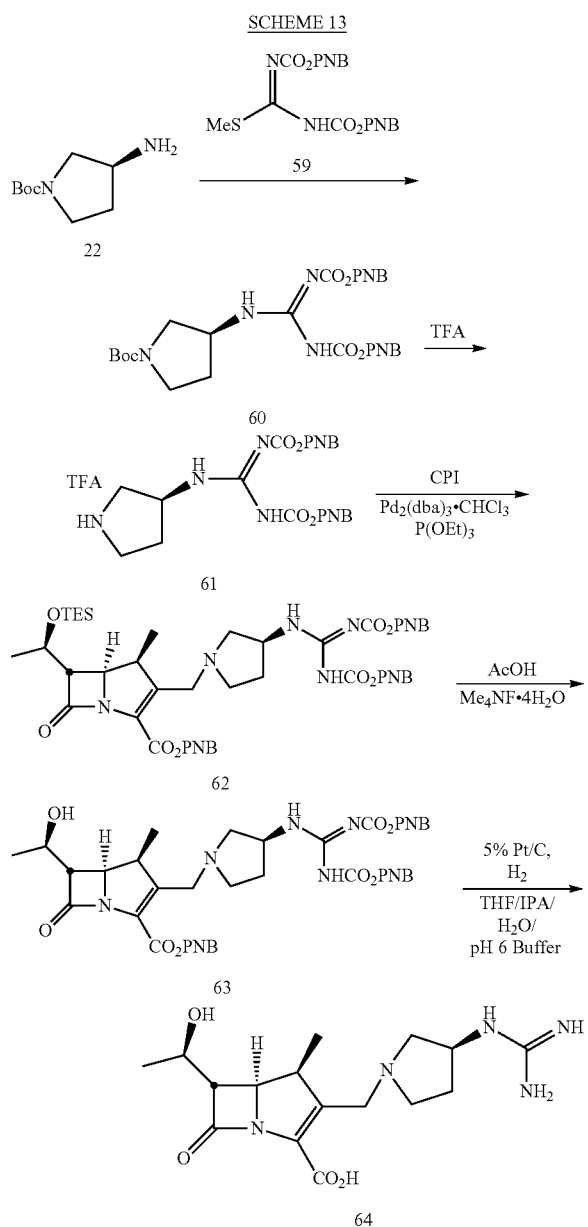

Step 1:

N,N'-bis(p-nitrobenzyloxycarbonyl)-S-methylisothiourea 59 was synthesized as described in U.S. Pat. Publication No. 2005-020519 and WO 2005/123069 A02. To a solution of compound 22 (18.7 g, 100 mmol) in THF (1 L) was added methylisothiourea 59 (39.05 g, 80 mmol), aged overnight at rt and then concentrated down to about 200 mL volume. The residue was triturated with MeOH (200 mL) and concentrated to about 200 mL volume again (repeated the trituration and concentration twice). The precipitated solid was filtered off, washed with MeOH (50 mL) twice and dried overnight at high vacuum to give the desired guanidine 60 (40 g, 80%) as a white solid.

$^1$H NMR (CDCl$_3$, 400 MHz): δ 11.76 (s, 1H), 8.42 (s, 1H), 8.23 (dd, J=15.2, 8.8 Hz, 4H), 7.54 (dd, J=8.8, 7.2 Hz, 4H), 5.27 (s, 2H), 5.22 (s, 2H), 4.72-4.60 (m, 1H), 3.72-3.60 (m, 1H), 3.52-3.38 (m, 2H), 3.26-3.16 (m, 1H), 2.26-2.16 (m, 1H), 1.95-1.84 (m, 1H), 1.45 (s, 9H).

Step 2:

To a solution of TFA (52.1 mL, 677 mmol) in CH$_2$Cl$_2$ (250 mL) at 0° C. was added the guanidine 60 (28.25 g, 45.13 mmol) as a solid, the reaction mixture was aged at 0° C. overnight, then it was concentrated and the residue was purified by silica gel column chromatography. The fractions are collected and concentrated and then triturated with EtOAc (50 mL) twice. The precipitated solid was collected by filtration, washed the cake with EtOAc (30 mL) twice and dried under high vacuum to afford the desired amine TFA salt 61 (20 g, 70%) as a white solid.

$^1$H NMR (CDCl$_3$, 400 MHz): δ 9.48-9.28 (br s, 1H), 9.20-9.00 (br s, 1H), 8.22 (dd, J=16.8, 8.8 Hz, 4H), 7.53 (dd, J=8.8, 6.4 Hz, 4H), 5.60-5.50 (br s, 2H), 5.30 (s, 2H), 5.21 (d, J=1.6 Hz, 2H), 4.61-4.53 (m, 1H), 3.80-3.68 (m, 1H), 3.66-3.54 (m, 2H), 3.44-3.30 (m, 1H), 2.62-2.48 (m, 1H), 2.32-2.18 (m, 1H).

Step 3 & 4:

In a degassed DMF (20 mL), Pd$_2$(dba)$_3$-CHCl$_3$(76 mg, 0.073 mmol) and triethyl phosphite (78 μL, 0.454 mmol) were added and mixed a catalyst until forming a deep yellow solution at rt. To the catalytic solution was added CPI (400 mg, 0.67 mmol), amine•TFA salt 61 (350 mg, 0.58 mmole) and 2,6-lutidine (200 μL, 2.96 mmol) and the resulting mixture was stirred 2 days at rt. After concentration under vacuum, the mixture was purified with 65% Ethyl acetate in Hexane to afford a 1:1 mixture of 62 & 63 (670 mg). The mixture was dissolved in THF and DMF (15 mL/5 mL) and followed by addition of acetic acid (200 μL, 3.5 mmol) and Me$_4$NF.4H$_2$O (200 mg, 1.2 mmol) at 4° C. After stirring overnight, the mixture was quenched with sat. NaHCO$_3$ and extracted with DCM twice. The extract was dried over anhydrous MgSO$_4$ and concentrated under a reduced pressure. The concentrate was purified by a silica column chromatography to afford the pure alcohol 63 (420 mg, 86% over two-steps).

$^1$H NMR (CDCl$_3$, 400 MHz): δ 11.73 (s, 1H), 8.54 (d, J=8.0 Hz, 1H), 8.2 (m, 6H), 7.63 (d, J=9.2 Hz, 2H), 7.52 (d, J=8.8 Hz, 2H), 7.51 (d, J=8.8 Hz, 2H), 5.46 (d, J=14.0 Hz, 1H), 5.23 (s, 2H), 5.19 (s, 2H), 5.18 (d, J=14.4 Hz, 1H) 4.60 (m, 1H), 4.21 (m, 2H), 3.82 (d, J=14.4 Hz, 2H), 3.37 (d, J=14.4 Hz, 1H), 3.36 (m, 1H), 3.26 (dd, J=5.8, 3.2 Hz, 1H), 2.57 (dd, J=9.6, 2.4 Hz, 2H), 2.50 (dd, J=9.6, 5.6 Hz, 1H), 2.40 (q, J=5.8 Hz, 1H), 2.26 (m, 1H), 1.90 (m, 1H), 1.69 (m, 1H), 1.30 (d, J=7.2 Hz, 3H), 1.18 (d, J=7.2 Hz, 3H)

Step 5:

According to General Method F, OH compound 63 (0.37 g, 0.438 mmol), 5% Pt/C (270 mg) in IPA (5 mL), THF (10 mL), and 0.35 M phosphate buffer (pH 6, 10 mL) were reacted for 7 h to afford the desired final product 64 (25 mg, 16.3%).

$^1$H NMR (D$_2$O, 400 MHz): δ 4.08 (m, 1H), 4.02 (dd, J=9.6, 2.8 Hz, 1H), 3.54 (d, J=13.2 Hz, 1H), 3.26 (dd, J=5.4, 2.8 Hz, 1H), 3.22 (d, J=13.6 Hz, 1H), 3.68 (dd, J=11.2, 7.2

Hz, 1H), 2.60 (m, 1H), 2.46 (m, 2H), 2.17 (m, 1H), 2.63 (m, 1H), 1.12 (d, J=6.0 Hz, 3H), 0.95 (d, J=7.6 Hz, 3H).

Example 12

Synthesis of Compound 67

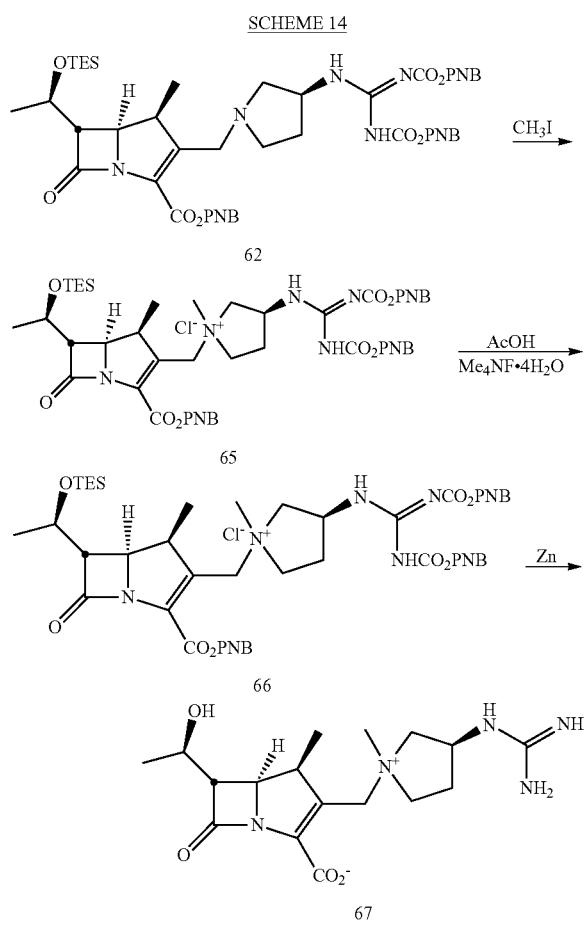

Step 1:

To a solution of amine 62 (1.39 g, 1.45 mmol) in THF (7 mL) was added 350 μL of MeI (5.62 mmol) at 0° C. and warmed up to rt. After 3 days it was concentrated and washed with a saturated brine to exchange the counter anion. The extract was dried over anhydrous MgSO$_4$ and concentrated under a reduced pressure. The concentrate was purified by a silica column chromatography with 10% MeOH in DCM to afford the quarternary amine salt 65 (1 g, 49% yield).

$^1$H NMR (Acetone-d6/CDCl$_3$, 400 MHz): δ 11.53 (s, 1H), 8.66 (d, J=6.8 Hz, 0.6 H), 8.49 (d, J=5.6 Hz, 0.4 H), 8.10 (m, 6H), 7.62-7.45 (m, 6H), 5.40-4.87 (m, 6 H) 4.36-1.91 (m, 13 H), 3.38 (s, 0.4 H), 3.36 (s, 0.6 H), 1.28-1.05 (m, 6H), 0.84 (m, 9H), 0.49 (q, J=8.0 Hz, 6H).

Step 2:

According to General Method E, TES compound 65 (1.0 g, 1.0 mmol), Me$_4$NF·4H$_2$O (0.25 g, 1.5 mmol), AcOH (200 μL, 3.5 mmol) in THF (15 mL) and DMF (5 mL) were reacted overnight to afford the desired OH product 66 (0.40 g, 45%).

$^1$H NMR (CD$_3$OD/CDCl$_3$, 400 MHz): δ 8.22-8.15 (m, 6H), 7.63 (dd, J=5.6, 4.4 Hz, 2 H), 7.53-7.47 (m, 4H), 5.43-5.05 (m, 6H), 4.95-4.80 (2 m, 1H), 4.43 (m, 2H), 4.20-3.95 (m, 3H), 3.75-3.45 (m, 2H), 3.34 (s, 1.8H), 3.26 (m, 1H), 3.12 (s, 1.2H), 2.88 (m, 2H), 2.68 (m, 1H), 2.45 (m, 1H), 1.29-1.19 (m, 6H).

Step 3:

According to General Method G, OH compound 66 (0.18 g, 0.201 mmol), Zinc dust (2.77 g) in THF (10 mL) and 0.35 M phosphate buffer (pH 6, 20 mL) were reacted for 7 h to afford the desired final product 67 (9 mg, 12.3%).

$^1$H NMR (D$_2$O, 400 MHz): δ 4.90 (m, 1H), 4.40 (br s, 1H), 4.15 (m, 2H), 3.78 (m, 1H), 3.60 (m, 2H), 3.45 (m, 1H), 3.35 (br s, 1H), 3.25-3.05 (m, 2H), 3.02 (s, 1.2H), 3.85 (s, 1.8H), 2.55 (m, 1H), 2.06 (m, 1H), 1.10 (m, 3H), 0.92 (m, 3H).

Example 13

Synthesis of Compound 72

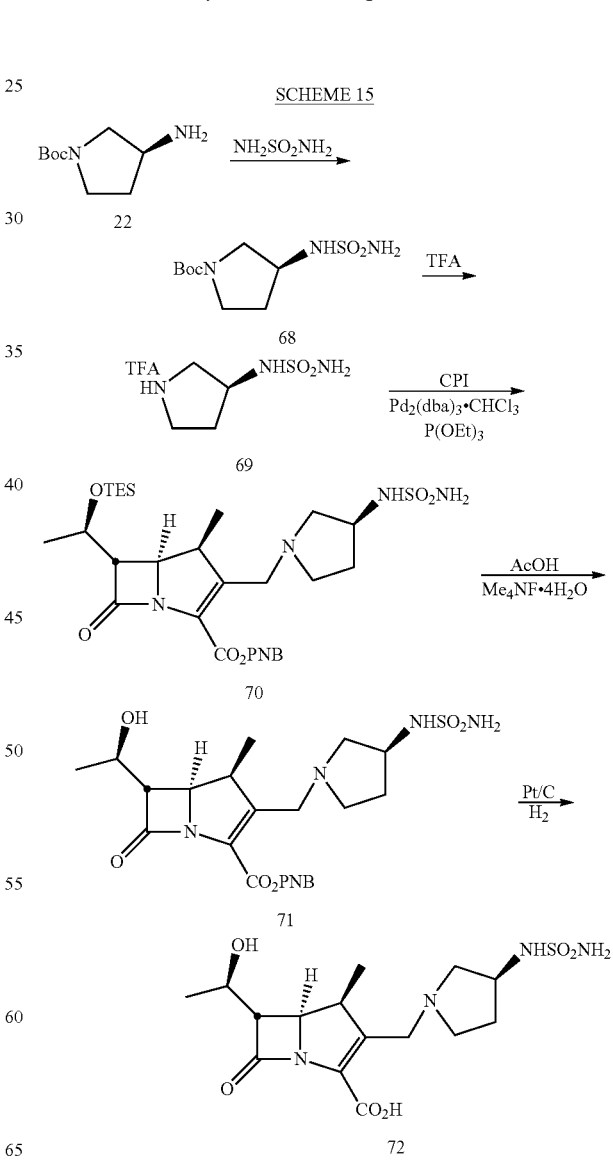

Step 1:

The similar procedure with side chain, 54, synthesis was used for the substitution reaction to afford the desired sulfonamide 68 in 24% yield.

$^1$H NMR (CDCl$_3$, 400 MHz): δ 5.29-4.94 (m, 3H), 4.05-3.95 (m, 1H), 3.70-3.55 (m, 1H), 3.53-3.25 (m, 3H), 2.22-2.11 (m, 1H), 2.05-1.90 (m, 1H), 1.45 (s, 9H).

Step 2:

The similar procedure with side chain, 24, synthesis was used for the deprotection of Boc group to afford a desired amine 69 as a TFA salt in quantitative yield.

$^1$H NMR (CD$_3$OD, 400 MHz): δ 4.14-4.09 (m, 1H), 3.46-3.32 (m, 4H), 2.34-2.23 (m, 1H), 2.14-2.05 (m, 1H).

Step 3 & 4:

The similar procedures (coupling & deprotection) with the synthesis of carbapenem 63 were used to afford the desired carbapenem 71 in 42% yield over two-steps.

$^1$H NMR (Acetone-D$_6$, 400 MHz,): δ 8.25 (d, J=8.8 Hz, 2H), 7.82 (d, J=9.2 Hz, 2H), 5.99 (br s, 1H), 5.55 (d, J=14.0 Hz, 1H), 5.34 (d, J=14.4 Hz, 1H), 4.28 (dd, J=8.4, 2.8 Hz, 1H), 4.15 (p, J=6.0 Hz, 1H), 4.05 (m, 1H), 3.66-3.48 (m, 2H), 3.34 (dd, J=6.4, 2.4 Hz, 1H), 3.27-2.63 (m, 6H), 2.32 (br s, 1H), 1.89 (br s, 1H), 1.26 (d, J=6.8 Hz, 3H), 1.21 (d, J=7.6 Hz, 3H).

Step 5:

According to General Method F, OH compound 71 (0.23 g, 0.438 mmol), 5% Pt/C (270 mg) in IPA (6 mL), THF (12 mL), and 0.35 M phosphate buffer (pH 6, 12 mL) were reacted for 7 h to afford the desired final product 72 (30 mg, 18%).

$^1$H NMR (D$_2$O in buffer at pH 7, 400 MHz): δ 4.10-3.91 (m, 4H), 3.59-3.40 (m, 6H), 3.07 (m, 1H), 2.35 (m, 1H), 1.97 (m, 1H), 1.11 (d, J=6.8 Hz, 3H), 1.01 (d, J=7.2 Hz, 3H).

Example 14

Synthesis of Compound 78

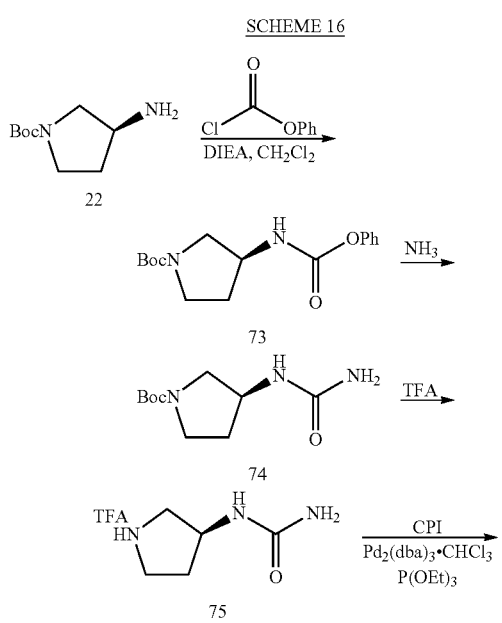

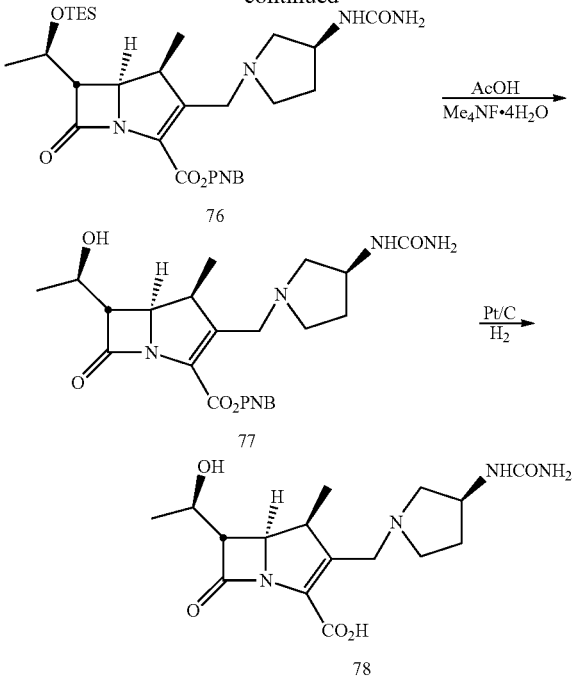

Step 1:

A solution of compound 22 (0.8 g, 4.3 mmol) in dry CH$_2$Cl$_2$ (40 mL) was cooled to 0° C., then DIEA (1.5 mL, 8.6 mmol) and ClCO$_2$Ph (630 μL, 5 mmol) were added into the solution, slowly warm up to rt. After overnight, the mixture was treated with H$_2$O (20 mL), separated and extracted with CH$_2$Cl$_2$ (20 mL) twice. The combined organic layers were washed with brine (30 mL), concentrated and purified by silica gel column chromatography to give the desired carbamate 73 (1.2 g, 91%).

$^1$H NMR (CDCl$_3$, 400 MHz): δ 7.36 (dd, J=8.0, 7.6 Hz, 2H), 7.21 (dd, J=7.6, 7.2 Hz, 1H), 7.12 (d, J=8.0 Hz, 2H), 5.13 (d, J=6.8 Hz, 1H), 4.36-4.27 (m, 1H), 3.65 (dd, J=11.6, 6.0 Hz, 1H), 3.55-3.39 (m, 2H), 3.37-3.22 (m, 1H), 2.26-2.14 (m, 1H), 2.03-1.85 (m, 1H), 1.47 (s, 9H).

Step 2:

The carbamate 73 (918 mg, 3 mmol) and 30 mL of NH$_3$ (7 M solution in MeOH, 210 mmol) were loaded to a sealed tube and aged at 90° C. for 60 h. After cooling down to rt, the reaction mixture was concentrated and the residue was triturated with EtOAc (10 mL×5). The precipitated solid was collected by filtration, washed the cake with CH$_2$Cl$_2$ (5 mL) twice and dried under high vacuum to give the desired urea 74 (0.547 g, 80%).

$^1$H NMR (DMSO-d$_6$, 400 MHz): δ 6.21 (s, 1H), 5.41 (s, 2H), 4.02-3.92 (m, 1H), 3.41-3.17 (m, 3H), 2.96 (dd, J=10.8, 4.4 Hz, 1H), 2.00-1.88 (m, 1H), 1.71-1.58 (m, 1H), 1.37 (s, 9H).

Step 3:

The similar procedure with side chain, 24, synthesis was used for deprotection of Boc group to afford the desired amine 75 as a TFA salt in quantitative yield.

$^1$H NMR (DMSO-d$_6$, 400 MHz): δ 8.79-8.73 (br, 2H), 6.38 (d, J=6.0 Hz, 1H), 5.80-5.40 (br s, 2H), 4.13-4.04 (m, 1H), 3.30-3.19 (m, 2H), 3.19-3.09 (m, 1H), 2.99-2.90 (m, 1H), 2.11-2.02 (m, 1H), 1.77-1.68 (m, 1H).

Step 4:

According to General Method A, CPI (0.59 g, 1.0 mmol), side chain 75 (0.243 g, 1.0 mmol), Pd$_2$(dba)$_3$CHCl$_3$ (76 mg, 0.073 mmol) and P(OEt)₃ (78 µL, 0.454 mmol) in DMF (20 mL) were reacted overnight to afford the desired TES product 76 (0.30 g, 50%).

¹H NMR (CDCl₃, 400 MHz): δ 8.21 (d, J=8.8 Hz, 2H), 7.65 (d, J=8.8 Hz, 2H), 5.43 (d, J=13.6 Hz, 1H), 5.21 (d, J=14.0 Hz, 1H), 4.78 (m, 1H), 4.28-4.11 (m, 3H), 3.86 (d, J=14.4 Hz, 1H), 3.34 (d, J=14.4 Hz, 1H), 3.31-3.22 (m, 2H), 2.82 (m, 1H), 2.58 (m, 2H), 2.41 (q, J=8.4 Hz, 1H), 2.24 (m, 1H), 1.66 (m, 1H), 1.24 (d, J=6.4 Hz, 3H), 1.15 (d, J=7.2 Hz, 3H), 0.93 (t, J=7.6 Hz, 9H), 0.59 (d, J=7.6 Hz, 6H)

Step 5:

The general method E was used for deprotection of TES group to afford the desired OH compound 77 in 85% yield.

¹H NMR (CD₃OD/CDCl₃, 400 MHz): δ 8.14 (d, J=6.8 Hz, 2 H), 7.57 (d, J=6.8 Hz, 2 H), 5.38 (d, J=14.0 Hz, 1 H), 5.16 (d, J=13.6 Hz, 1 H), 4.09 (m, 2H), 3.86 (d, J=13.2 Hz, 1 H), 3.31-3.21 (m, 3 H), 3.15 (dd, J=2.8, 7.2 Hz, 1 H), 2.53 (br s, 2H), 2.38 (m, 1H), 2.18 (m, 1H), 1.24 (d, J=6.8 Hz, 3 H), 1.08 (d, J=7.2 Hz, 3 H).

Step 6:

The general method F was used for deprotection of p-nitrobenzyloxycarbonyl group to afford the desired final product 78 in 33% yield.

¹H NMR (D₂O, 400 MHz): δ 4.16 (br s, 1H), 4.07 (m, 2H), 3.83 (br s, 2H), 3.31 (dd, J=6.0, 2.8 Hz, 1 H), 3.35-3.02 (m, 5H), 2.26 (br s, 1H), 1.81 (m, 1H), 1.12 (d, J=6.4 Hz, 3 H), 1.01 (d, J=7.2 Hz, 3 H).

Example 15

Synthesis of Compound 83

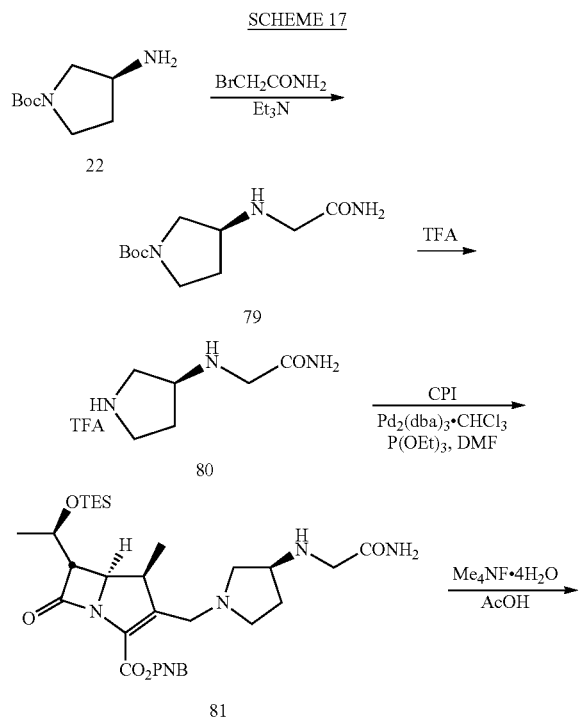

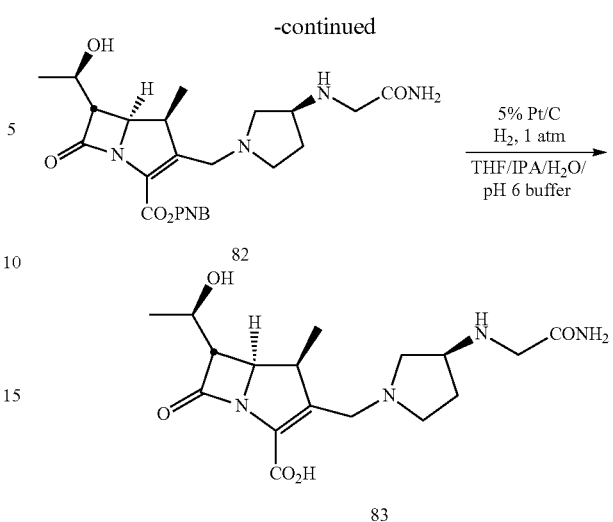

Step 1:

A solution of compound 22 (1.12 g, 6 mmol) in dry CH₃CN (20 mL) was cooled to 0° C., then Et₃N (1.4 mL, 10 mmol) was added to the reaction mixture followed by bromoacetamide (0.69 g, 5 mmol), and slowly warmed up to rt overnight. After removing the solvent, the residue was treated with H₂O (20 mL) and CH₂Cl₂ (50 mL) and separated. The aqueous layer was extracted by CH₂Cl₂ (20 mL) twice, and the combined organic layers was washed with brine (40 mL) and concentrated. The concentrate was purified by a silica gel column chromatography to give the desired mono-alkylation product 79 (0.55 g, 45%).

¹H NMR (DMSO-d₆, 400 MHz): δ 7.22 (s, 1H), 7.05 (s, 1H), 3.32-3.22 (m, 2H), 3.22-3.08 (m, 2H), 2.98-3.04 (m, 2H), 2.95 (dd, J=10.4, 4.4 Hz, 1H), 2.30-2.20 (m, 1H), 1.91-1.80 (m, 1H), 1.67-1.54 (m, 1H), 1.36 (s, 9H).

Step 2:

The similar procedure with side chain, 24, synthesis was used for de-protection of Boc group to afford the desired amine 80 as a TFA salt in quantitative yield.

¹H NMR (CDCl₃, 400 MHz): δ 3.34-3.28 (m, 1H), 3.26-3.18 (m, 2H), 3.10-3.00 (m, 3H), 2.95 (d, J=4.8 Hz, 2H), 2.18-1.86 (m, 1H), 1.74-1.65 (m, 1H).

Step 3:

According to General Method B, CPI (0.59 g, 1.0 mmol), side chain 80 (0.30 g, 2.1 mmol), Pd₂(dba)₃·CHCl₃ (76 mg, 0.073 mmol), P(OEt)₃ (78 µL, 0.454 mmol) and 2,6-lutidine (0.232 mL, 2.0 mmol) in DMF (20 mL) were reacted for 4 h to afford the desired coupling product 81 (0.30 g, 49%).

¹H NMR (CDCl₃, 400 MHz): δ 8.20 (d, J=8.8 Hz, 2H), 7.65 (d, J=8.8 Hz, 2H), 7.20 (br s, 1H), 6.00 (br s, 1H), 5.43 (d, J=14.0 Hz, 1H), 5.21 (d, J=14.4 Hz, 1H), 4.28-4.06 (m, 2H), 3.92 (m, 1H), 3.39-3.23 (m, 5H), 2.79 (br s, 1H), 2.58 (br s, 2H), 2.11 (m, 1H), 1.62 (br s, 1H), 1.23 (d, J=6.0 Hz, 3H), 1.15 (d, J=7.2 Hz, 3H), 0.92 (t, J=8.0 Hz, 9H), 0.56 (q, J=8.0 Hz, 6H).

Step 4:

The general method E was used for deprotection of TES group to afford the desired OH compound 82 in 49% yield.

¹H NMR (Acetone-d6/CDCl₃, 400 MHz): δ 8.08 (br s, 2H), 7.55 (d, J=6.4 Hz, 2 H), 7.14 (br s, 1H), 6.19 (br s, 1H), 5.36 (d, J=14.0 Hz, 1 H), 5.09 (d, J=13.6 Hz, 1 H), 4.10 (br s, 1H), 3.73 (d, J=13.2 Hz, 1H), 3.52 (br s, 1H), 3.27-3.05 (m, 6H), 2.69 (br s, 1H), 2.45 (br s, 1H), 2.32 (br s, 2H), 1.99 (br s, 1H), 1.47 (br s. 1H), 1.20 (br s, 3H), 1.03 (br s, 3H)

Step 5:

The general method F was used for deprotection of p-nitrobenzyloxycarbonyl group to afford the desired final product 83 in 16% yield.

$^1$H NMR (D$_2$O, 400 MHz): δ 4.04-4.00 (m, 2H), 3.88-3.71 (m, 3H), 3.36 (br s, 1H), 3.27 (dd, J=2.8, 6.0 Hz, 1 H), 3.13 (m, 1H), 3.10 (d, J=11.2 Hz, 2 H), 3.05-2.90 (m, 3H), 2.55 (br s, 1H), 1.68 (br s, 1H), 1.06 (d, J=6.4 Hz, 3 H), 0.95 (d, J=7.2 Hz, 3 H).

Example 16

Synthesis of Compound 84

SCHEME 18

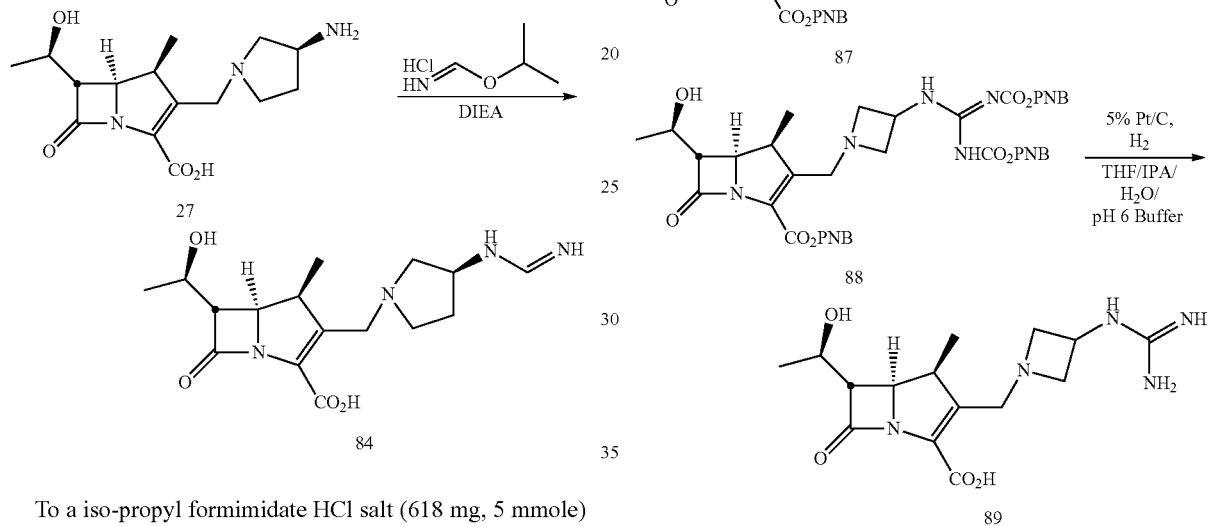

To a iso-propyl formimidate HCl salt (618 mg, 5 mmole) in iso-propanol (12 mL) was added 870 μL of DIEA (5 mmole) at −15° C. After 10 minute, it was transferred into a buffer solution (pH 7, 0.25 M, 25 mL) of amine 27 (100 mg, 0.32 mmole) at ice-bath and stirred over 3 hrs. The mixture was diluted cold DI water (25 mL) and washed with cold ethyl acetate twice. The aqueous layer was lyophilized and then purified on SP-207 resin with a solvent gradient system (from 100% water to 45% i-PrOH in water). The column fractions containing product were then concentrated under vacuum and lyophilized to afford the desired amidine carbapenem 84 (19 mg, 17.5%).

$^1$H NMR (D$_2$O, 400 MHz): δ 7.66 (s, 0.3H), 7.55 (s, 0.7H), 4.15 (m, 1H), 4.04-3.98 (m, 2H), 3.63-3.42 (m, 3H), 3.24 (m, 1H), 3.03-2.66 (m, 4H), 2.27 (m, 1H), 1.77 (m, 1H), 1.12 (d, J=6.4 Hz, 0.9 H), 1.07 (d, J=6.4 Hz, 2.1 H), 0.95 (d, J=7.2 Hz, 0.9 H), 0.92 (d, J=7.2 Hz, 2.1H).

Example 17

Synthesis of Compound 89

SCHEME 19

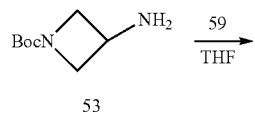

Step 1:

The similar procedure with side chain, 60, synthesis was used for guanidation to afford the desired guanidine 85 in 70% yield.

$^1$H NMR (CDCl$_3$, 400 MHz): δ 11.73 (s, 1H), 8.66 (d, J=6.4 Hz, 1H), 8.24 (dd, J=8.8, 17.2 Hz, 4H), 7.54 (dd, J=8.8, 6.4 Hz, 4H), 5.29 (s, 2H), 5.21 (s, 2H), 4.78-4.68 (m, 1H), 4.28 (dd, J=9.6, 7.6 Hz, 2H), 3.79 (dd, J=9.6, 5.2 Hz, 2H), 1.43 (s, 9H).

Step 2:

The similar procedure with side chain, 61, synthesis was used for de-protection of Boc group to afford the desired amine 86 as a TFA salt in 60% yield.

$^1$H NMR (DMSO-d$_6$, 400 MHz): δ 11.44 (s, 1H), 8.87 (d, J=6.4 Hz, 1H), 8.68-8.40 (m, 2H), 8.23 (dd, J=11.2, 8.8 Hz, 4H), 7.67 (d, J=8.8 Hz, 2H), 7.60 (d, J=8.8 Hz, 2H), 5.36 (s, 2H), 5.17 (s, 2H), 4.86-4.79 (m, 1H), 4.07 (d, J=7.6 Hz, 4H).

Step 3 & 4:

The similar procedures (coupling & deprotection) with the synthesis of carbapenem 63 were used to afford the desired carbapenem 87 in 44% yield over two-steps except that DIEA was used instead of lutidine base in THF/toluene mixed solvent (1/10 ratio).

$^1$H NMR (CDCl$_3$, 400 MHz): δ 11.67 (s, 1H), 8.48 (d, J=6.8 Hz, 1H), 8.21-8.13 (m, 6H), 7.60 (dt, J=6.8, 2.0 Hz, 2H), 7.49 (dt, J=5.2, 2.0 Hz, 2H), 7.46 (dt, J=4.8, 2.0 Hz, 2H), 5.43 (d, J=13.6 Hz, 1H), 5.23 (s, 2H), 5.16 (d, J=13.6

Hz, 1H), 5.14 (s, 2H), 4.56 (s, J=6.4 Hz, 1H), 4.20 (p, J=6.4 Hz, 1H), 4.12 (dd, J=10.0, 3.2 Hz, 1H), 3.83 (d, J=14.4 Hz, 1H), 3.58 (m, 1H), 3.22 (d, J=13.2 Hz, 1H), 3.21 (m, 1H), 2.95 (t, J=5.1 Hz, 1H), 2.83 (t, J=5.1 Hz, 1H), 1.28 (d, J=6.4 Hz, 3H), 1.09 (d, J=7.2 Hz, 3H).

Step 5:

According to General Method H, OH compound 87 (200 mg, 0.24 mmol), 5% Pt/C (280 mg) in IPA (5 mL), THF (12 mL), DI water (6 mL) and pH 6 buffer (4 mL) were reacted for 0.5 h afford the desired final product 88 (30 mg, 37%).

$^1$H NMR (D$_2$O, 400 MHz): δ 4.04-3.94 (m, 3H), 3.61 (d, J=12.8 Hz, 1H), 3.51 (t, J=7.6 Hz, 1H), 3.46 (t, J=7.6 Hz, 1H), 3.20 (dd, J=6.0, 2.8 Hz, 1H), 3.11 (d, J=13.2 Hz, 1H), 2.98 (t, J=7.2 Hz, 1H), 2.93 (dd, J=9.6, 7.2 Hz, 1H), 2.85 (d, J=7.2 Hz, 1H), 1.07 (d, J=6.4 Hz, 3H), (d, J=7.6 Hz, 3H).

Example 18

Synthesis of Compound 93

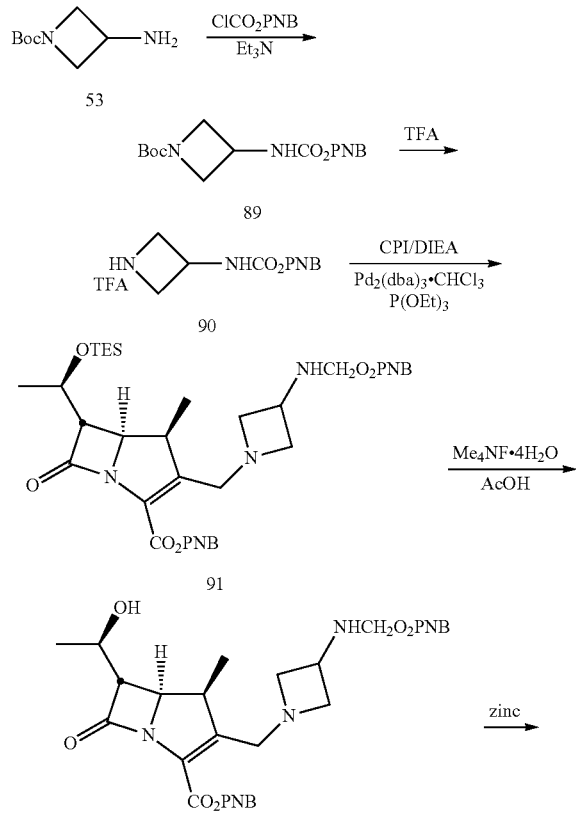

Step 1:

The similar procedure with side chain, 23, synthesis was used for protection of nitrogen atom to afford the desired carbamate 89 in 98% yield.

$^1$H NMR (CDCl$_3$, 400 MHz): δ 8.22 (d, J=8.8 Hz, 2H), 7.50 (d, J=8.4 Hz, 2H), 5.21 (br s, 1H), 5.19 (s, 2H), 4.47 (m, 1H), 4.24 (t, J=9.2 Hz, 2H), 3.76 (dd, J=8.8, 1.2 Hz, 2H), 1.45 (s, 9H).

Step 2:

The similar procedure with side chain, 61, synthesis was used for de-protection of Boc group to afford the desired amine 90 as a TFA salt in 92% yield.

$^1$H NMR (DMSO-d6/CDCl$_3$, 400 MHz): δ 10.25 (br s, 1H), 9.35 (br s, 1H), 8.03 (d, J=8.8 Hz, 2H), 7.76 (d, J=8.8 Hz, 1H), 7.35 (d, J=8.8 Hz, 2H), 5.02 (s, 2H), 4.53 (s, J=8.4 Hz, 1H), 4.07 (t, J=10.8 Hz, 2H), 3.99 (d, J=10.8 Hz, 2H).

Step 3:

According to the general coupling method D, the desired TES compound 91 was synthesized in 67% yield.

$^1$H NMR (CDCl$_3$, 400 MHz): δ 8.21 (d, J=8.8 Hz, 2H), 8.20 (d, J=8.8 Hz, 2H), 7.66 (d, J=8.8 Hz, 2H), 7.49 (d, J=8.4 Hz, 2H), 5.45 (d, J=13.2 Hz, 1H), 5.22 (br s, 1H), 5.21 (d, J=13.6 Hz, 1H), 5.17 (s, 2H), 4.34 (s, J=7.6 Hz, 1H), 4.23 (p, J=6.0 Hz, 1H), 4.16 (dd, J=10.4, 3.2 Hz, 1H), 3.92 (d, J=10.4 Hz, 1H), 3.67 (t, J=7.2 Hz, 1H), 3.63 (t, J=7.2 Hz, 1H), 3.27-3.21 (m, 3H), 2.99 (t, J=6.4 Hz, 1H), 2.88 (t, J=6.4 Hz, 1H), 1.25 (d, J=6.0 Hz, 3H), 1.13 (d, J=7.6 Hz, 3H), 0.93 (t, J=8.0 Hz, 9H), 0.58 (q, J=8.0 Hz, 6H).

Step 4:

According to the general procedure for the removal of TES group (Method E), the desired OH compound 92 was synthesized in 81% yield.

$^1$H NMR (CDCl$_3$, 400 MHz): δ 8.21 (d, J=8.8 Hz, 2H), 8.20 (d, J=8.8 Hz, 2H), 7.65 (d, J=8.4 Hz, 2H), 7.48 (d, J=8.4 Hz, 2H), 5.47 (d, J=13.6 Hz, 1H), 5.27 (br s, 1H), 5.19 (d, J=14.0 Hz, 1H), 5.17 (s, 2H), 4.33 (s, J=6.8 Hz, 1H), 4.25 (p, J=6.4 Hz, 1H), 4.19 (dd, J=6.0, 3.2 Hz, 1H), 3.93 (d, J=14.0 Hz, 1H), 3.67-3.60 (m, 2H), 3.32-3.24 (m, 3H), 3.01 (t, J=6.8 Hz, 1H), 2.92 (t, J=6.8 Hz, 1H), 2.31 (br s, 1H), 1.33 (d, J=6.4 Hz, 3H), 1.14 (d, J=7.2 Hz, 3H).

Step 5:

According to the general procedure for the removal of PNB groups (Method G), the desired final product 92 was synthesized in 22% yield.

$^1$H NMR (D$_2$O, 400 MHz): δ 4.04-3.95 (m, 2H), 3.87-3.76 (m, 3H), 3.67 (s, J=5.4 Hz, 1H), 3.52 (d, J=12.8 Hz, 1H), 3.37 (t, J=7.6 Hz, 1H), 3.25 (m, 1H), 3.22 (dd, J=6.0, 2.8 Hz, 1H), 2.93 (m, 1H), 1.05 (d, J=6.4 Hz, 3H), 0.89 (d, J=7.6 Hz, 3H).

Example 19

Synthesis of Compound 99

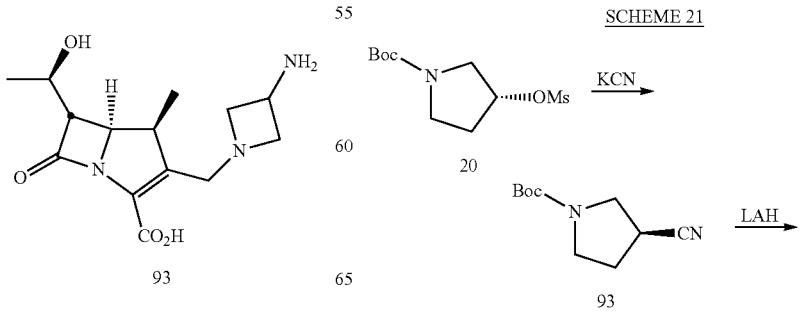

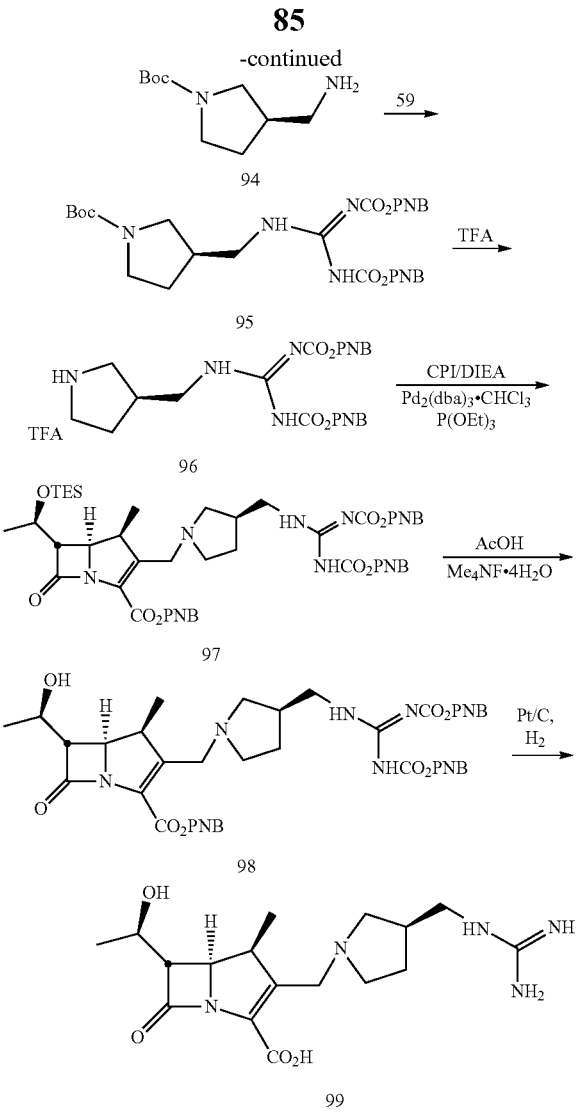

Step 1:

The similar procedure with side chain, 3, synthesis was used for the substitution reaction of the mesylate group to afford the desired nitrile compound 93 in 73% yield.

¹H NMR (CDCl₃, 400 MHz): δ 3.78-3.37 (m, 4H), 3.12-3.07 (m, 1H), 2.27-2.16 (m, 2H), 1.49 (s, 9H).

Step 2:

To a solution of LAH (1.22 g, 32.1 mmol) in ether (15 mL) was added a solution of the nitrile compound 93 (2.5 g, 12.8 mmol) in ether (15 mL) at ice-bath. After overnight at 0° C., it was quenched with 25% NaOH and extracted with ether three times. The extract was dried over anhydrous MgSO₄ and concentrated under a reduced pressure. The crude 94 (1.56 g, 61%) was used on the next reaction without further purification.

¹H NMR (CDCl₃, 400 MHz): δ 3.56-3.36 (m, 2H), 3.28 (m, 1H), 2.98 (m, 1H), 2.70 (m, 2H), 2.20 (m, 1H), 1.98 (br s, 1H), 1.58 (m, 1H), 1.45 (s, 9H), 1.06 (br s, 2H).

Step 3:

The similar procedure with side chain, 60, synthesis was used for guanidation to afford the desired guanidine 95 in 82% yield.

¹H NMR (CDCl₃, 400 MHz): δ 11.77 (s, 1H), 8.39 (t, J=5.2 Hz, 1H), 8.26-8.20 (m, 4H), 7.55 (d, J=8.4 Hz, 2H), 7.53 (d, J=8.4 Hz, 2H), 5.27 (s, 2H), 5.22 (s, 2H), 3.57-3.42 (m, 2H), 3.31 (m, 1H), 3.49 (m, 1H), 2.02 (m, 1H), 1.61 (m, 1H), 1.45 (s, 9H).

Step 4:

The similar procedure with side chain, 24, synthesis was used for de-protection of Boc group to afford the desired amine 96 as a TFA salt in quantitative yield.

¹H NMR (CDCl₃, 400 MHz): δ 11.71 (br s, 1H), 8.51 (t, J=5.6 Hz, 1H), 8.23 (d, J=8.8 Hz, 2H), 8.19 (d, J=8.8 Hz, 2H), 7.53 (d, J=8.4 Hz, 4H), 5.27 (s, 2H), 5.20 (s, 2H), 3.62-3.42 (m, 2H), 3.44-3.34 (m, 2H), 3.29 (m, 1H), 3.05 (dd, J=11.6, 7.6 Hz, 1H), 2.75 (m, 1H), 2.18 (s, J=7.6 Hz, 1H), 1.78 (dq, J=13.6, 8.0 Hz, 1H).

Step 5:

According to the general coupling method B, the desired TES compound 97 was synthesized in 42% yield.

¹H NMR (CDCl₃, 400 MHz): δ 11.78 (br s, 1H), 8.47 (t, J=4.8 Hz, 1H), 8.26-8.19 (m, 6H), 7.67 (d, J=8.8 Hz, 2H), 7.65 (d, J=9.2 Hz, 2H), 7.54 (d, J=8.8 Hz, 2H), 5.45 (d, J=14.0 Hz, 1H), 5.32 (s, 2H), 5.27 (S, 2H), 5.22 (d, J=14.0 Hz, 1H), 4.26 (p, J=6.0 Hz, 1H), 4.19 (dd, J=10.4, 3.2 Hz, 1H), 4.06 (m, 1H), 3.82 (d, J=14.4 Hz, 1H), 3.43 (m, 2H), 3.34 (d, J=14.4 Hz, 1H), 3.30 (m, 1H), 3.22 (dd, J=5.6, 3.2 Hz, 1H), 2.63 (m, 1H), 2.63-2.35 (m, 4H), 1.19 (d, J=7.2 Hz, 3H), 1.15 (d, J=6.4 Hz, 3H), 0.93 (t, J=7.6 Hz, 92H), 0.59 (q, J=7.6 Hz, 6H).

Step 6:

According to the general procedure for the removal of TES group (Method E), the desired OH compound 98 was synthesized in 77% yield.

¹H NMR (CDCl₃, 400 MHz): δ 11.75 (s, 1H), 8.47 (t, J=4.8 Hz, 1H), 8.25-8.19 (m, 6H), 7.65 (d, J=8.8 Hz, 2H), 7.55 (d, J=7.6 Hz, 2H), 7.53 (d, J=8.4 Hz, 2H), 5.49 (d, J=14.0 Hz, 1H), 5.27 (s, 2H), 5.22 (s, 2H), 5.21 (d, J=13.6 Hz, 1H), 4.26 (d, J=6.0 Hz, 1H), 4.18 (dd, J=10.0, 3.2 Hz, 1H), 4.06 (m, 1H), 3.80 (d, J=14.4 Hz, 1H), 3.51-3.20 (m, 3H), 3.35 (d, J=14.4 Hz, 1H), 3.25 (dd, J=6.8, 2.8 Hz, 1H), 2.69 (m, 1H), 2.50-2.41 (m, 3H), 1.99 (m, 1H), 1.52 (m, 1H), 1.35 (d, J=6.4 Hz, 3H), 1.14 (d, J=7.2 Hz, 3H).

Step 7:

According to the general procedure for the removal of PNB groups (Method F), the desired final product 99 was synthesized in 15% yield.

¹H NMR (D₂O, 400 MHz): δ 4.01 (m, 2H), 3.89 (m, 1H), 3.48 (d, J=13.2 Hz, 1H), 3.20 (m, 2H), 3.00 (m, 2H), 2.58 (m, 2H), 2.40 (m, 2H), 2.13 (m, 1H), 1.60 (m, 1H), 1.07 (br s, 3H), 0.96 (m, 1H), 0.90 (br s, 3H).

Example 20

Synthesis of Compound 106

SCHEME 22

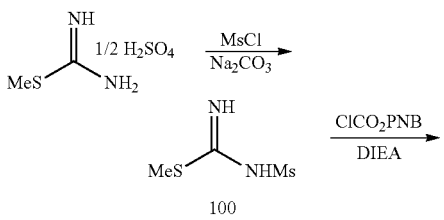

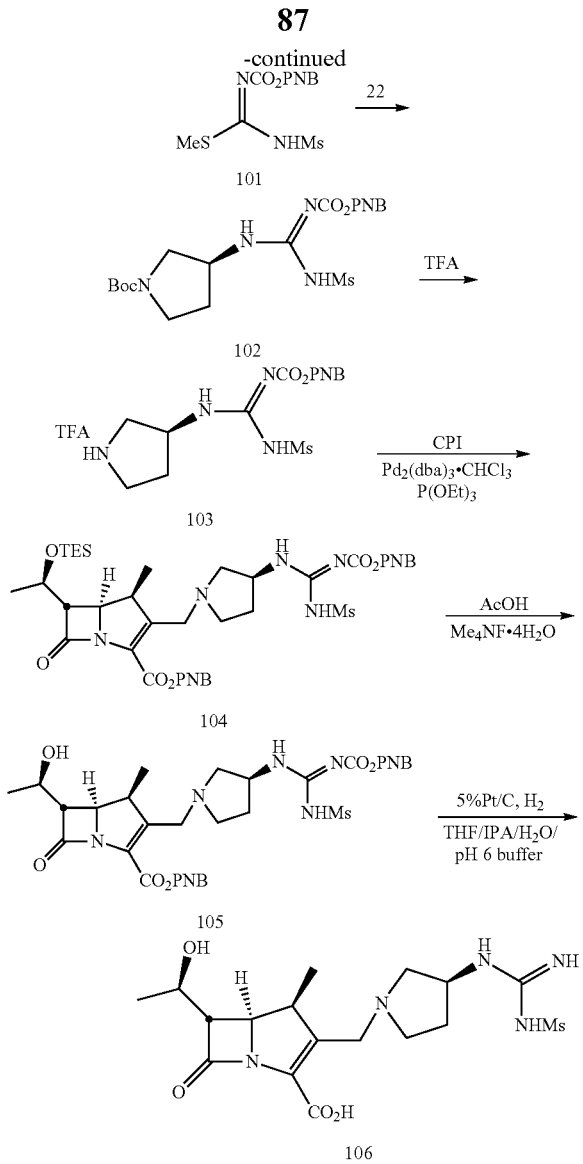

¹H NMR (CDCl₃, 400 MHz): δ 10.23 (s, 1H), 8.34 (s, 1H), 8.22 (d, J=8.8 Hz, 2H), 7.51 (d, J=8.8 Hz, 2H), 5.26 (s, 2H), 4.43 (br s, 1H), 3.62 (m, 1H), 3.43 (m, 2H), 3.29-3.20 (m, 1H), 3.00 (s, 3H), 2.16 (m, 1H), 1.87 (m, 1H).

Step 4:

The similar procedure with side chain, 61, synthesis was used for de-protection of Boc group to afford the desired amine 103 as a TFA salt in quantitative yield.

¹H NMR (CDCl₃, 400 MHz): δ 10.16 (s, 1H), 9.96 (br s, 1H), 9.74 (br s, 1H), 8.48 (d, J=6.0 Hz, 1H), 8.21 (d, J=8.8 Hz, 2H), 7.52 (d, J=8.8 Hz, 2H), 5.26 (s, 2H), 4.55 (m, 1H), 3.58-3.35 (m, 3H), 3.00 (s, 3H), 2.58 (br s, 1H), 2.42 (s, J=6.8 Hz, 1H), 2.07 (m, 1H).

Step 5 & 6:

The similar procedures (coupling & deprotection) with the synthesis of carbapenem 63 were used to afford the desired OH compound 105 in 56% yield over two-steps.

¹H NMR (CDCl₃, 400 MHz): δ 10.20 (s, 1H), 8.45 (d, J=7.2 Hz, 1H), 8.22 (d, J=8.8 Hz, 2H), 8.19 (d, J=8.4 Hz, 2H), 7.63 (d, J=8.8 Hz, 2H), 7.52 (d, J=8.8 Hz, 2H), 5.46 (d, J=13.6 Hz, 1H), 5.25 (s, 2H), 5.19 (d, J=14.0 Hz, 1H), 4.39 (m, 1H), 4.25 (m, 1H), 4.22 (dd, J=10.0, 3.2 Hz, 1H), 3.84 (d, J=14.8 Hz, 1H), 3.37 (d, J=14.8 Hz, 1H), 3.36 (m, 1H), 3.27 (dd, J=6.8, 3.2 Hz, 1H), 2.99 (s, 3H), 2.82 (m, 1H), 2.58-2.51 (m, 2H), 2.42 (q, J=6.8 Hz, 1H), 2.43 (m, 2H), 1.68 (m, 1H), 1.34 (d, J=6.0 Hz, 3H), 1.18 (d, J=7.2 Hz, 3H).

Step 7:

According to the general procedure for the removal of PNB groups (Method F), the desired final product 106 was synthesized in 33% yield.

¹H NMR (D₂O, 400 MHz): δ 4.30 (br s, 1H), 4.10-4.05 (m, 2H), 3.98 (m, 1H), 3.65 (m, 1H), 3.32 (dd, J=5.6, 2.8 Hz, 1H), 3.06 (p, J=6.0 Hz, 1H), 3.50-3.00 (m, 4H), 2.87 (s, 3H), 2.37 (br s, 1H), 1.92 (m, 1H), 1.12 (d, J=6.4 Hz, 3H), 1.02 (d, J=7.6 Hz, 3H).

Step 1:

To a slurry of S-methylisothiourea hemisulfate (10 g, 71.9 mmol) and sodium carbonate (35 g, 330 mmol) in DCM (75 mL) was added slowly water (15 mL) at rt and followed by a dropwise addition of methanesulfonyl chloride (5.56 mL, 71.8 mmol). After overnight at rt, the liquid was decanted and the solid was extracted with DCM. The combined organic layer was washed with 10% citric acid in water, dried over anhydrous MgSO₄ and concentrated to afford a white solid 100 (6 g, 50%).

¹H NMR (CDCl₃, 400 MHz): δ 3.02 (s, 3H), 2.40 (s, 3H).

Step 2:

The similar procedure with side chain, 23, synthesis was used for protection of nitrogen atom to afford the desired product 101 in 85% yield.

¹H NMR (CDCl₃, 400 MHz): δ 10.45 (s, 1H), 8.24 (d, J=8.8 Hz, 2H), 7.54 (d, J=8.8 Hz, 2H), 5.29 (s, 2H), 3.11 (s, 3H), 2.37 (s, 3H).

Step 3:

The similar procedure with side chain, 60, synthesis was used for guanidation to afford the desired guanidine 102 in 52% yield.

Example 21

Synthesis of Compound 111

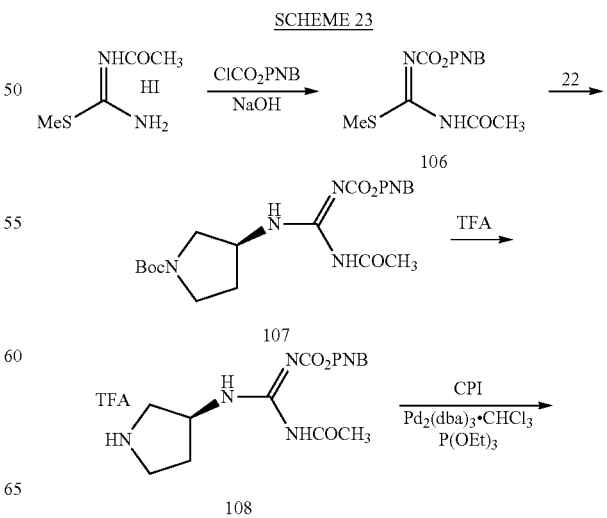

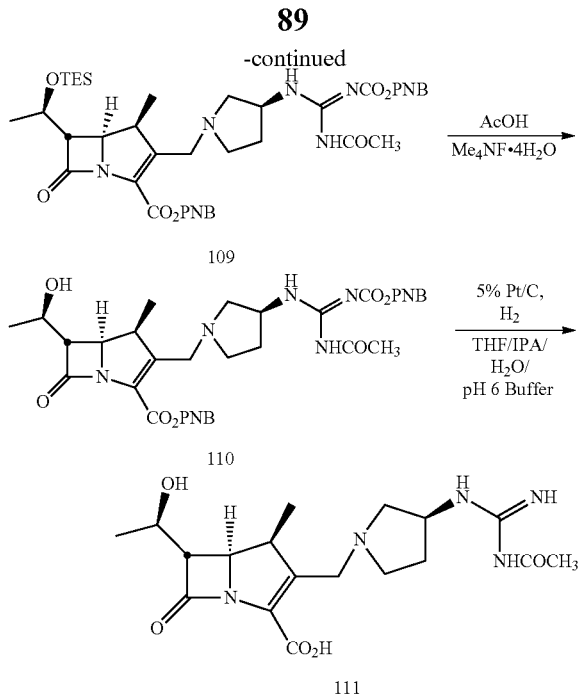

Step 1:
To a suspended mixture of iso-S-methylthiourea HI salt (5.7 g, 21.9 mmol) in DCM (100 mL) was added 220 mL of NaOH (0.1 N) at 0° C. To the mixture was added dropwise a solution of p-nitrobenzylchloro formate (4.96 g, 23 mmol) in DCM (20 ml) and 1.0 N NaOH (23 mL) simultaneously while keeping pH above 10. The mixture was warmed up gradually to rt overnight, extracted with DCM and concentrated to afford a white solid 106 (2.9 g, 43%).

$^1$H NMR (CDCl$_3$, 400 MHz): δ 12.29 (br s, 1H), 8.23 (d, J=8.8 Hz, 2H), 7.57 (d, J=8.4 Hz, 2H), 5.28 (s, 2H), 2.42 (s, 3H), 2.21 (s, 3H).

Step 2:
The similar procedure with side chain, 60, synthesis was used for guanidation to afford the desired guanidine 107 in 37% yield.

$^1$H NMR (CDCl$_3$, 400 MHz): δ 12.21 (br s, 1H), 9.32 (br s, 1H), 8.21 (d, J=8.8 Hz, 2H), 7.58 (d, J=8.8 Hz, 2H), 5.22 (br s, 2H), 4.65 (br s, 1H), 3.68 (m, 1H), 3.50-3.25 (m, 3H), 2.28 (s, 3H), 1.90 (m, 1H), 1.42 (s, 9H).

Step 3:
The similar procedure with side chain, 61, synthesis was used for de-protection of Boc group to afford the desired amine 108 as a TFA salt in 92% yield.

$^1$H NMR (CDCl$_3$, 400 MHz): δ 11.96 (s, 1H), 10.45 (br s, 1H), 9.78 (br s, 1H), 9.40 (d, J=6.0 Hz, 1H), 8.21 (d, J=8.8 Hz, 2H), 7.52 (d, J=8.8 Hz, 2H), 5.20 (s, 2H), 4.60 (br s, 1H), 3.58 (m, 2H), 3.37 (m, 2H), 2.45 (m, 1H), 2.20 (s, 3H), 2.12 (m, 1H).

Step 4 & 5:
The similar procedures (coupling & deprotection) with the synthesis of carbapenem 63 were used to afford the desired OH compound 110 in 29% yield over two-steps.

$^1$H NMR (CDCl$_3$, 400 MHz): δ 12.03 (s, 1H), 9.35 7.52 (d, J=8.0 Hz, 1H), 8.17 (d, J=8.8 Hz, 4H), 7.61 (d, J=8.4 Hz, 2H), 7.52 (d, J=8.4 Hz, 2H), 5.44 (d, J=13.6 Hz, 1H), 5.18 (s, 2H), 5.16 (d, J=13.6 Hz, 1H), 4.59 (m, 1H), 4.21 (m, 2H), 3.81 (d, J=14.8 Hz, 1H), 3.36 (d, J=14.8 Hz, 1H), 3.35 (m, 1H), 3.26 (dd, J=2.8, 6.4 Hz, 1H), 2.85 (m, 1H), 2.60-2.24 (m, 5H), 2.16 (s, 3H), 1.70 (m, 1H), 1.30 (d, J=6.0 Hz, 3H), 1.17 (d, J=7.2 Hz, 3H).

Step 6:
According to the general procedure for the removal of PNB groups (Method F), the desired final product 111 was synthesized in 18% yield.

$^1$H NMR (D$_2$O, 400 MHz): δ 4.15 (br s, 1H), 4.02 (br s, 2H), 3.69 (br s, 1H), 3.59 (br s, 1H), 3.25 (br s, 1H), 3.10-2.70 (m, 4H), 2.28 (br s, 1H), 2.05 (m, 1H), 1.95 (s, 3H), 1.84 (br s, 1H), 1.08 (br s, 3H), 0.94 (br s, 3H).

Example 22

Synthesis of Compound 115

SCHEME 24

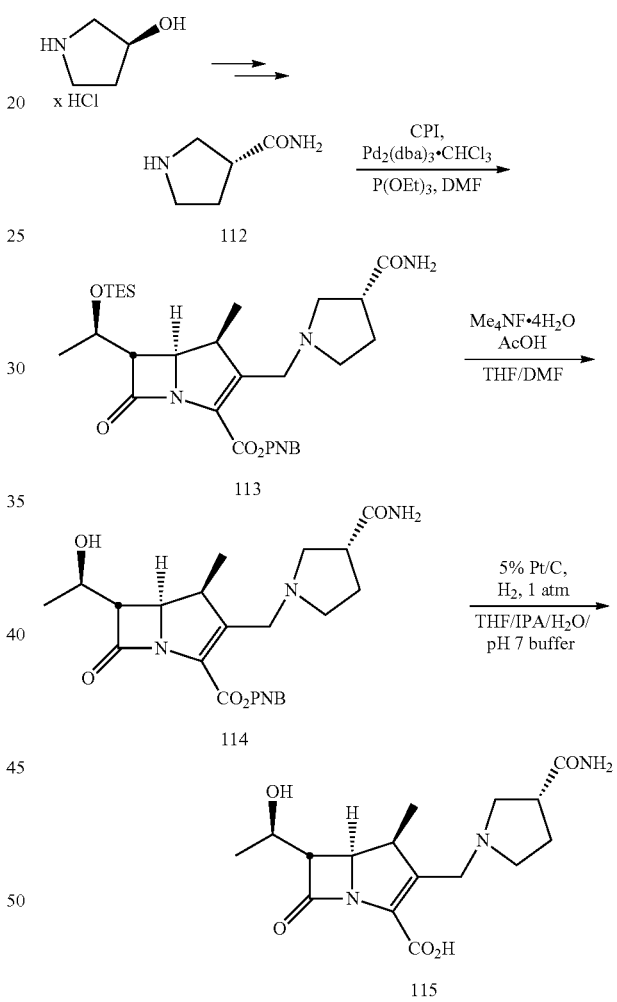

Step 1:
(R)-3-Pyrrolidinecarboxamide 112 was prepared using a similar synthetic method as described for the preparation of (S)-3-pyrrolidinecarboxamide 9 (Scheme 3 & 4). The amide 112 was obtained from (S)-3-hydroxypyrrolidine HCl salt in 49% yield (five steps).

$^1$H NMR (CDCl$_3$, 400 MHz): δ 6.75 (br s, 1H), 6.44 (br s, 1H), 2.98-2.80 (m, 4H), 2.70-2.62 (m, 1H), 1.92-1.74 (m, 2H).

Step 2:
Compound 113 was achieved in 64% yield using general Method A as described for the Pd coupling reaction.

¹H NMR (CDCl₃, 400 MHz): δ 8.21 (d, J=8.8 Hz, 2H), 7.66 (d, J=8.8 Hz, 2H), 6.45 (br s, 1H), 5.54 (br s, 1H), 5.44 (d, J=14.0 Hz, 1H), 5.22 (d, J=14.0 Hz, 1H), 4.27-4.20 (m, 2H), 3.90 (d, J=14.4 Hz, 1H), 3.39 (d, J=14.4 Hz, 1H), 3.31-3.23 (m, 2H), 2.92-2.82 (m, 3H), 2.64-2.60 (m, 1H), 2.36-2.29 (m, 1H), 2.22-2.13 (m, 1H), 2.05-1.96 (m, 1H), 1.24 (d, J=6.4 Hz, 3H), 1.17 (d, J=7.2 Hz, 3H), 0.93 (t, J=8.0 Hz, 9H), 0.59 (q, J=8.0 Hz, 6H).

Step 3:

Compound 114 was prepared in 89% yield using general Method E as described for the removal of the TES group.

¹H NMR (CDCl₃, 400 MHz): δ 8.22 (d, J=8.8 Hz, 2H), 7.65 (d, J=8.8 Hz, 2H), 6.47 (br s, 1H), 5.55 (br s, 1H), 5.48 (d, J=13.6 Hz, 1H), 5.20 (d, J=13.6 Hz, 1H), 4.28-4.23 (m, 2H), 3.90 (d, J=14.4 Hz, 1H), 3.39 (d, J=14.4 Hz, 1H), 3.37-3.27 (m, 2H), 2.95-2.81 (m, 3H), 2.63-2.59 (m, 1H), 2.36-2.30 (m, 1H), 2.22-2.13 (m, 1H), 2.04-1.96 (m, 1H), 1.34 (d, J=6.4 Hz, 3H), 1.18 (d, J=7.6 Hz, 3H).

Step 4:

The final product 115 was obtained in 76% yield according to a similar procedure as described for general Method F using THF, IPA and 0.25 M phosphate buffer solution (pH 7).

¹H NMR (D₂O, 400 MHz): δ 4.05-3.99 (m, 2H), 3.84-3.74 (m, 2H), 3.27-3.25 (m, 1H), 3.22-2.97 (m, 6 H), 2.23-2.13 (m, 1H), 1.98-189 (m, 1H), 1.06 (d, J=6.4 Hz, 3H), 0.95 (d, J=7.2 Hz, 3H).

Example 23

Synthesis of Compound 120

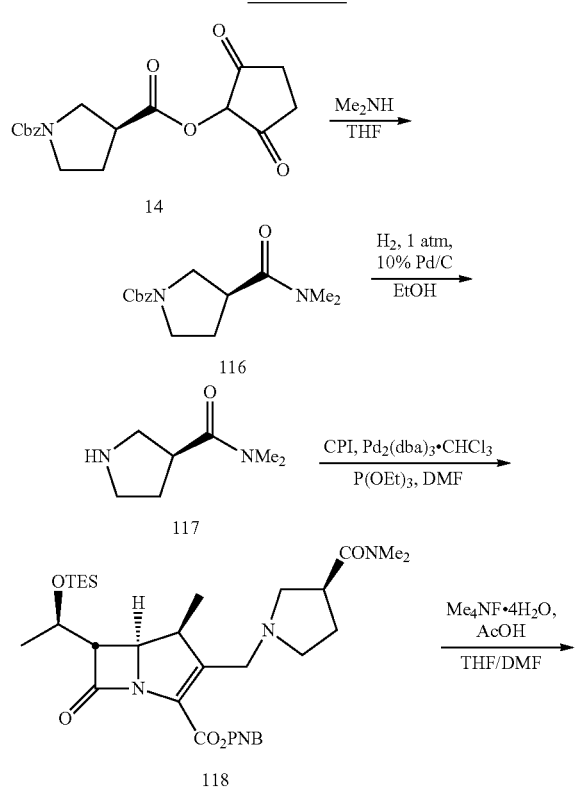

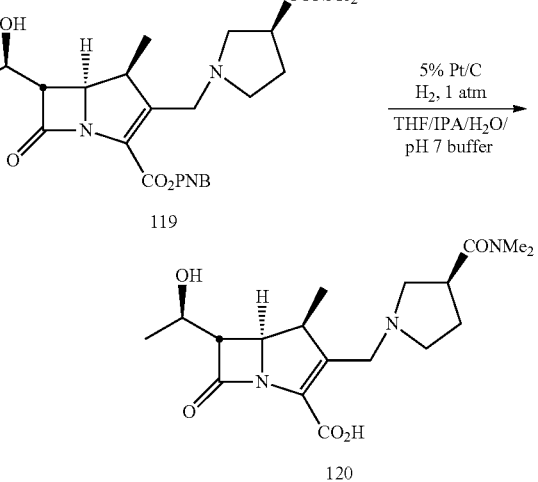

Step 1:

To a stirred solution of ester 14 (0.693 g, 2.0 mmol) in THF (20 mL) at 0° C. was added 2.0 M solution of Me₂NH in THF dropwise. The resulting solution was gradually warmed up to room temperature, and stirring was continued overnight. The reaction mixture was then filtered, and the filtrate was evaporated under reduced pressure. The residue was treated with DCM and DI water. The aqueous layer was separated and extracted with DCM. The combined organic layer was washed with brine, dried over Na₂SO₄ and evaporated under reduced pressure. The crude material was purified by silica gel column chromatography, using DCM/MeOH with gradient as an eluent, to give the desired amide 116 (0.486 g, 88%).

¹H NMR (CDCl₃, 400 MHz): δ 7.30-7.22 (m, 5H), 5.06 (s, 2H), 3.68-3.44 (m, 3H), 3.40-3.33 (m, 1H), 3.24-3.13 (m, 1H), 2.99 (s, 3H), 2.89 (s, 3H), 2.20-1.96 (m, 2H).

Step 2:

Amine 117 was achieved in quantitative yield upon a standard hydrogenolytic Cbz-deprotection.

¹H NMR (CDCl₃, 400 MHz): δ 7.99 (br s, 1H), 3.38-3.14 (m, 5H), 3.02 (s, 3H), 2.88 (s, 3H), 2.88 (s, 3H), 2.22-2.09 (m, 1H), 2.03-1.92 (m, 1H).

Step 3:

The desired coupling product 118 was obtained in 60% yield using general Method A as described for the Pd coupling reaction.

¹H NMR (CDCl₃, 400 MHz): δ 8.20 (d, J=8.4 Hz, 2H), 7.65 (d, J=8.8 Hz, 2H), 5.43 (d, J=13.6 Hz, 1H), 5.23 (d, J=13.6 Hz, 1H), 4.26-4.18 (m, 2H), 4.11-4.04 (m, 1H), 3.46-3.37 (m, 2H), 3.30-3.21 (m, 2H), 3.08-2.88 (m, 3H), 3.02 (s, 3H), 2.93 (s, 3H), 2.84-2.58 (m, 2H), 2.08-1.98 (m, 2H), 1.23 (d, J=6.0 Hz, 3H), 1.15 (dd, J=7.2, 2.0 Hz, 3H), 0.93 (t, J=8.0 Hz, 9H), 0.59 (t, J=8, 0 Hz, 6H).

Step 4:

The TES group in compound 118 was removed using general Method E to afford the OH-compound 119 in 63% yield.

¹H NMR (CDCl₃, 400 MHz): δ 8.21 (dd, J=6.8, 2.0 Hz, 2H), 7.64 (d, J=8.8 Hz, 2H), 5.46 (d, J=14.0 Hz, 1H), 5.21 (d, J=14.0 Hz, 1H), 4.27-4.19 (m, 2H), 3.91-3.84 (m, 1H), 3.52-3.31 (m, 2H), 3.25 (dd, J=6.4, 2.8 Hz, 1H), 3.21-3.13 (m, 1H), 3.01 (s, 3H), 3.93 (s, 3H), 2.88-2.82 (m, 3H), 2.72-2.56 (m, 3H), 2.27 (br s, 1H), 2.10-1.95 (m, 2H), 2.0-1.95 (m, 2H), 1.33 (dd, J=6.4, 1.2 Hz, 3H), 1.16 (dd, J=7.6, 3.2 Hz, 3H).

93

Step 5:

The PNB group in compound 119 was removed using general Method F, running hydrogenation in THF, IPA and 0.25 M phosphate buffer solution (pH 7), to afford the desired product 120 in 62% yield.

$^1$H NMR (D$_2$O, 400 MHz): δ 4.11-4.02 (m, 2H), 3.81-3.68 (m, 2H), 3.52-3.43 (m, 1H), 3.32-3.28 (m, 1H), 3.20-2.97 (m, 5H), 2.93 (s, 3H), 2.76 (s, 3H), 2.26-2.15 (m, 1H), 1.92-1.84 (m, 1H), 1.12 (d, J=6.0 Hz, 3H), 0.99 (d, J=7.2 Hz, 3H).

Example 24

Synthesis of Compound 127

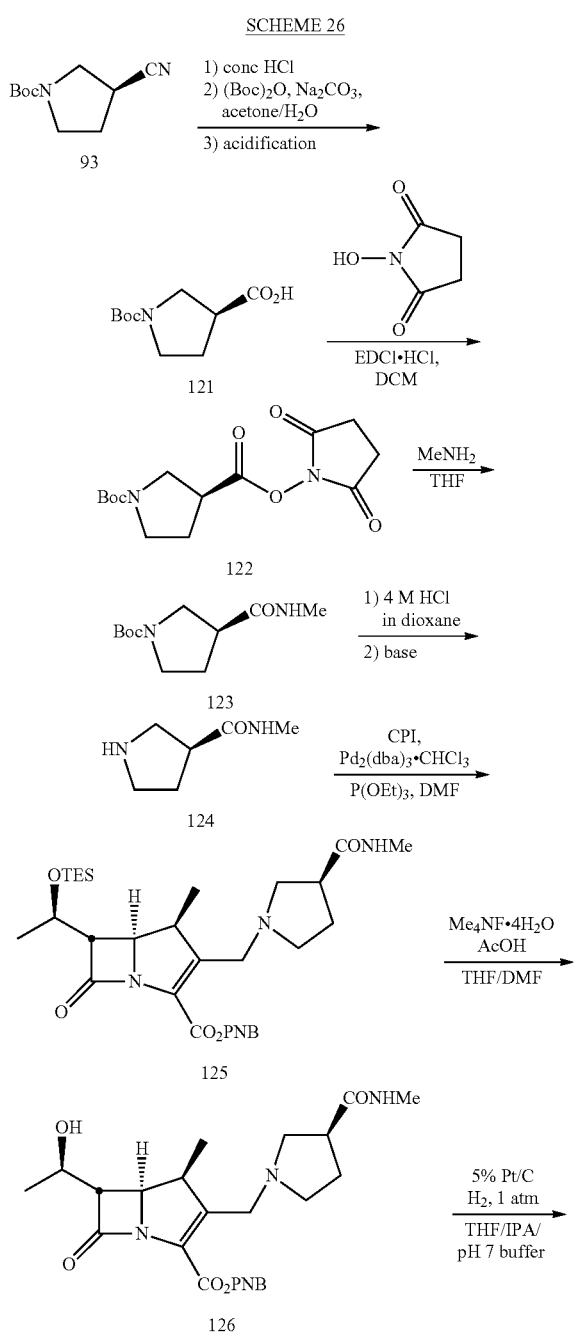

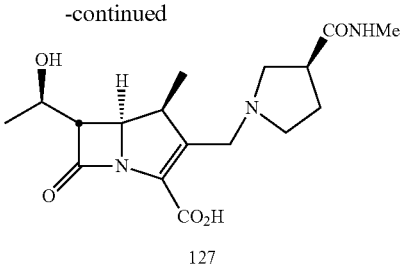

127

Step 1:

Boc-Protected nitrile 93 (3.93 g, 20.0 mmol) was dissolved in conc. HCl (20 mL). The resulting solution was heated at 100° C. for 3 h. Then the reaction mixture was cooled down and evaporated under reduced pressure. The residue was dried under high vacuum and then dissolved in the mixture of acetone (50 mL) and water (50 mL). The resulting solution was cooled to 0° C. and treated slowly with Na$_2$CO$_3$ (6.36 g, 60.0 mmol), as a solid, followed by (Boc)$_2$O (4.80 g, 22.0 mmol). The reaction mixture was stirred and allowed to warm up rt overnight. Then acetone was removed under reduced pressure and an aqueous solution was acidified with 6 N HCl to pH 1, and extracted with EtOAc (×4). The combined organic layers were washed with brine, dried over Na$_2$SO$_4$, and concentrated under reduced pressure to give the desired acid 121 (3.49 g, 81%).

$^1$H NMR (CDCl$_3$, 400 MHz): δ 9.30 (br s, 1H), 3.66-3.32 (m, 4H), 3.12-3.04 (m, 1H), 2.18-2.12 (m, 2H), 1.45 (s, 9H).

Step 2:

Compound 122 was prepared in 74% yield using a similar procedure as described for Cbz-protected analog 14 (Scheme 3).

$^1$H NMR (CDCl$_3$, 400 MHz): δ 3.73-3.32 (m, 5H), 2.84 (s, 4H), 2.32-2.26 (m, 2H), 1.45 (s, 9H).

Step 3:

Amide 123 was synthesized in quantitative yield according to procedure described in Scheme 23 for preparation of compound 116.

$^1$H NMR (CDCl$_3$, 400 MHz): δ 6.51 (br s, 1H), 3.57-3.36 (m, 3H), 3.27-3.20 (m. 1H), 2.87-2.79 (m, 1H), 2.73 (d, J=4.8 Hz, 3H), 2.12-1.97 (m. 2H), 1.38 (s, 9H).

Step 4:

Compound 123 (0.685 g, 3.0 mmol) was treated with cold 4 M HCl in dioxane (10.0 mL). The reaction mixture was stirred at 0° C. for 3 h (monitoring by TLC). The HCl salt of the desired amine 124 gradually precipitated from the reaction mixture as a white solid which was filtered off, washed with fresh dioxane followed by diethyl ether and dried (0.384 g, quantitative yield).

$^1$H NMR (DMSO-d$_6$, 400 MHz): δ 9.48 (br s, 1H), 9.20 (br s, 1H), 8.20 (d, J=4.0 Hz, 1H), 3.31-3.23 (m, 1H), 3.18-3.07 (m, 2H), 2.99 (q, J=7.6 Hz, 1H), 2.57 (d, J=4.8 Hz, 3H), 2.13-2.04 (m, 1H), 1.92-1.83 (m, 1H).

Step 5:

Compound 125 was synthesized in 29% yield by the Pd coupling reaction of CPI intermediate with free amine 124 using general Method A.

$^1$H NMR (CDCl$_3$, 400 MHz): δ 8.19 (dd, J=7.2, 2.0 Hz, 2H), 7.65 (d, J=8.8 Hz, 2H), 6.50 (d, J=2.0 Hz, 1H), 5.43 (d, J=14.0 Hz, 1H), 5.20 (d, J=14.0 Hz, 1H), 4.26-4.17 (m, 2H), 3.93 (d, J=14.0 Hz, 1H), 3.35 (d, J=14.4 Hz, 1H), 3.28-3.22 (m, 2H), 2.89-2.78 (m, 3H), 2.75 (d, J=4.8 Hz, 3H), 2.53-2.47 (m, 2H), 2.16-2.07 (m, 1H), 2.02-1.93 (m, 1H), 1.24 (d, J=7.2 Hz, 3H), 1.17 (d, J=7.2 Hz, 2H), 0.92 (t, J=8.0 Hz, 9H), 0.60 (q, J=8.0 Hz, 6H).

Step 6:

Using general Method E, the TES group was removed from compound 125 to afford the OH-compound 126 in 81% yield.

$^1$H NMR (CDCl$_3$, 400 MHz): δ 8.20 (d, J=8.8 Hz, 2H), 7.63 (d, J=8.8 Hz, 2H), 6.40 (d, 4.8 Hz, 1H), 5.46 (d, J=14.0 Hz, 1H), 5.19 (d, J=14.0 Hz, 1H), 4.27-4.20 (m, 2H), 3.89 (d, J=14.8 Hz, 1H), 3.34-3.26 (m, 3H), 2.87-2.77 (m, 3H), 2.75 (d, J=4.8 Hz, 3H), 2.55 (br s, 1H), 2.49-2 43 (m, 2H), 2.15-2.05 (m, 1H), 2.00-1.92 (m, 1H), 1.33 (d, J=6.4 Hz, 3H), 1.18 (d, J=7.2 Hz, 3H).

Step 7:

The final product 127 was obtained in 69% yield by a similar procedure as described for general Method F using THF, IPA and 0.25 M phosphate buffer pH 7.0.

$^1$H NMR (D$_2$O, 400 MHz): δ 4.09-4.04 (m, 2H), 3.83-3.73 (m, 2H), 3.31-2.98 (m, 6H), 2.56 (s, 3H), 2.20-2.10 (m, 1H), 1.98-1.90 (m, 1H), 1.11 (d, J=6.4 Hz, 3H), 0.99 (d, J=7.2 Hz, 3H).

Example 25

Synthesis of Compound 132

SCHEME 27

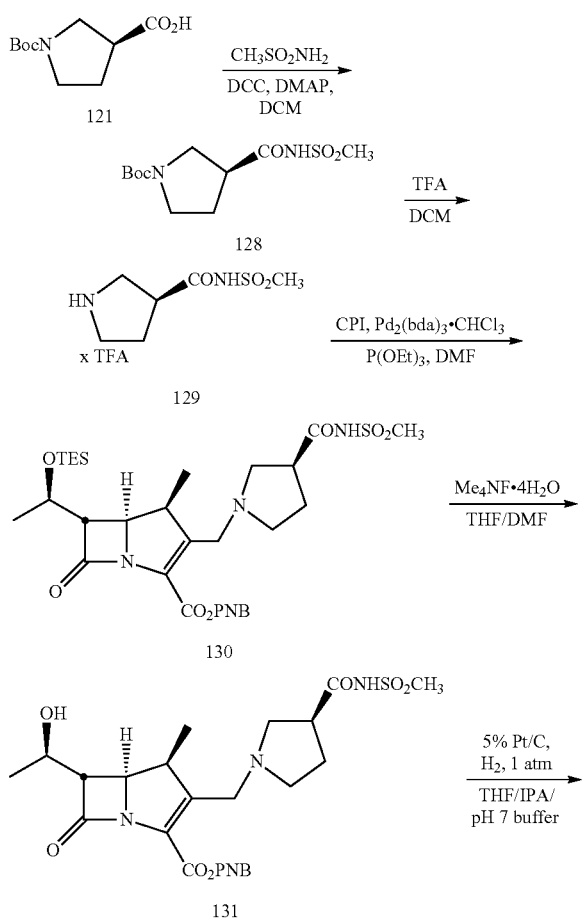

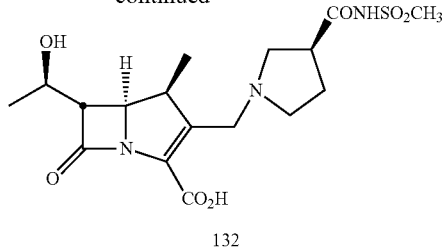

Step 1:

To a solution of acid 121 (0.646 g, 3.0 mmol) in anhydrous DCM (50 mL), a 1.0 M solution of DCC in DCM (4.5 mL, 0.928 g, 4.5 mmol) was added, followed by methanesulfonamide (0.285 g, 3.0 mmol) and DMAP (0.366 g 3.0 mmol). The reaction mixture was stirred at room temperature overnight. Then resulting precipitate was removed by filtration. The filtrate was evaporated under reduced pressure to dryness. The residue was purified by silica gel flash chromatography to give the desired product 128 in 52% yield.

$^1$H NMR (CDCl$_3$, 400 MHz): δ 3.68-3.44 (m, 3H), 3.38-3.31 (m, 1H), 3.27 (s, 3H), 3.11-3.03 (m, 1H), 2.25-2.08 (m, 1H), 1.43 (s, 9H).

Step 2:

Upon a standard Boc-deprotection procedure with TFA, as described earlier, TFA salt 129 of the desired amine was prepared in 92% yield and used for the next step.

$^1$H NMR (DMSO-d$_6$, 400 MHz): δ 8.88 (br s, 2H), 3.35-3.30 (m, 2H), 3.25 (s, 3H), 3.22-3.13 (m, 3H), 2.24-2.15 (m, 1H), 2.02-1.93 (m, 1H).

Step 3:

General Method B for the Pd coupling reaction gave the desired TES-protected product 130 in 48% yield together with TES-deprotected product 131 (21% yield).

Product 130: $^1$H NMR (CDCl$_3$, 400 MHz): δ 8.19 (d, J=8.8 Hz, 2H), 7.65 (d, J=8.8 Hz, 2H), 5.42 (d, J=14.0 Hz, 1H), 5.25 (d, J=14.0 Hz, 1H), 4.58 (d, J=13.2 Hz, 1H), 4.32-4.22 (m, 2H), 3.73 (d, J=13.6 Hz, 1H), 3.45-3.36 (m, 3H), 3.29-3.22 (m, 3H), 3.14 (s, 3H), 3.14-3.08 (m, 1H), 2.42-2.32 (m, 1H), 2.26-2.18 (m, 1H), 1.20 (d, J=6.0 Hz, 3H), 1.15 (d, J=7.2 Hz, 3H), 0.90 (t, J=8.0 Hz, 9H), 0.56 (q, J=8.0 Hz, 6H).

Step 4:

The TES product was deprotected using general Method E to give compound 131 in 93% yield.

$^1$H NMR (CDCl$_3$, 400 MHz): δ 8.15 (d, J=8.8 Hz, 2H), 7.60 (d, J=8.8 Hz, 2H), 5.40 (d, J=14.0 Hz, 1H), 5.19 (d, J=13.6 Hz, 1H), 4.30 (d, J=13.6 Hz, 1H), 4.22 (dd, J=10.0, 2.8 Hz, 1H), 4.10 (q, J=6.4 Hz, 1H), 3.59 (d, J=13.6 Hz, 1H), 3.37-3.24 (m, 3H), 3.21 (dd, J=6.8, 2.8 Hz, 1H), 3.08-2.96 (m, 1H), 3.04 (s, 3H), 2.86-2.78 (m, 2H), 2.30-2.21 (m, 1H), 2.13-2.04 (m, 1H), 1.25 (d, J=6.4 Hz, 3H), 1.11 (d, J=7.6 Hz, 3H).

Step 5:

The final product 132 was obtained using general Method F in 68% yield.

$^1$H NMR (D$_2$O, 400 MHz): δ 4.08-4.02 (m, 2H), 3.92 (s, 2H), 3.70-3.36 (m, 2H), 3.30 (dd, J=6.0, 2.8 Hz, 1H), 3.26-3.10 (m, 3H), 3.08-2.98 (m, 3H), 2.84 (s, 3H), 2.30-1.94 (m, 2H), 1.08 (d, J=6.4 Hz, 3H), 0.98 (d, J=7.2 Hz, 3H).

Example 26

Synthesis of Compound 137

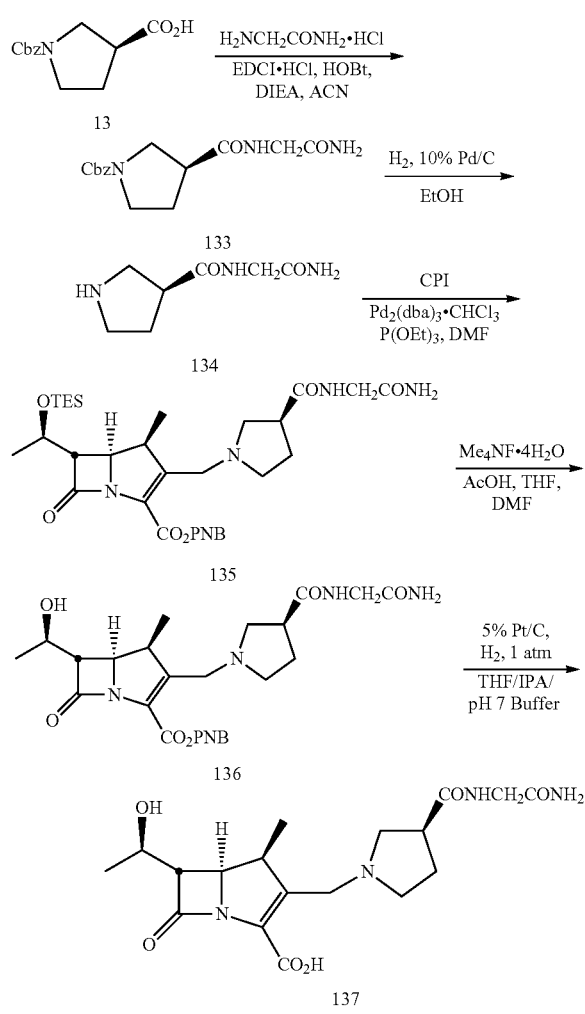

Step 1:

Compound 13 (0.400 g, 1.6 mmol) was dissolved in anhydrous ACN (20 mL) and cooled to 0° C. To the resulting solution glycinamide hydrochloride (0.230 g, 2.08 mmol), EDCI×HCl (0.461 g, 2.4 mmol), HOBt (0.324 g, 2.4 mmol) and DIEA (0.836 mL, 4.8 mmol) were added, and the reaction mixture was stirred under $N_2$ atmosphere at room temperature for 24 h. Then the solution was evaporated under reduced pressure. The residue was dissolved in EtOAc and washed with 1 M HCl and brine. The organic layer was dried over $Na_2SO_4$ and concentrated. The crude product was purified by silica gel flash chromatography eluting with DCM/MeOH with gradient to afford the desired amide 133 (0.480 g, 98%).

$^1$H NMR (CDCl$_3$, 400 MHz): δ 7.61 and 7.45 (t+t, J=5.2 Hz, 1H), 7.30-7.24 (m, 5H), 7.01 and 6.96 (br s+br s, 1H), 6.61 and 6.54 (br s+br s, 1H), 5.06 (d, J=3.2 Hz, 2H), 3.93-3.76 (m, 2H), 3.66-3.44 (m, 3H), 3.37-3.29 (m, 1H), 3.00-2.91 (m, 1H), 2.12-2.01 (m, 2H).

Step 2:

Upon a standard hydrogenolytic Cbz-deprotection the corresponding amine 134 was achieved in quantitative yield.

$^1$H NMR (DMSO-d$_6$, 400 MHz): δ 9.11 (br s, 1H), 8.39 (t, J=1.6 Hz, 1H), 7.36 (s, 1H), 7.03 (s, 1H), 3.68-3.57 (m, 2H), 3.31-3.26 (m, 1H), 3.21-3.07 (m, 4H), 2.15-2.06 (m, 1H), 1.97-1.88 (m, 1H).

Step 3:

The desired coupling product 135 was prepared in 28% yield using general Method A.

$^1$H NMR (CDCl$_3$, 400 MHz): δ 8.20 (dd, J=6.8, 2.0 Hz, 2H), 7.66 (dd, J=8.8 Hz, 2H), 7.32 (br s, 1H), 6.37 (br s, 1H), 5.64 (br s, 1H), 5.44 (d, J=14.0 Hz, 1H), 5.22 (d, J=14.0 Hz, 1H), 4.27-4.20 (m, 2H), 3.94-3.81 (m, 3H), 3.42-3.31 (m, 2H), 3.25-3.23 (m, 1H), 2.92-2.83 (m, 3H), 2.27-2.12 (m, 2H), 2.03-1.94 (m, 2H), 1.24 (d, J=6.0 Hz, 3H), 1.17 (d, J=7.2 Hz, 3H), 0.93 (t, J=8.0 Hz, 9H), 0.59 (q, J=8.0 Hz, 6H).

Step 4:

The TES compound 135 was deprotected using general Method E to give compound 136 in 61% yield.

$^1$H NMR (CDCl$_3$, 400 MHz): δ 8.22 (dd, J=7.6, 2.0 Hz, 2H), 7.70 and 7.41 (t+t, J=4.8 Hz, 1H), 7.65 (d, J=8.8 Hz, 2H), 6.70 and 6.61 (br s+br s, 1H), 6.57 and 6.40 (br s+br s, 1H), 5.47 (dd, J=13.6, 3.6 Hz, 1H), 5.22 (dd, J=13.6, 2.4 Hz, 1H), 4.25-4.19 (m, 2H), 4.05-3.73 (br m, 3H), 3.61-3.48 (m, 1H), 3.38 (t, J=14.4 Hz, 1H), 3.25 (dd, J=7.2, 2.8 Hz, 1H), 3.03-2.85 (m, 3H), 2.32-2.15 (m, 2H), 2.01-1.91 (m, 2H), 1.36 (dd, J=9.6, 6.0 HZ, 3H), 1.17 (dd, J=7.6, 2.8 Hz, 3H).

Step 5:

The final desired product 137 was obtained in 55% yield using a similar procedure as described for general Method F.

$^1$H NMR (D$_2$O, 400 MHz): δ 4.10-4.04 (m, 2H), 3.86-3.80 (m, 2H), 3.75 (s, 2H), 3.34-3.30 (m, 2H), 3.24-3.01 (m, 5H), 2.28-2.18 (m, 1H), 2.06-1.97 (m, 1H), 1.12 (d, J=5.6 Hz, 3H), 1.00 (d, J=6.4 Hz, 3H).

Example 27

Synthesis of Compound 143

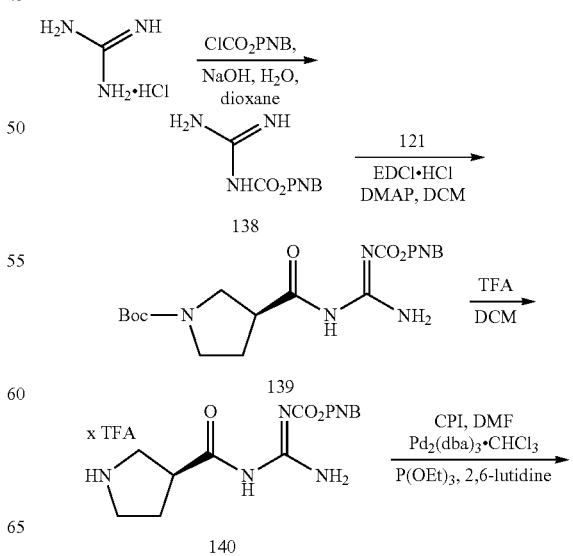

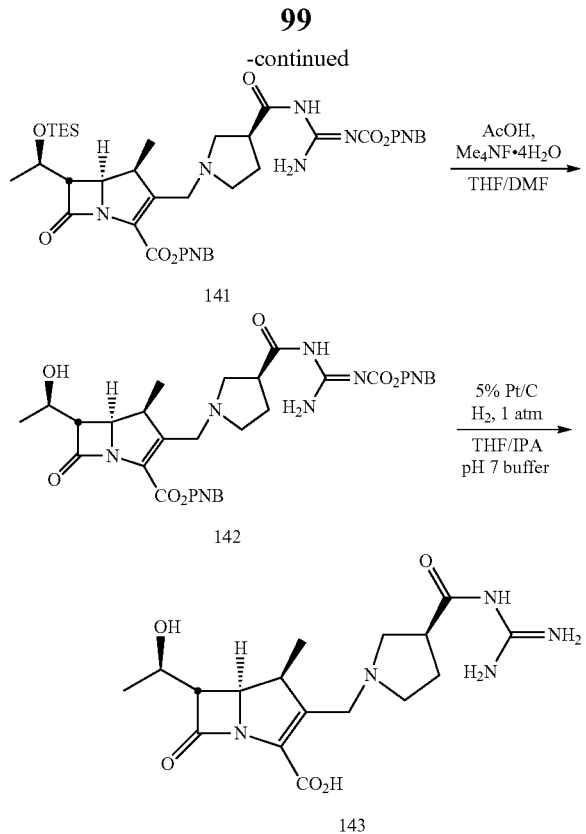

141

142

143

Step 1:

1,4-Dioxane (10 mL) was added to a solution of guanidine hydrochloride (0.96 g, 10.0 mmol) and NaOH (0.80 g, 20.0 mmol) in H$_2$O (10 mL), and the resulting mixture was cooled to 0° C. Next, a solution of 4-nitrobenzyl chloroformate (1.66 g, 7.7 mmol) in 1,4-dioxane (15 mL) was slowly added at 0-5° C. under vigorous stirring. After stirring for an additional 10 h at room temperature, the mixture was concentrated under reduced pressure to one-third its original volume and extracted with EtOAc three times. The combined extracts were washed with brine and dried over Na$_2$SO$_4$. After filtering and a removal of the solvent under reduced pressure, the pure mono-protected guanidine 138 (1.56 g, 85%) was obtained.

$^1$H NMR (DMSO-d$_6$, 400 MHz): δ 8.18 (d, J=2.0 Hz, 2H), 7.57 (d, J=2.0 Hz, 2H), 5.69 (br s, 4H), 4.62 (s, 2H).

Step 2:

To a cold solution of acid 121 (0.646 g, 3.0 mmol) in anhydrous DCM (60 mL), guanidine 138 (0.929 g, 3.9 mmol), EDCI×HCl (0.863 g, 4.5 mmol) and DMAP (0.586 g, 4.8 mmol) were added. The reaction mixture was stirred under N$_2$ atmosphere and allowed to warm up. After 24 h the solvent was evaporated under reduced pressure. The residue was dissolved in EtOAc and washed with 1 N HCl and brine. The organic layer was dried over Na$_2$SO$_4$ and evaporated under reduced pressure. The residue was purified by silica gel flash chromatography to give the desired product 139 in 70% yield.

$^1$H NMR (DMSO-d$_6$, 400 MHz): δ 10.15 (br s, 1H), 8.40 (br s, 1H), 8.22 (d, J=8.8 Hz, 2H), 7.62 (d, J=8.8 Hz, 2H), 5.74 (br s, 1H), 5.25 (s, 2H), 3.49-3.38 (m, 2H), 3.30-3.21 (m, 2H), 3.30-3.21 (m, 2H), 3.14-3.07 (m, 1H), 2.15-1.97 (m, 2H), 1.40 (s, 9H).

Step 3:

Compound 140 was achieved in 91% yield upon a standard TFA deprotection.

$^1$H NMR (CDCl$_3$, 400 MHz): δ 9.95 (br s, 2H), 8.22 (d, J=6.8 Hz, 2H), 7.51 (d, J=6.8 Hz, 2H), 5.24 (s, 2H), 3.60-3.51 (m, 2H), 3.38-3.30 (m, 3H), 2.41-2.25 (m, 2H).

Step 4:

General Method B for the Pd coupling reaction gave a mixture of TES-protected product 141 (26%) together with TES-deprotected product 142 (40%).

Product 141: $^1$H NMR (CDCl$_3$, 400 MHz): δ 11.50 (br s, 1H), 10.10 (br s, 1H), 8.40 (br s, 1H), 8.20-8.16 (m, 4H), 7.63 (d, J=8.8 Hz, 2H), 7.51 (d, J=8.8 Hz, 2H), 5.45 (d, J=13.6 Hz, 1H), 5.24 (s, 2H), 5.20 (d, J=13.6 Hz, 1H), 4.77-4.71 (m, 1H), 4.34-4.19 (m, 3H), 3.88-3.83 (m, 2H), 3.56-3.28 (m, 5H), 2.49-2.39 (m, 1H), 2.36-2.24 (m, 1H), 1.28 (d, J=6.4 Hz, 3H), 1.14 (d, J=7.2 Hz, 3H), 0.91 (t, J=8.0 Hz, 9H), 0.57 (q, J=8.0 Hz, 6H).

Step 5:

The TES product was deprotected using general Method E to give an additional amount of compound 142 in 94% yield.

$^1$H NMR (CDCl$_3$, 400 MHz): δ 8.60 (d, J=3.2 Hz, 1H), 8.22-8.17 (m, 4H), 7.61 (d, J=8.4 Hz, 2H), 7.52 (d, J=8.8 Hz, 2H), 5.44 (d, J=13.6 Hz, 1H), 5.25 (s, 2H), 5.17 (d, J=14.0 Hz, 1H), 4.77-4.74 (m, 1H), 4.35 (dd, J=10.4, 3.2 Hz, 1H), 4.27-4.22 (m, 1H), 3.88 (d, J=13.2 Hz, 1H), 3.55-3.38 (m, 4H), 3.32 (dd, J=5.2, 2.8 Hz, 1H), 3.20-3.10 (m, 1H), 2.50-2.41 (m, 1H), 2.34-2.25 (m, 1H), 2.34-2.25 (m, 1H), 1.29 (d, J=6.4 Hz, 3H), 1.15 (d, J=7.2 Hz, 3H).

Step 6:

The final product 143 was obtained in 61% yield using a similar procedure as described for general Method F.

$^1$H NMR (D$_2$O, 400 MHz): δ 4.04-4.01 (m, 2H), 3.90 (br s, 2H), 3.29-3.27 (m, 2H), 3.23-3.21 (m, 1H), 3.18-3.11 (m, 1H), 3.05-2.95 (m, 3H), 2.22-2.10 (m, 1H), 2.04-1.93 (m, 1H), 1.06 (d, J=6.4 Hz, 3H), 0.96 (d, J=7.2 Hz, 3H).

Example 28

Synthesis of Compound 146

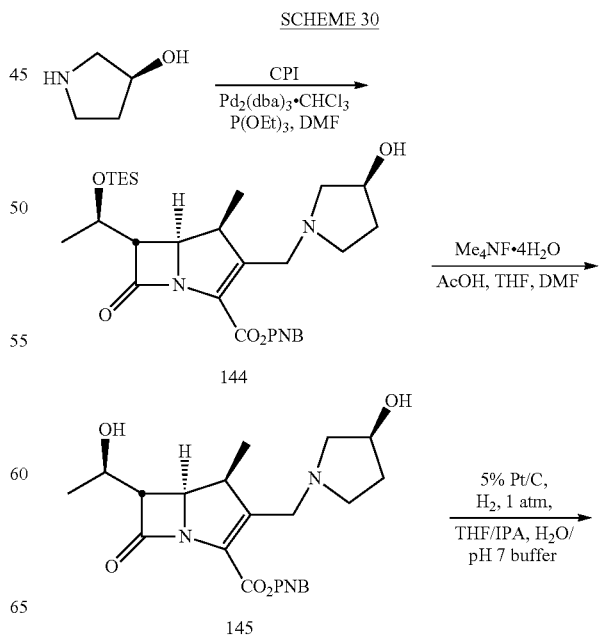

SCHEME 30

144

145

101

-continued

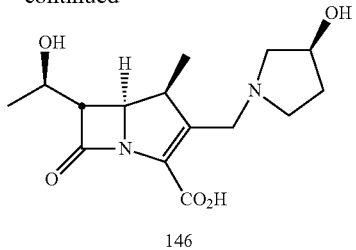

146

Step 1:

Compound 144 was synthesized in 82% yield by using general Method A as described for the Pd coupling reaction.

$^1$H NMR (CDCl$_3$, 400 MHz): δ 8.21 (dd, J=6.8, 2.0 Hz, 2H), 7.66 (d, J=8.8 Hz, 2H), 5.45 (d, J=14.0 Hz, 1H), 5.21 (d, J=14.0 Hz, 1H), 4.33-4.30 (m, 1H), 4.24 (t, J=6.0 Hz, 1H), 4.19 (dd, J=10.4, 3.2 Hz, 1H), 3.86 (d, J=14.4 Hz, 1H), 3.38-3.33 (m, 2H), 3.26 (dd, J=5.6, 2.8 Hz, 1H), 2.90-2.87 (m, 1H), 2.66 (d, J=10.0 Hz, 1H), 2.44-2.34 (m, 2H), 2.21-2.13 (m, 1H), 1.77-1.71 (m, 1H), 1.25 (d, J=6.4 Hz, 3H), 1.17 (d, J=7.6 Hz, 3H), 0.93 (t, J=7.6 Hz, 9H), 0.59 (q, J=7.6 Hz, 6H).

Step 2:

The TES group in compound 144 was removed using general Method E to afford product 145 in 54% yield.

$^1$H NMR (CDCl$_3$, 400 MHz): δ 8.21 (dd, J=6.8, 2.0 Hz, 2H), 7.64 (d, J=8.8 Hz, 2H), 5.47 (d, J=14.0 Hz, 1H), 5.20 (d, J=14.0 Hz, 1H0, 4.32-4.29 (m, 1H), 4.28-4.20 (m, 1H), 3.85 (d, J=14.4 Hz, 1H), 3.43-3.37 (m, 1H), 3.35 (d, J=14.4 Hz, 1H), 3.26 (dd, J=6.0, 2.8 Hz, 1H), 2.92-2.87 (m, 1H), 2.66 (d, J=6.0 Hz, 1H), 2.45 (br s, 1H), 2.39-2.30 (m, 2H), 2.21-2.12 (m, 1H), 1.77-1.70 (m, 1H), 1.31 (d, J=6.0 Hz, 3H), 1.16 (d, J=7.2 Hz, 3H).

Step 3:

The final product 146 was obtained in 64% yield using a similar procedure as described for general Method F.

$^1$H NMR (D$_2$O, 400 MHz): δ 4.44 (br s, 1H), 4.11-4.05 (m, 2H), 3.91-3.81 (m, 2H), 3.32-3.29 (m, 2H), 3.14-3.03 (m, 4H), 2.20-2.09 (m, 1H), 1.89-1.82 (m, 1H), 1.12 (d, J=6.0 Hz, 3H), 1.00 (d, J=6.8 Hz, 3H).

Example 29

Synthesis of Compound 151

SCHEME 31

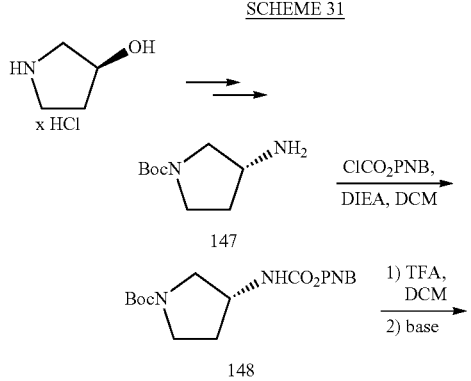

102

-continued

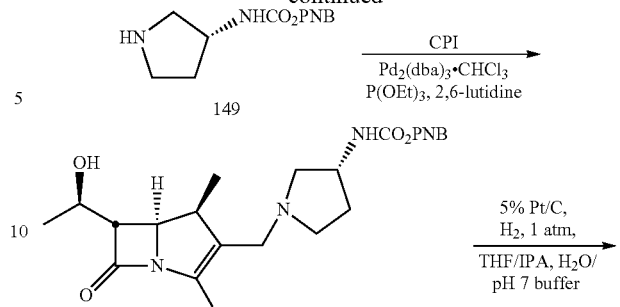

Steps 1

According to the procedures described in Scheme 6 for the preparation of (S)-3-aminopyrrolidine 22, (S)-3-hydroxypyrrolidine hydrochloride was converted to (R)-3-aminopyrrolidine 147 in 91% yield (four steps).

$^1$H NMR (CDCl$_3$, 400 MHz): δ 3.58-3.31 (m, 4H), 3.07-2.97 (m, 1H), 2.07-1.99 (m, 1H), 1.68-1.60 (m, 1H), 1.45 (s, 9H).

Step 2:

Amine 147 was protected with the PNB group to give compound 148 in 79% yield.

$^1$H NMR (CDCl$_3$, 400 MHz): δ 8.21 (d, J=8.8 Hz, 2H), 7.50 (d, J=8.8 Hz, 2H), 5.18 (s, 2H), 5.03 (br s, 1H), 4.25-4.22 (m, 1H), 3.60 (dd, J=11.2, 6.0 Hz, 1H), 3.43-3.39 (m, 2H), 3.27-3.17 (m, 1H), 2.18-2.10 (m, 1H), 1.90-1.78 (m, 1H), 1.44 (s, 9H).

Step 3:

A standard Boc-deprotection procedure afforded pyrrolidine 149 in 87% yield.

$^1$H NMR (DMSO-d$_6$, 400 MHz): δ 8.80 (br s, 1H), 8.22 (d, J=8.4 Hz, 2H), 7.82 (d, J=6.0 Hz, 1H), 7.60 (d, J=8.4 Hz, 2H), 5.17 (s, 2H), 4.15-4.11 (m, 1H), 3.34-3.14 (m, 4H), 3.02 (dd, J=11.6, 4.8 Hz, 1H), 2.12-2.02 (m, 1H), 1.87-1.79 (m, 1H).

Step 4:

General Method B for the Pd coupling reaction gave de-TES compound 150 as a major product (54% yield), together with a small amount of TES-protected product.

$^1$H NMR (CDCl$_3$, 400 Hz): δ 8.13-8.09 (m, 4H), 7.56 (d, J=8.8 Hz, 2H), 7.43 (d, J=8.8 Hz, 2H), 5.40 (d, J=13.6 Hz, 1H), 5.13 (d, J=13.6 Hz, 1H), 5.11 (s, 2H), 4.60 (d, J=12.8 Hz, 1H), 4.48 (br s, 1H), 4.30 (d, J=10.4 Hz, 1H), 4.22-4.16 (m, 1H), 3.76 (d, J=13.2 Hz, 1H), 3.54-3.48 (m, 3H), 3.31-3.18 (m, 3H), 3.06-2.94 (m, 1H), 2.48-2.38 (m, 1H), 2.06-1.97 (m, 1H), 1.25 (d, J=6.4 Hz, 3H), 1.11 (d, J=6.8 Hz, 3H).

Step 5:

The final product 151 was obtained in 29% yield using general Method F.

$^1$H NMR (D$_2$O, 400 MHz): δ 4.09-4.03 (m, 2H), 3.64 (d, J=12.8 Hz, 2H), 3.41 (d, J=14.4 Hz, 1H), 3.08-3.02 (m, 2H), 2.80-2.70 (m, 2H), 2.47-2.42 (m, 1H), 2.23-2.13 (m, 1H), 1.71-1.64 (m, 1H), 1.12 (d, J=6.4 Hz, 3H), 0.96 (d, J=7.2 Hz, 3H).

Example 30

Synthesis of Compound 156

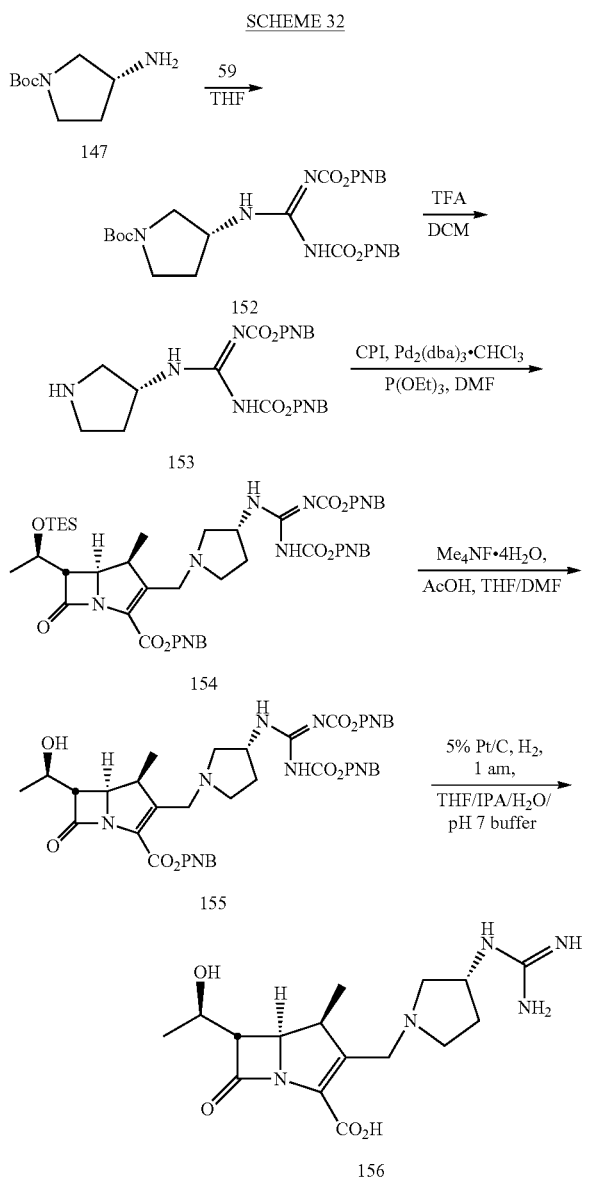

Synthetic methodology and procedures shown above are similar to those presented in Scheme 13 for the preparation of carbapenem 64.

Step 1:

The reaction of (R)-1-Boc-3-aminopyrrolidine 147 with PNB-protected S-methylisothiourea 59 afforded guanidine 152 in 93% yield.

$^1$H NMR (CDCl$_3$, 400 MHz): δ 8.42 (br s, 1H), 8.25-8.19 (m, 4H), 7.54 (d, J=8.0 Hz, 2H), 7.52 (d, J=8.0 Hz, 2H), 5.26 (s, 2H), 5.22 (s, 2H), 4.68-4.62 (m, 1H), 3.70-3.65 (m, 1H), 3.48-3.40 (m, 2H), 3.33-3.20 (m, 1H), 2.24-2.16 (m, 1H), 1.93-1.85 (m, 1H), 1.45 (s, 9H).

Step 2:

A standard procedure for Boc-deprotection, with TFA afforded the desired amine 153 isolated as a TFA salt in 98% yield.

$^1$H NMR (DMSO-d$_6$, 400 MHz): δ 11.45 (br s, 1H), 8.80 (br s, 2H), 8.43 (d, J=7.2 Hz, 1H), 8.25-8.21 (m, 4H), 7.67 (d, J=8.8 Hz, 2H), 7.60 (d, J=8.8 Hz, 2H), 5.35 (s, 2H), 5.19 (s, 2H), 4.69-4.61 (m, 1H), 3.40-3.27 (m, 2H), 3.18-3.12 (m, 2H), 2.26-2.17 (m, 1H), 1.95-1.86 (m, 1H).

Step 3:

General Method B for the Pd coupling reaction afforded a mixture of TES-protected product 154 (28% yield), together with de-TES product 155 (46% yield).

Product 154: $^1$H NMR (CDCl$_3$, 400 MHz): δ 11.75 (s, 1H), 8.57 (d, J=7.6 Hz, 1H), 8.25-8.18 (m, 6H), 7.65 (d, J=8.4 Hz, 2H), 7.56-7.49 (m, 4H), 5.45 (d, J=13.6 Hz, 1H), 5.26-5.20 (m, 5H), 4.63 (br s, 1H), 4.29-4.19 (m, 2H), 3.86 (d, J=14.4 Hz, 1H), 3.41-3.32 (m, 2H), 3.25 (dd, J=6.4, 2.8 Hz, 1H), 3.09 (dd, J=6.8, 2.8 Hz, 1H), 2.85-2.74 (m, 2H), 2.58-2.50 (m, 1H), 2.32-2.28 (m, 2H), 1.26 (d, J=6.0 Hz, 3H), 1.18 (d, J=7.6 Hz, 3H), 0.95 (t, J=7.6 Hz, 9H), 0.60 (q, J=7.6 Hz, 6H).

Step 4:

The TES product was deprotected using general Method E to obtain the OH product 155 in 94% yield.

$^1$H NMR (CDCl$_3$, 400 MHz): δ 11.74 (s, 1H), 8.62 (br s, 1H), 8.22-8.16 (m, 6H), 7.61 (d, J=8.4 Hz, 2H) 7.52 (d, J=8.4 Hz, 2H), 7.51 (d, J=8.8 Hz, 2H), 5.43 (d, J=14.0 Hz, 1H), 5.25 (s, 2H), 5.19 (s, 2H), 5.18 (d, J=14.0 Hz, 1H), 4.88 (br s, 1H), 4.69 (d, J=13.2 Hz, 1H), 4.34 (dd, J=10.4, 2.8 Hz, 1H), 4.24 (q, J=6.0 Hz, 1H), 3.86 (d, J=13.2 Hz, 1H), 3.76-3.64 (m, 1H), 3.58-3.44 (m, 2H), 3.33-3.20 (m, 2H), 3.10-2.80 (m, 2H), 2.60-2.52 (m, 1H), 2.19-2.10 (m, 1H), 1.29 (d, J=6.0 Hz, 3H), 1.14 (d, J=7.2 Hz, 3H).

Step 5:

The desired final product 156 was achieved in 35% yield using general Method F.

$^1$H NMR (D$_2$O, 400 MHz): δ 4.04-3.96 (m, 2H), 3.92-3.86 (m, 1H), 3.54 (d, J=13.6 Hz, 1H), 3.25-3.20 (m, 2H), 3.03-2.99 (m, 1H), 2.87-2.83 (m, 1H), 2.68-2.60 (m, 1H), 2.51-2.44 (m, 1H), 2.40-2.34 (m, 1H), 2.16-2.11 (m, 1H), 1.62-1.57 (m, 1H), 1.06 (d, J=6.4 Hz, 3H), 0.89 (d, J=7.2 Hz, 3H).

Example 31

Synthesis of Compound 163

SCHEME 33

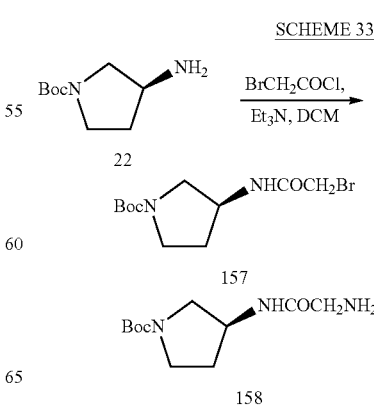

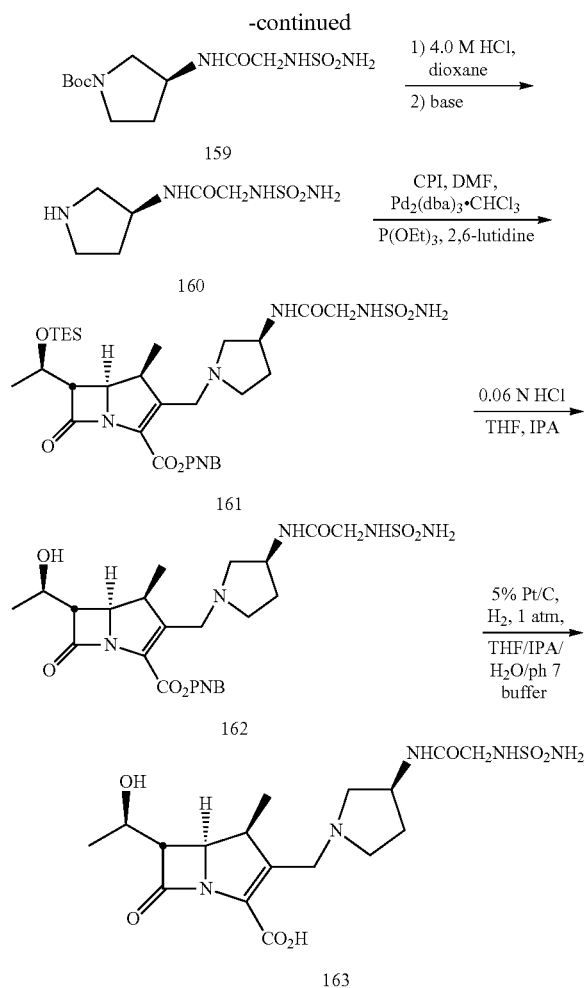

Step 3:

To a solution of compound 158 (0.730 g, 3.0 mmol) in dioxane (20 mL) was added sulfamide (0.577 g, 6.0 mmol). The resulting mixture was stirred under reflux. Progress of the reaction was monitored by TLC. When reaction was complete the mixture was cooled down and insoluble material was filtered off. The filtrate was concentrated under reduced pressure. The residue was treated with EtOAc, and insoluble material was filtered off again. The filtrate was evaporated under reduced pressure. The residue was purified by silica gel flash chromatography using DCM/MeOH with gradient as an eluent. The desired product 159 was obtained in 56% yield (0.542 g).

$^1$H NMR (CDCl$_3$, 400 MHz): δ 7.40 (br s, 1H), 6.08 (br s, 1H), 5.79 (br s, 2H), 4.45-4.35 (m, 1H), 3.78-3.20 (m, 6H), 2.15-2.04 (m, 1H), 1.92-1.85 (m, 1H), 1.44 (s, 9H).

Step 4:

A standard procedure for Boc-deprotection, with 4 M HCl in dioxane followed by liberation of free amine with base, afforded the desired amine 160 in 89% yield.

HCl salt of 160: $^1$H NMR (DMSO-d$_6$, 400 MHz): δ 9.24 (br s, 3H), 8.20 (d, J=2.8 Hz, 1H), 6.70 (br s, 2H), 4.36-4.30 (m, 1H), 3.32-3.23 (m, 2H), 3.20-3.14 (m, 1H), 3.04-2.98 (m, 1H), 2.13-2.04 (m, 1H), 1.87-1.79 (m, 1H).

Step 5:

General Method B for the Pd coupling reaction afforded the desired product 161 in 41% yield.

$^1$H NMR (CDCl$_3$, 400 MHz): δ 8.21 (d, J=8, 8 Hz, 2H), 7.66 (d, J=8.4 Hz, 2H), 6.91 (d, J=7.6 Hz, 1H), 5.81 (br s, 2H), 5.50 (br s, 1H), 5.43 (d, J=14.0 Hz, 1H), 5.23 (d, J=14.0 Hz, 1H), 4.44-4.37 (m, 1H), 4.27-4.21 (m, 2H), 3.88 (d, J=14.4 Hz, 1H), 3.74 (s, 2H), 3.34-3.28 (m, 2H), 3.24 (dd, J=4.8, 2.8 Hz, 1H), 2.81-2.75 (m, 1H), 2.69-2.65 (m, 1H), 2.57-2.54 (m, 1H), 2.51-2.44 (m, 1H), 2.28-2.19 (m, 1H), 1.70-1.62 (m, 1H), 1.24 (d, J=6.4 Hz, 3H), 1.16 (d, J=7.2 Hz, 3H), 0.93 (t, J=8.0 Hz, 9H), 0.59 (q, J=8.0 Hz, 6H).

Step 6:

Compound 161 (0.32 g, 0.46 mmol) was dissolved in THF (15 mL) and IPA (4 mL), and cooled to 0° C. Then, 0.06 N HCl solution was added gradually to maintain pH value 2.4. The resulting mixture was aged at 0° C. After reaction completion, the reaction mixture was neutralized with 0.25 M sodium phosphate buffer pH 7.0 (10 mL), stirred for 10 minutes and treated with EtOAc. After separation, the aqueous layer was extracted with EtOAc twice. The combined organic layer was dried over Na$_2$SO$_4$ and evaporated under reduced pressure. The residue was purified by flash chromatography on silica gel eluting with DCM/MeOH with gradient to give the desired OH compound 162 in 60% yield.

$^1$H NMR (CDCL$_3$, 400 MHz): δ 8.21 (d, J=8.8 Hz, 2H), 7.63 (d, J=8.8 Hz, 2H), 7.20 (d, J=3.6 Hz, 1H), 6.01 (br s, 2H), 5.44 (d, J=13.6 Hz, 1H), 5.22 (d, J=13.6 Hz, 1H), 4.36-4.29 (m, 1H), 4.27-4.19 (m, 2H), 3.82 (d, J=14.4 Hz, 1H), 3.69 (s, 2H), 3.53-3.29 (m, 2H), 3.22 (dd, J=6.8, 2.8 Hz, 1H), 3.03-3.00 (m, 1H), 2.67 (d, J=9.6 Hz, 1H), 2.29-2.19 (m, 2H), 1.73-1.64 (m, 1H), 1.30 (d, J=6.0 Hz, 3H), 1.14 (d, J=7.2 Hz, 3H).

Step 7:

General Method F for the removal of the PNB protecting group afforded the desired final product 163 in 64% yield.

$^1$H NMR (D$_2$O, 400 MHz): δ 4.30-4.23 (m, 1H), 4.07-3.99 (m, 2H), 3.73-3.63 (m, 2H), 3.57 (s, 2H), 3.26 (dd, J=6.0, 2.8 Hz, 1H), 3.06-2.98 (m, 3H), 2.92-2.83 (m, 2H), 2.26-2.17 (m, 1H), 1.81-1.73 (m, 1H), 1.08 (d, J=6.4 Hz, 3H), 0.95 (d, J=7.2 Hz, 3H).

Step 1:

To a cold solution of (S)-1-Boc-3-aminopyrrolidine (6.15 g, 33.0 mmol) in anhydrous DCM (60 mL) was added DIEA (7.5 mL, 42.9 mmol) under N$_2$ atmosphere at 0° C. and followed by addition of bromoacetyl chloride (3.3 mL, 39.6 mmol) dropwise. The reaction mixture was allowed to warm up, and stirring was continued at room temperature for 24 h. Then, the mixture was diluted with EtOAc, washed with aqueous NaHCO$_3$ and brine, dried over Na$_2$SO$_4$, filtered, and evaporated under reduced pressure to give a crude material which was purified by flash chromatography on silica gel eluting with hexane/EtOAc with gradient. The desired product 157 was obtained in 80% yield (8.1 g).

$^1$H NMR (CDCl$_3$, 400 MHz): δ 6.62 (br s, 1H), 4.48-4.41 (m, 1H), 4.04 (s, 1H), 3.86 (s, 1H), 3.66-3.61 (m, 1H), 3.46-3.41 (m, 2H), 3.28-3.17 (m, 1H), 2.22-2.12 (m, 1H), 1.93-1.82 (m, 1H), 1.45 (s, 9H).

Step 2:

To a solution of compound 157 (6.0 g, 19.53 mmol) in MeOH (110 mL) was added NaI (8.78 g, 58.6 mmol) and 28% aqueous NH$_4$OH (110 mL). The resulting mixture was stirred at room temperature for 48 h. The mixture was evaporated under reduced pressure to dryness. The residue was purified by silica gel flash chromatography eluting with ACN to give 4.6 g of the desired product 158 (96.8%).

$^1$H NMR (CDCl$_3$, 400 MHz): δ 8.38 and 8.28 (s+s, 1H), 7.64 (br s, 2H), 4.51-4.42 (m, 1H), 4.25-4.00 (m, 2H), 3.66-3.34 (m, 4H), 2.20-2.00 (m, 2H), 1.41 (s, 9H).

Example 32

Synthesis of Compound 167

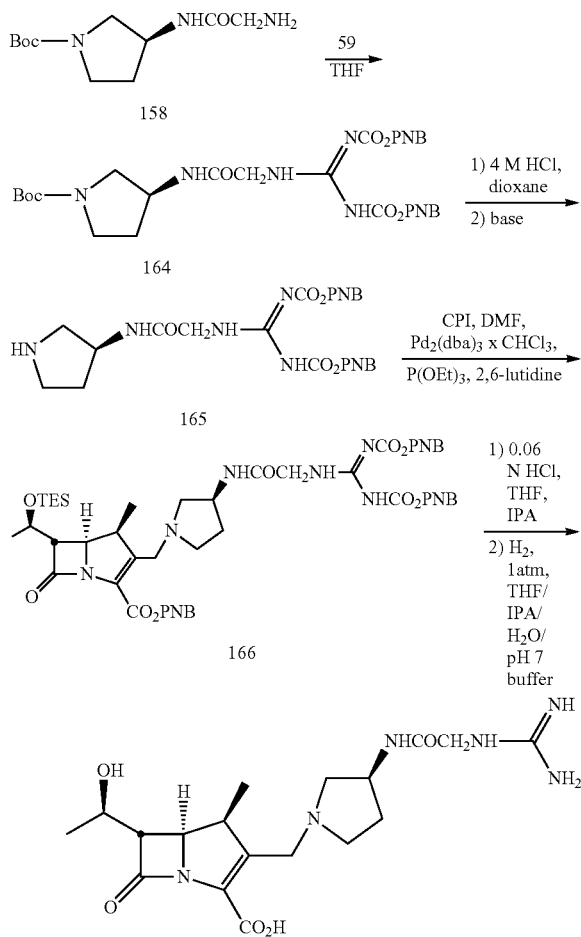

Step 1:
A standard guanidation reaction with 59 afforded the desired product 164 in 52% yield.

$^1$H NMR (DMSO-d$_6$, 400 MHz): δ 11.50 (br s, 1H), 8.94 (t, J=4.4 Hz, 1H), 8.23-8.12 (m, 4H), 7.54-7.50 (m, 4H), 6.68 and 6.62 (br s+br s, 1H), 5.28 (s, 2H), 5.18 (s, 2H), 4.44-4.40 (m, 1H), 4.06 (d, J=4.8 Hz, 2H), 3.59-3.55 (m, 1H), 3.40-3.15 (m, 3H), 2.17-2.06 (m, 1H), 1.90-1.80 (m, 1H), 1.47 (s, 9H).

Step 2:
According to a standard Boc-deprotection procedure, pyrrolidine 165 was prepared in 88% yield.

HCl salt of 172: $^1$H NMR (CDCl$_3$, 400 MHz): δ 11.52 (br s, 1H), 9.23 (br s, 1H), 9.09 (br s, 1H), 8.77 (br s, 1H), 8.54 (d, J=6.4 Hz, 2H), 8.25-8.21 (m, 4H), 7.68 (d, J=8.4 Hz, 2H), 7.59 (d, J=8.4 Hz, 2H), 5.36 (s, 2H), 5.17 (s, 2H), 4.30-4.25 (m, 1H), 3.97 (d, J=4.8 Hz, 2H), 3.33-3.12 (m, 3H), 3.00-2.93 (m, 1H), 2.12-2.03 (m, 1H), 1.83-1.75 (m, 1H).

Step 3:
General Method A for the Pd coupling reaction afforded product 166 in 71% yield.

$^1$H NMR (CDCl$_3$, 400 MHz): δ 11.46 (br s, 1H), 8.99 Br s, 1H), 8.20-8.14 (m, 6H), 7.63 (d, J=8.8 Hz, 2H), 7.53-7.49 (m, 1H), 5.41 (d, J=14.0 Hz, 1H), 5.27 (s, 2H), 5.24 (d, J=14.0 Hz, 1H), 5.17 (s, 2H), 4.42-4.38 (m, 1H), 4.27-4.16 (m, 2H), 4.08-3.99 (m, 3H), 3.90-3.80 (m, 2H), 3.56-3.46 (m, 1H), 3.34-3.20 (m, 3H), 2.75-2.61 (m, 1H), 2.51-2.43 (m, 1H), 2.28-2.20 (m, 1H), 1.22 (d, J=6.0 Hz, 3H), 1.13 (d, J=7.2 Hz, 3H), 0.90 (t, J=8.0 Hz, 9H), 0.57 (q, J=8.0 Hz, 6H).

Step 4:
General method for the removal of the TES protecting group with 0.06 N HCl (described in step 6 of Scheme 33) gave the OH-product, which was used for next step—PNB-deprotection (described in general Method F)—without further isolation or purification to obtain the desired final product 167 in 20% yield.

$^1$H NMR (D$_2$O, 400 MHz): δ 4.03-3.94 (m, 2H), 3.89 (dd, J=8.8, 2.8 Hz, 1H), 3.83-3.77 (m, 1H), 3.60 (d, J=8.8 Hz, 2H), 3.11 (dd, J=6.4, 2.4 Hz, 1H), 3.00-2.98 (m, 1H), 2.78-2.69 (m, 2H), 2.56-2.21 (br m, 3H), 2.09-2.04 (m, 1H), 1.76-1.67 (m, 1H), 1.06 (d, J=6.4 Hz, 3H), 0.87 (d, J=7.2 Hz, 3H).

Example 33

Synthesis of Compound 176 & 178

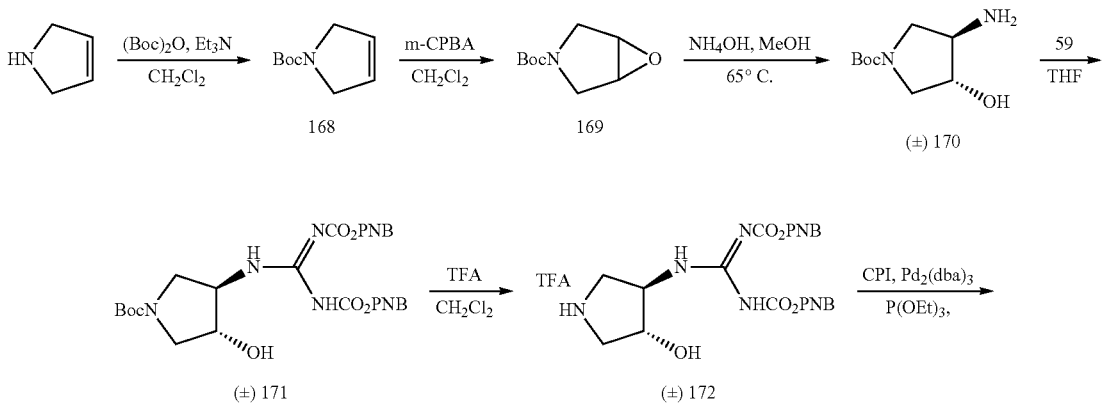

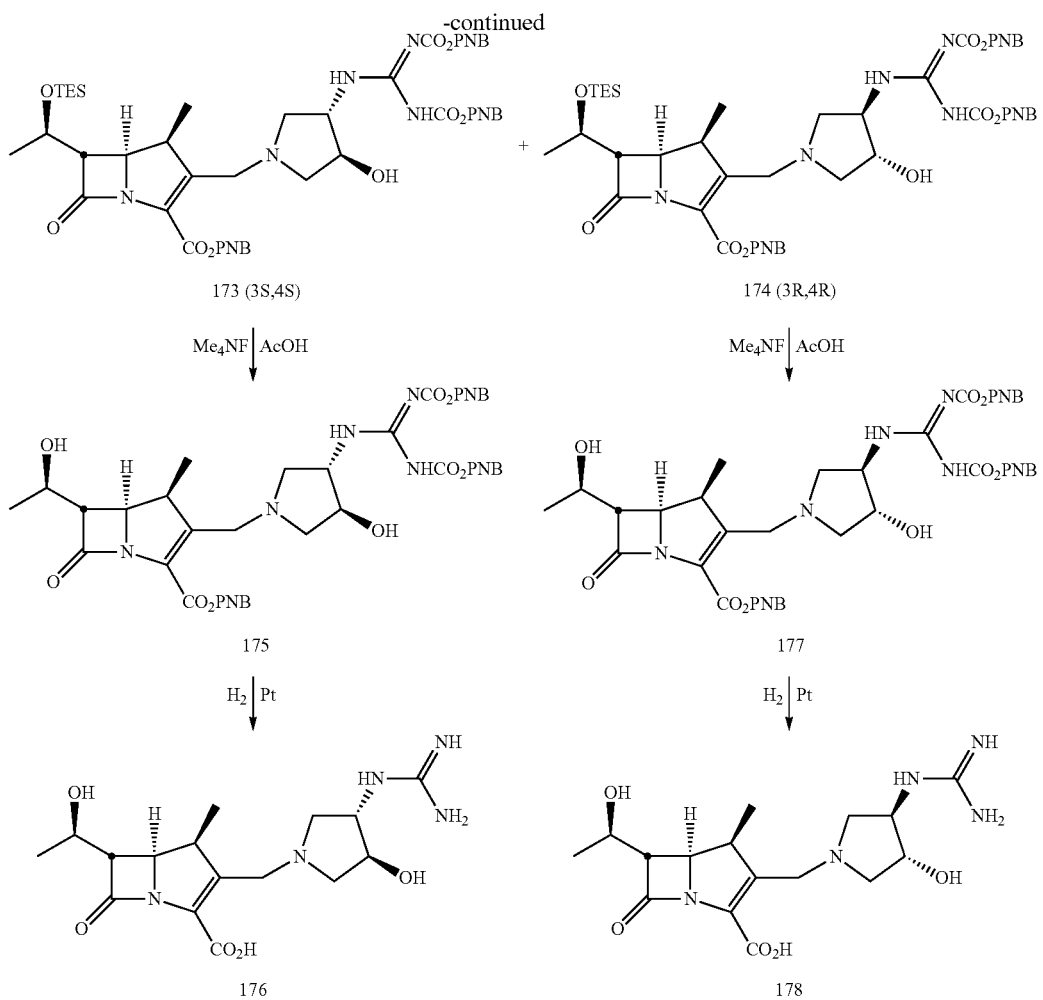

173 (3S,4S)   174 (3R,4R)

175   177

176   178

Step 1:

To solution of 3-pyrroline (4.68 g, 67.8 mmol) in $CH_2Cl_2$ (100 mL) at 0° C. was added $Et_3N$ (14.2 mL, 102 mmol), followed by dropwise addition of a solution of $(Boc)_2O$ (16.28 g, 74.6 mol) in $CH_2C_2$ (25 mL). After addition, the reaction mixture was stirred at room temperature for 15 h. Then the reaction mixture was treated with $H_2O$ and separated. After extraction twice with $CH_2Cl_2$, the combined organic layers dried over $Na_2SO_4$, and concentrated in vacuo to give compound 168 (crude 12.2 g).

$^1H$ NMR ($CDCl_3$, 400 MHz): δ 5.82-5.70 (m, 2H), 4.18-4.03 (m, 4H), 1.46 (s, 9H).

Step 2:

The Boc-protected pyrroline 168 (crude 12.2 g, 67.8 mmol) was dissolved in $CH_2Cl_2$ (200 mL), and m-CPBA (maximum 77% pure, 22.56 g, 101 mmol) was added in portions. After the mixture was stirred at room temperature for 3 days, the precipitate was filtered off and the filtrate was treated with 6N NaOH to PH≈9, after separation, the aqueous phase was extracted twice with $CH_2Cl_2$. The combined organic layers washed with brine, concentrated and purified by a silica gel column chromatography with hexane-EtOAc (from 7:3 to 1:1) to afford a pale yellow oil 169 (7.93 g, 66% yield over 2 steps).

$^1H$ NMR ($CDCl_3$, 400 MHz): δ 3.83-3.67 (m, 4H), 3.33-3.30 (m, 2H), 1.45 (s, 9H).

Step 3:

A solution of the epoxide 169 (6.48 g, 35 mmol) in a mixture of 28% $NH_4OH$ (70 ml) and MeOH (70 ml) in a sealed thick-wall reactor was allowed to stand at 65° C. for 40 h. Then the mixture was cooled down to room temperature and the solvent was evaporated. The oily racemic mixture (±)-170 (7.70 g) was used directly for next step without further purification.

$^1H$ NMR ($CDCl_3$, 400 MHz): δ 4.00 (m, 1H), 3.66 (m, 2H), 3.30 (m, 2H), 3.12 (m, 1H), 2.10 (br s, 3H), 1.46 (s, 9H).

Step 4:

To a solution of hydroxylamine (±)-170 (crude 7.70 g, 35 mmol) in THF (250 ml) was added bis-PNB protected methyl thiourea guanidine 59 (15.37 g, 31.5 mmol), the reaction mixture was aged at rt. for 4 days and then concentrated. The residue was purified by silica gel column chromatography with MeOH—$CH_2Cl_2$ (from 2:98 to 5:95) to give (±)-171 (15.33 g, 80% yield) as a white solid.

$^1H$ NMR ($CDCl_3$, 400 MHz): δ 11.70 (d, J=10.7 Hz, 1H), 8.50 (d, J=14.8 Hz, 1H), 8.24 (dd, J=9.0, 8.8 Hz, 4H), 7.54 (dd, J=8.8, 5.9 Hz, 4H), 5.29 (s, 2H), 5.21 (s, 2H), 4.32-4.20 (m, 2H), 3.98-3.74 (m, 2H), 3.34-3.20 (m, 2H).

Step 5:

A 500 ml flask loaded with $CH_2Cl_2$ (150 mL) was cooled with ice-bath, to this was added TFA (17.3 ml, 0.23 mol)

followed by compound (±)-171 (9.03 g, 15 mmol) as a solid. The reaction mixture was aged at 0° C. overnight and then concentrated in vacuo. The concentrate was washed with hexane and dry Et$_2$O to afford TFA•salt (±)-172 (8.68 g).

$^1$H NMR (CDCl$_3$, 400 MHz): δ 11.50 (s, 1H), 10.20 (br s, 2H), 8.37 (d, J=6.3 Hz, 1H), 8.08 (t, J=8.8 Hz, 4H), 7.42 (dd, J=8.8, 3.0 Hz, 4H), 5.15 (s, 2H), 5.08 (s, 2H), 4.42-4.27 (m, 2H), 3.60 (dd, J=12.4, 6.6 Hz, 1H), 3.46-3.30 (m, 2H), 3.16 (dd, J=12.4, 2.0 Hz, 1H).

Step 6:

According to General Method D, CPI (1.8 g, 3.0 mmol), side chain 172 (1.85 g, 3.0 mmol), Pd$_2$(dba)$_3$CHCl$_3$ (199 mg, 0.192 mmol) and P(OEt)$_3$ (203 µL, 1.18 mmol) in THF/Toluene (10/90 mL) were reacted overnight to afford the desired TES product 173 (3S,4S) (less polar isomer: 1.3 g, 45%) and 174 (3R,4R) (polar isomer: 1.38 g, 48%).

173 (3S,4S): $^1$H NMR (CDCl$_3$, 400 MHz): δ 11.63 (br s, 1H), 8.42 (d, J=4.4 Hz, 1H), 8.22 (m, 6H), 7.66 (d, J=8.4 Hz, 2H), 7.53 (d, J=9.2 Hz, 2H), 7.51 (d, J=8.8 Hz, 2H), 5.44 (d, J=14.0 Hz, 1H), 5.28-5.16 (m, 5H), 4.89 (s, 1H), 4.25 (t, J=6.0 Hz, 1H), 4.19 (dd, J=6.4, 2.8 Hz, 1H), 4.16-4.02 (m, 2H), 3.88 (d, J=14.4 Hz, 1H), 3.32 (d, J=14.4 Hz, 1H), 3.31 (m, 1H), 3.24 (dd, J=5.6, 2.8 Hz, 1H), 3.09 (dd, J=9.6, 7.6 Hz, 1H), 2.97 (dd, J=10.0, 7.2 Hz, 1H), 2.62 (dd, J=10.0, 4.8 Hz, 1H), 2.44 (dd, J=9.6, 6.4 Hz, 1H), 1.25 (d, J=6.4 Hz, 3H), 1.17 (d, J=7.2 Hz, 3H), 0.94 (t, J=8.0 Hz, 9H), 0.60 (q, J=8.0 Hz, 6H).

174 (3R,4R): $^1$H NMR (CDCl$_3$, 400 MHz): δ 11.64 (br s, 1H), 8.42 (d, J=4.4 Hz, 1H), 8.22 (m, 6H), 7.66 (d, J=8.8 Hz, 2H), 7.53 (d, J=8.4 Hz, 2H), 7.51 (d, J=8.8 Hz, 2H), 5.44 (d, J=13.6 Hz, 1H), 5.33-5.16 (m, 5H), 4.95 (s, 1H), 4.25 (t, J=6.0 Hz, 1H), 4.21 (dd, J=6.4, 2.8 Hz, 1H), 4.16-4.02 (m, 2H), 3.86 (d, J=14.4 Hz, 1H), 3.32 (d, J=14.0 Hz, 1H), 3.31 (m, 1H), 3.24 (dd, J=5.6, 2.8 Hz, 1H), 3.06 (dd, J=9.6, 7.6 Hz, 1H), 2.86 (dd, J=10.0, 7.2 Hz, 1H), 2.70 (dd, J=10.0, 4.4 Hz, 1H), 2.52 (dd, J=9.6, 7.2 Hz, 1H), 1.25 (d, J=6.4 Hz, 3H), 1.16 (d, J=7.2 Hz, 3H), 0.94 (t, J=8.0 Hz, 9H), 0.60 (q, J=8.0 Hz, 6H).

Step 7:

According to General Method E, TES compound 173 (3S,4S) (1.3 g, 1.35 mmol), Me$_4$NF.4H$_2$O (0.40 g, 2.42 mmol), AcOH (350 µL, 5.83 mmol) in THF (20 mL) and IPA (5 mL) were reacted for 24 h to afford the desired OH product 175 (3S,4S) (1.0 g, 85%).

$^1$H NMR (CDCl$_3$, 400 MHz): δ 11.62 (br s, 1H), 8.44 (d, J=4.4 Hz, 1H), 8.23 (d, J=8.8 Hz, 2H), 8.22 (d, J=8.8 Hz, 2H), 8.19 (d, J=7.6 Hz, 2H), 7.64 (d, J=8.8 Hz, 2H), 7.52 (d, J=8.4 Hz, 2H), 7.50 (d, J=8.4 Hz, 2H), 5.46 (d, J=14.0 Hz, 1H), 5.27 (s, 2H), 5.20 (d, J=15.2 Hz, 1H), 5.19 (s, 2H), 4.89 (s, 1H), 4.24 (t, J=6.4 Hz, 1H), 4.20 (dd, J=10.0, 6.8 Hz, 1H), 4.16-4.02 (m, 2H), 3.87 (d, J=14.4 Hz, 1H), 3.35 (m, 1H), 3.31 (d, J=14.4 Hz, 1H), 3.24 (dd, J=6.4, 2.8 Hz, 1H), 3.04 (dd, J=9.6, 7.6 Hz, 1H), 2.98 (dd, J=9.6, 7.2 Hz, 1H), 2.54 (dd, J=9.6, 4.8 Hz, 1H), 2.45 (dd, J=9.6, 5.6 Hz, 1H), 1.31 (d, J=6.0 Hz, 3H), 1.17 (d, J=7.2 Hz, 3H).

Step 9

According to General Method H, OH compound 175 (3S,4S) (0.44 g, 0.50 mmol), 5% Pt/C (300 mg) in IPA (5 mL), THF (12 mL), DI water (4 mL) and pH=6 buffer (6 mL) were reacted for 0.5 h to afford the desired product 176 (3S,4S) (60 mg, 31%).

$^1$H NMR (D$_2$O, 400 MHz): δ 4.09-3.98 (m, 3H), 3.65 (q, J=5.2 Hz, 1H), 3.55 (d, J=13.2 Hz, 1H), 3.21 (dd, J=6.0, 3.2 Hz, 1H), 3.13 (d, J=13.2 Hz, 1H), 3.02 (dd, J=9.6, 7.2 Hz, 1H), 2.94 (dd, J=10.8, 8.0 Hz, 1H), 2.86 (dd, J=10.8, 7.2 Hz, 1H), 2.39 (m, 2H), 1.08 (d, J=6.4 Hz, 3H), 0.90 (d, J=7.2 Hz, 3H).

Step 10:

According to General Method E, TES compound 174 (3R,4R) (1.38 g, 1.44 mmol), Me$_4$NF.4H$_2$O (0.36 g, 2.18 mmol), AcOH (343 µL, 5.72 mmol) in THF (20 mL) and IPA (5 mL) were reacted for 24 h to afford the desired OH product 177 (3R,4R) (1.14 g, 91%).

$^1$H NMR (CDCl$_3$, 400 MHz): δ 11.63 (br s, 1H), 8.42 (d, J=4.0 Hz, 1H), 8.25-8.17 (m, 6H), 7.64 (dd, J=8.8, 3.6 Hz, 2H), 7.55-7.49 (m, 4H), 5.47 (d, J=14.4 Hz, 1H), 5.28 (s, 2H), 5.23-5.19 (m, 3H), 4.92 (s, 1H), 4.26-4.20 (m, 2H), 4.16-4.02 (m, 2H), 3.86 (d, J=14.0 Hz, 1H), 3.37 (d, J=13.6 Hz, 1H), 3.28 (m, 1H), 3.26 (m, 1H), 3.04 (m, 2H), 2.87 (dd, J=9.6, 7.2 Hz, 1H), 2.66 (m, 1H), 2.50 (dd, J=9.6, 5.6 Hz, 1H), 1.31 (d, J=6.0 Hz, 3H), 1.17 (d, J=7.2 Hz, 3H).

Step 11:

According to General Method H, OH compound 177 (3R,4R) (0.50 g, 0.57 mmol), 5% Pt/C (400 mg) in IPA (5 mL), THF (12 mL), DI water (6 mL) and pH=6 buffer (4 mL) were reacted for 0.5 h to afford the desired product 176 (3R,4R) (75 mg, 35%).

$^1$H NMR (D$_2$O, 400 MHz): δ 4.06-3.96 (m, 3H), 3.65 (br s, 1H), 3.51 (d, J=13.2 Hz, 1H), 3.21 (dd, J=6.0, 2.8 Hz, 1H), 3.16 (d, J=13.2 Hz, 1H), 3.00 (dd, J=10.0, 6.8 Hz, 1H), 2.84 (dd, J=10.8, 8.0 Hz, 1H), 2.77 (dd, J=10.8, 7.2 Hz, 1H), 2.40 (m, 2H), 1.07 (d, J=6.0 Hz, 3H), 0.90 (d, J=7.2 Hz, 3H).

Example 34

Synthesis of Compound 185a & 185b

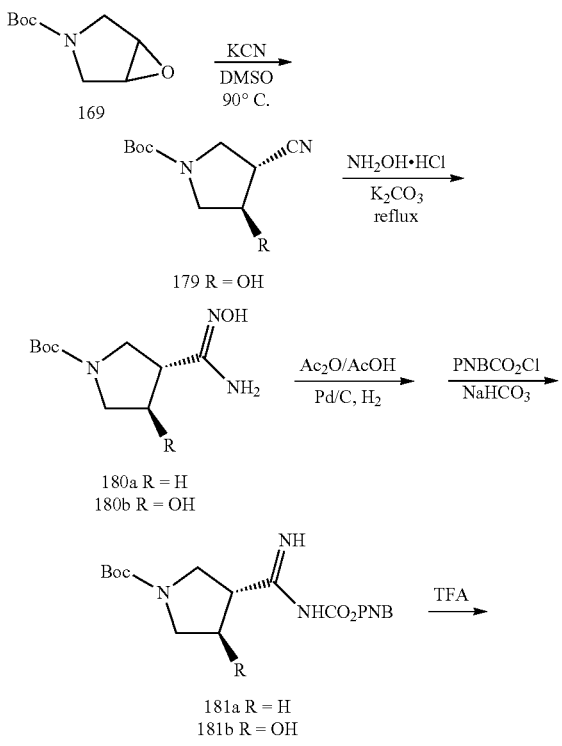

SCHEME 36

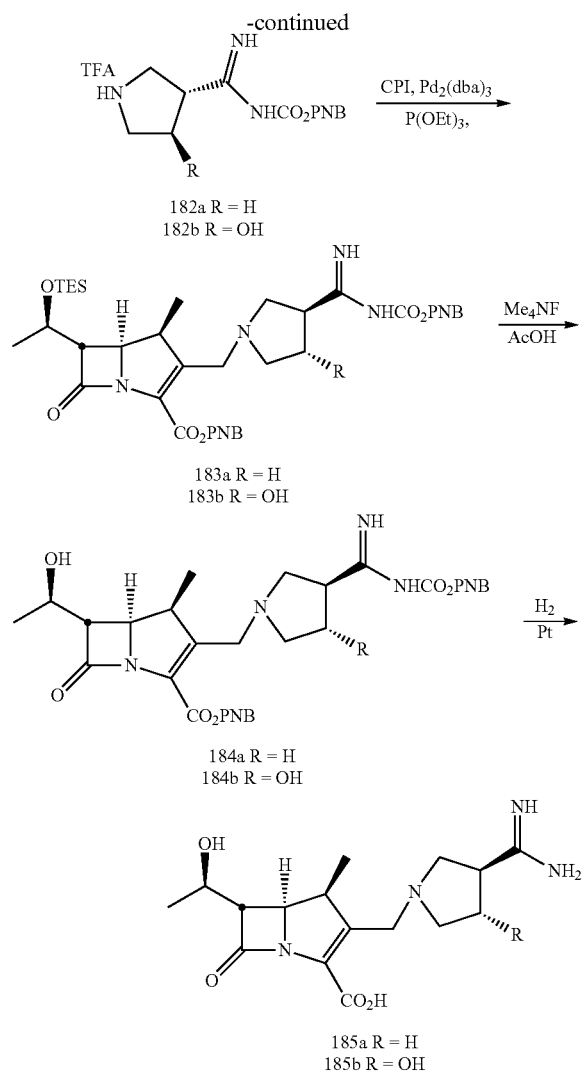

182a R = H
182b R = OH

183a R = H
183b R = OH

184a R = H
184b R = OH

185a R = H
185b R = OH

Step 1:

To a solution of epoxide 169 (4.0 g, 21.6 mmol) in dry DMSO (20 mL) was added KCN (2.8 g, 43.2 mmol), and the reaction mixture was stirred at 90° C. for 4 days. After cooling down to room temperature, the mixture was diluted with ethyl acetate (100 mL) and washed with water (100 mL). The organic phase was separated, washed again with brine, and dried over anhydrous MgSO$_4$. After concentration, the crude was purified by a flash column chromatography (EtOAc/Hexane 1:1) to afford the desired compound 179 (2.0 g, 48%) as colorless oil.

$^1$H NMR (CDCl$_3$, 400 MHz) δ, 4.60 (m, 1H), 3.78-3.60 (m, 3H), 3.40 (m, 1H), 3.04 (m, 1H), 2.42 (br s, 1H), 1.49 (s, 9H)

Step 2: General Procedures for Hydroxyamilation of Nitrile

A solution of 93 (2.80 g, 14.2 mmol), hydroxylamine hydrochloride (1.98 g, 28.4 mmol) and potassium carbonate (3.92 g, 28.4 mmol) in absolute ethanol (50 mL) was heated under reflux for 3 h and allowed to stir at room temperature overnight and filtered. Evaporation of the filtrate and purification of the residue by flash chromatography using ethyl acetate as the elute gave 2.50 g (78%) of 180a as foam.

$^1$H NMR (CDCl$_3$, 400 MHz) δ 4.51 (s, 2H), 3.59-3.30 (m, 5H), 2.89 (m, 1H), 2.11-2.01 (m, 2H), 1.41 (s, 9H)

According to the general procedure as above, 179 (2.0 g, 9.44 mmol), NH$_2$OH.HCl (2.0 g, 28 mmol) and K$_2$CO$_3$ (3.88 g, 28 mmol) were reacted in ethanol to afford the desired product 180b (2.0 g, 86%).

$^1$H NMR (DMSO, 400 MHz) δ 9.00 (br s, 1H), 5.38 (br s, 2H), 5.19 (m, 1H), 4.22 (m, 1H), 4.00 (m, 1H), 3.41-3.20 (m, 2H), 3.07 (m, 1H), 2.60 (m, 1H), 1.39 (s, 9H)

Step 3: General Procedures for De-Hydroxylation & Protection

A mixture of 180a (2.10 g, 10.5 mmol), acetic anhydride (1.98 mL, 21 mmol), Pd/C (5%, 210 mg) and acetic acid (0.5 mL) in ethanol (100 mL) was shaken under hydrogen (50 psi) on a Parr hydrogenator for 15 h. The catalyst was removed by filtration and the filtrate was evaporated to dryness. The residue was dissolved in a mixture of dry ethanol (50 mL) and toluene (50 mL), and evaporated to dryness. This process was repeated three times and the crude amidine residue was used without further purification.

To a cooled (0° C.) solution of amidine salt and sodium bicarbonate (1.93 g, 23.1 mmol) in dichloromethane/water (30 mL/30 mL) was added 4-nitrobenzyl chloroformate (2.71 g, 12.6 mmol). After stirring at room temperature for 2 h, the layers were separated and the aqueous was extracted with CH$_2$Cl$_2$ (3×25 mL). The combined organics were dried over NaSO$_4$ and concentrated to afford crude material. Flash column chromatography (EtOAc/Hexane 3:1) provided title compound 181a (1.60 g, 41%) as white foam solid.

$^1$H NMR (CDCl$_3$, 400 MHz) δ 8.85 (br s, 1H), 8.72 (br s, 1H), 8.22 (d, J=7.2 Hz, 2H), 7.60 (d, J=7.2 Hz, 2H), 5.08 (s, 2H), 3.40 (m, 2H), 3.20 (m, 2H), 2.99 (m, 1H), 2.03-1.82 (m, 2H), 1.39 (s, 9H).

According to the general procedure as above, 181b was prepared with 31% yield (1 g) from 2.0 g of 180b.

$^1$H NMR (CDCl$_3$, 400 MHz) δ 9.26 (br s, 1H), 8.12 (d, J=7.2 Hz, 2H), 7.59 (d, J=7.2 Hz, 2H), 5.10 (s, 2H), 4.50 (m, 1H), 3.79 (m, 2H), 3.52 (m, 2H), 3.20 (m, 1H), 2.91 (m, 1H), 1.39 (s, 9H).

Step 4:

Compound 181a (1.60 g, 4.23 mmol) was added portionwise to a stirred, cooled (0° C.) solution of trifluoroacetic acid (5.0 mL) in CH$_2$Cl$_2$ (20 mL). This mixture was stirred under nitrogen for 2 h and then evaporated to dryness. The residue was purified by flash chromatography using CH$_2$Cl$_2$: MeOH (7:3) as the elute to yield trifluoroacetic acid salt 182a (1.5 g, 92%) as foam.

$^1$H NMR (DMSO, 400 MHz) δ 8.10 (d, J=7.2 Hz, 2H), 7.63 (d, J=7.2 Hz, 2H), 5.13 (s, 2H), 3.99 (br s, 4H), 3.40-3.18 (m, 5H), 2.28 (m, 1H), 2.03 (m, 1H).

In a similar manner as above, 181b (1.0 g, 2.53 mmol) and trifluoroacetic acid (2.9 mL, 37.95 mmol) were reacted to afford the desired product 182b (0.9 g, 88%).

$^1$H NMR (CDCl$_3$, 400 MHz) δ 8.10 (d, J=7.2 Hz, 2H), 7.63 (d, J=7.2 Hz, 2H), 5.13 (s, 2H), 4.20 (br s, 4H), 3.88-3.52 (m, 4H), 3.00 (m, 2H).

Step 5:

According to General Method D, CPI (524 mg, 0.89 mmol), side chain 182a (360 mg, 0.89 mmol), DIEA (154 mL, 0.89 mmol) Pd$_2$(dba)$_3$CHCl$_3$ (83.5 mg, 0.081 mmol) and P(OEt)$_3$ (87 μL, 0.51 mmol) in THF/Toluene (3/25 mL) were reacted for 5 h to afford the desired TES product 183a (0.3 g, 44%).

$^1$H NMR (CDCl$_3$, 400 MHz) δ 8.88 (br s, 1H), 8.20 (m, 4H), 7.98 (br s, 1H), 7.65 (d, J=8.8 Hz, 2H), 7.56 (d, J=8.4 Hz, 2H), 5.43 (d, J=13.6 Hz, 1H), 5.21 (d, J=14.0 Hz, 1H), 5.20 (s, 2H), 4.28-4.22 (m, 2H), 3.95 (d, J=13.6 Hz, 0.7H), 3.90 (d, J=14.4 Hz, 0.3H), 3.42 (d, J=14.0 Hz, 0.3H), 3.32 (d, J=14.0 Hz, 0.7H), 3.27-2.89 (m, 5H), 2.55-2.17 (m, 3H), 1.96 (m, 1H), 1.24 (d, J=6.0 Hz, 3H), 1.18 (d, J=7.2 Hz, 3H), 0.95-0.91 (m, 9H), 0.62-0.56 (m, 6H)

According to General Method D, CPI (1.2 g, 2.0 mmol), side chain 182b (880 mg, 2.09 mmole), DIEA (450 μL, 2.59 mmole), Pd$_2$(dba)$_3$CHCl$_3$ (145.5 mg, 0.14 mmol) and P(OEt)$_3$ (151 μL, 0.88 mmol) in THF/Toluene (10/40 mL) were reacted for 5 h to afford the desired TES product 183b (diastereomer mixture, 0.33 g, 21%).

$^1$H NMR (CDCl$_3$, 400 MHz) δ 8.92 (br s, 1H), 8.22 (d, J=8.8 Hz, 2H), 8.19 (d, J=9.6 Hz, 2H), 7.92 (br s, 1H), 7.65 (d, J=8.8 Hz, 2H), 7.53 (d, J=8.0 Hz, 2H), 5.43 (d, J=13.2 Hz, 1H), 5.22 (d, J=13.2 Hz, 1H), 5.20 (s, 2H), 4.45 (br s, 1H), 4.27-4.20 (m, 2H), 4.00 (d, J=13.2 Hz, 0.5H), 3.90 (d, J=14.0 Hz, 0.5H), 3.39 (d, J=14.0 Hz, 0.5H), 3.30-2.89 (m, 7.5H), 2.41-2.31 (m, 1H), 1.24 (d, J=6.0 Hz, 3H), 1.18 (d, J=7.2 Hz, 3H), 0.93 (t, J=8.0 Hz, 9H), 0.59 (q, J=8.0 Hz, 6H)

Step 6:

According to General Method E, TES compound 183a (0.6 g, 0.79 mmol), Me$_4$NF.4H$_2$O (0.36 g, 2.18 mmol), AcOH (300 μL, 5.00 mmol) in THF (20 mL) and IPA (5 mL) were reacted for 24 h to afford the desired OH product 184a (270 mg, 53%).

$^1$H NMR (CDCl$_3$, 400 MHz): δ 8.92 (br s, 1H), 8.20 (m, 4H), 7.98 (br s, 1H), 7.66 (d, J=8.8 Hz, 2H), 7.57 (d, J=7.6 Hz, 2H), 5.47 (d, J=13.6 Hz, 1H), 5.25-5.17 (m, 3H), 4.30-4.23 (m, 2H), 3.96 (d, J=14.4 Hz, 0.5H), 3.91 (d, J=14.8 Hz, 0.5H), 3.43 (d, J=14.8 Hz, 0.5H), 3.34 (d, J=14.0 Hz, 0.5H), 3.27-2.89 (m, 6H), 2.55-2.17 (m, 3H), 1.96 (m, 1H), 1.24 (d, J=6.0 Hz, 3H), 1.18 (d, J=7.2 Hz, 3H)

According to General Method E, TES compound 183b (0.33 g, 0.42 mmol), Me$_4$NF.4H$_2$O (0.40 g, 2.42 mmol), AcOH (400 μL, 6.67 mmol) in THF (20 mL) and IPA (5 mL) were reacted for 24 h to afford the desired OH product 184a (180 mg, 64%).

$^1$H NMR (CDCl$_3$, 400 MHz) δ 8.92 (br s, 1H), 8.22-8.17 (m, 4H), 7.92 (br s, 1H), 7.63 (d, J=8.0 Hz, 2H), 7.53 (m, 2H), 5.48-5.43 (m, 1H), 5.22 (d, J=14.8 Hz, 1H), 5.19 (s, 2H), 4.42 (br s, 1H), 4.29-4.20 (m, 2H), 4.03-3.87 (m, 2H), 3.39-2.72 (m, 8H), 2.41-2.31 (m, 1H), 1.24 (d, J=6.0 Hz, 3H), 1.18 (d, J=7.2 Hz, 3H)

Step 7:

According to General Method H, OH compound 184a (0.27 g, 0.42 mmol), 5% Pt/C (400 mg) in IPA (5 mL), THF (12 mL), DI water (10 mL) were reacted for 0.5 h to afford the desired product 185a (35 mg, 25%).

$^1$H NMR (D$_2$O, 400 MHz): δ 4.07-3.98 (m, 2H), 3.54 (d, J=14.0 Hz, 1H), 3.23 (m, 2H), 3.04 (m, 2H), 2.84-2.53 (m, 4H), 2.14 (br s, 1H), 1.80 (m, 1H), 1.08 (d, J=6.4 Hz, 3H), 0.91 (d, J=7.2 Hz, 3H)

According to General Method H, OH compound 184b (0.18 g, 0.27 mmol), 5% Pt/C (400 ing) in IPA (5 mL), THF (12 mL), DT water (10 mL) were reacted for 0.5 h to afford the desired product 185b (22 mg, 23%).

$^1$H NMR (D$_2$O, 400 MHz) δ 4.31 (br s, 1H), 4.03-3.96 (m, 2H), 3.53 (d, J=13.2 Hz, 1H), 3.21 (m, 1H), 3.15 (d, J=13.6 Hz, 1H), 3.03-2.80 (m, 5H), 2.64 (m, 1H), 2.39-2.27 (m, 1H), 1.07 (d, J=4.8 Hz, 3H), 0.96-0.88 (m, 3H)

Example 35

Dilution Antimicrobial Susceptibility Tests

The MIC (minimum inhibitory concentration) was determined by the NCCLS (National Committee for Clinical Laboratory Standards) methods 2000. Methods for dilution antimicrobial susceptibility testing for bacteria that growth aerobically (M7-A5, vol. 20, No. 2). The agar dilution method for determining antimicrobial susceptibility was carried out using Mueller-Hinton agar. A final inoculum of $10^4$ CFU/spot was applied with an inoculation device. Broth dilution tests were performed with 5×10$^5$ CFU/well in 96 well plates. The susceptibilities of streptococci were determined by Mueller-Hinton agar supplemented with 5% sheep blood. All assays were run with the indicated control strains, available from the ATCC (American Type Culture Collection, Rockville, Md.). Results of the antimicrobial susceptibility tests of certain compounds against Gram-negative organisms are shown in Table 1.

Abbreviations used in Table 1 are defined as follows: Cf-R: Ceftazidime Resistance, Ci-R: Ciprofloxacin Resistance, Gen-R: Gentamycin Resistance, Imp-R: Imipenem Resistance, Mp-R: Meropenem Resistance, Ofx-R: Ofloxacin Resistance, B+: β-lactamase Production, AmpC: AmpC-lactamase Hyper production, CBPase: Carbapenemase Production.

TABLE 1

| | | | | Antibacterial activity (MIC$^a$) data on G(−) bacterial strains | | | | | | | | |
|---|---|---|---|---|---|---|---|---|---|---|---|---|
| # | Genus | Species | Resistance $^b$ | 7 | 12 | 19 | 27 | 32 | 37 | 43 | 46 | Meropenem |
| 1 | Acinetobacter | calcoaceticus | | 4 | 0.5 | 0.5 | 0.25 | 2 | 2 | 0.5 | 1 | 0.5 |
| 2 | Acinetobacter | baumannii | Cf-R, Ci-R | 2 | 0.5 | 0.5 | 0.5 | 2 | 4 | 1 | 2 | 1 |
| 3 | Acinetobacter | baumannii | Cf-R, Ci-R, Mp-I | 4 | 2 | 2 | 2 | 4 | 8 | 4 | 4 | 8 |
| 4 | Acinetobacter | baumannii | Cf-R, Imp-I, CBPase | 4 | 1 | 1 | 1 | 2 | 4 | 4 | 4 | 4 |
| 5 | Citrobacter | diversus | | 0.063 | 0.13 | 0.25 | 0.25 | 1 | 0.5 | 0.25 | 0.25 | 0.016 |
| 6 | Citrobacter | freundii | | 0.13 | 0.25 | 0.25 | 0.25 | 1 | 0.5 | 0.25 | 0.5 | 0.016 |
| 7 | Enterobacter | aerogenes | | 0.5 | 1 | 1 | 1 | 4 | 2 | 1 | 1 | 0.063 |
| 8 | Enterobacter | cloacae | Cf-R, B+ | 0.13 | 0.13 | 0.25 | 0.25 | 1 | 0.5 | 0.25 | 0.25 | 0.016 |
| 9 | Enterobacter | cloacae | Cf-R | 0.25 | 0.25 | 0.5 | 0.5 | 2 | 1 | 0.5 | 0.5 | 0.063 |
| 10 | Escherichia | coli | Ci-R | 0.13 | 0.13 | 0.25 | 0.25 | 1 | 0.5 | 0.25 | 0.25 | 0.016 |
| 11 | Escherichia | coli | Ci-R, AmpC | 0.13 | 0.13 | 0.25 | 0.25 | 0.5 | 0.5 | 0.25 | 0.25 | 0.016 |
| 12 | Escherichia | coli | | 0.13 | 0.13 | 0.25 | 0.25 | 1 | 0.5 | 0.25 | 0.25 | 0.016 |
| 13 | Escherichia | coli | | 0.13 | 0.25 | 0.25 | 0.25 | 1 | 0.5 | 0.25 | 0.25 | 0.016 |
| 14 | Klebsiella | oxytoca | | 0.25 | 0.5 | 0.5 | 0.5 | 2 | 0.5 | 0.5 | 0.5 | 0.031 |
| 15 | Klebsiella | pneumoniae | | 0.25 | 0.5 | 0.5 | 0.5 | 2 | 1 | 0.5 | 0.5 | 0.031 |
| 16 | Moraxella | catarrhalis | | ≤0.008 | ≤0.008 | ≤0.008 | ≤0.008 | 0.016 | ≤0.008 | ≤0.008 | ≤0.008 | ≤0.008 |
| 17 | Morganella | Morganii | | 1 | 2 | 4 | 4 | 8 | 2 | 2 | 2 | 0.13 |
| 18 | Morganella | Morganii | | 1 | 1 | 2 | 2 | 4 | 2 | 2 | 2 | 0.13 |
| 19 | Proteus | vulgaris | | 0.5 | 0.5 | 1 | 1 | 4 | 1 | 1 | 1 | 0.13 |

TABLE 1-continued

Antibacterial activity (MIC$^a$) data on G(−) bacterial strains

| # | Genus | Species | Resistance | | | | | | | | |
|---|---|---|---|---|---|---|---|---|---|---|---|
| 20 | Proteus | mirabilis | | 0.13 | 0.25 | 0.25 | 0.25 | 1 | 0.5 | 0.25 | 0.25 | 0.031 |
| 21 | Providencia | rettgeri | | 0.5 | 1 | 1 | 1 | 4 | 1 | 1 | 1 | 0.031 |
| 22 | Salmonella | typhimurium | | 0.13 | 0.25 | 0.25 | 0.25 | 1 | 0.5 | 0.5 | 0.25 | 0.016 |
| 23 | Serratia | marcescens | | 0.25 | 0.5 | 1 | 0.5 | 2 | 1 | 1 | 1 | 0.031 |
| 24 | Serratia | marcescens | | 0.5 | 1 | 1 | 1 | 2 | 2 | 1 | 1 | 0.031 |
| 25 | Shigella | dysenteriae | | 0.25 | 0.25 | 0.25 | 0.5 | 1 | 0.5 | 0.5 | 0.5 | 0.016 |
| 26 | Shigella | sonnei | | 0.13 | 0.25 | 0.25 | 0.25 | 1 | 0.5 | 0.25 | 0.25 | 0.016 |
| 27 | Shigella | flexneri | | 0.13 | 0.25 | 0.25 | 0.13 | 0.5 | 0.25 | 0.25 | 0.25 | 0.016 |
| 28 | Stenotrophomonas | maltophilia | | 0.5 | 0.25 | 0.25 | 0.13 | 1 | 1 | 0.5 | 0.5 | 0.25 |
| 29 | Pseudomonas | aeruginosa | | 16 | 4 | 4 | 2 | 16 | 8 | 4 | 4 | 0.25 |
| 30 | Pseudomonas | aeruginosa | | 8 | 4 | 4 | 2 | 16 | 8 | 2 | 4 | 0.5 |
| 31 | Pseudomonas | aeruginosa | Ofx-R | 2 | 1 | 1 | 0.5 | 4 | 4 | 1 | 1 | 0.5 |
| 32 | Pseudomonas | aeruginosa | Cf-R | 8 | 4 | 4 | 2 | 16 | 8 | 4 | 4 | 0.13 |
| 33 | Pseudomonas | aeruginosa | Ci-R | 8 | 4 | 4 | 2 | 16 | 8 | 4 | 4 | 1 |
| 34 | Pseudomonas | aeruginosa | Gen-R | 8 | 4 | 4 | 2 | 16 | 8 | 4 | 4 | 0.5 |
| 35 | Pseudomonas | aeruginosa | Ip-R | 32 | 8 | 8 | 4 | 32 | 16 | 8 | 16 | 4 |
| 36 | Pseudomonas | aeruginosa | Cf-R, Ci-R, Mp-R | >32 | 32 | 32 | 8 | >32 | 32 | 16 | 32 | 8 |

| # | Genus | Species | Resistance | 49 | 58 | 64 | 67 | 72 | 78 | 83 | 84 | Meropenem |
|---|---|---|---|---|---|---|---|---|---|---|---|---|
| 1 | Acinetobacter | calcoaceticus | | 0.25 | 0.5 | 0.13 | 2 | 1 | 2 | 2 | 0.25 | 0.5 |
| 2 | Acinetobacter | baumannii | Cf-R, Ci-R | 0.5 | 2 | 1 | 8 | 2 | 2 | 4 | 0.5 | 1 |
| 3 | Acinetobacter | baumannii | Cf-R, Ci-R, Mp-I | 2 | 4 | 1 | 8 | 4 | 4 | 8 | 1 | 8 |
| 4 | Acinetobacter | baumannii | Cf-R, Imp-I, CBPase | 1 | 2 | 0.5 | 4 | 4 | 4 | 8 | 1 | 4 |
| 5 | Citrobacter | diversus | | 0.063 | 0.13 | 0.5 | 0.13 | 0.5 | 0.5 | 0.5 | 0.25 | 0.016 |
| 6 | Citrobacter | freundii | | 0.13 | 0.25 | 0.5 | 0.25 | 0.5 | 0.5 | 1 | 0.5 | 0.016 |
| 7 | Enterobacter | aerogenes | | 0.25 | 0.5 | 1 | 4 | 1 | 2 | 4 | 1 | 0.063 |
| 8 | Enterobacter | cloacae | Cf-R, B+ | 0.063 | 0.13 | 0.5 | 0.13 | 0.25 | 0.5 | 0.5 | 0.25 | 0.016 |
| 9 | Enterobacter | cloacae | Cf-R | 0.13 | 0.25 | 0.5 | 0.25 | 1 | 1 | 1 | 0.5 | 0.063 |
| 10 | Escherichia | coli | Ci-R | 0.063 | 0.13 | 0.25 | 0.13 | 0.25 | 0.5 | 0.5 | 0.25 | 0.016 |
| 11 | Escherichia | coli | Ci-R, AmpC | 0.063 | 0.13 | 0.25 | 0.13 | 0.25 | 0.5 | 0.5 | 0.25 | 0.016 |
| 12 | Escherichia | coli | | 0.063 | 0.13 | 0.5 | 0.13 | 0.25 | 0.5 | 0.5 | 0.25 | 0.016 |
| 13 | Escherichia | coli | | 0.13 | 0.25 | 0.5 | 0.25 | 0.5 | 1 | 1 | 0.5 | 0.016 |
| 14 | Klebsiella | oxytoca | | 0.25 | 0.25 | 1 | 0.25 | 1 | 1 | 2 | 0.5 | 0.031 |
| 15 | Klebsiella | pneumoniae | | 0.25 | 0.25 | 1 | 4 | 0.5 | 1 | 1 | 0.5 | 0.031 |
| 16 | Moraxella | catarrhalis | | ≤0.008 | ≤0.008 | ≤0.008 | 0.016 | 0.016 | 0.016 | 0.031 | ≤0.008 | ≤0.008 |
| 17 | Morganella | Morganii | | 2 | 1 | 4 | 16 | 4 | 8 | 8 | 4 | 0.13 |
| 18 | Morganella | Morganii | | 1 | 1 | 2 | 16 | 4 | 4 | 8 | 2 | 0.13 |
| 19 | Proteus | vulgaris | | 0.5 | 0.5 | 1 | 16 | 2 | 4 | 4 | 1 | 0.13 |
| 20 | Proteus | mirabilis | | 0.13 | 0.25 | 0.5 | 0.25 | 0.5 | 1 | 1 | 0.5 | 0.031 |
| 21 | Providencia | rettgeri | | 0.5 | 0.5 | 2 | 16 | 2 | 4 | 4 | 2 | 0.031 |
| 22 | Salmonella | typhimurium | | 0.13 | 0.25 | 0.5 | 0.25 | 0.5 | 1 | 1 | 0.5 | 0.016 |
| 23 | Serratia | marcescens | | 0.25 | 0.5 | 1 | 0.5 | 1 | 2 | 2 | 1 | 0.031 |
| 24 | Serratia | marcescens | | 0.25 | 0.5 | 2 | 0.5 | 1 | 2 | 2 | 1 | 0.031 |
| 25 | Shigella | dysenteriae | | 0.13 | 0.25 | 0.5 | 0.25 | 0.5 | 1 | 1 | 0.5 | 0.016 |
| 26 | Shigella | sonnei | | 0.13 | 0.25 | 0.5 | 0.25 | 0.5 | 1 | 1 | 0.5 | 0.016 |
| 27 | Shigella | flexneri | | 0.063 | 0.13 | 0.25 | 0.13 | 0.25 | 0.5 | 0.5 | 0.25 | 0.016 |
| 28 | Stenotrophomonas | maltophilia | | 0.13 | 0.25 | 0.25 | 2 | 0.5 | 1 | 1 | 0.25 | 0.25 |
| 29 | Pseudomonas | aeruginosa | | 4 | 8 | 1 | 1 | 8 | 8 | 16 | 2 | 0.25 |
| 30 | Pseudomonas | aeruginosa | | 4 | 8 | 1 | 2 | 8 | 8 | 16 | 2 | 0.5 |
| 31 | Pseudomonas | aeruginosa | Ofx-R | 2 | 4 | 0.25 | 2 | 2 | 2 | 8 | 0.5 | 0.5 |
| 32 | Pseudomonas | aeruginosa | Cf-R | 4 | 8 | 2 | 2 | 4 | 16 | 16 | 2 | 0.13 |
| 33 | Pseudomonas | aeruginosa | Ci-R | 4 | 8 | 2 | 2 | 8 | 16 | 16 | 2 | 1 |
| 34 | Pseudomonas | aeruginosa | Gen-R | 4 | 8 | 2 | 2 | 8 | 16 | 32 | 2 | 0.5 |
| 35 | Pseudomonas | aeruginosa | Ip-R | 8 | 16 | 2 | 4 | 8 | 16 | 32 | 4 | 4 |
| 36 | Pseudomonas | aeruginosa | Cf-R, Ci-R, Mp-R | 32 | 32 | 16 | 16 | 32 | >32 | >32 | 16 | 8 |

| # | Genus | Species | Resistance | 89 | 93 | 99 | 106 | 111 | 115 | 120 | 127 | Meropenem |
|---|---|---|---|---|---|---|---|---|---|---|---|---|
| 1 | Acinetobacter | calcoaceticus | | 0.13 | 1 | 0.25 | 4 | 1 | 0.5 | 4 | 1 | 0.5 |
| 2 | Acinetobacter | baumannii | Cf-R, Ci-R | 1 | 2 | 1 | 2 | 4 | 1 | 8 | 1 | 1 |
| 3 | Acinetobacter | baumannii | Cf-R, Ci-R, Mp-I | 1 | 8 | 2 | 8 | 4 | 2 | 16 | 4 | 8 |
| 4 | Acinetobacter | baumannii | Cf-R, Imp-I, CBPase | 0.5 | 2 | 2 | 2 | 4 | 1 | 4 | 2 | 4 |
| 5 | Citrobacter | diversus | | 0.13 | 0.25 | 0.5 | 1 | 0.5 | 0.25 | 0.5 | 0.5 | 0.016 |
| 6 | Citrobacter | freundii | | 0.25 | 0.5 | 1 | 1 | 0.5 | 0.25 | 0.5 | 0.5 | 0.016 |
| 7 | Enterobacter | aerogenes | | 1 | 2 | 2 | 2 | 2 | 1 | 2 | 2 | 0.063 |
| 8 | Enterobacter | cloacae | Cf-R, B+ | 0.13 | 0.25 | 0.5 | 1 | 0.5 | 0.13 | 0.5 | 0.5 | 0.016 |
| 9 | Enterobacter | cloacae | Cf-R | 0.25 | 0.5 | 1 | 2 | 1 | 0.25 | 1 | 1 | 0.063 |
| 10 | Escherichia | coli | Ci-R | 0.13 | 0.25 | 0.5 | 1 | 0.5 | 0.25 | 0.5 | 0.5 | 0.016 |
| 11 | Escherichia | coli | Ci-R, AmpC | 0.13 | 0.25 | 0.5 | 0.5 | 0.5 | 0.25 | 0.5 | 0.5 | 0.016 |
| 12 | Escherichia | coli | | 0.13 | 0.25 | 0.5 | 1 | 0.5 | 0.25 | 0.5 | 0.5 | 0.016 |
| 13 | Escherichia | coli | | 0.25 | 0.5 | 1 | 1 | 0.5 | 0.25 | 0.5 | 0.5 | 0.016 |

TABLE 1-continued

Antibacterial activity (MIC$^a$) data on G(−) bacterial strains

| # | Genus | Species | Resistance | | | | | | | | | |
|---|---|---|---|---|---|---|---|---|---|---|---|---|
| 14 | Klebsiella | oxytoca | | 0.5 | 0.5 | 2 | 2 | 1 | 0.25 | 1 | 1 | 0.031 |
| 15 | Klebsiella | pneumoniae | | 0.25 | 0.5 | 1 | 1 | 1 | 0.5 | 1 | 1 | 0.031 |
| 16 | Moraxella | catarrhalis | | ≤0.008 | 0.031 | ≤0.008 | ≤0.008 | ≤0.008 | ≤0.008 | 0.016 | ≤0.008 | ≤0.008 |
| 17 | Morganella | Morganii | | 2 | 8 | 4 | 4 | 4 | 2 | 8 | 4 | 0.13 |
| 18 | Morganella | Morganii | | 2 | 4 | 4 | 4 | 2 | 2 | 4 | 4 | 0.13 |
| 19 | Proteus | vulgaris | | 0.5 | 2 | 2 | 2 | 2 | 1 | 4 | 2 | 0.13 |
| 20 | Proteus | mirabilis | | 0.25 | 0.5 | 1 | 1 | 0.5 | 0.25 | 0.5 | 0.5 | 0.031 |
| 21 | Providencia | rettgeri | | 1 | 2 | 4 | 4 | 2 | 1 | 2 | 2 | 0.031 |
| 22 | Salmonella | typhimurium | | 0.25 | 0.5 | 1 | 1 | 0.5 | 0.25 | 0.5 | 0.5 | 0.016 |
| 23 | Serratia | marcescens | | 0.5 | 1 | 2 | 2 | 1 | 0.5 | 1 | 1 | 0.031 |
| 24 | Serratia | marcescens | | 0.5 | 1 | 4 | 2 | 2 | 1 | 2 | 2 | 0.031 |
| 25 | Shigella | dysenteriae | | 0.25 | 0.5 | 1 | 1 | 0.5 | 0.25 | 0.5 | 1 | 0.016 |
| 26 | Shigella | sonnei | | 0.25 | 0.5 | 1 | 1 | 0.5 | 0.25 | 0.5 | 0.5 | 0.016 |
| 27 | Shigella | flexneri | | 0.13 | 0.25 | 1 | 0.5 | 0.5 | 0.25 | 0.5 | 0.5 | 0.016 |
| 28 | Stenotrophomonas | maltophilia | | 0.13 | 0.5 | 0.25 | 1 | 0.5 | 0.25 | 1 | 0.5 | 0.25 |
| 29 | Pseudomonas | aeruginosa | | 1 | 4 | 2 | 8 | 4 | 4 | 16 | 8 | 0.25 |
| 30 | Pseudomonas | aeruginosa | | 1 | 4 | 2 | 8 | 4 | 4 | 16 | 8 | 0.5 |
| 31 | Pseudomonas | aeruginosa | Ofx-R | 0.5 | 4 | 1 | 4 | 1 | 1 | 4 | 2 | 0.5 |
| 32 | Pseudomonas | aeruginosa | Cf-R | 1 | 4 | 4 | 8 | 4 | 4 | 16 | 8 | 0.13 |
| 33 | Pseudomonas | aeruginosa | Ci-R | 1 | 8 | 4 | 8 | 8 | 8 | 16 | 8 | 1 |
| 34 | Pseudomonas | aeruginosa | Gen-R | 1 | 8 | 4 | 8 | 4 | 8 | 16 | 8 | 0.5 |
| 35 | Pseudomonas | aeruginosa | Ip-R | 4 | 16 | 4 | 16 | 8 | 8 | >32 | 16 | 4 |
| 36 | Pseudomonas | aeruginosa | Cf-R, Ci-R, Mp-R | 8 | 16 | >32 | >32 | >32 | >32 | >32 | >32 | 8 |

| # | Genus | Species | Resistance | 132 | 137 | 143 | 146 | 151 | 156 | 163 | 167 | Meropenem |
|---|---|---|---|---|---|---|---|---|---|---|---|---|
| 1 | Acinetobacter | calcoaceticus | | 4 | 1 | 8 | 1 | 0.25 | 0.5 | 2 | 32 | 0.5 |
| 2 | Acinetobacter | baumannii | Cf-R, Ci-R | 16 | 2 | 32 | 1 | 0.5 | 2 | 4 | >32 | 1 |
| 3 | Acinetobacter | baumannii | Cf-R, Ci-R, Mp-I | 16 | 8 | 32 | 2 | 2 | 4 | 8 | >32 | 8 |
| 4 | Acinetobacter | baumannii | Cf-R, Imp-I, CBPase | 32 | 2 | >32 | 4 | 1 | 2 | 16 | >32 | 4 |
| 5 | Citrobacter | diversus | | 0.25 | 0.5 | 0.5 | 0.5 | 0.25 | 0.5 | 0.5 | 1 | 0.016 |
| 6 | Citrobacter | freundii | | 0.25 | 1 | 1 | 0.5 | 0.5 | 0.5 | 1 | 2 | 0.016 |
| 7 | Enterobacter | aerogenes | | 1 | 2 | 4 | 2 | 2 | 2 | 2 | 4 | 0.063 |
| 8 | Enterobacter | cloacae | Cf-R, B+ | 0.25 | 0.5 | 0.5 | 0.25 | 0.25 | 0.5 | 0.5 | 2 | 0.016 |
| 9 | Enterobacter | cloacae | Cf-R | 0.5 | 1 | 1 | 1 | 0.5 | 1 | 1 | 2 | 0.063 |
| 10 | Escherichia | coli | Ci-R | 0.25 | 0.5 | 0.5 | 0.25 | 0.25 | 0.5 | 0.5 | 1 | 0.016 |
| 11 | Escherichia | coli | Ci-R, AmpC | 0.25 | 0.5 | 0.5 | 0.25 | 0.25 | 0.5 | 0.5 | 1 | 0.016 |
| 12 | Escherichia | coli | | 0.25 | 0.5 | 0.5 | 0.5 | 0.25 | 0.5 | 0.5 | 1 | 0.016 |
| 13 | Escherichia | coli | | 0.25 | 1 | 0.5 | 0.5 | 0.5 | 0.5 | 0.5 | 1 | 0.016 |
| 14 | Klebsiella | oxytoca | | 0.5 | 1 | 1 | 1 | 0.5 | 1 | 1 | 2 | 0.031 |
| 15 | Klebsiella | pneumoniae | | 0.5 | 1 | 2 | 1 | 0.5 | 1 | 1 | 2 | 0.031 |
| 16 | Moraxella | catarrhalis | | 0.016 | ≤0.008 | 0.063 | 0.016 | ≤0.008 | ≤0.008 | ≤0.008 | 2 | ≤0.008 |
| 17 | Morganella | Morganii | | 4 | 4 | 16 | 8 | 4 | 4 | 8 | 8 | 0.13 |
| 18 | Morganella | Morganii | | 4 | 4 | 8 | 8 | 4 | 4 | 8 | 8 | 0.13 |
| 19 | Proteus | vulgaris | | 1 | 2 | 8 | 4 | 1 | 2 | 4 | 4 | 0.13 |
| 20 | Proteus | mirabilis | | 0.25 | 0.5 | 1 | 0.5 | 0.5 | 0.5 | 0.5 | 2 | 0.031 |
| 21 | Providencia | rettgeri | | 1 | 2 | 2 | 2 | 2 | 2 | 1 | 2 | 0.031 |
| 22 | Salmonella | typhimurium | | 0.25 | 1 | 0.5 | 0.5 | 0.5 | 1 | 0.5 | 2 | 0.016 |
| 23 | Serratia | marcescens | | 0.5 | 2 | 1 | 2 | 1 | 2 | 2 | 2 | 0.031 |
| 24 | Serratia | marcescens | | 1 | 2 | 2 | 2 | 1 | 2 | 2 | 4 | 0.031 |
| 25 | Shigella | dysenteriae | | 0.25 | 1 | 1 | 0.5 | 0.5 | 1 | 1 | 1 | 0.016 |
| 26 | Shigella | sonnei | | 0.25 | 1 | 1 | 0.5 | 0.5 | 0.5 | 0.5 | 1 | 0.016 |
| 27 | Shigella | flexneri | | 0.13 | 0.5 | 0.5 | 0.25 | 0.25 | 0.5 | 0.5 | 1 | 0.016 |
| 28 | Stenotrophomonas | maltophilia | | 2 | 0.5 | 4 | 0.5 | 0.25 | 0.5 | 1 | 16 | 0.25 |
| 29 | Pseudomonas | aeruginosa | | >32 | 8 | >32 | 8 | 2 | 4 | 16 | >32 | 0.25 |
| 30 | Pseudomonas | aeruginosa | | >32 | 8 | >32 | 8 | 2 | 4 | 16 | >32 | 0.5 |
| 31 | Pseudomonas | aeruginosa | Ofx-R | 32 | 4 | 32 | 2 | 1 | 2 | 4 | 32 | 0.5 |
| 32 | Pseudomonas | aeruginosa | Cf-R | >32 | 8 | >32 | 8 | 2 | 8 | 16 | >32 | 0.13 |
| 33 | Pseudomonas | aeruginosa | Ci-R | >32 | 16 | >32 | 8 | 2 | 8 | 16 | >32 | 1 |
| 34 | Pseudomonas | aeruginosa | Gen-R | >32 | 16 | >32 | 8 | 2 | 8 | 16 | >32 | 0.5 |
| 35 | Pseudomonas | aeruginosa | Ip-R | >32 | 32 | >32 | 16 | 4 | 8 | 16 | >32 | 4 |
| 36 | Pseudomonas | aeruginosa | Cf-R, Ci-R, Mp-R | >32 | >32 | >32 | 32 | 8 | >32 | >32 | >32 | 8 |

| # | Genus | Species | Resistance | 176 | 178 | 185a | 185b | Meropenem |
|---|---|---|---|---|---|---|---|---|
| 1 | Acinetobacter | calcoaceticus | | 0.13 | 0.13 | 0.13 | 0.13 | 0.5 |
| 2 | Acinetobacter | baumannii | Cf-R, Ci-R | 0.5 | 1 | 0.5 | 0.50 | 1 |
| 3 | Acinetobacter | baumannii | Cf-R, Ci-R, Mp-I | 1 | 1 | 1 | 2 | 8 |
| 4 | Acinetobacter | baumannii | Cf-R, Imp-I, CBPase | 1 | 1 | 1 | 1 | 4 |
| 5 | Citrobacter | diversus | | 0.063 | 0.25 | 0.13 | 0.063 | 0.016 |
| 6 | Citrobacter | freundii | | 0.13 | 0.5 | 0.13 | 0.063 | 0.016 |
| 7 | Enterobacter | aerogenes | | 0.25 | 1 | 0.5 | 0.25 | 0.063 |

TABLE 1-continued

Antibacterial activity (MIC$^a$) data on G(−) bacterial strains

| 8 | Enterobacter | cloacae | Cf-R, B+ | 0.063 | 0.25 | 0.063 | 0.063 | 0.016 |
|---|---|---|---|---|---|---|---|---|
| 9 | Enterobacter | cloacae | Cf-R | 0.13 | 0.5 | 0.13 | 0.13 | 0.063 |
| 10 | Escherichia | coli | Ci-R | 0.063 | 0.25 | 0.063 | 0.031 | 0.016 |
| 11 | Escherichia | coli | Ci-R, AmpC | 0.063 | 0.25 | 0.063 | 0.031 | 0.016 |
| 12 | Escherichia | coli | | 0.063 | 0.5 | 0.063 | 0.031 | 0.016 |
| 13 | Escherichia | coli | | 0.13 | 0.5 | 0.13 | 0.063 | 0.016 |
| 14 | Klebsiella | oxytoca | | 0.13 | 0.5 | 0.25 | 0.13 | 0.031 |
| 15 | Klebsiella | pneumoniae | | 0.13 | 0.5 | 0.25 | 0.13 | 0.031 |
| 16 | Moraxella | catarrhalis | | ≤0.008 | ≤0.008 | ≤0.008 | ≤0.008 | ≤0.008 |
| 17 | Morganella | Morganii | | 1 | 2 | 1 | 0.5 | 0.13 |
| 18 | Morganella | Morganii | | 0.5 | 2 | 1 | 0.5 | 0.13 |
| 19 | Proteus | vulgaris | | 0.25 | 2 | 0.5 | 0.25 | 0.13 |
| 20 | Proteus | mirabilis | | 0.063 | 0.5 | 0.13 | 0.063 | 0.031 |
| 21 | Providencia | rettgeri | | 0.25 | 1 | 0.5 | 0.25 | 0.031 |
| 22 | Salmonella | typhimurium | | 0.13 | 0.5 | 0.13 | 0.063 | 0.016 |
| 23 | Serratia | marcescens | | 0.25 | 1 | 0.25 | 0.13 | 0.031 |
| 24 | Serratia | marcescens | | 0.25 | 2 | 0.5 | 0.13 | 0.031 |
| 25 | Shigella | dysenteriae | | 0.13 | 0.5 | 0.13 | 0.063 | 0.016 |
| 26 | Shigella | sonnei | | 0.063 | 0.5 | 0.13 | 0.063 | 0.016 |
| 27 | Shigella | flexneri | | 0.063 | 0.25 | 0.063 | 0.063 | 0.016 |
| 28 | Stenotrophomonas | maltophilia | | 0.063 | 0.13 | 0.063 | 0.13 | 0.25 |
| 29 | Pseudomonas | aeruginosa | | 1 | 1 | 1 | 1 | 0.25 |
| 30 | Pseudomonas | aeruginosa | | 1 | 2 | 1 | 1 | 0.5 |
| 31 | Pseudomonas | aeruginosa | Ofx-R | 0.5 | 1 | 0.5 | 0.5 | 0.5 |
| 32 | Pseudomonas | aeruginosa | Cf-R | 1 | 2 | 1 | 1 | 0.13 |
| 33 | Pseudomonas | aeruginosa | Ci-R | 1 | 2 | 1 | 1 | 1 |
| 34 | Pseudomonas | aeruginosa | Gen-R | 1 | 2 | 1 | 1 | 0.5 |
| 35 | Pseudomonas | aeruginosa | Ip-R | 2 | 2 | 2 | 4 | 4 |
| 36 | Pseudomonas | aeruginosa | Cf-R, Ci-R, Mp-R | 8 | 16 | 8 | 8 | 8 |

The compositions, methods and/or processes disclosed and claimed herein can be made and executed without undue experimentation in light of the present disclosure. While the compositions and methods of this invention have been described in terms of preferred embodiments, it will be apparent to those of skill in the art that variations may be applied to the compositions, methods and/or processes and in the steps or in the sequence of steps of the methods described herein without departing from the concept and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope and concept of the invention.

We claim:

1. A method of treating a bacterial infection in a host comprising administering a therapeutic amount of a compound of Formula I:

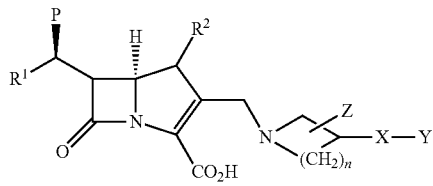

or a pharmaceutically acceptable salt, ester or prodrug thereof,
wherein
$R^1$ and $R^2$ are each independently selected from H or alkyl;
P is H, OH, halogen, or hydroxyl protected by a hydroxyl protecting group;
n is 1 or 2;
X is —(CR$_2$)$_m$— or —C(═O)—;
m is 0, 1 or 2;
Y is CN, SR' or NRR';
each R is independently selected from H, alkyl or haloalkyl;
R' is alkyl, NR$_2$; C(═O)R; SO$_2$R; SO$_2$NR$_2$; C(═NR)NR$_2$; C(═O)NR$_2$; CR$_2$C(═O)NR$_2$; C(═NR)R; C(═NR)NRSO$_2$R; C(═NR)NRC(═O)R; C(═O)CR$_2$NRSO$_2$NR$_2$; or C(═O)CR$_2$NRC(═NR)NR$_2$; and
Z is H, alkyl, halo, CN, SR' or NRR'; optionally in a pharmaceutically acceptable carrier or diluent.

2. A method of treating a bacterial infection in a host comprising administering a therapeutic amount of a compound of Formula II:

or a pharmaceutically acceptable salt, ester or prodrug thereof,
wherein
$R^1$ and $R^2$ are each independently selected from H or alkyl;
P is H, OH, halogen, or hydroxyl protected by a hydroxyl protecting group;
X is —(CR$_2$)$_m$— or —C(═O)—;
m is 0, 1 or 2;

Y is CN, OR, SR' or NRR';
each R is independently selected from H, alkyl or haloalkyl;
R' is H, alkyl, NR$_2$; C(=O)R; SO$_2$R; SO$_2$NR$_2$; C(=NR)NR$_2$; C(=O)NR$_2$; CR$_2$C(=O)NR$_2$; C(=NR)R; C(=NR)NRSO$_2$R; C(=NR)NRC(=O)R; C(=O)CR$_2$NRSO$_2$NR$_2$; or C(=O)CR$_2$NRC(=NR)NR$_2$; and
Z is H, alkyl, halo, CN, OR, SR' or NRR'; optionally in a pharmaceutically acceptable carrier or diluent.

3. A method of treating a bacterial infection in a host comprising administering a therapeutic amount of a compound of Formula III:

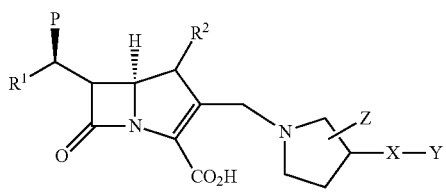

or a pharmaceutically acceptable salt, ester or prodrug thereof,
wherein
R$^1$ and R$^2$ are each independently selected from H or alkyl;
P is H, OH, halogen, or hydroxyl protected by a hydroxyl protecting group;
X is —(CR$_2$)$_m$— or —C(=O)—;
m is 0, 1 or 2;
Y is CN, SR' or NRR';
each R is independently selected from H, alkyl or haloalkyl;
R' is alkyl, NR$_2$; C(=O)R; SO$_2$R; SO$_2$NR$_2$; C(=NR)NR$_2$; C(=O)NR$_2$; CR$_2$C(=O)NR$_2$; C(=NR)R; C(=NR)NRSO$_2$R; C(=NR)NRC(=O)R; C(=O)CR$_2$NRSO$_2$NR$_2$; or C(=O)CR$_2$NRC(=NR)NR$_2$; and
Z is H, alkyl, halo, CN, SR' or NRR'; optionally in a pharmaceutically acceptable carrier or diluent.

4. A method of treating a bacterial infection in a host comprising administering a therapeutic amount of a compound of Formula IV:

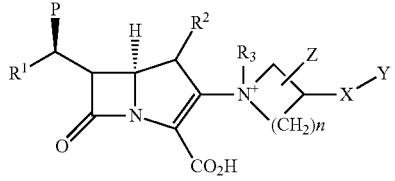

or a pharmaceutically acceptable salt, ester or prodrug thereof,
wherein
R$^1$, R$^2$ and R$^3$ are each independently selected from H or alkyl;
P is H, OH, halogen, or hydroxyl protected by a hydroxyl protecting group;
n is 1, or 2
X is —(CR$_2$)$_m$— or —C(=O)—;
m is 0, 1 or 2;
Y is CN, OR, SR' or NRR';
each R is independently selected from H, alkyl or haloalkyl;

R' is H, alkyl, NR$_2$; C(=O)R; SO$_2$R; SO$_2$NR$_2$; C(=NR)NR$_2$; C(=O)NR$_2$; CR$_2$C(=O)NR$_2$; C(=NR)R; C(=NR)NRSO$_2$R; C(=NR)NRC(=O)R; C(=O)CR$_2$NRSO$_2$NR$_2$; or C(=O)CR$_2$NRC(=NR)NR$_2$; and
Z is H, alkyl, halo, CN, OR, SR' or NRR'; optionally in a pharmaceutically acceptable carrier or diluent.

5. A method of treating a bacterial infection in a host comprising administering a therapeutic amount of a compound of Formula V:

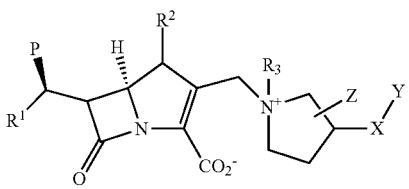

or a pharmaceutically acceptable salt, ester or prodrug thereof,
wherein
R$^1$, R$^2$ and R$^3$ are each independently selected from H or alkyl;
P is H, OH, halogen, or hydroxyl protected by a hydroxyl protecting group;
X is —(CR$_2$)$_m$— or —C(=O)—;
m is 0, 1 or 2;
Y is CN, OR, SR' or NRR';
each R is independently selected from H, alkyl or haloalkyl;
R' is H, alkyl, NR$_2$; C(=O)R; SO$_2$R; SO$_2$NR$_2$; C(=NR)NR$_2$; C(=O)NR$_2$; CR$_2$C(=O)NR$_2$; C(=NR)R; C(=NR)NRSO$_2$R; C(=NR)NRC(=O)R; C(=O)CR$_2$NRSO$_2$NR$_2$; or C(=O)CR$_2$NRC(=NR)NR$_2$; and
Z is H, alkyl, halo, CN, OR, SR' or NRR'; optionally in a pharmaceutically acceptable carrier or diluent.

6. A method of treating a bacterial infection in a host comprising administering a therapeutic amount of a compound of Formula VI:

(VI)

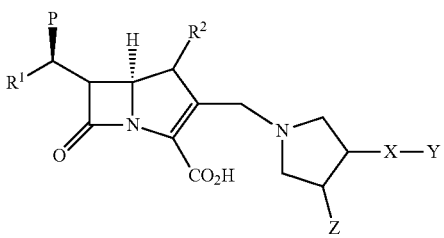

or a pharmaceutically acceptable salt, ester or prodrug thereof,
wherein
R$^1$ and R$^2$ are each independently selected from H or alkyl;
P is H, OH, halogen, or hydroxyl protected by a hydroxyl protecting group;
X is —(CR$_2$)$_m$— or —C(=O)—;
m is 0, 1 or 2;
Y is CN, SR' or NRR';
each R is independently selected from H, alkyl or haloalkyl;

R' is alkyl, NR$_2$; C(=O)R; SO$_2$R; SO$_2$NR$_2$; C(=NR)NR$_2$; C(=O)NR$_2$; CR$_2$C(=O)NR$_2$; C(=NR)R; C(=NR)NRSO$_2$R; C(=NR)NRC(=O)R; C(=O)CR$_2$NRSO$_2$NR$_2$; or C(=O)CR$_2$NRC(=NR)NR$_2$; and
Z is H, alkyl, halo, CN, SR' or NRR'.
7. A method of treating a bacterial infection in a host comprising administering a therapeutic amount of a compound selected from the group consisting of:
49
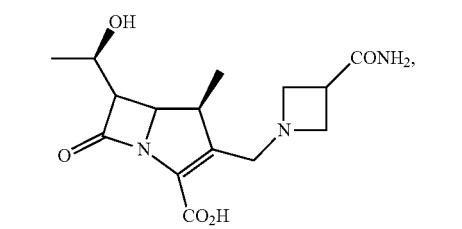
58
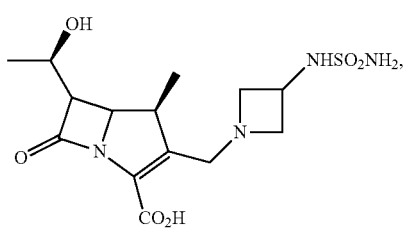
89
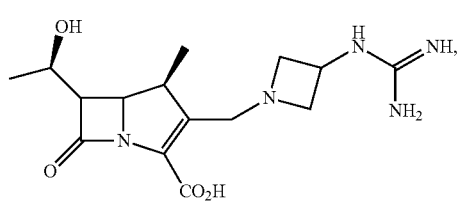
93
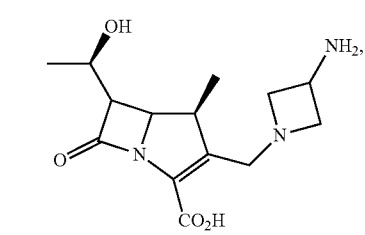
7
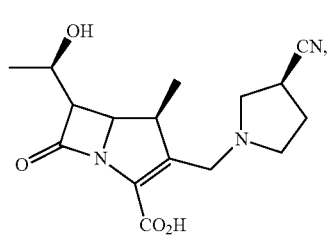
12
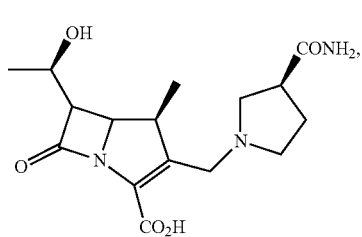
-continued
19
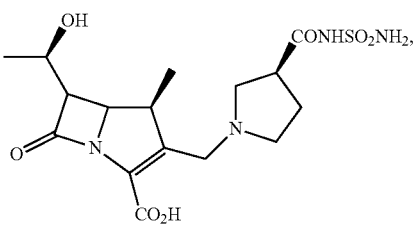
27
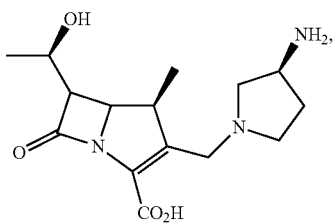
32
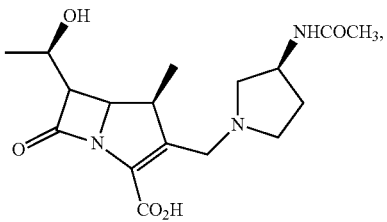
37
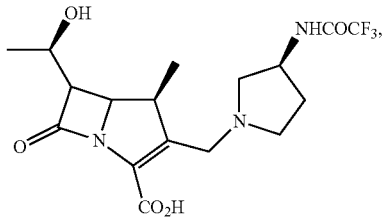
43
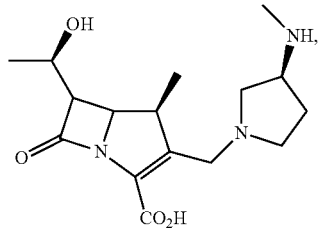
46
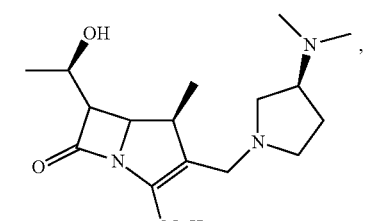
64
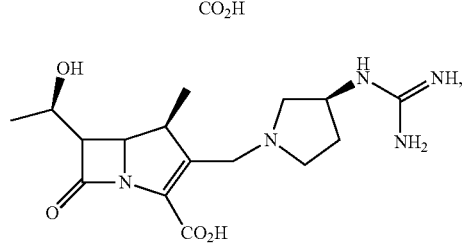

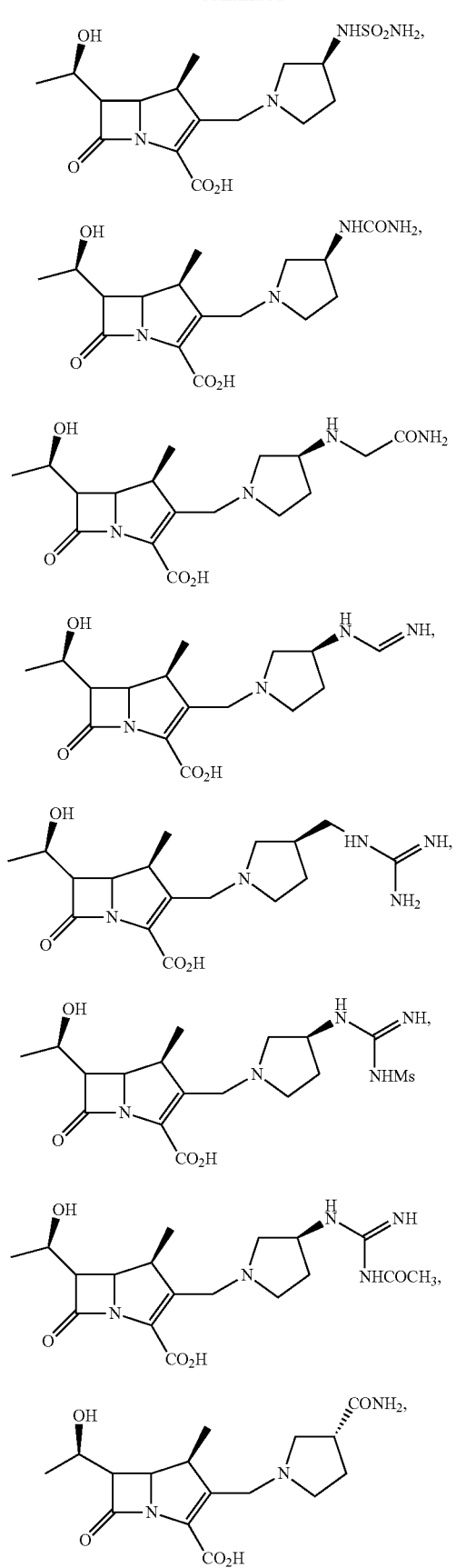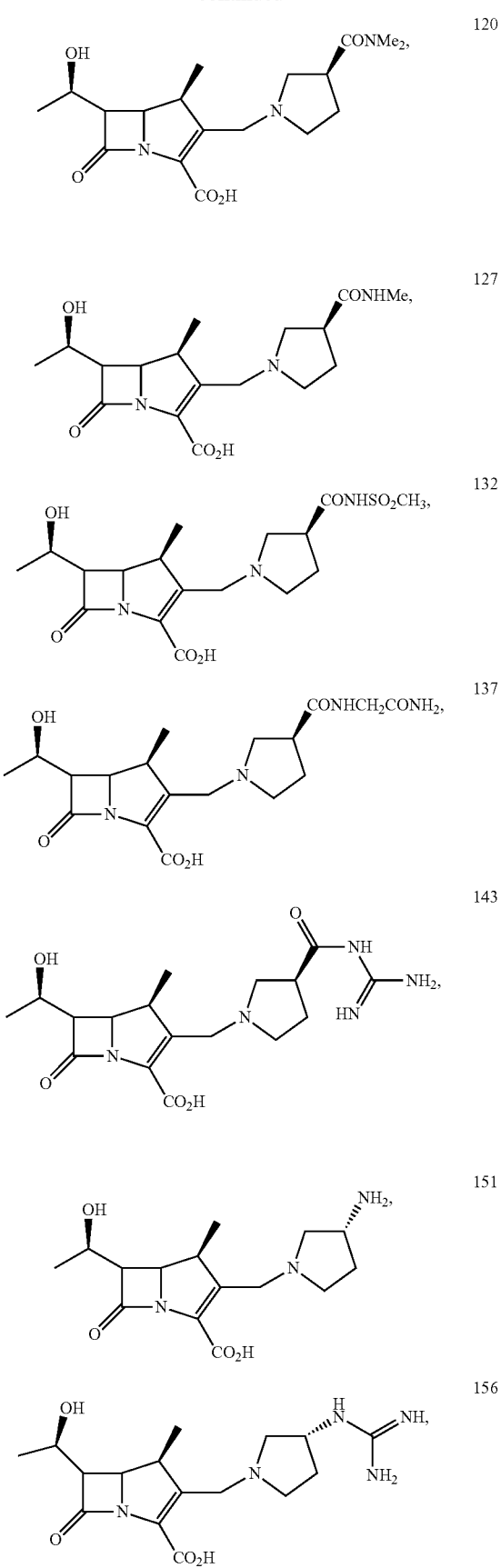

-continued

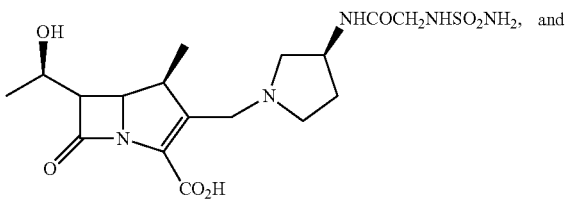
163

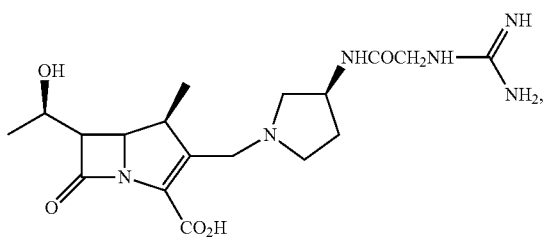
167 pharmaceutically acceptable salt, ester or prodrug thereof.

8. A method of treating a bacterial infection in a host comprising administering a therapeutic amount of a compound selected from the group consisting of:

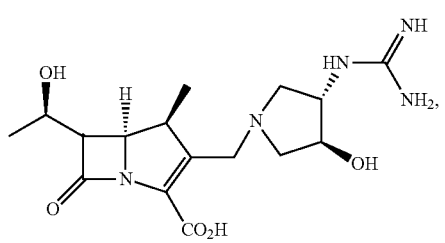
176

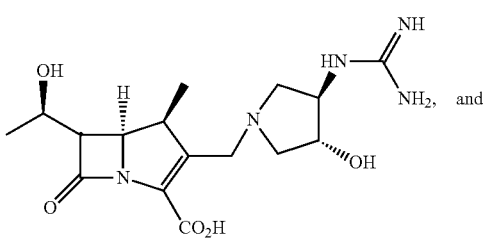
178

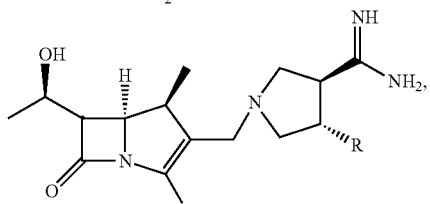
185a R = H
185b R = OH

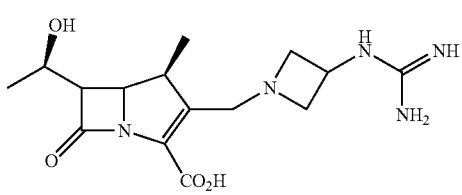
89 or a pharmaceutically acceptable salt, ester or prodrug thereof.

9. The method of claim 1, wherein the host is a human.

10. The method of claim 1, wherein the compound is administered orally, parenterally, intravenously, intradermally, subcutaneously or topically.

11. The method of claim 1, wherein the bacterial infection is due to gram-negative bacteria.

12. The method of claim 1, wherein the bacterial infection is a drug resistant or multiple-drug resistant bacterial infection.

13. The method of claim 1, where in the compound is administered in combination or alternation with another anti-bacterial agent.

14. The method of claim 13, wherein the other anti-bacterial agent is a β-lactamase inhibitor.

15. The method of claim 2, wherein the host is a human.

16. The method of claim 2, wherein the compound is administered orally, parenterally, intravenously, intradermally, subcutaneously or topically.

17. The method of claim 2, wherein the bacterial infection is due to gram-negative bacteria.

18. The method of claim 2, wherein the bacterial infection is a drug resistant or multiple-drug resistant bacterial infection.

19. The method of claim 2, where in the compound is administered in combination or alternation with another anti-bacterial agent.

20. The method of claim 19, wherein the other anti-bacterial agent is a β-lactamase inhibitor.

21. The method of claim 6, wherein the host is a human.

22. The method of claim 6, wherein the compound is administered orally, parenterally, intravenously, intradermally, subcutaneously or topically.

23. The method of claim 6, wherein the bacterial infection is due to gram-negative bacteria.

24. The method of claim 6, wherein the bacterial infection is a drug resistant or multiple-drug resistant bacterial infection.

25. The method of claim 6, where in the compound is administered in combination or alternation with another anti-bacterial agent.

26. The method of claim 25, wherein the other anti-bacterial agent is a β-lactamase inhibitor.

27. The method of claim 1, wherein the host is a human.

28. The method of claim 1, wherein the compound is administered orally, parenterally, intravenously, intradermally, subcutaneously or topically.

29. The method of claim 1, wherein the bacterial infection is due to gram-negative bacteria.

30. The method of claim 1, wherein the bacterial infection is a drug resistant or multiple-drug resistant bacterial infection.

31. The method of claim 1, where in the compound is administered in combination or alternation with another anti-bacterial agent.

32. The method of claim 31, wherein the other anti-bacterial agent is a β-lactamase inhibitor.

* * * * *